United States Patent
Jacobson et al.

(10) Patent No.: US 10,947,210 B2
(45) Date of Patent: *Mar. 16, 2021

(54) INHIBITORS OF HEPATITIS C VIRUS POLYMERASE

(71) Applicant: COCRYSTAL PHARMA, INC., Bothell, WA (US)

(72) Inventors: Irina C. Jacobson, Sammamish, WA (US); Michael D. Feese, Seattle, WA (US); Sam S K Lee, Edmonds, WA (US)

(73) Assignee: COCRYSTAL PHARMA, INC., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/582,468

(22) Filed: Sep. 25, 2019

(65) Prior Publication Data

US 2020/0255393 A1   Aug. 13, 2020

Related U.S. Application Data

(63) Continuation of application No. 15/556,653, filed as application No. PCT/US2016/023664 on Mar. 23, 2016, now Pat. No. 10,464,914.

(60) Provisional application No. 62/136,857, filed on Mar. 23, 2015.

(51) Int. Cl.
C07D 307/84    (2006.01)
A61K 31/343    (2006.01)
A61K 45/06     (2006.01)

(52) U.S. Cl.
CPC .......... *C07D 307/84* (2013.01); *A61K 31/343* (2013.01); *A61K 45/06* (2013.01)

(58) Field of Classification Search
CPC .................................................. C07D 307/84
See application file for complete search history.

(56) References Cited

U.S. PATENT DOCUMENTS

| | | | |
|---|---|---|---|
| 6,350,458 B1 | 2/2002 | Modi | |
| 6,881,741 B2 | 4/2005 | Chan Chun Kong et al. | |
| 6,887,877 B2 | 5/2005 | Chan Chun Kong et al. | |
| 6,936,629 B2 | 8/2005 | Chan Chun Kong et al. | |
| 7,402,608 B2 | 7/2008 | Chan Chun Kong et al. | |
| 7,569,600 B2 | 8/2009 | Denis et al. | |
| 9,707,215 B2 | 7/2017 | Lee et al. | |
| 10,464,914 B2 * | 11/2019 | Jacobson | A61P 43/00 |
| 2007/0293484 A1 | 12/2007 | Guan et al. | |
| 2009/0136448 A1 | 5/2009 | Corfield et al. | |

FOREIGN PATENT DOCUMENTS

| | | |
|---|---|---|
| JP | 2013-521237 A | 6/2013 |
| JP | 2013-527842 A | 7/2013 |
| WO | WO-96/29075 A1 | 9/1996 |
| WO | WO-02/100846 A1 | 12/2002 |
| WO | WO-02/100851 A2 | 12/2002 |
| WO | WO-2004/041201 A2 | 5/2004 |
| WO | WO-2004/052879 A1 | 6/2004 |
| WO | WO-2004/052885 A1 | 6/2004 |
| WO | WO-2006/072347 A2 | 7/2006 |
| WO | WO-2006/119646 A1 | 11/2006 |
| WO | WO-2008/017688 A1 | 2/2008 |
| WO | WO-2008/024843 A2 | 2/2008 |
| WO | WO-2008/043791 A2 | 4/2008 |
| WO | WO-2008/058393 A1 | 5/2008 |
| WO | WO-2008/059042 A1 | 5/2008 |
| WO | WO-2008/125599 A1 | 10/2008 |
| WO | WO-2009/000818 A1 | 12/2008 |
| WO | WO-2009/101022 A1 | 8/2009 |
| WO | WO-2009/137500 A1 | 11/2009 |
| WO | WO-2011/106929 A1 | 9/2011 |
| WO | WO-2012/067663 A1 | 5/2012 |
| WO | WO-2012/083105 A1 | 6/2012 |

OTHER PUBLICATIONS

"Evaluation of Acute Hepatitis C Infection Surveillance—United States, 2008" MMWR 59(43):1407-10 (Nov. 5, 2010).
Appleby et al., "Viral RNA polymerase inhibitors", Chapter 23 (pp. 527-546) In: Cameron et al. (eds.), Viral Genome Replication, Springer Science+Business Media (2009).
Bartenschlager et al., Replication of the hepatitis C virus in cell culture, Antiviral Res., 60(2):91-102 (2003).

(Continued)

*Primary Examiner* — Paul V Ward
(74) *Attorney, Agent, or Firm* — Marshall, Gerstein & Borun LLP

(57) ABSTRACT

The present invention provides, among other things, compounds represented by the general Formula I: (I) and pharmaceutically acceptable salts thereof, wherein L and A (and further substituents) are as defined in classes and subclasses herein and compositions (e.g., pharmaceutical compositions) comprising such compounds, which compounds are useful as inhibitors of hepatitis C virus polymerase, and thus are useful, for example, as medicaments for the treatment of HCV infection.

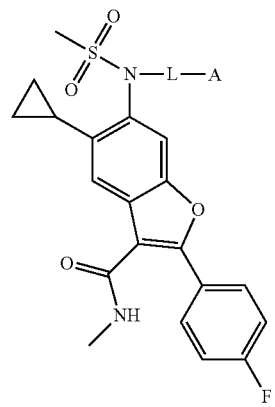

(I)

8 Claims, No Drawings

(56) References Cited

OTHER PUBLICATIONS

Biswal et al., Crystal structures of the RNA-dependent RNA polymerase genotype 2a of hepatitis C virus reveal two conformations and suggest mechanisms of inhibition by non-nucleoside inhibitors, J. Biol. Chem., 280(18):18202-10 (2005).
Chan et al., Discovery of thiophene-2-carboxylic acids as potent inhibitors of HCV NS5B polymerase and HCV subgenomic RNA replication. Part 1: Sulfonamides, Bioorg. Med. Chem. Letter. 14(3):793-6 (2004).
Ghany et al., An update on treatment of genotype 1 chronic hepatitis C virus infection: 2011 practice guideline by the American Association for the Study of Liver Diseases, Hepatology, 54(4):1433-44 (2011).
Gubert et al., A convenient synthesis of parent and 2-substituted octahydro-2H-pyrazino[1,2-a]-pyrazines, Synthesis, 22(44):318 (1991).
Hodgson, The Sandmeyer reaction, Chem. Rev., 40(2):251-77 (1947).
Huang et al., "Hepatitis C virus related assays", Chapter 2, pp. 56-57, In: Tan et al. (eds.), Hepatitis C: Antiviral Drug Discovery and Development, Caister Academic Press (2011).
International Application No. PCT/US2016/023664, International Preliminary Report on Patentability, dated Sep. 26, 2017.
International Preliminary Report on Patentability, International Application No. PCT/US2013/046758, dated Dec. 23, 2014.
International Search Report and Written Opinion, International Application No. PCT/US2013/046758, dated Nov. 15, 2013.
International Search Report and Written Opinion, International Application No. PCT/US2016/023664, dated Aug. 18, 2016.
Li et al., Allosteric inhibitors of hepatitis C polymerase: discovery of potent and orally bioavailable carbon-linked dihydropyrones, J. Med. Chem., 50(17):3969-72 (2007).
Li et al., Discovery of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one (PF-00868554) as a potent and orally available hepatitis C virus polymerase inhibitor, J. Med. Chem., 52(5):1255-8 (2009).
Lohmann et al., Replication of subgenomic hepatitis C virus RNAs in a hepatoma cell line, Science, 285(5424):110-3 (1999).
Maynard et al., Supporting Information to: Discovery of a potent boronic acid derived inhibitor of the HCV RNA-dependent RNA polymerase, J. Med. Chem., 57(5):1902-13 (2014).
McKercher et al., Specific inhibitors of HCV polymerase identified using an NS5B with lower affinity for template/primer substrate, Nucleic Acids Res., 32(2):422-31 (2004).
Morrison et al., In HCV, protease race heats up with combo therapy looming, In Vivo: The Business & Medicine Report, 27(5):42-7 (May 2009).
Powdrill et al., Inhibitors of the Hepatitis C Virus RNA-Dependent RNA Polymerase NS5B, Viruses, 2(10):2169-95 (2010).
Rautio et al., Prodrugs: design and clinical applications, Nat. Rev. Drug Discov., 7(3):255-70 (2008).
Soriano et al., Hepatitis C therapy with HCV NS5B polymerase inhibitors, Expert Opin. Pharmacother., 14(9):1161-70 (2013).
Suzuki et al., Recent advances in the cross-coupling reactions of organoboron derivatives with organic electrophiles, 1995-1998, J. Organometallic Chem., 576:147-68 (1999).
Tan (ed.), Hepatitis C Viruses: Genomes and Molecular Biology, Norfolk, UK: Horizon Bioscience (2006).
Wang et al., Non-nucleoside analogue inhibitors bind to an allosteric site on HCV NS5B polymerase. Crystal structures and mechanism of inhibition, J. Biol. Chem., 278(11):9489-95 (2003).
Woerz et al., Hepatitis C virus replicons: dinosaurs still in business?, J. Viral Hepat., 16(1):1-9 (2009).
Yang et al., Cyclic amide bioisosterism: strategic application to the design and synthesis of HCV NS5B polymerase inhibitors, Bioorg. Med. Chem. Lett., 20(15):4614-9 (2010).
Zhu et al., Design and synthesis of HCV agents with sequential triple inhibitory potentials, Bioorg. Med. Chem. Lett., 20(17):5212-6 (2010) Supplemental Data.

* cited by examiner

INHIBITORS OF HEPATITIS C VIRUS POLYMERASE

The invention provides compounds, compositions, and methods for inhibition of the hepatitis C virus.

BACKGROUND

Hepatitis C virus (HCV) is an enveloped, positive-sense, single-stranded RNA virus, of the genus Hepacivirus, belonging to the family Flaviviridae. Infection by HCV is a leading cause of liver disease and cirrhosis in humans. Transmission occurs primarily by way of percutaneous exposure to infected blood, typically involving use of injected drugs or injury with objects contaminated with blood, but is also associated with sexual contact with infected partners. Thanks to viral testing, risk of transmission by blood transfusion or by transplant is extremely low. Infection is often asymptomatic, or symptoms are mild, and about 15-20% of infected persons are able to clear the virus without treatment. However, infection in the remaining 80-85% of infected persons develops into persistent infection, which may be life-long, causing liver disease, which can lead to cirrhosis and hepatocellular carcinoma. HCV infection is the most common chronic blood-borne disease in the United States, affecting about 4 million people and causing about 12,000 deaths per year. "Evaluation of Acute Hepatitis C Infection Surveillance—United States, 2008," *MMWR*, Nov. 5, 2010, 59(43). Approximately 170 million persons around the world have chronic hepatitis C infection. Chen et al., *Int J Med Sci,* 2006, 3(2):47-52. Personal consequences of HCV infection include decreased life expectancy, chronic debilitating liver disease and possibly liver cancer, and risk of infection of sexual partners and health care workers. Economic consequences of chronic HCV infection in the United States are exceedingly large. Direct medical costs have been estimated at $10.7 billion per year for the 10-year period 2010-2019, with societal costs projected to be $54.2 billion, and the cost of morbidity from disability projected to be $21.3 billion. Id.

The hepatitis C virus has been intensively studied, and much is known about its genetics and biology. For an overview of this subject, see Tan, Ed., *Hepatitis C Viruses: Genomes and Molecular Biology,* Horizon Bioscience, Norfolk, UK (2006). HCV has a simple genome that resides in a single open reading frame of about 9.6 kb. The genome is translated in the infected cell to yield a single polyprotein consisting of about 3000 amino acids, which is then proteolytically processed by host and viral enzymes to produce at least 10 structural and non-structural (NS) proteins. The virus is diversified in infected humans into 16 different antigenically and/or genetically identifiable subtypes or genotypes, some of which are further subdivided into subtypes.

HCV rapidly mutates as it replicates, and is believed to exist as a viral quasispecies, meaning that it mutates rapidly as it replicates to generate many competing genetic varieties of the virus having comparable evolutionary fitness. This intrinsic generation of many varieties in a single infected person makes it very difficult to isolate a single variety for development of a vaccine, and is believed to be associated with the difficulty in developing a vaccine, development of resistance of the virus to specific pharmaceuticals, and persistence of the virus in the host. It is possible that the virus able to develop into immunologically distinct quasispecies under the pressure of the immune response of the host, thereby allowing it to survive and persist.

Another factor making it difficult to develop treatments for HCV infection is the narrow range of hosts and a notoriously difficult problem of propagating the virus in cell culture. Most research has been done using pseudoparticle systems. Pseudoparticles consist primarily of nucleocapsids surrounded by a lipid envelope and contain HCV glycoprotein complexes. These pseudoparticles have been used to elucidate the early stages of the viral replication cycle and receptor binding, and to study neutralizing antibodies. Notwithstanding, pseudoparticles have a significant limitation in that they cannot recapitulate the full replication cycle. Other systems described for investigation of HCV include culture of subgenomic RNAs in Huh-7 cells, and culture in primary human hepatocytes, and surrogate models such as the bovine viral diarrhea virus (BVDV).

Significant research has also been done in synthetic RNA replicons, which self-amplify in human hepatoma cells and recapitulate much, but not all, of the HCV replication cycle. Heretofore, such replicons have been subgenomic, and have also been unable to yield infectious viral particles. Moreover, such a replicon system appears to function only using the 1b genotype of HCV (HCV1b). More recently, HCV cell culture has become possible through the isolation of the JFH-1 clone (HCV 2a). While its uniqueness remains incompletely understood, JFH-1 replicates to high levels in Huh-7 (hepatocellular carcinoma) cells and other cell types in culture, and produces infectious particles. Serial passage of JFH-1 has caused it to become genetically conditioned to cell culture conditions and it may no longer be representative of clinical isolates of the virus, but the viral particles are apparently functional virions, insofar as they are infectious in culture and in inoculated animals bearing human liver xenografts. Apparently, the efficiency of JFH-1 replication depends significantly upon the NS5B gene of the clone. Replacement with NS5B genes from other genotypes is difficult. Woerz et al., 2009, *J Viral Hepat,* 16(1):1-9. Other replicon systems have been developed with various replication markers and for different HCV genotypes, including HCV 1a and HCV 2a. See, Huang et al., "Hepatitis C Virus-related Assays," Chapter 2 in *Hepatitis C: Antiviral Drug Discovery and Development,* S-L Tan and Y He, eds., Caister Academic Press (2011), at pp 56-57.

Approved pharmaceutical treatments include injection of interferon, typically pegylated versions including peginterferon alfa-2a (Pegasys®) or peginterferon alfa-2b (PegIntron®). Clinical use of pegylated interferon was approved by FDA in 2001. Ribavirin (e.g., Ribasphere®, Virazole®, Copegus®, Rebetol®), a guanosine analog that has broad-spectrum activity against viruses, is used to treat HCV infection, but appears not to be effective against HCV when used as a monotherapy. Current standard-of-care therapy includes administering peginterferon in combination with ribavirin. This regimen is limited because of side effects (e.g., flu-like symptoms, leukopenia, thrombocytopenia, depression, and anemia) and only moderate efficacy; success is dependent in part on the genotype predominating in the patient. See Ghany et al., *Hepatology,* 2011, 54(4):1433-44.

In addition to the pegylated interferon/ribavirin regimen, three different direct-acting antiviral agents have been approved for use in humans having HCV infection. These include sofosbuvir (Sovaldi®; Gilead Sciences), an NS5B polymerase inhibitor; simeprevir (Olysio®; Janssen Pharmaceuticals), an NS3 protease inhibitor and ledipasvir (Gilead Sciences), an NS5A inhibitor. Numerous alternative pharmaceutical approaches to treatment of HCV infection are still in research and development. For example, recombinant and modified interferon molecules have also been the subject of development programs, including, e.g., recombinant alfa interferon (BLX-883; Locteron®; Biolex/Octoplus) and albinterferon alfa 2b (Zalbin®; Human Genome Sciences).

The HCV protein NS3-4A, a serine protease, which is an enzyme essential for replication of the virus, has been the subject of intensive pharmaceutical research. A number of companies are seeking to develop inhibitors of this enzyme. Some of the earlier molecules are telaprevir (Incivek®, VX-950; Vertex) and boceprevir (Victrelis®, SCH503034; Merck & Co.), each of which was approved as direct-acting antiviral agent. These various molecules may be useful as single therapeutics, but some are also being investigated in combination with interferon/ribavirin therapies and/or compounds that may be effective against HCV via other mechanisms. However, viral resistance to individual protease inhibitors is believed to occur easily. Morrison and Haas, In Vivo, May 2009, 42-47.

The NS5B polymerase of HCV is also undergoing study. This protein is an RNA-dependent RNA polymerase (RdRp), which is essential for the synthesis of viral RNA, and consequently, for the completion of the viral life cycle. An overview of the NS5B protein is available at Chapter 10 of Tan, supra.

Many groups are currently working on developing inhibitors of the NS5B polymerase. Wang et al. (*J Biol Chem* 2003, 278(11), 9489-95) report that certain non-nucleoside molecules bind to an allosteric site on the polymerase, interfering with a conformational change required for activity. Biswal et al. (*J Biol Chem*, 2005, 280(18), 18202-10) report crystal structures indicating that the NS5B polymerase exhibits two conformations, with a gross structure resembling the classical fingers, palm, and thumb domains of other polymerases. This paper also show cocrystal structures for two inhibitors bound to the polymerase, and offers hypotheses on the mechanism of polymerase inhibition. Li et al. (*J Med Chem*, 2007, 50(17):3969-72) report on some dihydropyrone compounds that are said to be orally available allosteric inhibitors. See also Li et al., *J Med Chem*, 2009, 52:1255-58.

Inhibitors of NS5B may be classified broadly into three groups: nucleoside analogues (NI), non-nucleoside analogues (NNI), and pyrophosphate compounds (PPi). See, Powdrill et al., *Viruses*, 2010, 2:2169-95 and Appleby et al., "Viral RNA Polymerase Inhibitors," Chapter 23 in *Viral Genome Replication*, Cameron et al., eds., Springer Science+Business Media 2009.

Nucleoside analogue compounds (NI), which bind at the enzyme active site and compete with natural nucleoside triphosphates, interfere with viral RNA synthesis. A number of these compounds have entered clinical trials. Nucleoside inhibitors include, for example, IDX184 (Idenix), RG7128 (RO5024048; Pharmasset/Roche), and most notably the recently-approved sofosbuvir (SOVALDI®, PSI-7977; Gilead/Pharmasset).

Non-nucleoside inhibitors, by contrast, appear to bind at allosteric sites on NS5B—of which about 4 are well characterized. Id. NNI compounds include, for example, filibuvir (Pfizer), tegobuvir (GS 9190; Gilead), VX-222 (Vertex), A-837093 (Abbott), ABT-072 (Abbott), ABT-333 (Abbott), and PF-868554 (Pfizer).

Also among the non-nucleoside inhibitors of NS5B are a series of thiophene-2-carboxylic acids and derivatives thereof. See, e.g., Chan et al., *Bioorg Med Chem Lett*, 2004, 14, 793-96; International patent publications WO 02/100846 A1, WO 02/100851 A2, WO 2004/052879 A2, WO 2004/052885 A1, WO 2006/072347 A2, WO 2006/119646 A1, WO 2008/017688 A1, WO 2008/043791 A2, WO 2008/058393 A1, WO 2008/059042 A1, WO 2008/125599 A1, and WO 2009/000818 A1. See also U.S. Pat. Nos. 6,881,741 B2, 7,402,608 B2, and 7,569,600 B2. See also, Yang et al., *Bioorg Med Chem Lett* 2010, 20, 4614-19, relating to some bioisosteres of such compounds. Other similar compounds are described, for example, in U.S. Pat. Nos. 6,887,877 B2 and 6,936,629 B2.

Pyrophosphate compounds (PPi) mimic natural pyrophosphates released during nucleotidyl transfer reactions.

Various NI and NNI compounds have shown safety or efficacy in clinical trials, but few have yet reached approval for use in treating humans. PPi compounds, by contrast, are generally in the investigational stage.

There remains a profound need for more effective pharmaceutical therapies, including medicaments that are useful as single agents or in combination with other active agents, for the treatment of hepatitis C infection in humans.

SUMMARY OF THE INVENTION

The present invention provides compounds represented by the general Formula I:

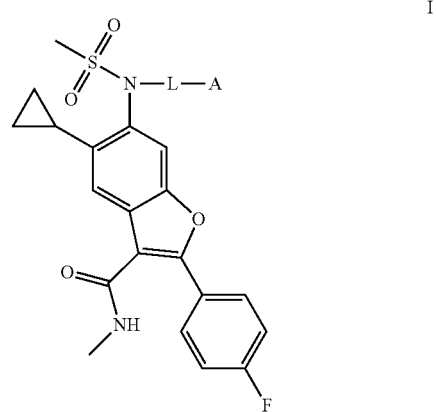

and salts (e.g., pharmaceutically acceptable salts) thereof, wherein L, A, D, and E are as defined in classes and subclasses herein, and compositions (e.g., pharmaceutical compositions) comprising such compounds, which compounds are useful as inhibitors of hepatitis C virus polymerase, and thus are useful, for example, as medicaments for the treatment of HCV infection and diseases associated with or consequent to such infection.

In certain other embodiments, the invention provides pharmaceutical compositions comprising a compound of the invention, wherein the compound is present in an amount effective to inhibit HCV polymerase activity. In certain other embodiments, the invention provides pharmaceutical compositions comprising a compound of Formula I and optionally further comprising an additional active agent to achieve therapeutic effect. In yet other embodiments, the additional active agent is an agent that has anti-HCV activity or function.

In yet another aspect, the present invention provides methods for inhibiting HCV polymerase activity in a subject (or optionally in a biological sample ex vivo or in vitro), comprising administering to the subject (or contacting the biological sample) with an effective inhibitory amount of a compound of Formula I.

In still another aspect, the present invention provides methods for treating any disorder constitutively associated with HCV infection or replication or involving HCV polymerase activity, comprising administering to a subject in need thereof a therapeutically effective amount of a compound of Formula I.

DETAILED DESCRIPTION

In one aspect, the invention provides compounds having the structure given as Formula I:

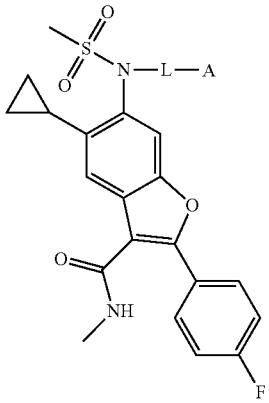

I or a pharmaceutically acceptable salt thereof,
in which:
L is (a): —(CH$_2$)$_x$—[O(CH$_2$)$_w$]$_y$—O—(CR$^d$$_2$)$_z$—
each R$^d$ is selected from hydrogen, methyl, and phenyl, or both R$^d$ together with the carbon to which they are attached form C$_{3-5}$cycloalkyl;
w is 2 to 4;
x is 2 to 6; and
y and z are each independently 0 to 5, with the proviso that when y is 0, then (x+z) is 4 to 11; or
(b): —(CH$_2$)$_m$-G$^1$-C(O)-G$^2$-C(R$^b$)$_2$-G$^3$-C(O)-G$^4$-(CR$^c$$_2$)$_n$, in which
m is 1 or 2;
n is 0 to 5;
each of G$^1$, G$^2$, G$^3$, and G$^4$ is independently null, O, or NR$^a$;
R$^a$ is independently hydrogen or C$_{1-4}$alkyl,
each R$^b$ is selected from hydrogen and methyl, or both R$^b$ together with the carbon to which they are attached form C$_{3-5}$cycloalkyl,
each R$^c$ is independently hydrogen or methyl; and
A is selected from C$_{1-3}$alkyl, —C(O)CH$_3$, —CO$_2$H, —CONHOH, —CO$_2$—C$_{1-4}$alkyl, —C(O)NH$_2$, —NH$_2$, hydroxyl, chloropyridinyl, —OC$_{1-2}$alkylene-CO$_2$H, —OC$_{1-2}$alkylene-CO$_2$C$_{1-4}$alkyl, —SC(O)CH$_3$,

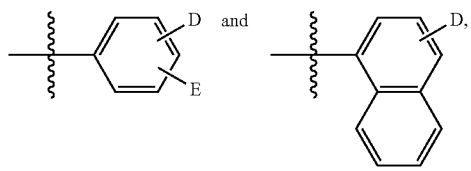

in which D is —C(O)CH$_3$, —(C$_{0-3}$alkylene)-CO$_2$H, —(C$_{0-3}$alkylene)-CO$_2$C$_{1-5}$alkyl, —(C$_{0-3}$alkylene)-CONHOH, —C(O)CH=C(OH)CO$_2$H, —C(O)CH=C(OH)CO$_2$C$_{1-4}$alkyl, —CO$_2$CH$_2$C(O)NH$_2$, —CO$_2$CH$_2$SC$_{1-4}$alkyl, —CO$_2$Bn, or —CO$_2$CH$_2$CO$_2$C$_{1-4}$alkyl, and E is null, halo, C$_{1-4}$alkyl, —OC$_{1-4}$alkyl, —NH—C$_{1-4}$alkyl, —C$_{0-3}$alkylene-NH$_2$, or NO$_2$.

In some embodiments, the invention provides compounds of Formula I:

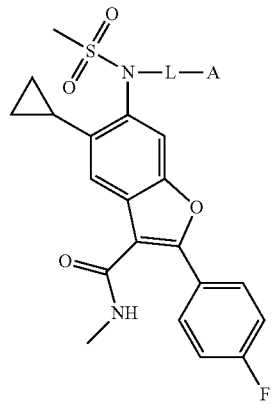

I or a pharmaceutically acceptable salt thereof,
wherein:
L is —(CH$_2$)$_x$(OCH$_2$CH$_2$)$_y$—O—(CH$_2$)$_z$—, in which x=2-6, y=0-5, and z=0-5; provided that when y is 0, then (x+z) is 4 to 11; and
A is selected from —CO$_2$H, —CO$_2$—C$_{1-4}$alkyl, chloropyridinyl

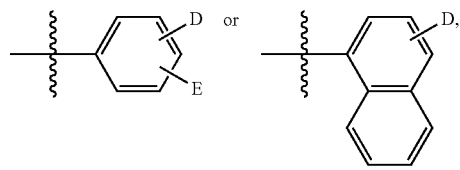

in which D is —CO$_2$H or —CO$_2$—C$_{1-4}$alkyl, and E is null, halo, C$_{1-4}$alkyl, —NH—C$_{1-4}$alkyl, —C$_{0-3}$alkylene-NH$_2$, or NO$_2$.

In some embodiments, the invention provides compounds of Formula I, in which E is null, fluoro, methyl, NH$_2$ or NO$_2$.

In some embodiments, the invention provides compounds of Formula I, in which x=2, w=2, y=1, and z=1.

In some embodiments, the invention provides compounds of Formula I, in which x=3, y=1, and z=1.

In some embodiments, the invention provides compounds of Formula I, in which y is 1 to 4.

In some embodiments, the invention provides compounds of Formula I, in which L is —(CH$_2$)$_x$—(OCH$_2$CH$_2$)$_y$—O—(CH$_2$)$_z$—.

In some embodiments, the invention provides compounds of Formula I, in which L is —(CH$_2$)$_m$-G$^1$-C(O)-G$^2$-C(OR$^b$-G$^3$-C(O)-G$^4$-(CH$_2$)$_n$. In some embodiments, the invention provides compounds of Formula I, in which (i) G$^1$ is null and G$^2$ is NH and/or (ii) G$^3$ is null and G$^4$ is NH.

In some embodiments, the invention provides compounds of Formula I, in which A is —CO$_2$H, —CONHOH, —CO$_2$—C$_{1-4}$alkyl, —C(O)NH$_2$, —OC$_{1-2}$alkylene-CO$_2$H, or —OC$_{1-2}$alkylene-CO$_2$C$_{1-4}$alkyl.

In some embodiments, the invention provides compounds of Formula I, in which A is

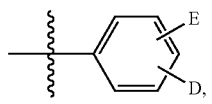

D is —(C$_{0-3}$alkylene)-CO$_2$H, —(C$_{0-3}$alkylene)-CO$_2$C$_{1-5}$alkyl, or —(C$_{0-3}$alkylene)-CONHOH, and E is null. In some embodiments, the invention provides compounds of Formula I, in which A is

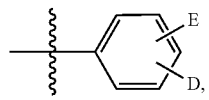

D is —CO$_2$H, —CO$_2$CH$_3$, —CO$_2$Et, —CO$_2$iPr, or —CO$_2$-nBu, and E is null.

In some embodiments, the invention provides compounds of Formula I, in which D is at the para or meta position on the phenyl group.

In various embodiments, the invention provides compounds of Formula I, in which each R$^d$ is independently selected from hydrogen, methyl, and phenyl, or both R$^d$ together with the carbon to which they are attached form cyclopropyl, cyclobutyl, or cyclopentyl; w is 2, 3, or 4; x is 2, 3, 4, 5, or 6; y is 0, 1, 2, 3, 4, or 5; and z is 0, 1, 2, 3, 4, or 5. In some embodiments, when y is 0, (x+z) is 4, 5, 6, 7, 8, 9, 10, or 11. In various embodiments, the invention provides compounds of Formula I, in which m is 1 or 2; n is 0, 1, 2, 3, 4, or 5; each R$^a$ is independently hydrogen, methyl, ethyl, propyl, or butyl; each R$^b$ is independently selected from hydrogen and methyl, or both R$^b$ together with the carbon to which they are attached form cyclopropyl, cyclobutyl, or cyclopentyl; and each R$^c$ is independently hydrogen or methyl. In various embodiments, the invention provides compounds of Formula I, wherein L is —(CH$_2$)$_x$[O(CH$_2$)$_w$]$_y$—O—(CR$^d$$_2$)$_z$—; A is

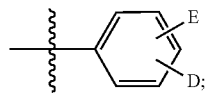

D is —CO$_2$H, —CO$_2$C$_{1-5}$alkyl, or —CONHOH; E is null; x is 4 to 6 (e.g., 5); y is 0 to 1 and w is 2 (e.g., y is 0); z is 0 to 2 (e.g., 1); and/or both R$^d$ are hydrogen. In various embodiments, the invention provides compounds of Formula I, wherein x is 5, y is 0, z is 1, both R$^d$ are hydrogen, A is

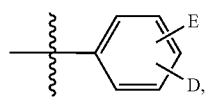

D is —CO$_2$H (e.g., —CO$_2$H at the para position on the phenyl group), and E is null.

In another aspect, the invention provides a compound selected from:

6-(N-(2-(2-(3-Acetylbenzyloxy)-ethoxy)-ethyl)-methylsulfonamido)-5-cyclopropyl-2-(4-fluorophenyl)-N-methylbenzofuran-3-carboxamide (2-8A);
6-[(2-{2-[2-(3-Acetyl-benzyloxy)-ethoxy]-ethoxy}-ethyl)-methanesulfonyl-amino]-5-cyclopropyl-2-(4-fluoro-phenyl)-benzofuran-3-carboxylic acid methylamide (2-8B);
6-{[2-(2-{2-[2-(3-Acetyl-benzyloxy)-ethoxy]-ethoxy}-ethoxy)-ethyl]-methanesulfonyl-amino}-5-cyclopropyl-2-(4-fluoro-phenyl)-benzofuran-3-carboxylic acid methylamide (2-8C);
6-({2-[2-(2-{2-[2-(3-Acetyl-benzyloxy)-ethoxy]-ethoxy}-ethoxy)-ethoxy]-ethyl}-methanesulfonyl-amino)-5-cyclopropyl-2-(4-fluoro-phenyl)-benzofuran-3-carboxylic acid methylamide (2-8D);
6-[(2-{2-[2-(2-{2-[2-(3-Acetyl-benzyloxy)-ethoxy]-ethoxy}-ethoxy)-ethoxy]-ethoxy}-ethyl)-methanesulfonyl-amino]-5-cyclopropyl-2-(4-fluoro-phenyl)-benzofuran-3-carboxylic acid methylamide (2-8E);
6-({2-[2-(4-Acetyl-benzyloxy)-ethoxy]-ethyl}-methanesulfonyl-amino)-5-cyclopropyl-2-(4-fluoro-phenyl)-benzofuran-3-carboxylic acid methylamide (2-8F);
6-[(2-{2-[2-(4-Acetyl-benzyloxy)-ethoxy]-ethoxy}-ethyl)-methanesulfonyl-amino]-5-cyclopropyl-2-(4-fluoro-phenyl)-benzofuran-3-carboxylic acid methylamide (2-9G);
6-{[2-(2-{2-[2-(4-Acetyl-benzyloxy)-ethoxy]-ethoxy}-ethoxy)-ethyl]-methanesulfonyl-amino}-5-cyclopropyl-2-(4-fluoro-phenyl)-benzofuran-3-carboxylic acid methylamide (2-8H);
6-({2-[2-(2-{2-[2-(4-Acetyl-benzyloxy)-ethoxy]-ethoxy}-ethoxy)-ethoxy]-ethyl}-methanesulfonyl-amino)-5-cyclopropyl-2-(4-fluoro-phenyl)-benzofuran-3-carboxylic acid methylamide (2-8I);
6-[(2-{2-[2-(2-{2-[2-(4-Acetyl-benzyloxy)-ethoxy-ethoxy}-ethoxy)-ethoxy]-ethoxy}-ethyl)-methanesulfonyl-amino]-5-cyclopropyl-2-(4-fluoro-phenyl)-benzofuran-3-carboxylic acid methylamide (2-8J);
4-{3-2-(2-{[5-Cyclopropyl-2-(4-fluoro-phenyl)-3-methylcarbamoyl-benzofuran-6-yl]-methanesulfonyl-amino}-ethoxy)-ethoxymethyl]-phenyl}-2-hydroxy-4-oxo-but-2-enoic acid ethyl ester (2-9A);
4-(3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-phenyl)-2-hydroxy-4-oxo-but-2-enoic acid ethyl ester (2-9B);
4-[3-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxymethyl)-phenyl]-2-hydroxy-4-oxo-but-2-enoic acid ethyl ester (2-9C);
4-{3-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxymethyl]-phenyl}-2-hydroxy-4-oxo-but-2-enoic acid ethyl ester (2-9D);
4-(3-{2-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxy]-ethoxymethyl}-phenyl)-2-hydroxy-4-oxo-but-2-enoic acid ethyl ester (2-9E);
4-{4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-phenyl}-2-hydroxy-4-oxo-but-2-enoic acid ethyl ester (2-9F);
4-(4-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-phenyl)-2-hydroxy-4-oxo-but-2-enoic acid ethyl ester (2-9G);

4-[4-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxymethyl)-phenyl]-2-hydroxy-4-oxo-but-2-enoic acid ethyl ester (2-9H);

4-{4-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxymethyl]-phenyl}-2-hydroxy-4-oxo-but-2-enoic acid ethyl ester (2-9I);

4-(4-{2-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxy]-ethoxymethyl}-phenyl)-2-hydroxy-4-oxo-but-2-enoic acid ethyl ester (2-9J);

4-{3-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-phenyl}-2-hydroxy-4-oxo-but-2-enoic acid (2-10A);

4-(3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-phenyl)-2-hydroxy-4-oxo-but-2-enoic acid (2-10B);

4-[3-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxymethyl)-phenyl]-2-hydroxy-4-oxo-but-2-enoic acid (2-10C);

4-{3-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxymethyl]-phenyl}-2-hydroxy-4-oxo-but-2-enoic acid (2-10D);

4-(3-{2-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxy]-ethoxymethyl}-phenyl)-2-hydroxy-4-oxo-but-2-enoic acid (2-10E);

4-{4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-phenyl}-2-hydroxy-4-oxo-but-2-enoic acid (2-10F);

4-(4-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-phenyl)-2-hydroxy-4-oxo-but-2-enoic acid (2-10G);

4-[4-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxymethyl)-phenyl]-2-hydroxy-4-oxo-but-2-enoic acid (2-10H);

4-{4-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxymethyl]-phenyl}-2-hydroxy-4-oxo-but-2-enoic acid (2-10I);

4-(4-{2-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxy]-ethoxymethyl}-phenyl)-2-hydroxy-4-oxo-but-2-enoic acid (2-10J);

6-(N-(3-(2-((3-acetylbenzyl)-oxy)-ethoxy)-propyl)-methylsulfonamido)-5-cyclopropyl-2-(4-fluorophenyl)-N-methylbenzofuran-3-carboxamide (3-6A);

4-{3-[2-(3-{[5-Cyclopropyl-2-(4-fluoro-phenyl)-3-methylcarbamoyl-benzofuran-6-yl]-methanesulfonyl-amino}-propoxy)-ethoxymethyl]-phenyl}-2-hydroxy-4-oxo-but-2-enoic acid ethyl ester (3-7A);

4-{3-[2-(3-{[5-Cyclopropyl-2-(4-fluoro-phenyl)-3-methylcarbamoyl-benzofuran-6-yl]-methanesulfonyl-amino}-propoxy)-ethoxymethyl]-phenyl}-2-hydroxy-4-oxo-but-2-enoic acid (3-8A);

6-({2-[3-(3-Acetyl-benzyloxy)-propoxy]-ethyl}-methanesulfonyl-amino)-5-cyclopropyl-2-(4-fluoro-phenyl)-benzofuran-3-carboxylic acid methylamide (3-6B);

4-{3-[3-(2-{[5-Cyclopropyl-2-(4-fluoro-phenyl)-3-methylcarbamoyl-benzofuran-6-yl]-methanesulfonyl-amino}-ethoxy)-propoxymethyl]-phenyl}-2-hydroxy-4-oxo-but-2-enoic acid (3-8B);

5-Cyclopropyl-2-(4-fluorophenyl)-6-(N-(2-(2-(2-(2-hydroxyethoxy)-ethoxy)-ethoxy)-ethyl) methylsulfonamido)-N-methylbenzofuran-3-carboxamide (4-5);

6-(N-(2-(2-(2-(2-Aminoethoxy)-ethoxy)-ethoxy)-ethyl)-methylsulfonamido)-5-cyclopropyl-2-(4-fluorophenyl)-N-methylbenzofuran-3-carboxamide (4-10);

6-(N-(2,5,8,11-Tetraoxatridecan-13-yl)-methylsulfonamido)-5-cyclopropyl-2-(4-fluorophenyl)-N-methylbenzofuran-3-carboxamide (5-4A);

6-({2-[2-(2-Butoxy-ethoxy)-ethoxy]-ethyl}-methanesulfonyl-amino)-5-cyclopropyl-2-(4-fluoro-phenyl)-benzofuran-3-carboxylic acid methylamide (5-4B);

2-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid methyl ester (6-6A);

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid methyl ester (6-6B);

3-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid methyl ester (6-6C);

2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-benzoic acid methyl ester (6-6D);

4-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-benzoic acid methyl ester (6-6E);

3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-benzoic acid methyl ester (6-6F);

2-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid (6-7A);

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid (6-7B);

3-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid (6-7C);

2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-benzoic acid (6-7D);

4-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-benzoic acid (6-7E);

3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-benzoic acid (6-7F);

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid ethyl ester (6-8B1);

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid propyl ester (6-8B2);

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid butyl ester (6-8B3);

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid pentyl ester (6-8B4);

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid carbamoylmethyl ester (6-8B5);

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid methylsulfanylmethyl ester (6-8B6);

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid benzyl ester (6-8B7);

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid ethoxycarbonylmethyl ester (6-8B8);

4-{[(2-{[5-Cyclopropyl-2-(4-fluoro-phenyl)-3-methylcarbamoyl-benzofuran-6-yl]-methanesulfonyl-amino}-ethylcarbamoyl)-methyl]-carbamoyl}-butyric acid (7-7);

4-(3-{[(2-{[5-Cyclopropyl-2-(4-fluoro-phenyl)-3-methylcarbamoyl-benzofuran-6-yl]-methanesulfonyl-amino}-ethylcarbamoyl)-methyl]-carbamoyl}-phenyl)-butyric acid ethyl ester (7-9);

4-(3-{[(2-{[5-Cyclopropyl-2-(4-fluoro-phenyl)-3-methylcarbamoyl-benzofuran-6-yl]-methanesulfonyl-amino}-ethylcarbamoyl)-methyl]-carbamoyl}-phenyl)-butyric acid (7-10);

4-[(2-{[5-Cyclopropyl-2-(4-fluoro-phenyl)-3-methylcarbamoyl-benzofuran-6-yl]-methanesulfonyl-amino}-ethoxycarbonylmethyl)-carbamoyl]-butyric acid (8-6);

4-(3-{[2-(2-{[5-Cyclopropyl-2-(4-fluoro-phenyl)-3-methyl-carbamoyl-benzofuran-6-yl]-methanesulfonyl-amino}-acetylamino)-acetylamino]-methyl}-phenyl)-2-hydroxy-4-oxo-but-2-enoic acid ethyl ester (9-13A);

4-[3-({2-[(2-{[5-Cyclopropyl-2-(4-fluoro-phenyl)-3-methylcarbamoyl-benzofuran-6-yl]-methanesulfonyl-amino}-acetyl)-methyl-amino]-acetylamino}-methyl)-phenyl]-2-hydroxy-4-oxo-but-2-enoic acid ethyl ester (9-13B);

4-(3-{[2-(2-{[5-Cyclopropyl-2-(4-fluoro-phenyl)-3-methyl-carbamoyl-benzofuran-6-yl]-methanesulfonyl-amino}-acetylamino)-2-methyl-propionylamino]-methyl}-phenyl)-2-hydroxy-4-oxo-but-2-enoic acid ethyl ester (9-13C);

4-[3-({[1-(2-{[5-Cyclopropyl-2-(4-fluoro-phenyl)-3-methylcarbamoyl-benzofuran-6-yl]-methanesulfonyl-amino}-acetylamino)-cyclopropanecarbonyl]-amino}-methyl)-phenyl]-2-hydroxy-4-oxo-but-2-enoic acid ethyl ester (9-13D);

4-[3-({[1-(2-{[5-Cyclopropyl-2-(4-fluoro-phenyl)-3-methylcarbamoyl-benzofuran-6-yl]-methanesulfonyl-amino}-acetylamino)-cyclopentanecarbonyl]-amino}-methyl)-phenyl]-2-hydroxy-4-oxo-but-2-enoic acid ethyl ester (9-13E);

4-(3-{[2-(2-{[5-Cyclopropyl-2-(4-fluoro-phenyl)-3-methyl-carbamoyl-benzofuran-6-yl]-methanesulfonyl-amino}-acetylamino)-propionylamino]-methyl}-phenyl)-2-hydroxy-4-oxo-but-2-enoic acid ethyl ester (9-13F);

4-(3-{[2-(2-{[5-Cyclopropyl-2-(4-fluoro-phenyl)-3-methyl-carbamoyl-benzofuran-6-yl]-methanesulfonyl-amino}-acetylamino)-acetylamino]-methyl}-phenyl)-2-hydroxy-4-oxo-but-2-enoic acid (9-14A);

4-[3-({2-[(2-{[5-Cyclopropyl-2-(4-fluoro-phenyl)-3-methylcarbamoyl-benzofuran-6-yl]-methanesulfonyl-amino}-acetyl)-methyl-amino]-acetylamino}-methyl)-phenyl]-2-hydroxy-4-oxo-but-2-enoic acid (9-14B);

4-(3-{[2-(2-{[5-Cyclopropyl-2-(4-fluoro-phenyl)-3-methyl-carbamoyl-benzofuran-6-yl]-methanesulfonyl-amino}-acetylamino)-2-methyl-propionylamino]-methyl}-phenyl)-2-hydroxy-4-oxo-but-2-enoic acid (9-14C);

4-[3-({[1-(2-{[5-Cyclopropyl-2-(4-fluoro-phenyl)-3-methylcarbamoyl-benzofuran-6-yl]-methanesulfonyl-amino}-acetylamino)-cyclopropanecarbonyl]-amino}-methyl)-phenyl]-2-hydroxy-4-oxo-but-2-enoic acid (9-14D);

4-[3-({[1-(2-{[5-Cyclopropyl-2-(4-fluoro-phenyl)-3-methylcarbamoyl-benzofuran-6-yl]-methanesulfonyl-amino}-acetylamino)-cyclopentanecarbonyl]-amino}-methyl)-phenyl]-2-hydroxy-4-oxo-but-2-enoic acid (9-14E);

4-(3-{[2-(2-{[5-Cyclopropyl-2-(4-fluoro-phenyl)-3-methyl-carbamoyl-benzofuran-6-yl]-methanesulfonyl-amino}-acetylamino)-propionylamino]-methyl}-phenyl)-2-hydroxy-4-oxo-but-2-enoic acid (9-14F);

5-[2-(2-{[5-Cyclopropyl-2-(4-fluoro-phenyl)-3-methylcarbamoyl-benzofuran-6-yl]-methanesulfonyl-amino}-acetylamino)-acetylamino]-pentanoic acid methyl ester (10-3A);

5-[2-(2-{[5-Cyclopropyl-2-(4-fluoro-phenyl)-3-methylcarbamoyl-benzofuran-6-yl]-methanesulfonyl-amino}-acetylamino)-acetylamino]-2-methyl-pentanoic acid methyl ester (10-3B);

5-[2-(2-{[5-Cyclopropyl-2-(4-fluoro-phenyl)-3-methylcarbamoyl-benzofuran-6-yl]-methanesulfonyl-amino}-acetylamino)-acetylamino]-pentanoic acid (10-4A);

5-[2-(2-{[5-Cyclopropyl-2-(4-fluoro-phenyl)-3-methylcarbamoyl-benzofuran-6-yl]-methanesulfonyl-amino}-acetylamino)-acetylamino]-2-methyl-pentanoic acid (10-4B);

2-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethyl}-benzoic acid methyl ester (11-5A);

3-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethyl}-benzoic acid ethyl ester (11-5B);

4-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethyl}-benzoic acid methyl ester (11-5C);

2-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethyl}-benzoic acid (11-6A);

3-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethyl}-benzoic acid (11-6B);

4-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethyl}-benzoic acid (11-6C);

2-{3-[2-(2-{[5-Cyclopropyl-2-(4-fluoro-phenyl)-3-methyl-carbamoyl-benzofuran-6-yl]-methanesulfonyl-amino}-ethoxy)-ethoxy]-propyl}-benzoic acid methyl ester (12-6A);

2-{3-[2-(2-{[5-Cyclopropyl-2-(4-fluoro-phenyl)-3-methyl-carbamoyl-benzofuran-6-yl]-methanesulfonyl-amino}-ethoxy)-ethoxy]-propyl}-benzoic acid (12-7A);

3-{3-[2-(2-{[5-Cyclopropyl-2-(4-fluoro-phenyl)-3-methyl-carbamoyl-benzofuran-6-yl]-methanesulfonyl-amino}-ethoxy)-ethoxy]-propyl}-benzoic acid (12-7B);

4-{3-[2-(2-{[5-Cyclopropyl-2-(4-fluoro-phenyl)-3-methyl-carbamoyl-benzofuran-6-yl]-methanesulfonyl-amino}-ethoxy)-ethoxy]-propyl}-benzoic acid (12-7C);

4-[2-(4-{[5-Cyclopropyl-2-(4-fluoro-phenyl)-3-methylcar-bamoyl-benzofuran-6-yl]-methanesulfonyl-amino}-bu-toxy)-ethyl]-benzoic acid methyl ester (13-7C);

4-[4-(2-{[5-Cyclopropyl-2-(4-fluoro-phenyl)-3-methylcar-bamoyl-benzofuran-6-yl]-methanesulfonyl-amino}-ethoxy)-butyl]-benzoic acid methyl ester (13-7A);

4-[3-(3-{[5-Cyclopropyl-2-(4-fluoro-phenyl)-3-methylcar-bamoyl-benzofuran-6-yl]-methanesulfonyl-amino}-propoxy)-propyl]-benzoic acid methyl ester (13-7B);

4-(7-{[5-Cyclopropyl-2-(4-fluoro-phenyl)-3-methylcar-bamoyl-benzofuran-6-yl]-methanesulfonyl-amino}-hep-tyl)-benzoic acid methyl ester (13-7D);

4-(2-(4-(N-(5-cyclopropyl-2-(4-fluorophenyl))-3-(methyl-carbamoyl)benzofuran-6-yl)-methylsulfonamido)bu-toxy)-ethyl)benzoic acid (13-8C);

4-[4-(2-{[5-Cyclopropyl-2-(4-fluoro-phenyl)-3-methylcar-bamoyl-benzofuran-6-yl]-methanesulfonyl-amino}-ethoxy)-butyl]-benzoic acid (13-8A);

4-[3-(3-{[5-Cyclopropyl-2-(4-fluoro-phenyl)-3-methylcar-bamoyl-benzofuran-6-yl]-methanesulfonyl-amino}-propoxy)-propyl]-benzoic acid (13-8B);

4-(7-{[5-Cyclopropyl-2-(4-fluoro-phenyl)-3-methylcar-bamoyl-benzofuran-6-yl]-methanesulfonyl-amino}-hep-tyl)-benzoic acid (13-8D);

2-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-benzoic acid ethyl ester (14-6A);

3-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-benzoic acid ethyl ester (14-6B);

4-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-benzoic acid ethyl ester (14-6C);

2-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-benzoic acid (14-7A);

3-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-benzoic acid (14-7B);

4-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-benzoic acid (14-7C);

4-(6-{[5-Cyclopropyl-2-(4-fluoro-phenyl)-3-methylcar-bamoyl-benzofuran-6-yl]-methanesulfonyl-amino}-hexyloxy)-benzoic acid ethyl ester (15-7);

4-(6-{[5-Cyclopropyl-2-(4-fluoro-phenyl)-3-methylcar-bamoyl-benzofuran-6-yl]-methanesulfonyl-amino}-hexyloxy)-benzoic acid (15-8);

4-(5-{[5-Cyclopropyl-2-(4-fluoro-phenyl)-3-methylcar-bamoyl-benzofuran-6-yl]-methanesulfonyl-amino}-pen-tyloxymethyl)-benzoic acid methyl ester (16-6);

4-(5-{[5-Cyclopropyl-2-(4-fluoro-phenyl)-3-methylcar-bamoyl-benzofuran-6-yl]-methanesulfonyl-amino}-pen-tyloxymethyl)-benzoic acid [16-7];

5-[2-(2-{[5-Cyclopropyl-2-(4-fluoro-phenyl)-3-methylcar-bamoyl-benzofuran-6-yl]-methanesulfonyl-amino}-ethoxy)-ethoxymethyl]-2-fluoro-benzoic acid ethyl ester (17A-7);

5-[2-(2-{[5-Cyclopropyl-2-(4-fluoro-phenyl)-3-methylcar-bamoyl-benzofuran-6-yl]-methanesulfonyl-amino}-ethoxy)-ethoxymethyl]-2-fluoro-benzoic acid (17A-8A);

5-Cyclopropyl-6-({2-[2-(4-fluoro-3-hydroxycarbamoyl-benzyloxy)-ethoxy]-ethyl}-methanesulfonyl-amino)-2-(4-fluoro-phenyl)-benzofuran-3-carboxylic acid methyl-amide (17A-8B);

5-[2-(2-{[5-Cyclopropyl-2-(4-fluoro-phenyl)-3-methylcar-bamoyl-benzofuran-6-yl]-methanesulfonyl-amino}-ethoxy)-ethoxymethyl]-2-methoxy-benzoic acid (17B-8);

4-[2-(2-{[5-Cyclopropyl-2-(4-fluoro-phenyl)-3-methylcar-bamoyl-benzofuran-6-yl]-methanesulfonyl-amino}-ethoxy)-ethoxymethyl]-3-methyl-benzoic acid methyl ester (18-9B);

4-[2-(2-{[5-Cyclopropyl-2-(4-fluoro-phenyl)-3-methylcar-bamoyl-benzofuran-6-yl]-methanesulfonyl-amino}-ethoxy)-ethoxymethyl]-2-methyl-benzoic acid methyl ester (18-9A);

4-[2-(2-{[5-Cyclopropyl-2-(4-fluoro-phenyl)-3-methylcar-bamoyl-benzofuran-6-yl]-methanesulfonyl-amino}-ethoxy)-ethoxymethyl]-3-methyl-benzoic acid (18-10B);

4-[2-(2-{[5-Cyclopropyl-2-(4-fluoro-phenyl)-3-methylcar-bamoyl-benzofuran-6-yl]-methanesulfonyl-amino}-ethoxy)-ethoxymethyl]-2-methyl-benzoic acid (18-10A);

2-(2-((6-Chloropyridin-3-yl)-methoxy)-ethoxy)-ethyl)-methylsulfonamido)-5-cyclopropyl-2-(4-fluorophenyl)-N-methylbenzofuran-3-carboxamide (19-8B);

6-({2-[2-(2-Chloro-pyridin-4-ylmethoxy)-ethoxy]-ethyl}-methanesulfonyl-amino)-5-cyclopropyl-2-(4-fluoro-phe-nyl)-benzofuran-3-carboxylic acid methylamide (19-8A);

4-[2-(2-{[5-Cyclopropyl-2-(4-fluoro-phenyl)-3-methylcar-bamoyl-benzofuran-6-yl]-methanesulfonyl-amino}-ethoxy)-ethoxymethyl]-naphthalene-1-carboxylic acid ethyl ester (20-7);

4-[2-(2-{[5-Cyclopropyl-2-(4-fluoro-phenyl)-3-methylcar-bamoyl-benzofuran-6-yl]-methanesulfonyl-amino}-ethoxy)-ethoxymethyl]-naphthalene-1-carboxylic acid (20-8);

Thioacetic acid S-[2-(2-{[5-cyclopropyl-2-(4-fluoro-phe-nyl)-3-methylcarbamoyl-benzofuran-6-yl]-methanesulfo-nyl-amino}-ethoxy)-ethyl]ester (21-5);

6-(N-(2-(3-(3-Acetylphenyl)-propoxy)-ethyl)-methylsulfo-namido)-5-cyclopropyl-2-(4-fluorophenyl)-N-methyl-benzofuran-3-carboxamide (22-10);

4-{3-[3-(2-{[5-Cyclopropyl-2-(4-fluoro-phenyl)-3-methyl-carbamoyl-benzofuran-6-yl]-methanesulfonyl-amino}-ethoxy)-propyl]-phenyl}-2-hydroxy-4-oxo-but-2-enoic acid ethyl ester (22-11);

4-(3-(3-(2-(N-(5-cyclopropyl-2-(4-fluorophenyl))-3-(meth-ylcarbamoyl)benzofuran-6-yl) methyl sulfonamido)-ethoxy)-propyl)-phenyl)-2-hydroxy-4-oxobut-2-enoic acid (22-12);

{2-[2-(2-{[5-Cyclopropyl-2-(4-fluoro-phenyl)-3-methylcar-bamoyl-benzofuran-6-yl]-methanesulfonyl-amino}-ethoxy)-ethoxy]-ethoxy}-acetic acid tert-butyl ester [23-5A];

2-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-propionic acid ethyl ester (23-5B);

{2-[2-(2-{[5-Cyclopropyl-2-(4-fluoro-phenyl)-3-methylcar-bamoyl-benzofuran-6-yl]-methanesulfonyl-amino}-ethoxy)-ethoxy]-ethoxy}-acetic acid ethyl ester (23-5C);

{2-[2-(2-{[5-Cyclopropyl-2-(4-fluoro-phenyl)-3-methylcar-bamoyl-benzofuran-6-yl]-methanesulfonyl-amino}-ethoxy)-ethoxy]-ethoxy}-acetic acid (23-6A);

2-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-propionic acid (23-6B);

5-Cyclopropyl-2-(4-fluoro-phenyl)-6-({2-[2-(2-hydroxycar-bamoylmethoxy-ethoxy)-ethoxy]-ethyl}-methanesulfonyl-amino)-benzofuran-3-carboxylic acid methylamide (23-6C);

6-({2-[2-(2-Carbamoylmethoxy-ethoxy)-ethoxy]-ethyl}-methanesulfonyl-amino)-5-cyclopropyl-2-(4-fluoro-phenyl)-benzofuran-3-carboxylic acid methylamide (23-7A);

3-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-propionic acid ethyl ester (24-3);

3-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-propionic acid (24-4);

{2-[2-(2-{[5-Cyclopropyl-2-(4-fluoro-phenyl)-3-methylcar-bamoyl-benzofuran-6-yl]-methanesulfonyl-amino}-ethoxy)-ethoxy]-ethoxy}-phenyl-acetic acid ethyl ester (25-4);

{2-[2-(2-{[5-Cyclopropyl-2-(4-fluoro-phenyl)-3-methylcar-bamoyl-benzofuran-6-yl]-methanesulfonyl-amino}-ethoxy)-ethoxy]-ethoxy}-phenyl-acetic acid (25-5);

5-Cyclopropyl-2-(4-fluoro-phenyl)-6-[(2-{2-[2-(hydroxy-carbamoyl-phenyl-methoxy)-ethoxy]-ethoxy}-ethyl)-methanesulfonyl-amino]-benzofuran-3-carboxylic acid methylamide (25-6);

1-[2-(2-{2-[(5-Cyclopropyl-3-methylcarbamoyl-2-p-tolyl-benzofuran-6-yl)-methanesulfonyl-amino]-ethoxy}-ethoxy)-ethoxy]-cyclopentanecarboxylic acid tert-butyl ester (26-6A);

2-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-2-methyl-propionic acid tert-butyl ester (26-6B);

1-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-cyclopentanecarboxylic acid (26-7A);

2-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-2-methyl-propionic acid (26-7B);

5-Cyclopropyl-2-(4-fluoro-phenyl)-6-[(2-{2-[2-(1-hydroxy-carbamoyl-1-methyl-ethoxy)-ethoxy]-ethoxy}-ethyl)-methanesulfonyl-amino]-benzofuran-3-carboxylic acid methylamide (26-8B);

[5-(2-{[5-Cyclopropyl-2-(4-fluoro-phenyl)-3-methylcar-bamoyl-benzofuran-6-yl]-methanesulfonyl-amino}-ethoxy)-pentyloxy]-acetic acid tert-butyl ester (27-8A);

[5-(2-{[5-Cyclopropyl-2-(4-fluoro-phenyl)-3-methylcar-bamoyl-benzofuran-6-yl]-methanesulfonyl-amino}-ethoxy)-pentyloxy]-acetic acid (27-9A);

2-[5-(2-{[5-Cyclopropyl-2-(4-fluoro-phenyl)-3-methylcar-bamoyl-benzofuran-6-yl]-methanesulfonyl-amino}-ethoxy)-pentyloxy]-propionic acid (27-9B);

5-(5-{[5-Cyclopropyl-2-(4-fluoro-phenyl)-3-methylcar-bamoyl-benzofuran-6-yl]-methanesulfonyl-amino}-pentyloxy)-pentanoic acid tert-butyl ester (28-7A);

5-((5-(N-(5-cyclopropyl-2-(4-fluorophenyl)-3-(methylcar-bamoyl)benzofuran-6-yl)-methyl sulfonamido)-pentyl)-oxy)-pentanoic acid (28-8A);

5-(5-{[5-Cyclopropyl-2-(4-fluoro-phenyl)-3-methylcar-bamoyl-benzofuran-6-yl]-methanesulfonyl-amino}-pentyloxy)-2-methyl-pentanoic acid (28-8B);

4-[2-(2-{[5-Cyclopropyl-2-(4-fluoro-phenyl)-3-methylcar-bamoyl-benzofuran-6-yl]-methanesulfonyl-amino}-ethoxy)-ethoxymethyl]-2-nitro-benzoic acid methyl ester (29-7);

4-[2-(2-{[5-Cyclopropyl-2-(4-fluoro-phenyl)-3-methylcar-bamoyl-benzofuran-6-yl]-methanesulfonyl-amino}-ethoxy)-ethoxymethyl]-2-nitro-benzoic acid (29-8);

2-Amino-4-[2-(2-{[5-cyclopropyl-2-(4-fluoro-phenyl)-3-methylcarbamoyl-benzofuran-6-yl]-methanesulfonyl-amino}-ethoxy)-ethoxymethyl]-benzoic acid methyl ester (29-9);

2-Amino-4-[2-(2-{[5-cyclopropyl-2-(4-fluoro-phenyl)-3-methylcarbamoyl-benzofuran-6-yl]-methanesulfonyl-amino}-ethoxy)-ethoxymethyl]-benzoic acid (29-10);

5-Cyclopropyl-2-(4-fluoro-phenyl)-6-[methanesulfonyl-(2-{2-[2-(2-oxo-propoxy)-ethoxy]-ethoxy}-ethyl)-amino]-benzofuran-3-carboxylic acid methylamide (30-1);

2-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-propionic acid ethyl ester (30-2);

3-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxy}-propionic acid ethyl ester (30-3);

3-(2-{2-[2-(2-{[5-Cyclopropyl-2-(4-fluoro-phenyl)-3-meth-ylcarbamoyl-benzofuran-6-yl]-methanesulfonyl-amino}-ethoxy)-ethoxy]-ethoxy}-ethoxymethyl)-benzoic acid (30-4);

6-({2-[3-(3-Acetyl-phenyl)-propoxy]-ethyl}-methanesulfo-nyl-amino)-5-cyclopropyl-2-(4-fluoro-phenyl)-benzo-furan-3-carboxylic acid methylamide (30-5);

6-[({[(3-Acetyl-benzylcarbamoyl)-methyl]-carbamoyl}-methyl)-methanesulfonyl-amino]-5-cyclopropyl-2-(4-fluoro-phenyl)-benzofuran-3-carboxylic acid methylam-ide (30-6);

4-{2-[2-(2-{[5-Cyclopropyl-2-(4-fluoro-phenyl)-3-methyl-carbamoyl-benzofuran-6-yl]-methanesulfonyl-amino}-ethoxy)-ethoxy]-ethoxymethyl}-benzoic acid (30-7);

4-(3-{3-[2-(2-{[5-Cyclopropyl-2-(4-fluoro-phenyl)-3-meth-ylcarbamoyl-benzofuran-6-yl]-methanesulfonyl-amino}-ethoxy)-ethoxy]-propyl}-phenyl)-2,4-dioxo-butyric acid (30-8);

4-{3-[4-(2-{[5-Cyclopropyl-2-(4-fluoro-phenyl)-3-methyl-carbamoyl-benzofuran-6-yl]-methanesulfonyl-amino}-ethoxy)-butoxy]-phenyl}-2,4-dioxo-butyric acid (30-9);

4-[3-(3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-propyl)-phenyl]-2,4-di-oxo-butyric acid (30-10);

5-[2-(2-{[5-Cyclopropyl-2-(4-fluoro-phenyl)-3-methylcar-bamoyl-benzofuran-6-yl]-methanesulfonyl-amino}-ethoxy)-ethoxymethyl]-2-methoxy-benzoic acid methyl ester (30-11);

4-(3-{4-[2-(2-{[5-Cyclopropyl-2-(4-fluoro-phenyl)-3-meth-ylcarbamoyl-benzofuran-6-yl]-methanesulfonyl-amino}-ethoxy)-ethoxy]-butyl}-phenyl)-2,4-dioxo-butyric acid (30-12);

4-{2-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxy]-ethoxymethyl}-benzoic acid (30-13);

5-[2-(2-{[5-Cyclopropyl-2-(4-fluoro-phenyl)-3-methylcar-bamoyl-benzofuran-6-yl]-methanesulfonyl-amino}-ethoxy)-ethoxymethyl]-2-fluoro-benzoic acid ethyl ester (30-14);

4-[3-(5-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-pentyl)-phenyl]-2,4-dioxo-butyric acid (30-15); and 4-[3-(4-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-butyl)-phenyl]-2,4-dioxo-butyric acid (30-16);

and pharmaceutically acceptable salts thereof.

In another aspect, the invention provides compounds having the structure given as Formula I:

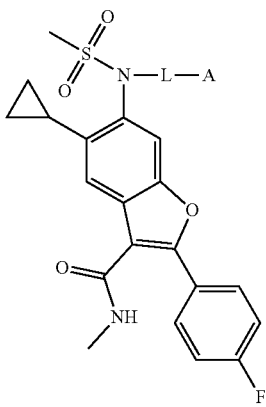

I or a pharmaceutically acceptable salt thereof,
in which:
L is $C_{7-20}$alkylene (e.g., $C_{7-10}$alkylene); and
A is selected from $C_{1-3}$alkyl, —C(O)CH$_3$, —CO$_2$H, —CONHOH, —CO$_2$—C$_{1-4}$alkyl, —C(O)NH$_2$, —NH$_2$, hydroxyl, chloropyridinyl, —OC$_{1-2}$alkylene-CO$_2$H, —OC$_{1-2}$alkylene-CO$_2$C$_{1-4}$alkyl, —SC(O)CH$_3$,

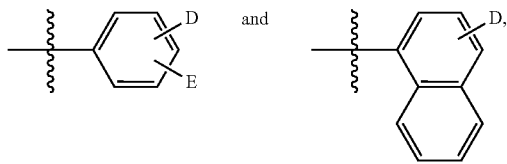

in which D is —C(O)CH$_3$, —(C$_{0-3}$alkylene)-CO$_2$H, —(C$_{0-3}$alkylene)-CO$_2$C$_{1-5}$alkyl, —(C$_{0-3}$alkylene)-CONHOH, —C(O)CH=C(OH)CO$_2$H, —C(O)CH=C(OH)CO$_2$C$_{1-4}$alkyl, —CO$_2$CH$_2$C(O)NH$_2$, —CO$_2$CH$_2$SC$_{1-4}$alkyl, —CO$_2$Bn, or —CO$_2$CH$_2$CO$_2$C$_{1-4}$alkyl, and E is null, halo, $C_{1-4}$alkyl, —OC$_{1-4}$alkyl, —NH—C$_{1-4}$alkyl, —C$_{0-3}$alkylene-NH$_2$, or NO$_2$.

In another aspect, the invention provides a composition comprising any of the foregoing compounds and at least one pharmaceutically acceptable excipient.

In another aspect, the invention provides a method for treating or preventing hepatitis C virus infection or reactivation in a host, comprising administering to the host a therapeutic amount of a compound or composition as disclosed herein.

In another aspect, the invention provides a method for reducing a hepatitis C virus polymerase activity in a host, comprising administering to the host a therapeutic amount of a compound or composition as disclosed herein.

In another aspect, the invention provides a method for reducing hepatitis C virus replication in a host, comprising administering to the host a therapeutic amount of a compound or composition as disclosed herein.

In the foregoing methods, the invention provides embodiments in which the method further comprises administering to the host at least one other active agent. Such active agents may be active agents that have antiviral, e.g., anti-HCV, activity or function. For example, such active agents may be selected from the group consisting of interferons, ribavirin, nucleoside HCV NS5B polymerase inhibitors, non-nucleoside HCV NS5B polymerase inhibitors, HCV NS3-4A protease inhibitors, HCV NS5A inhibitors, HCV entry inhibitors, HCV NS3 inhibitors, HCV NS3 helicase inhibitors, HCV NS4B inhibitors, and human cyclophilin inhibitors.

In another aspect, the invention provides a combination, comprising a compound as disclosed herein together with at least one other active agent. Such active agents may be active agents that have antiviral, e.g., anti-HCV, activity or function. For example, such active agents may be selected from the group consisting of interferons, ribavirin, nucleoside HCV NS5B polymerase inhibitors, non-nucleoside HCV NS5B polymerase inhibitors, HCV NS3-4A protease inhibitors, HCV NS5A inhibitors, HCV entry inhibitors, HCV NS3 inhibitors, HCV NS3 helicase inhibitors, HCV NS4B inhibitors, and human cyclophilin inhibitors.

In another aspect, the invention provides a combination, comprising a composition comprising a compound as disclosed herein and a pharmaceutically acceptable excipient, together with a composition comprising at least one other active agent and a pharmaceutically acceptable excipient. Such active agents may be active agents that have antiviral, e.g., anti-HCV, activity or function. For example, such active agents may be selected from the group consisting of interferons, ribavirin, nucleoside HCV NS5B polymerase inhibitors, non-nucleoside HCV NS5B polymerase inhibitors, HCV NS3-4A protease inhibitors, HCV NS5A inhibitors, HCV entry inhibitors, HCV NS3 inhibitors, HCV NS3 helicase inhibitors, HCV NS4B inhibitors, and human cyclophilin inhibitors. For example, such combinations may comprise a composition comprising a compound of Formula I and a pharmaceutically acceptable excipient, together with two or more other compositions comprising other such active agents and pharmaceutically acceptable excipients.

The invention further provides compounds that can be useful as prodrugs. For example, compounds that contain a carboxyl group may be modified to a variety of promoieties using conventional techniques. For example, a carboxyl moiety in a compound of Formula I may be replaced by or modified to a corresponding amides, carbamates, carbonates, or esters, provided that biotransformation processes can yield the appropriate carboxyl form of the parent compound. Ideally the prodrug form will, upon biotransformation, yield the parent compound in a high recovery ratio, and will be non-toxic or have no significant safety concerns.

Accordingly, in one aspect, there are provided compounds of Formula I in which D is a carboxyl group is esterified, e.g., the group —C(O)OH is replaced by the group —C(O)O—R$^P$, wherein R$^P$ is —C$_{1-4}$alkyl, —C$_{1-4}$alkyl-OC(O)O—C$_{1-4}$alkyl, 5-methyl-2-oxo-[1,3]dioxol-4-ylmethyl, or —C$_{1-4}$alkyl-NR'R", wherein R' and R" are independently hydrogen or —C$_{1-4}$alkyl.

In some embodiments, prodrug forms of a compound of Formula I can have reduced potency for inhibition of HCV polymerase activity. Alternatively, such prodrug forms can have an IC$_{50}$ against HCV polymerase that is at least 50-fold, at least 100-fold, at least 150-fold, at least 200-fold, or at least 500-fold higher than the $IC_{50}$ of the corresponding unmodified carboxyl form of the compound.

In one aspect of the invention, in the compounds of Formula I, the L group is comprises a carbon (alkylene) or carbon and oxygen (ether) backbone. In such cases the backbone can comprise 7 to 10 carbon or carbon and oxygen atoms. In some embodiments, L is —$(CH_2)_x(OCH_2CH_2)_y$—O—$(CH_2)_z$—, in which x=2-6, y=0-5, and z=0-5; provided that when y is 0, then (x+z) is 4 to 11.

In some embodiments, x=2, y=0 to 2, and z=2 to 4.
In some embodiments, x=2, y=0, and z=4.
In some embodiments, x=2, y=1, and z=1 to 3.
In some embodiments x=2, y=1, and z=1.
In some embodiments x=2, y=1, and z=2.
In some embodiments x=2, y=1, and z=3.
In some embodiments, x=2, y=2, and z=0 to 1.
In some embodiments, x=2, y=2, and z=0.
In some embodiments, x=2, y=2, and z=1.
In some embodiments, x=3, y=0, and z=3.
In some embodiments, x=4, y=0, and z=2.
In some embodiments, x=5, y=0, and z=0 to 4.
In some embodiments, x=5, y=0, and z=1.
In some embodiments, x=5, y=0, and z=4.
In some embodiments, x=6, y=0, and z=0.
In some embodiments, L is $C_7$alkylene.

Throughout the description of this invention, any scope of any variable, including m, n, w, x, y, and z, can, unless otherwise specified, be used independently with the scope of any other instance of a variable.

General Preparation of Compounds

The compounds of the invention may be prepared by any suitable synthetic route, using chemical techniques and apparatus known to the skilled organic chemist. Details of the syntheses of exemplary compounds are provided in the Examples below. General outlines of such synthetic processes are provided to aid the understanding of the invention.

It will be appreciated that the compounds of Formula I may contain one or more asymmetric carbon atoms and may exist in racemic, diastereomeric, and optically active forms. All of these racemic compounds, enantiomers, and diastereomers are contemplated to be within the scope of the present invention. Methods are known in the art for separating isomers such as enantiomers and diastereomers, including physical and chemical methods. It will further be appreciated that certain compounds of the present invention may exist in different tautomeric forms. All tautomers are contemplated to be within the scope of the present invention.

Certain compounds of the present invention may occur as atropisomers, which are stereoisomers that exhibit hindered rotation about a single bond, in which the steric interconversion barrier to such rotation is high enough to permit isolation of individual conformers. Atropisomers may be equilibrated thermally, and the interconversion barrier may be measured kinetically.

The present invention also includes isotopically-labeled compounds of Formula I. The isotopically-labeled compounds are identical to the compounds of this invention, but for being manufactured to replace one or more atoms with another isotope of the same element. For example, a selected atom may be changed from a naturally abundant isotope to a rare isotope. Exemplary isotopes that can be incorporated into compounds of the invention include isotopes of hydrogen, carbon, nitrogen, oxygen, sulfur, chlorine, such as $^2H$, $^3H$, $^{11}C$, $^{13}C$, $^{14}C$ $^{13}N$, $^{15}O$, $^{17}O$, $^{35}S$, $^{18}F$, $^{36}Cl$. Certain isotope-labeled compounds (e.g., $^3H$ and $^{14}C$) are useful in compound or substrate tissue distribution studies. Certain heavier isotopes (e.g., $^2H$) may afford therapeutic advantages resulting from possible greater metabolic stability.

Also included within the present invention are salts, (e.g., pharmaceutically acceptable salts) of the compounds of Formula I. Any salt that is consistent with the overall stability and utility of the compounds of Formula I may be provided using conventional methods. Suitable salts include, without limitation, salts of acidic or basic groups that can be present in the compounds provided herein. Under certain acidic conditions, the compound can form a wide variety of salts with various inorganic and organic acids. Acids that can be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate (methylenesulfonate), methylsulfate, muscate, napsylate, nitrate, panthothenate, phosphate/diphosphate, polygalacturonate, salicylate, stearate, succinate, sulfate, tannate, tartrate, teoclate, triethiodide, and pamoate. Under certain basic conditions, the compound can form base salts with various pharmacologically acceptable cations. Non-limiting examples of such salts include alkali metal or alkaline earth metal salts and, particularly, calcium, magnesium, sodium, lithium, zinc, potassium and iron salts, as well as tetraalkylammonium salts. General information regarding pharmaceutically acceptable salts may be found in Stahl P H, and Wermuth C G, eds., *Handbook of Pharmaceutical Salts: Properties, Selection and Use*, 2002, Wiley-VCH/VHCA Weinheim/Zürich.

The present invention also relates provides hydrates and other solvates of the compounds of Formula I. Thus, hydrates and other solvates of the compounds of Formula I and hydrates and other solvates of the salts of the compounds of Formula I are included within the scope of the present invention.

Esters, including pharmaceutically acceptable esters, of the compounds of Formula I are included within the scope of the present invention. Esters include stable carboxylic acid esters —COOR, for example, in which R is selected from optionally substituted straight or branched chain alkyl, alkoxyalkyl, aralkyl, aryloxyalkyl, aryl; or for example, —$CH_2OC(O)R'$ or —$CH_2OCO_2R'$ in which R' is alkyl (e.g., R' is tert-butyl). Unless otherwise specified, any alkyl moiety present in such esters suitably contains 1 to 6 carbon atoms, preferably 1 to 4 carbon atoms.

If there should be, in this specification, a discrepancy between a depicted structure and a name given to that structure, the depicted structure is to be accorded more weight. In addition, if the stereochemistry of a structure or a portion of a structure is not indicated with conventionally accepted notation, for example, bold or dashed lines, the structure or portion thereof is to be interpreted as encompassing all stereoisomers of such structure.

A compound of Formula I and its salts (e.g., pharmaceutically acceptable salts) may exist in crystalline forms, which may appear as different polymorphs or pseudopolymorphs. As used herein, crystalline "polymorphism" means the ability of a crystalline compound to exist in different crystal structures. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubilities, and melting points. Polymorphism may result from differences in crystal packing (packing polymorphism) or differences in packing between different conformers of the same molecule (conformational polymorphism). As used herein, crystalline "pseudopolymorphism" means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The present invention comprises all polymorphs and pseudopolymorphs of the compounds of Formula I and their pharmaceutically acceptable salts.

A compound of Formula I and its salts or solvates may also exist as amorphous solids. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I and their salts, (e.g., pharmaceutically acceptable salts) and solvates.

In one aspect the invention provides a composition comprising a compound according to Formula I or a salt (e.g., a pharmaceutically acceptable salt) or solvate thereof. Such compositions may further comprise at least one further component, such as a pharmaceutically acceptable excipient.

Methods of Use

In another aspect, the invention provides a method for treating a hepatitis C virus infection in a host, comprising administering to the host a therapeutic amount of at least one compound according to Formula I, or a pharmaceutically acceptable salt thereof. There is likewise provided a compound according to Formula I or a pharmaceutically acceptable salt of such compound, for use in the treatment of a HCV infection in a host. In some embodiments, the method further comprises administering to the host at least one other therapeutically active agent selected from the group consisting of interferons, ribavirin, taribavirin, nucleoside HCV polymerase inhibitors, non-nucleoside HCV polymerase inhibitors, HCV NS3-4A protease inhibitors, HCV NS5A inhibitors, HCV entry inhibitors, HCV NS3 inhibitors, and HCV NS4B inhibitors. In some embodiments, the compound may be used for preventing HCV infection in a host. In some embodiments, the compound may be used to limit infection in a host. In some embodiments, the host is a human subject.

In another aspect, the invention provides a method for treating a hepatitis C virus reactivation in a host, comprising administering to the host a therapeutic amount of at least one compound according to Formula I, or a pharmaceutically acceptable salt thereof. There is likewise provided a compound according to Formula I or a pharmaceutically acceptable salt of such compound, for use in the treatment of a HCV infection in a host. In some embodiments, the method further comprises administering to the host at least one other therapeutically active agent selected from the group consisting of interferons, ribavirin, taribavirin, nucleoside HCV polymerase inhibitors, non-nucleoside HCV polymerase inhibitors, HCV NS3-4A protease inhibitors, HCV NS5A inhibitors, HCV entry inhibitors, HCV NS3 inhibitors, and HCV NS4B inhibitors. In some embodiments, the compound may be used for preventing HCV infection in a host. In some embodiments, the compound may be used to limit infection in a host. In some embodiments, the host is a human subject.

In another aspect, the invention provides a method for inhibiting or reducing the activity of hepatitis C virus polymerase in a host, comprising administering to the host a therapeutic amount of at least one compound according to Formula I or a pharmaceutically acceptable salt thereof. There is likewise provided a compound according to Formula I, or a pharmaceutically acceptable salt of such compound, for use in inhibiting or reducing the activity of HCV polymerase in a host. In some embodiments, the method further comprises administering to the host at least one other therapeutically active agent selected from the group consisting of interferons, ribavirin, taribavirin, nucleoside HCV polymerase inhibitors, non-nucleoside HCV polymerase inhibitors, HCV NS3-4A protease inhibitors, HCV NS5A inhibitors, HCV entry inhibitors, HCV NS3 inhibitors, and HCV NS4B inhibitors. In some embodiments, the host is a human subject.

In a further aspect, the invention provides a method for inhibiting or reducing hepatitis C virus polymerase replication in a host, comprising administering to the host a therapeutic amount of at least one compound according to Formula I or a pharmaceutically acceptable salt thereof. There is likewise provided a compound according to Formula I, or a pharmaceutically acceptable salt of such compound, for use in inhibiting or reducing HCV polymerase replication in a host. In some embodiments, the method further comprises administering to the host at least one other therapeutically active agent selected from the group consisting of interferons, ribavirin, taribavirin, nucleoside HCV polymerase inhibitors, non-nucleoside HCV polymerase inhibitors, HCV NS3-4A protease inhibitors, HCV NS5A inhibitors, HCV entry inhibitors, HCV NS3 inhibitors, and HCV NS4B inhibitors. In some embodiments, the host is a human subject.

In another aspect, the invention provides a method of treating HCV-associated liver cirrhosis, chronic liver disease, hepatocellular carcinoma, cryoglobulinaemia, and/or liver fibrosis in a host, which comprises administering to the host a therapeutic amount of at least one compound according to Formula I or a pharmaceutically acceptable salt thereof. There is likewise provided a compound according to Formula I, or a pharmaceutically acceptable salt of such compound, for use in HCV-associated liver cirrhosis, chronic liver disease, hepatocellular carcinoma, cryoglobulinaemia, and/or liver fibrosis in a host. In some embodiments, the method further comprises administering to the host at least one other therapeutically active agent selected from the group consisting of interferons, ribavirin, taribavirin, nucleoside HCV polymerase inhibitors, non-nucleoside HCV polymerase inhibitors, HCV NS3-4A protease inhibitors, HCV NS5A inhibitors, HCV entry inhibitors, HCV NS3 inhibitors, and HCV NS4B inhibitors.

In another aspect, the invention provides a use of a compound according to Formula I or a pharmaceutically acceptable salt thereof in the manufacture of a medicament for treating a hepatitis C virus infection in a host. In some embodiments, the host is a human subject.

In another aspect, the invention provides a use of a compound according to Formula I or a pharmaceutically acceptable salt thereof in the manufacture of a medicament for inhibiting or reducing the activity of hepatitis C virus polymerase in a host. In some embodiments, the host is a human subject.

In another aspect, the invention provides a use of a compound according to Formula I or a pharmaceutically acceptable salt thereof in the manufacture of a medicament for inhibiting or reducing hepatitis C virus polymerase replication in a host. In some embodiments, the host is a human subject.

The invention provides, in a further aspect, a combination comprising at least one compound of Formula I or a pharmaceutically acceptable salt thereof together with at least one other active agent, especially interferon, ribavirin, and/ or an additional anti-HCV agent.

In a further aspect of the present invention there is provided a compound chosen from compounds of Formula I or a pharmaceutically acceptable salt thereof for use in human or veterinary medical therapy, particularly in the treatment or prevention of viral infection, particularly flavivirus infection, for example, HCV infection.

In another aspect, the invention provides for the use of a compound of Formula I or a pharmaceutically acceptable salt thereof in the manufacture of a medicament for the treatment and/or prophylaxis of viral infection, particularly HCV infection.

In another aspect, the invention provides a compound of Formula I or a pharmaceutically acceptable salt thereof for use in treating HCV disease in a human.

In another aspect, the invention provides a compound prepared to be administered in combination with at least one active agent selected from the group consisting of interferons, ribavirin, nucleoside HCV NS5B polymerase inhibitors, non-nucleoside HCV NS5B polymerase inhibitors, HCV NS3-4A protease inhibitors, HCV NS5A inhibitors, HCV entry inhibitors, HCV NS3 inhibitors, HCV NS3 helicase inhibitors, HCV NS4B inhibitors, and human cyclophilin inhibitors.

In another aspect, the invention provides a combination comprising: a) a therapeutically effective amount of a compound of Formula I or a pharmaceutically acceptable salt thereof and b) a therapeutically effective amount of at least one active agent selective from the group consisting of interferons, ribavirin, nucleoside HCV NS5B polymerase inhibitors, non-nucleoside HCV NS5B polymerase inhibitors, HCV NS3-4A protease inhibitors, HCV NS5A inhibitors, HCV entry inhibitors, HCV NS3 inhibitors, HCV NS3 helicase inhibitors, HCV NS4B inhibitors, and human cyclophilin inhibitors.

In another aspect, the invention provides a use of a compound of Formula I or a pharmaceutically acceptable salt thereof in combination with at least one active agent selected from the group consisting of interferons, ribavirin, nucleoside HCV NS5B polymerase inhibitors, non-nucleoside HCV NS5B polymerase inhibitors, HCV NS3-4A protease inhibitors, HCV NS5A inhibitors, HCV entry inhibitors, HCV NS3 inhibitors, HCV NS3 helicase inhibitors, HCV NS4B inhibitors, and human cyclophilin inhibitors, for manufacture of a medicament for treatment of HCV disease in a human.

In another aspect, the invention provides a use of a compound of Formula I or a pharmaceutically acceptable salt thereof in the manufacture of a dosage form for treatment of HCV disease in a human, wherein the dosage form comprises 1 to 1,000 mg of a compound of Formula I or a pharmaceutically acceptable salt thereof, and an effective amount of at least one active agent selected from the group consisting of interferons, ribavirin, nucleoside HCV NS5B polymerase inhibitors, non-nucleoside HCV NS5B polymerase inhibitors, HCV NS3-4A protease inhibitors, HCV NS5A inhibitors, HCV entry inhibitors, HCV NS3 inhibitors, HCV NS3 helicase inhibitors, HCV NS4B inhibitors, and human cyclophilin inhibitors, wherein the dosage form is suitable for administration to a human.

In yet another aspect, the invention provides methods for inhibiting HCV polymerase activity in a biological sample, comprising contacting the biological sample with an effective inhibitory amount of a compound of Formula I or a pharmaceutically acceptable salt thereof. In some embodiments, the biological sample is a blood, tissue, or other fluid sample. In some embodiments, the biological sample is a culture of host cells, e.g., hepatocytes, or hepatocellular carcinoma cells, infected with HCV. For a survey of biological assay systems in which the compounds of the invention may be demonstrated, see, Huang et al., "Hepatitis C Virus-related Assays," Chapter 2 in *Hepatitis C: Antiviral Drug Discovery and Development*, S-L Tan and Y He, eds., Caister Academic Press (2011).

Such methods may be useful in research or in the clinic, for example, in the identification of HCV genotypes amenable to inhibition with the compounds of the invention or the identification of subjects who may beneficially be treated using compounds or compositions of the invention. In some embodiments, the HCV genotype is 1, or the HCV genotype is 1a, or the HCV genotype is 1b.

In various embodiments of the methods, set forth above, of using the compounds of Formula I for treatment or prevention of HCV infection or the sequelae of such infection, the HCV may be genotypically unidentified. In other embodiments, the HCV is HCV genotype 1, optionally HCV genotype 1a or 1b. In other embodiments, the HCV may be selected from among other HCV genotypes, including HCV genotypes 2 and/or 3.

Without intending to be bound by theory, it is believed that the compounds of Formula I that exhibit inhibition of HCV replication or infectivity derive their activity through interaction with or binding to an allosteric site controlling the conformation of the HCV NS5B protein, and thereby inhibiting viral RNA synthesis in the host cell. It is believed that the compounds of Formula I that exhibit inhibition of HCV replication or infectivity interact with or bind to the NNI IV. As demonstrated in the Examples below, compounds of Formula I exhibit potent inhibition of the NS5B RdRp activity in a biochemical assay in vitro as well as inhibition of HCV replication as measured in an HCV replicon cell assay.

Definitions

It is understood that the compounds of the invention, as described herein, may be substituted with a variety of substituents or functional moieties. In general, the term "substituted," whether or not preceded by the term "optionally," and substituents contained in formulas of this invention, refer to the replacement of hydrogen radicals in a given structure with the radical of a specified substituent. When more than one position in any given structure may be substituted with more than one substituent selected from a specified group, the substituents are, unless otherwise indicated, to be understood as independent, i.e., they may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful as described herein, for example, in the treatment and prevention of disorders associated with HCV infection.

The term "aliphatic," as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl," "alkynyl" and the like. Furthermore, as used herein, the terms "alkyl," "alkenyl," "alkynyl," and the like encompass both substituted and unsubstituted groups.

In certain embodiments, the alkyl, alkenyl and alkynyl groups employed in the invention contain about 1-20 aliphatic carbon atoms ($C_{1-20}$). In certain other embodiments, the alkyl, alkenyl, and alkynyl groups employed in the invention contain about 1-10 aliphatic carbon atoms ($C_{1-10}$). In yet other embodiments, the alkyl, alkenyl, and alkynyl groups employed in the invention contain about 1-8 aliphatic carbon atoms ($C_{1-8}$). In still other embodiments, the alkyl, alkenyl, and alkynyl groups employed in the invention contain about 1-6 aliphatic carbon atoms ($C_{1-6}$). In yet other embodiments, the alkyl, alkenyl, and alkynyl groups employed in the invention contain about 1-4 carbon atoms ($C_{1-4}$). Aliphatic groups include, for example, for example, methyl, ethyl, n-propyl, isopropyl (iPr), allyl, n-butyl (nBu), sec-butyl, isobutyl, tert-butyl, n-pentyl, sec-pentyl, isopentyl, tert-pentyl, n-hexyl, sec-hexyl, and the like, which may bear one or more substituents. Alkenyl groups include, for example, ethenyl, propenyl, butenyl, 1-methyl-2-buten-1-yl, and the like. Alkynyl groups include, for example, ethynyl, 2-propynyl (propargyl), 1-propynyl, and the like.

The term "alkyl," as used herein, refers to a saturated straight chain or branched hydrocarbon. Alkyl groups may occur as monovalent or divalent radicals in compounds disclosed herein. In some embodiments, alkyl groups have 1 to 10 ($C_{1-10}$), 1 to 6 ($C_{1-6}$), 1 to 4 ($C_{1-4}$), or 1 to 3 ($C_{1-3}$) carbon atoms. Representative saturated straight chain alkyl substituents include methyl, ethyl, n-propyl, n-butyl, n-pentyl, and n-hexyl; while saturated branched alkyl substituents include isopropyl, sec-butyl, isobutyl, tert-butyl, isopentyl, 2-methylbutyl, 3-methylbutyl, and the like.

The term "Bn," as used herein, refers to a benzyl group.

The terms "amine" and "amino," as used herein, refer to a group having the formula —NR'R" wherein R' and R" are both hydrogen. The term "alkylamine," as used herein, refers to a group having the formula —NR'R" wherein R' is hydrogen or alkyl, and R" is alkyl. Thus, the term alkylamine includes monoalkylamine and dialkylamine. The term "aminoalkyl," as used herein, refers to a group having the formula -alkyl-NR'R" wherein R' and R" are independently hydrogen or alkyl.

The term "ether," as used herein, refers to a group having the formula R'—O—R", wherein R' and R" are independently alkyl or other substituent linked to the oxygen via a carbon atom, for example, —CH$_2$—O—CH$_2$ or —CH$_2$—O-aryl-(CH$_2$)$_3$. The term "thioether," as used herein, refers to a similar group having the formula R'—S—R". The term "(thio)ether," as used herein, refers to a group that comprises an ether or thioether functionality, or that has hybrid ether and thioether functionality, for example —CH$_2$—O—CH$_2$—S—CH$_2$—.

The term "excipient," as used herein, refers to is a natural or synthetic substance formulated alongside the active ingredient of a composition. Excipients may be included in a composition for various functions or to impart various properties to the composition. For example, excipients may be included for the purpose of bulking-up formulations that contain potent active ingredients (thus often referred to as "bulking agents," "fillers," or "diluents"). Alternatively excipients may be included in a formulation to confer a therapeutic enhancement on the active ingredient in the final dosage form, such as facilitating drug absorption or solubility. The selection of appropriate excipients also depends upon the route of administration and the dosage form, as well as the active ingredient and other factors. For example, for oral administration consideration may be given to colorants, flavorants, glidants, lubricants, and the like. Excipients can also be useful in the manufacturing process, to aid in the handling of the active substance concerned such as by facilitating powder flowability or non-stick properties. Excipients may be employed to aid in stability of the formulation such as prevention of denaturation over the expected shelf life, or to prevent or deter microbial (e.g., bacterial, fungal) growth (preservatives).

The term "IC$_{50}$," as used herein, refers to an amount, concentration, or dosage of a particular test compound that achieves a 50% inhibition of a maximal response in an in vitro assay-such as a biochemical or enzymatic assay—that measures such response.

The term "halo" or "halogen," as used herein, refers to F, Cl, Br, or I.

The term "HCV polymerase," as used herein, refers to the NS5B polymerase of HCV.

The term "pharmaceutically acceptable," as used herein in relation to an ingredient (such as an active ingredient, a salt or solvate thereof, or an excipient) that may be included in a pharmaceutical formulation for administration to a patient, refers to that ingredient being acceptable in the sense of being compatible with any other ingredients present in the pharmaceutical formulation and not being deleterious to the patient. Indeed, pharmaceutical regulations and standards require that all excipient in medicaments administered to humans and other animals, as well as the chemical decomposition or metabolism products of such excipients, be identified and shown to be safe. The acronym GRAS is often applied to such materials, meaning that they are "Generally Recognized As Safe."

The term "preventing," as used herein, means that the compounds of the present invention are useful when administered to a patient who has not been diagnosed as possibly having the disease at the time of administration, but who would normally be expected to develop the disease or be at increased risk for the disease. Generally, the term "preventing" refers to administration of a compound of the invention prior to the onset of symptoms, particularly to patients at risk of contracting HCV infection. The compounds of the invention will slow the development of disease symptoms, delay the onset of disease, or prevent the individual from developing the disease at all.

The term "prodrug," as used herein, refers to a chemical compound that has little or no pharmacological activity per se or that has properties that are preferred for administration, but that is capable of undergoing biotransformation to a therapeutically active metabolite of interest. For example, a prodrug form of a compound of Formula I may itself have little or no inhibitory activity against HCV polymerase, but would undergo biotransformation in the body of the patient to the active form of the compound. As another example, a prodrug form of a compound of Formula I may have one or more physicochemical properties, e.g., solubility, that imparts to the compound a different pharmacokinetic or pharmacodynamic profile. Biotransformation can include hydrolysis, oxidation, photolysis, or by means of physiological or metabolic processes, e.g., by enzymatic modification. A prodrug may be thought of as including the therapeutic compound covalently linked to a promoiety, and the biotransformation process removes or modifies the promoiety to yield the therapeutic compound. Common functional groups on compounds that may be replaced with or modified to contain a promoiety include, for example, amino, carbonyl, carboxyl, hydroxyl, phosphonyl, and thiolyl groups. See, e.g., Rautio et al., *Nat Rev Drug Discov,* 2008, 7:255-270. If a parent drug contains one of these moieties, the compound may be modified using bioreversible chemistry to contain a promoiety. Alternatively, the prodrug may be prepared with the promoiety incorporated at an earlier synthetic stage, as may be desired.

The term "solvate," as used herein, refers to a complex of variable stoichiometry formed by a solute (in this invention, a compound of Formula I or a salt thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. However, solvates having non-pharmaceutically acceptable solvents are within the scope of the present invention, for example, for use as intermediates in the preparation of other compounds of Formula I and their pharmaceutically acceptable salts. Most preferably the solvent used is water and the resulting solvate may also be referred to as a hydrate. As used herein and unless otherwise indicated, the term "hydrate" means a compound provided herein or a salt thereof that further includes a stoichiometric or nonstoichiometric amount of water bound by non-covalent intermolecular forces.

The term "stable," as used herein, refers to compounds that possess stability sufficient to allow their manufacture, and that maintain the integrity of the compound for a sufficient period of time to be detected and preferably for a sufficient period of time to be useful for the purposes detailed herein. For example, a compound of the invention should be sufficiently stable to permit its purification, or isolation, or identification; or should be sufficiently stable to permit formulation into a pharmaceutically acceptable dosage form.

The term "subject," as used herein, is an animal, typically a mammal, most typically a human, such as a patient. The term "host," as used herein, is a cell, such as a hepatocyte, or a human patient or other subject suspected of being, or determined to have been, infected with HCV, as determined through conventional genetic or serologic techniques.

The term "substituted," as used herein, refers to a moiety in which at least one hydrogen atom is replaced by a non-hydrogen substituent. For example if a phenyl group is said to be optionally substituted, at least one of the hydrogens in the phenyl ring is replaced with a substituent that is not hydrogen. Typically, such substituents are small moieties, such as halo, hydroxyl, $C_{1-4}$alkyl, $C_{1-4}$alkoxy, or cyano. Such substitutions generally either contribute to a desirable property for the molecule or at least do not substantially detract from the desirable properties of the molecule, and in any case should be sufficiently stable for use according to the purposes set forth herein.

The term "therapeutic amount," as used herein, refers to an amount of a compound that would be reasonably expected by the skilled medical practitioner to have a particular therapeutic effect in the patient, taking into consideration such factors as the sex, age, genetic background, body mass, body surface area, mode of administration, and the like, notwithstanding idiosyncrasies of the patient's physiology. The therapeutic effect may be realized in the treatment, prevention, and/or management of a HCV infection or a condition or symptom associated with such infection, or the delay or minimization of one or more symptoms associated therewith. The term "therapeutic amount" can therefore, encompass an amount that improves overall therapy, reduces or avoids symptoms or causes of HCV infection, or enhances the therapeutic efficacy of another therapeutic agent. It is possible that a therapeutic amount of a compound may achieve different results when administered to different patients. In some cases, an amount of a compound that produces therapeutic benefit to one patient may yield little or no benefit for another patient, but is still considered a therapeutic amount. In some embodiments, a therapeutic amount of an active compound is an amount determined by the US Food and Drug Administration (or a correlative organization in another country or region) to be safe and effective in the treatment of HCV infection or another specified disease or disorder in a human patient.

It will be appreciated that reference herein to "therapy" and/or "treatment" includes, but is not limited to prevention, retardation, prophylaxis, amelioration, and/or cure of the HCV infection or consequent or associated medical symptoms, conditions, or other sequelae (collectively, "HCV disease"). It will thus be appreciated that references herein to treatment or prevention of HCV infection include treatment or prevention of chronic HCV infection, acute HCV infection, or any of the HCV-associated diseases and disorders such as liver fibrosis, hepatic steatosis, cirrhosis, cryoglobulinemia, and hepatocellular carcinoma. Accordingly, the terms "treat," "treating," and "treatment," as used herein refer to alleviating or reducing the severity of a symptom associated with HCV infection or a condition consequent to such infection. In certain embodiments, compounds of the invention will delay or slow the progression of HCV infection, or a condition consequent to such infection, thereby making it possible for the subject to enjoy a longer life span or a better quality of life.

The term "subtherapeutic amount," as used herein, refers to an amount of a compound that, if administered alone, would be expected to exhibit no therapeutic effect or no significant therapeutic effect in the patient, taking into consideration the foregoing factors. Subtherapeutic amounts of a compound of Formula I may be useful in combination therapy, in which, for example, two or more active compounds are administered to achieve a therapeutic effect.

Therapeutic or treatment effect may be measured in any manner known in the art. Therapeutic effect may be observed in asymptomatic HCV patients by way of delaying, reducing, or preventing onset or development of one or more such symptoms characteristic of HCV disease. For example, therapeutic effect may be observed through delay, reduction, or prevention of a liver pathology. As another example, therapeutic effect may be observed through reduction of viral load (such as by qPCR assessment of the number of copies of HCV RNA in a patient's blood). See, e.g., Highleyman L. and Franciscus A., "HCV Diagnostic Tools: HCV Viral Load Tests," HCSP Fact Sheet, v.3 May 2011 [http://www.hcvadvocate.org/hepatitis/factsheets_pdf/viralload.pdf].

The term "effective amount," as used herein, refers to an amount of a compound that, when provided to a host cell or an in vitro or ex vivo system would be expected to exhibit an overt or measurable effect in the system. For example, in an acellular or cellular assay system suitable for measuring an activity of HCV polymerase, the compounds of Formula I may inhibit or reduce such activity of HCV polymerase when provided in an effective amount. As another example, in a cellular assay system suitable for measuring replication or infectivity of HCV, the compounds of Formula I may inhibit or reduce such activity of HCV when provided in an effective amount.

Pharmaceutical Compositions and Dosage Forms

The invention provides compositions, and in particular, pharmaceutical compositions, comprising any of the compounds of Formula I (e.g., a single enantiomer, a mixture of enantiomers, or a mixture of diastereomers thereof, or a pharmaceutically acceptable salt or solvate thereof) in combination with at least one pharmaceutically acceptable excipient. See, for example, R C Rowe, *Handbook of Pharmaceutical Excipients*, $6^{th}$ ed., 2009, Pharmaceutical Press.

While numerous embodiments of compositions according to the invention are set forth in detail below, it will be understood by the skilled person that compounds of Formula I are not limited to use in compositions specifically adapted for administration as medicaments, but that many other compositions comprising any of the compounds of Formula I may be made using conventional materials and methods. Accordingly, the invention provides compositions comprising any of the compounds of Formula I (e.g., a single enantiomer, a mixture of enantiomers, or a mixture of diastereomers thereof, or a salt or solvate thereof) in combination with at least one vehicle, carrier, diluent, excipient, or a mixture of one or more of the foregoing ingredients. For example, it is to be expected that any of the compounds of Formula I may appear in solution with a solvent that is considered not acceptable for administration to humans or other subjects. In addition, any of the compounds of Formula I may be prepared as a salt of a compound that is considered not acceptable for administration to humans or other subjects. The skilled person will understand how to prepare and interconvert such salt forms of the compounds, and such compositions comprising such compounds, by way of conventional techniques.

The amounts of various compounds of Formula I to be administered can be determined by standard procedures taking into account factors such as the compound ($IC_{50}$) potency, ($EC_{50}$) efficacy, and the biological half-life (of the compound), the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds of Formula I with low oral bioavailability, relatively higher doses will have to be administered. Oral administration is a convenient method of administration of the compounds of Formula I.

Suitably the pharmaceutical composition is in unit dosage form. For oral administration, for example, a tablet or capsule may be administered; for nasal application, a metered aerosol dose may be administered; for transdermal application, a topical formulation or patch may be administered; and for transmucosal delivery, a buccal patch may be administered.

Each dosage unit for oral administration may contain from 0.01 to 500 mg/Kg, for example from 0.1 to 50 mg/Kg, of a compound of Formula I or a pharmaceutically acceptable salt thereof, calculated as the free base. The daily dosage for parenteral, nasal, oral inhalation, transmucosal, or transdermal routes may contains from 0.01 mg to 100 mg/Kg, of a compound of Formula I. A topical formulation may contain 0.01 to 5.0% of a compound of Formula I. The active ingredient may be administered from 1 to 4 times per day, for example once, twice or three times per day, sufficient to achieve the desired pharmaceutical activity.

The pharmaceutical compositions may be formulated in various dosage forms, including, but not limited to, the dosage forms for oral, parenteral, or topical administration. The pharmaceutical compositions may also be formulated as modified release dosage forms, including, but not limited to, delayed, extended, prolonged, sustained, pulsatile, controlled, accelerated, fast, targeted, and programmed release, and gastric retention dosage forms. These dosage forms can be prepared according to conventional methods and techniques known to those skilled in the art. See, e.g., *Remington: The Science and Practice of Pharmacy*, $21^{st}$ ed., 2005, Lippincott Williams & Wilkins; *Ansel's Pharmaceutical Dosage Forms and Drug Delivery Systems*, $9^{th}$ ed., 2010, Lippincott Williams & Wilkins.

In one aspect of the invention, the pharmaceutical compositions are provided in a dosage form for oral administration, which comprise a compound provided herein, including a single enantiomer, a mixture of enantiomers, or a mixture of diastereomers thereof, or a pharmaceutically acceptable salt, solvate; and at least one pharmaceutically acceptable excipient.

In another aspect of the invention, the pharmaceutical compositions are provided in a dosage form for parenteral administration, which comprise a compound provided herein, including a single enantiomer, a mixture of enantiomers, or a mixture of diastereomers thereof, or a pharmaceutically acceptable salt or solvate thereof; and a at least one pharmaceutically acceptable excipient.

In yet another aspect of the invention, the pharmaceutical compositions are provided in a dosage form for topical administration, which comprise a compound provided herein, including a single enantiomer, a mixture of enantiomers, or a mixture of diastereomers thereof, or a pharmaceutically acceptable salt, solvate; and at least one pharmaceutically acceptable excipient.

The pharmaceutical compositions provided herein may be provided in a unit- or multiple-dosage form. A unit-dosage form, as used herein, refers to a physically discrete unit suitable for administration to a subject, and packaged individually as is known in the art. Each unit-dose contains a predetermined quantity of the active ingredient(s) sufficient to produce the desired therapeutic effect, in association with the required at least one pharmaceutically acceptable excipient. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in a segregated unit-dosage form. Examples of multiple-dosage forms include, without limitation, vials, bottles, blister-packs, and cardboard packages of tablets or capsules.

The pharmaceutical compositions provided herein may be administered at once, or multiple times at intervals of time. It is understood that the dosage and duration of treatment suitable for a particular patient may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the pharmaceutical compositions provided herein.

Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, wafers, sprinkles, elixirs, and syrups.

In addition to the active ingredient(s), the pharmaceutical compositions for oral administration may contain one or more pharmaceutically acceptable excipient, including, but not limited to, binders, fillers, diluents, disintegrants, wetting agents, lubricants, glidants, coloring agents, dye-migration inhibitors, sweetening agents, and flavoring agents. Suitable pharmaceutically acceptable excipients are known and described in the art. See, e.g., R C Rowe, *Handbook of Pharmaceutical Excipients,* 6$^{th}$ ed., 2009, Pharmaceutical Press.

Binders or granulators impart cohesiveness to a tablet to ensure the tablet remaining intact after compression. Suitable binders or fillers include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol (psyllium) husks, polyvinylpyrrolidone (PVP), Veegum, larch arabogalactan, powdered tragacanth, and guar gum; celluloses, such as ethyl cellulose (EC), cellulose acetate, carboxymethyl cellulose (CMC), methyl cellulose, hydroxyethyl cellulose (HEC), hydroxypropyl cellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. In certain embodiments, the binder or filler is present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methyl cellulose and CMC; wood products; natural sponge; cation exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pregelatinized starch; clays; aligns; and mixtures thereof. The amount of a disintegrant in the pharmaceutical compositions provided herein varies upon the type of formulation, and is readily discernible to those of ordinary skill in the art. In certain embodiments, the pharmaceutical compositions provided herein contain from about 0.5 to about 15% or from about 1 to about 5% by weight of a disintegrant.

Suitable lubricants include, but are not limited to, calcium stearate; magnesium stearate; sodium stearyl fumarate; mineral oil; light mineral oil; glycerin; sorbitol; mannitol; glycols, such as glycerol behenate and polyethylene glycol (PEG); stearic acid; stearyl fumaric acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co., Boston, Mass.); and mixtures thereof. In certain embodiments, the pharmaceutical compositions provided herein contain about 0.1 to about 5% by weight of a lubricant.

Suitable glidants include, but are not limited to, colloidal silicon dioxide, CAB-O-SIL®, and asbestos-free talc.

Suitable coloring agents include, but are not limited to, any of the approved, certified, water soluble FD&C dyes, water insoluble FD&C dyes suspended on alumina hydrate, and color lakes, and mixtures thereof. A color lake is the combination by adsorption of a water-soluble dye to a hydrous oxide of a heavy metal, resulting in an insoluble form of the dye.

Suitable flavoring agents include, but are not limited to, natural flavors extracted from plants, such as fruits, and synthetic blends of compounds which produce a pleasant taste sensation, such as peppermint and methyl salicylate.

Suitable sweetening agents include, but are not limited to, sucrose, lactose, mannitol, syrups, glycerin, and artificial sweeteners, such as saccharin and aspartame.

Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate.

Suitable suspending and dispersing agents include, but are not limited to, sodium CMC, pectin, tragacanth, Veegum, acacia, HPMC, and PVP.

Suitable preservatives include, but are not limited to, glycerin, esters of p-hydroxybenzoic acid (e.g., methyl- and propyl-paraben), benzoic add, sodium benzoate and alcohol.

Suitable wetting agents include, but are not limited to, propylene glycol monostearate, sorbitan monooleate, diethylene glycol monolaurate, and polyoxyethylene lauryl ether.

Suitable solvents include, but are not limited to, glycerin, sorbitol, ethyl alcohol, and syrup.

Suitable non-aqueous liquids utilized in emulsions include, but are not limited to, mineral oil and cottonseed oil.

Suitable organic acids include, but are not limited to, citric and tartaric acid.

Suitable sources of carbon dioxide include, but are not limited to, sodium bicarbonate and sodium carbonate.

It should be understood that a particular excipient may serve more than one function, even within the same formulation.

The pharmaceutical compositions provided herein may be provided as compressed tablets, tablet triturates, chewable lozenges, rapidly dissolving tablets, multiple compressed tablets, enteric coated tablets, sugar-coated tablets, or film-coated tablets. Enteric coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable taste or odor and in protecting the tablets from oxidation. Film-coated tablets are compressed tablets that are covered with a thin layer or film of a water-soluble material. Film coatings include, but are not limited to, hydroxyethyl cellulose, sodium CMC, polyethylene glycol 4000, and cellulose acetate phthalate. Film coating imparts the same general characteristics as sugar coating. Multiple compressed tablets are compressed tablets made by more than one compression cycle, including layered, press-coated, and dry-coated tablets.

The tablet dosage forms may be prepared from the active ingredient in powdered, crystalline, or granular forms, alone or in combination with at least one pharmaceutically acceptable excipient; including, e.g., a binder, disintegrant, controlled-release polymer, lubricant, diluent, and/or colorant. Flavoring and sweetening agents are especially useful in the formation of chewable tablets and lozenges.

The pharmaceutical compositions provided herein may be provided as soft or hard capsules, which can be made from, e.g., gelatin, methylcellulose, pullulan, starch, or calcium alginate. The hard gelatin capsule, also known as a dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including, but not limited to, methyl- and propylparabens and sorbic acid. The liquid, semisolid, and solid dosage forms provided herein may be encapsulated in a capsule using conventional methods. Suitable liquid and semisolid dosage forms include, but are not limited to, solutions and suspensions in propylene carbonate, vegetable oils, or triglycerides. The capsules may also be coated as known by those of skill in the art in order to modify or sustain dissolution of the active ingredient.

The pharmaceutical compositions provided herein may be provided in liquid and semisolid dosage forms, including, but not limited to, emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing an active ingredient, e.g., a compound of Formula I, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the form of liposomes, micelles, microspheres, or nanosystems. Micellar dosage forms can be prepared as described in U.S. Pat. No. 6,350,458.

The pharmaceutical compositions provided herein may be provided as noneffervescent or effervescent granules or powders, to be reconstituted into a liquid dosage form. Pharmaceutically acceptable excipients used in the noneffervescent granules or powders may include diluents, sweeteners, and wetting agents. Pharmaceutically acceptable excipients used in the effervescent granules or powders may include organic acids and a source of carbon dioxide.

The pharmaceutical compositions provided herein may be formulated as immediate or modified release dosage forms, including delayed, sustained, pulsed, controlled, targeted, and programmed release forms.

The pharmaceutical compositions provided herein may be co-formulated with other active ingredients which do not impair the desired therapeutic action, or with substances that supplement the desired action.

Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science. See, e.g., *Remington: The Science and Practice of Pharmacy*, supra; *Handbook of Pharmaceutical Excipients*; supra.

The pharmaceutical compositions intended for parenteral administration may include one or more pharmaceutically acceptable excipients, including, but not limited to, aqueous vehicles, water-miscible vehicles, non-aqueous vehicles, antimicrobial agents, or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases. Suitable pharmaceutically acceptable excipients are known and described in the art. See, e.g., *Handbook of Pharmaceutical Excipients*, supra.

Suitable aqueous vehicles include, but are not limited to, water, saline, physiological saline or phosphate buffered saline (PBS), sodium chloride injection, Ringer's injection, isotonic dextrose injection, sterile water injection, and dextrose and lactated Ringer's injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium CMC, HPMC, and PVP. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to, EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether-7-β-cyclodextrin (CAPTISOL®, CyDex, Lenexa, Kans.).

The pharmaceutical compositions provided herein may be formulated for single or multiple dosage administration. The single dosage formulations can be packaged in, e.g., an ampoule, a vial, or a syringe. In certain embodiments, the multiple dosage parenteral formulations contain an antimicrobial agent at bacteriostatic or fungistatic concentrations. In certain embodiments, the parenteral formulations provided herein are sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed, sustained, pulsed, controlled, targeted, and programmed release forms.

The pharmaceutical compositions may be formulated as a suspension, solid, semisolid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions to diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/vinyl acetate copolymers, ethylene/propylene copolymers, ethylene/ethyl acrylate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Topical Administration

The pharmaceutical compositions provided herein may be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein may also comprise liposomes, micelles, microspheres, nanosystems, and mixtures thereof.

Pharmaceutically acceptable excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases. Suitable pharmaceutically acceptable excipients are known and described in the art. See, e.g., *Handbook of Pharmaceutical Excipients*, supra.

The pharmaceutical compositions may also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the form of ointments, creams, or gels. Suitable ointment vehicles include oleaginous or hydrocarbon vehicles, including lard, benzoinated lard, olive oil, cottonseed oil, and other oils; white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; and emulsion vehicles, either water-in-oil (W/O) emulsions or oil-in-water (O/W) emulsions, including cetyl alcohol, glyceryl monostearate, lanolin, and stearic acid. These vehicles are emollient but generally require addition of antioxidants and preservatives.

Suitable cream bases can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout a liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinyl alcohol; cellulosic polymers, such as HPC, HEC, HPMC, hydroxypropyl methylcellulose phthalate, and methylcellulose; gums, such as tragacanth and xanthan gum; sodium alginate; and gelatin. To prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the form of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes, such as are described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable excipients utilized in rectal and vaginal suppositories include bases or vehicles, such as stiffening agents, which impart to the formulation a melting point in the proximity of body temperature. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; and glycerinated gelatin. Combinations of the various vehicles may be used. Rectal and vaginal suppositories may further comprise antioxidants as described herein, including bisulfite and sodium metabisulfite. Rectal and vaginal suppositories may be prepared by the compressed method or molding. The typical mass of a rectal and vaginal suppository is about 2 to about 3 g.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; or nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent, solvent or solvent system for dispersing, solubilizing, or extending release of the active ingredient provided herein; and/or a propellant as solvent; and/or a surfactant, such as sorbitan trioleate, oleic acid, or an oligolactic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of monohydrates. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavoring agent, such as menthol and levomenthol, or sweeteners, such as saccharin or saccharin sodium.

The pharmaceutical compositions provided herein for topical administration may be formulated to be immediate release or modified release, including delayed, sustained, pulsed, controlled, targeted, and programmed release.

Co-Administration and Combinations

The terms "co-administration" and "in combination with" include the administration of two or more pharmaceutically active agents (for example, a compound of Formula I and another antiviral agent or second agent) either simultaneously, concurrently, or sequentially with no specific time limits. In one embodiment, both agents are present in the cell or in the patient's body at the same time or exert their biological or therapeutic effect at the same time. In one embodiment, the two or more active agents are in the same composition or unit dosage form. In another embodiment, the two or more active agents are provided in separate compositions or unit dosage forms.

Combinations above may conveniently be presented for use in the form of a pharmaceutical formulation and, thus, pharmaceutical formulations comprising a combination as defined above together with at least one pharmaceutically acceptable excipient thereof represent a further aspect of the invention. Thus, in some embodiments, the invention provides compositions comprising a compound of Formula I, or a pharmaceutically acceptable salt thereof, and at least one pharmaceutically acceptable excipient, and further comprising one or two additional compounds having anti-HCV activity. Alternatively, in some embodiments, the invention provides combined use of a compound of Formula I, or a pharmaceutically acceptable salt thereof, and at least one pharmaceutically acceptable excipient, and further comprising use of one or two additional compounds having anti-HCV activity, each in a composition with at least one pharmaceutically acceptable excipient or together in a composition with at least one pharmaceutically acceptable excipient.

In some embodiments, the invention provides combined use of a compound of Formula I, or a pharmaceutically acceptable salt thereof, to prepare a composition comprising the compound of Formula I, one or two additional compounds having anti-HCV activity, and a pharmaceutically acceptable excipient.

The components of combinations may be administered either sequentially or simultaneously, or in subcombinations, in separate or combined pharmaceutical formulations. Appropriate combinations may be identified by those skilled in the art.

The compounds of Formula I and other individual components of such combinations may be provided in therapeutic or subtherapeutic amounts. Irrespective of whether each component in the combination is itself provided in an amount that would otherwise be considered therapeutic or subtherapeutic, and irrespective of whether the components are directed to the same or different specific therapeutic effects, a combination according to the invention is administered in an amount that a skilled practitioner would deem suitable for the treatment of HCV, as described herein. In such cases, the combination is said to be administered in a therapeutic amount. Accordingly, an amount of a compound of the invention might be considered subtherapeutic if administered alone, but would be considered to be a therapeutic amount if the combination or co-administration regimen is considered therapeutically effective. For example, an amount of a compound of Formula I may be administered in an amount that achieves a therapeutic effect, e.g., a reduction in hepatitis C viral load, in combination with one or more other active agents.

In some embodiments, a compound of Formula I may be administered in combination with one or more other antiviral agents. In some embodiments, a compound of Formula I may be administered in combination with two other antiviral agents. In some embodiments, a compound of Formula I may be administered in combination with three other antiviral agents. In some embodiments, a compound of Formula I may be administered in combination with four other antiviral agent. Such combinations are sometimes referred to as "cocktails." Some combinations of antiviral agents are being used in the clinic to ameliorate the ability of HCV to mutate to overcome the inhibitory activity of a single agent. Use of a compound of Formula I in such combinations can therefore impart useful therapeutic advantages.

Combinations or co-administration of the compounds of the invention with other active agents may desirably exhibit synergistic effects (i.e., the effect that is achieved when active ingredients are administered together is greater than the sum of the effects of each agent administered separately) and/or a higher barrier to drug resistance. For example, if two agents are co-administered, their combined effect may be synergistic if a therapeutic effect is achieved notwithstanding that the two agents would not be expected to yield an equivalent therapeutic effect if administered separately or together. On the contrary, antagonism of two agents may be said to exist if their combined effect is less than the sum of the effects of each agent administered separately. Synergy, drug resistance, and antagonism may be measured using any method that is generally accepted in the art, such as by way of concentration response curves for a parameter of interest. Synergy, drug resistance, or antagonism for a given combination may be determined for inhibition of HCV infection, HCV polymerase activity, a pharmacokinetic or pharmacodynamic effect, or the like.

Doses and dosing regimens of compounds of Formula I together with active second agents and combinations thereof should depend on the specific indication being treated, the age and condition of the patient, and the severity of adverse effects, and may be adjusted accordingly by those of skill in the art. Examples of doses and dosing regimens for other active moieties can be found, for example, in *Physician's Desk Reference*, and will require adaptation for use in the methods of the invention.

Accordingly, in some embodiments, there is administered to the patient a therapeutic amount of a combination comprising a compound of Formula I and at least one other active agent to a patient in need thereof. In some embodiments, the administered amount of at least one other active agent is subtherapeutic. In some embodiments, the administered amount of the at least one other active agent is therapeutic. In some embodiments, the administered amount of the compound of Formula I is subtherapeutic. In other embodiments, the administered amount of the compound of Formula I is therapeutic.

Active agents suitable for use in combination with a compound of Formula I may be agents that have activity against HCV directly or indirectly, e.g., compounds that inhibit or reduce the replication or infectivity of HCV. Such and HCV agents include, among others, interferons, antiviral agents (e.g., ribavirin, taribavirin (viramidine), amantadine), nucleoside HCV NS5B polymerase inhibitors, non-nucleoside HCV NS5B polymerase inhibitors, HCV protease inhibitors, HCV NS5A inhibitors, HCV NS4B inhibitors, HCV NS3 helicase inhibitors, host cell entry inhibitors, and human cyclophilin inhibitors.

In some embodiments, a compound of the invention may be administered in combination with one or more interferon molecules. Exemplary interferons include, without limitation, natural, recombinant, and modified (e.g., PEG-linked, albumin-linked) interferon molecules. Interferons include, but are not limited to, interferon alfa-2a (Roferon®), interferon alpha-2b (Intron®), interferon alfacon-1 (Infergen®), peginterferon alfa-2a (Pegasys®) or peginterferon alfa-2b (PegIntron®), recombinant alfa interferon (BLX-883; Locteron®), and albinterferon alfa 2b (Zalbin®).

In some embodiments, a compound of Formula I may be administered in combination with an interferon and ribavirin. In such cases, the compound of the invention may be said to be used to supplement the current standard of care. In some other embodiments, a compound of the invention is administered in combination with ribavirin.

In some embodiments, a compound of Formula I may be administered in combination with one or more compounds that inhibit the activity of the HCV serine protease (NS3-4A). Such protease inhibitors include, without limitation, telaprevir (Incivek™; VX-950; Vertex), boceprevir (Victrelis™; SCH503034; Merck), simeprevir (TMC435; Janssen/Tibotec/Medevir), danoprevir (ITMN-191/RG7227; Hoffmann-La Roche/Genentech), faldaprevir (BI 201335; Boehringer Ingelheim), BI 12202 (Boehringer Ingelheim), vaniprevir (MK-7009; Merck), MK-5172 (Merck), paritaprevir (ABT-450; Abbvie); VX500 (Vertex), PHX1766 (Phenomix), BILN2061 (Boehringer Ingelheim), GS-9256 (Gilead), GS-9451 (Gilead), asunaprevir (BMS-650032; Bristol-Myers Squibb), VX-985 (Vertex), sovaprevir (ACH-1625; Achillion), ACH-2684 (Achillion), and narlaprevir (SCH900518; Merck).

In some embodiments, a compound of Formula I may be administered in combination with one or more nucleoside inhibitors of the HCV polymerase (NS5B). Suitable NI compounds include, among others, IDX184 (Idenix), mericitabine (RG7128, R-7128, R05024048; Hoffmann-La Roche/Genentech), PSI-7851 (Pharmasset), PSI-938 (Pharmasset), sofosbuvir (SOVALDI®, PSI-7977; Gilead/Pharmasset), TMC647055 (Janssen); and VX-135 (Vertex), as well as phosphoramidate nucleotide analogs such as INX-189 (Inhibitex), TMC649128 (Tibotec/Medevir). Combinations of compounds of Formula I with other NS5B inhibitors may be used, for example, combinations with ALS-2200 or ALS-2158 (Vertex and Alios Biopharma)

In some embodiments, a compound of Formula I may be administered in combination with one or more non-nucleoside inhibitors of the HCV polymerase (NS5B). Suitable NNI compounds include, without limitation, compounds that bind to or inhibit activity through one of the identified NNI sites on the NS5B protein. See, Powdrill et al., *Viruses*, 2010, 2:2169-95 and Appleby et al., "Viral RNA Polymerase Inhibitors," Chapter 23 in *Viral Genome Replication*, Cameron et al., eds., Springer Science+Business Media 2009. These NNI compounds may be classified on the basis of the site with which they interact.

Accordingly, in some embodiments, a compound of Formula I may be co-administered, or provided in combination, with an NNI I inhibitor compound, an NNI II inhibitor compound, an NNI III inhibitor compound, or an NNI IV inhibitor compound, or a combination such compounds. Accordingly, in some embodiments, a compound of Formula I may be administered in combination with one or more compounds selected from among:

NNI I compounds including, among others, JTK-109 (Japan Tobacco), BILB-1941 (Boehringer Ingelheim), MK-3281 (Merck), BI 207127 (Boehringer Ingelheim);
NNI II compounds including, among others, filibuvir (PF-868554; Pfizer), VX-759 (VCH-759; Vertex), VCH-916 (Vertex), VX-222 (VCH-222; Vertex), GS-9669 (Gilead);
NNI III compounds including, among others, GSK625433 (Glaxo SmithKline), ANA-598 (Anadys/Roche), dasabuvir (ABT-333; Abbvie), ABT-072 (Abbott), setrobuvir (ANA-5981; Hoffmann-La Roche/Genentech); or
NNI IV compounds including, among others, HCV-796 (ViroPharma/Wyeth), tegobuvir (GS-9190; Gilead), IDX375 (Idenix).

In other embodiments, a compound of Formula I may be administered in combination with one or more other NS5B polymerase inhibitors including, among others, BMS 791325 (Bristol-Myers Squibb), R1626 (Roche), A-848837 (Abbott), and A-837093 (Abbott), as well as the compounds disclosed in International patent publications WO 02/100846 A1, WO 02/100851 A2, WO 2004/052879 A2, WO 2004/052885 A1, WO 2006/072347 A2, WO 2006/119646 A1, WO 2008/017688 A1, WO 2008/043791 A2, WO 2008/058393 A1, WO 2008/059042 A1, WO 2008/125599 A1, and WO 2009/000818 A1; U.S. Pat. Nos. 6,881,741 B2, 6,887,877 B2, and 6,936,629 B2, 7,402,608 B2, and 7,569,600 B2; and Yang et al., *Bioorg Med Chem Lett*, 2010, 20:4614-19.

In some embodiments, a compound of Formula I may be administered in combination with an active compound that inhibits another activity or function of a target selected from HCV metalloprotease, HCV serine protease, HCV polymerase, HCV helicase, HCV NS4B protein, HCV entry, HCV assembly, HCV egress, HCV NS5A protein, and inosine-5'-monophosphate dehydrogenase (IMPDH). For example, a compound of the invention may be administered in combination with one or more compounds selected from:

NS5A (regulatory protein) inhibitors, e.g., daclatasvir (BMS-790052; Bristol-Myers Squibb), BMS-824383 (Bristol-Myers Squibb), AZD7295 (AstraZeneca), PPI-461 (Presidio), PPI-688 (Presidio), GS-5885 (Gilead), ACH-2928 (Achillion), IDX-719 (Idenix), ombitasvir (ABT-267; Abbvie); ledipasvir (GS-5885; Gilead), ACH-3102 (Achillion), GS-5816 (Gilead), JNJ-56914845 (GSK 2336805; Janssen), MK-8742 (Merck);
NS3 (peptidase/helicase) inhibitors, e.g., BMS-650032 (Bristol-Myers Squibb);
NS4B (regulatory protein) inhibitors, e.g., clemizole (Eiger Biopharmaceuticals); Host-cell entry inhibitors, e.g., ITX5061 (iTherX); and
Cyclophilin inhibitors, such as cyclophilin-A inhibitors, e.g., Debio 025 (alisporivir), SCY-635, NIM811, and other cyclosporin (ciclosporin) derivatives.

In some embodiments, a compound of Formula I may be administered in combination with two or more compounds that inhibit activities or functions of HCV. For example, a compound of Formula I may be administered in combination with combinations of HCV NS5B (polymerase) inhibitors and NS5A (regulatory protein) inhibitors, such as sofosbuvir+ledipasvir (HARVONI®; Gilead), and sofosbuvir with GS-5816. As another example, a compound of Formula I may be administered in combination with combinations of HCV NS5B (polymerase) inhibitors, such as TMC435, and NS5A (regulatory protein) inhibitors, such as JNJ-56914845.

In some embodiments, a compound of Formula I may be administered in combination with one or more compounds that inhibit activities or functions of HCV and one or more compounds that have other activities. For example, a compound of Formula I may be administered in combination with combinations of a NS3-4A protease inhibitor, that is boosted with ritonavir (NORVIR®; Abbvie), which inhibits CYP3A4, a host enzyme that can metabolize protease inhibitors. These include, for example, ABT-450 boosted with ritonavir and danoprevir boosted with ritonavir.

In some embodiments, a compound of Formula I may be employed in combination with multiple active agents. As one example of such combinations, a compound of Formula I may be employed in combination with a protease inhibitor (e.g., paritaprevir) boosted with ritonavir, and a NS5A inhibitor (e.g., ombitasvir), optionally with ribavirin.

In some embodiments, a compound of Formula I may be administered in combination with a compound selected from interleukin 2, interleukin 6, interleukin 12, a compound that enhances the development of a type 1 helper T cell response, interfering RNA, anti-sense RNA, imiquimod, ribavirin, an IMPDH inhibitor, amantadine, and rimantadine.

The compounds of Formula I may also be used in combination with other therapeutic agents, for example, therapeutic vaccines, anti-fibrotic agents, anti-inflammatory agents such as corticosteroids or NSAIDs, bronchodilators such as beta-2 adrenergic agonists and xanthines (e.g., theophylline), mucolytic agents, anti-muscarinics, anti-leukotrienes, inhibitors of cell adhesion (e.g., ICAM antagonists), anti-oxidants (e.g., N-acetylcysteine), cytokine agonists, cytokine antagonists, lung surfactants and/or antimicrobial agents. The compounds of Formula I may also be used in combination with gene replacement therapy.

While the active moieties mentioned herein as second active agents may be identified as free active moieties, salt forms (including salts with hydrogen or coordination bonds), solvates, or as non-covalent derivatives (e.g., chelates, complexes, and clathrates) of such active moieties, it is to be understood that the given representative commercial drug products are not limiting, and free active moieties, or salts or other derivative forms of the active moieties may alternatively be employed. Accordingly, reference to an active moiety should be understood to encompass not just the free active moiety but any pharmacologically acceptable salt, solvate, or other derivative form that is consistent with the specified parameters of use.

EXAMPLES

The chemistry examples, synthetic schemata, and intermediates, provided herein are intended to illustrate synthetic routes suitable for preparation of the compounds of the invention (and their intermediates), to assist in understanding the present invention. With appropriate manipulation and protection of any chemical functionality, synthesis of compounds of Formula I is accomplished by methods analogous to those described herein. Suitable protecting groups can be found, for example, in P. G. M. Wuts and T. W. Greene, *Greene's Protective Groups in Organic Synthesis*, 4th Ed., 2006, Wiley Interscience.

Methods for testing for activity of the compounds of the invention are described in the examples. The skilled persons will know of other methods for identifying compounds having activity against the NS5B polymerase. For example, McKercher et al., *Nucl Acids Res*, 2004, 32(2):422-31, describes a method for identifying NS5B inhibitor compounds; Burton J R, Everson, G T, Clin Liver Dis. 2009, 13, 453-465; Soriano et al., *Expert Opin Pharmacother*, 2013, 14, 1161-1170.

Synthetic intermediates were analyzed LC-MS. Final products were analyzed and confirmed by LC-MS and $^1$H NMR. The LC-MS method: the instrument was Agilent 1100 HPLC and Agilent 3200 mass spectrometer with ESI(+) detector. The analytical column used was a Synergi Hydro-RP column (00B-4375-E0; Phenomenex), and the compounds were eluted for 3 minutes (10% to 95% acetonitrile (ACN) in water, containing 0.1% trifluoroacetic acid).

Example 1

Ethyl 3-(4-fluorophenyl)-3-oxopropanoate (1-2)

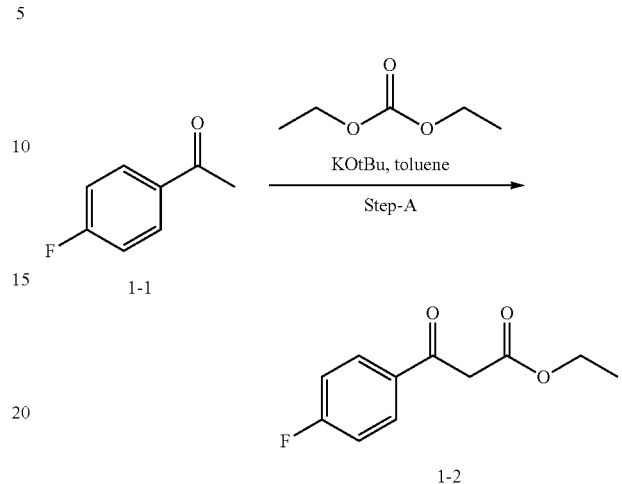

To a stirred solution of potassium-t-butoxide (323 g, 2.89 mol) in toluene (1 L) was added diethyl carbonate (533 g, 4.51 mol) at RT, and the mixture was heated to 80° C. for 1 hr. 1-(4-Fluorophenyl)-ethanone (250 g, 1.80 mol) in toluene (2 L) was added to the reaction mixture slowly and stirred at 70° C. for 2 hr, then cooled to RT and stirring was continued for 16 hr. The reaction mixture was quenched with dilute HCl, then diluted with water and extracted with ethyl acetate (EtOAc; 3×800 mL). The combined organic layer was washed with brine, dried over $Na_2SO_4$, and concentrated. The crude compound was purified by fractional distillation to give 1-2 (210 g, 55% yield, 1 mol) as pale yellow liquid. MS=211.2 $[M+1]^+$.

Ethyl 2-(4-fluorophenyl)-5-hydroxybenzofuran-3-carboxylate (1-3)

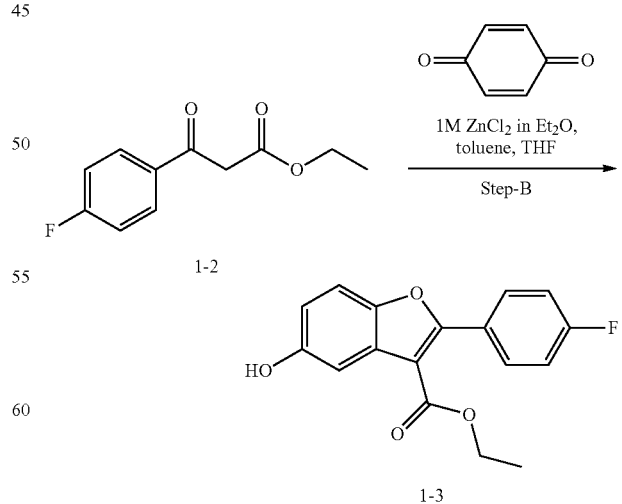

To a stirred solution of ethyl 3-(4-fluorophenyl)-3-oxopropanoate (5 g, 23 mmol) in toluene (75 mL) was added ZnCl$_2$ (1 M in diethyl ether) (34 mL, 34.5 mmol) slowly at 110° C. p-Benzoquinone (3.4 g, 30.9 mmol) in tetrahydrofuran (THF) was added dropwise and stirring was continued for 6 hr at 110° C. The reaction mixture was cooled to RT, water (100 mL) was added, and the mixture was extracted with EtOAc (100 mL). The organic layer was washed with brine, dried (Na$_2$SO$_4$) and concentrated. The crude compound was purified by column chromatography (100-200 silica) to afford 1-3 (2.6 g, 36% yield) as a brown solid. MS=301.0 [M+1]$^+$.

Ethyl 2-(4-fluorophenyl)-5-isopropoxybenzofuran-3-carboxylate (1-4)

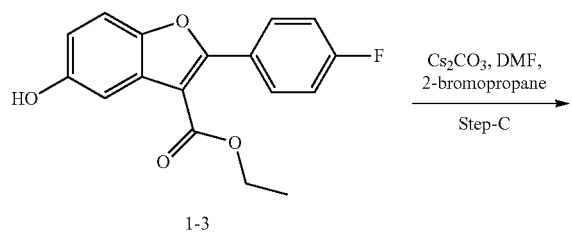

Cesium carbonate (Cs$_2$CO$_3$; 58.3 g, 33 mmol) was added to a solution of 1-3 (50 g, 166.6 mmol) in dimethylformamide (DMF) (250 mL) followed by the addition of 2-bromopropane (80 mL, 83 mmol) drop wise. Then, the reaction mixture was heated to 60° C. and stirred for 2 hr. After consumption of the starting material (by TLC), the reaction mixture was diluted with ice cold water (100 mL) and extracted with EtOAc (100 mL). The organic layer was washed with brine (50 mL), dried over Na$_2$SO$_4$ and concentrated. The crude compound was purified by washings with diethyl ether and pentane to afford 1-4 (45 g, 79% yield) as an off-white solid. MS=343.1 [M+1]$^+$.

Ethyl 2-(4-fluorophenyl)-5-isopropoxy-6-nitrobenzofuran-3-carboxylate (1-5)

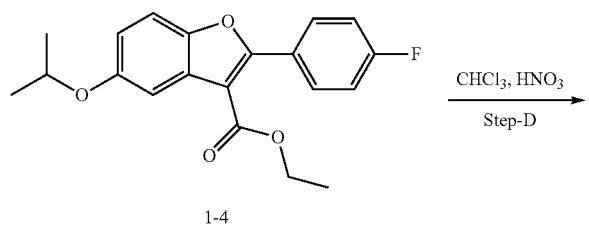

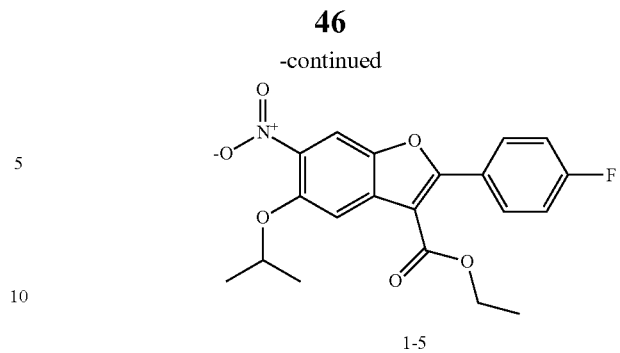

To a stirred solution of 1-4 (45 g, 131.5 mmol) in chloroform (500 mL) was added drop wise 70% HNO$_3$ (80 mL) in CHCl$_3$ (200 mL) at 0° C. and stirred at RT for 2 hr. After completion of the reaction as indicated by TLC, the mixture was poured into ice cold water (100 mL), extracted with EtOAc (100 mL). The organic layer was washed with brine (50 mL), dried over Na$_2$SO$_4$ and concentrated. The crude compound was purified by washing with diethyl ether and pentane to afford 1-5 (44 g, 86% yield) as a yellow solid.

Ethyl 2-(4-fluorophenyl)-5-hydroxy-6-nitrobenzofuran-3-carboxylate (1-6)

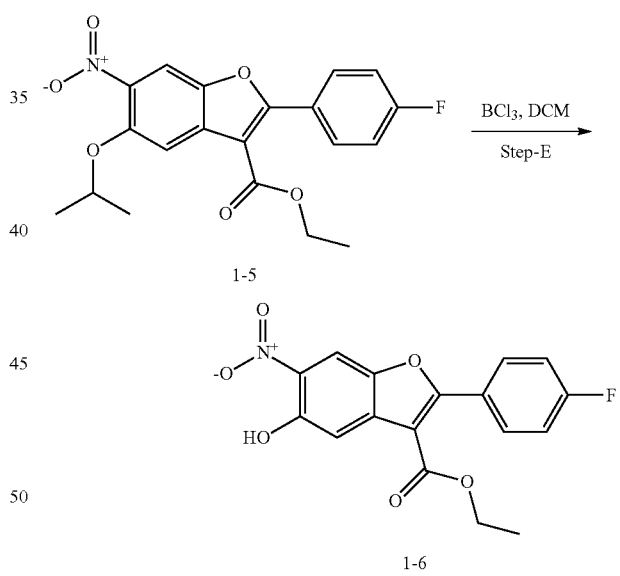

Boron trichloride (BCl$_3$; 500 mL, 85.7 mmol) was added to a stirred solution of 1-5 (44 g, 113.3 mmol) in dichloromethane (DCM; 900 mL) at 0° C. and the reaction was continued to stir at same temperature for 2 hr. After completion of the reaction as indicated by TLC, the mixture was poured in to ice cold water (200 mL), extracted with DCM (2×300 mL). The combined organic layer was washed with brine (100 mL), dried over Na$_2$SO$_4$ and concentrated. The crude compound was purified by washings with pentane to afford 1-6 (38 g, 110.14 mmol, 97%) as a yellow solid. MS=344.1 [M+1]$^+$.

Ethyl 2-(4-fluorophenyl)-6-nitro-5-(trifluoromethyl-sulfonyloxy)-benzofuran-3-carboxylate (1-7)

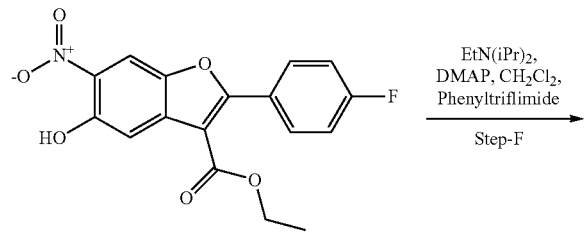

N-Phenylbis(trifloromethanesulfonamide) (phenyltriflimide; 24.8 g, 69.5 mmol) was added to a stirred solution of 1-6 (20 g, 57.9 mmol) in ACN/DMF (500 mL, 10:1) at 0° C. and the reaction was continued to stir at 0° C. for 2 hr. After completion of the reaction (by TLC), the reaction mixture was poured in to ice cold water (100 mL), extracted with EtOAc (3×100 mL). The combined organic layer was washed with water (50 mL), brine (50 mL), dried over Na₂SO₄ and concentrated. The crude compound washed with pentane (100 mL) and dried to afford 1-7 (27.6 g, quantitative yield) as an off-white solid.

Ethyl 5-cyclopropyl-2-(4-fluorophenyl)-6-nitrobenzofuran-3-carboxylate (1-8)

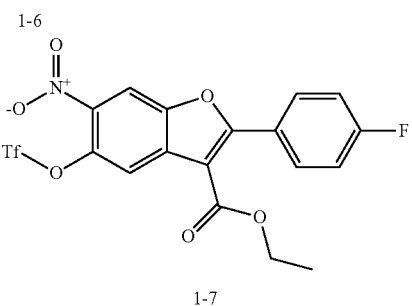

To a stirred, degassed solution of 1-7 (27.6 g, 57.9 mmol) in toluene (250 mL) was added cyclopropyl boronic acid (7.46 g, 86.79 mmol), sodium bromide (6.14 g, 59.6 mmol), potassium fluoride (11.4 g, 191.52 mmol). After degassing for 20 min, Pd(PPh₃)₄ (2 g, 1.73 mmol) was added and the reaction was continued to stir at 110° C. for 16 hr. After completion of the reaction was indicated by TLC, the mixture was poured into ice cold water (500 mL), extracted with EtOAc (3×250 mL). The combined organic layer was washed with brine (100 mL), dried over Na₂SO₄ and concentrated. The crude compound was purified by column chromatography (230-400 silica) using 13% DCM in hexane to afford 1-8 (8 g, 21.68 mmol, 38% yield) as a yellow solid. MS=370 [M+1]⁺.

Ethyl 6-amino-5-cyclopropyl-2-(4-fluorophenyl)benzofuran-3-carboxylate (1-9)

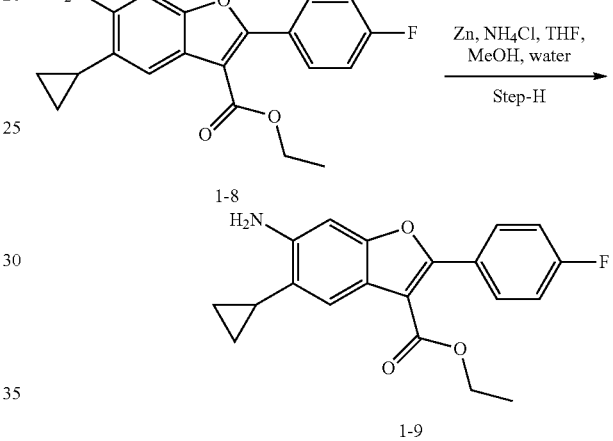

To a stirred solution of 1-8 (5.7 g, 15.43 mmol) in a mixture of methanol (MeOH), THF and water (3:3:1) was added zinc dust (4.03 g, 61.73 mmol) and NH₄Cl at RT and the mixture was heated at 80° C. for 6 hr. After completion of the reaction as indicated by TLC, the mixture was filtered through celite pad, washed with EtOAc. Filtrate concentrated under reduced pressure, crude residue was diluted with EtOAc (100 mL) and washed with water (100 mL), brine (50 mL), dried over Na₂SO₄ and concentrated. The crude compound was washed with pentane (30 mL) to afford 1-9 (5.2 g, quantitative) as an orange solid. MS=340 [M+1]⁺.

Ethyl 5-cyclopropyl-2-(4-fluorophenyl)-6-(N-(methylsulfonyl)-methylsulfonamido)-benzofuran-3-carboxylate (1-10)

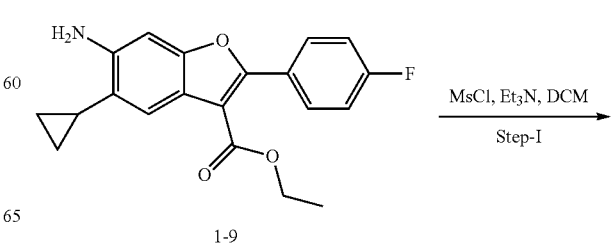

49

-continued

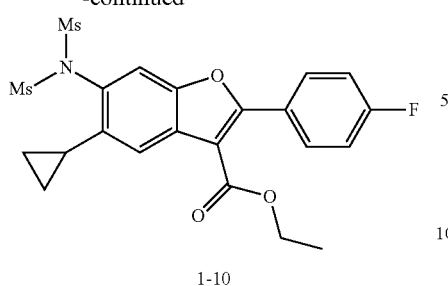

1-10

To a stirred solution of 1-9 (5.2 g, 15.33 mmol) in DCM (70 mL) was added mesylchloride (2.72 mL, 35.2 mmol), triethylamine (11.62 mL, 76.66 mmol) at 0° C. and the reaction was continued to stir at RT for 2 hr. After completion of starting material as indicated by TLC, the mixture was poured in to ice cold water (50 mL), extracted with DCM (100 mL). The organic layer was washed with brine (50 mL), dried over Na$_2$SO$_4$ and concentrated to afford 1-10 (6 g, 79% yield) as an orange solid. MS=496.4 [M+1]$^+$.

5-Cyclopropyl-2-(4-fluorophenyl)-6-(methylsulfonamido)benzofuran-3-carboxylic Acid (1-11)

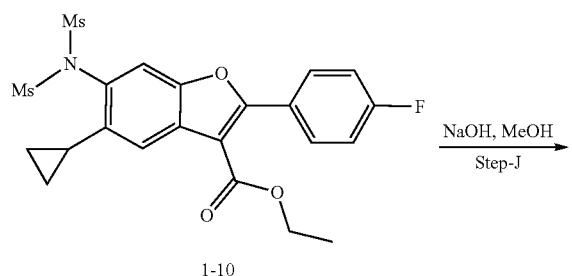

To a stirred solution of 1-10 (6 g, 12.12 mmol) in a mixture of MeOH, THF and H$_2$O (3:3:1, 75 mL) was added NaOH (1.93 g, 48.48 mmol) at RT and stirred for 6 hr at 80° C. After completion of reaction as indicated by TLC, the reaction mixture was concentrated to remove organic volatiles, crude compound was diluted with water (20 mL), and neutralized using 1 N HCl (pH ~3-4), extracted with EtOAc (100 mL). The organic layer was washed with brine (50 mL), dried over Na$_2$SO$_4$ and concentrated. The crude compound was washed with pentane to afford 1-11 (4.9 g, quantitative) as an off-white solid. MS=390.1 [M+1]$^+$.

50

5-Cyclopropyl-2-(4-fluorophenyl)-N-methyl-6-(methylsulfonamido)benzofuran-3-carboxamide (1-12)

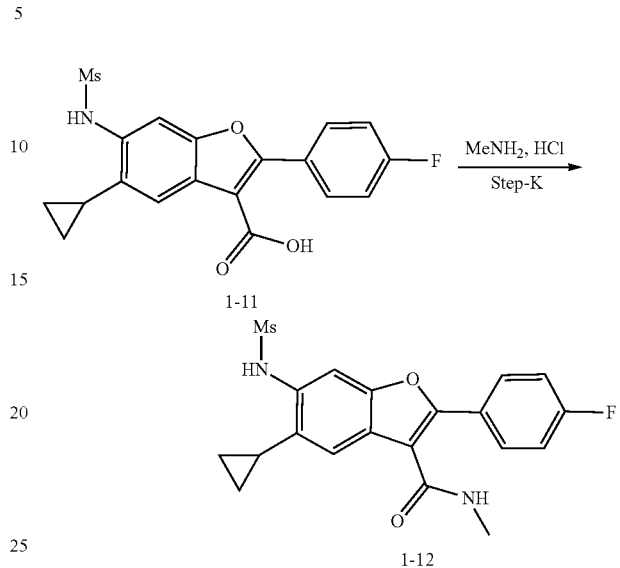

To a solution of 1-11 (14 g, 35.9 mmol) in DCM (150 mL) was added HATU (27.3 g, 71.9 mmol), DIPEA (18.8 mL, 107.9 mmol) at 0° C. and the reaction was continued to stir at RT for 16 hr. After completion of reaction as indicated by TLC, the mixture was poured in to ice cold water (100 mL), extracted with EtOAc (100 mL). The organic layer was washed with water (50 mL), brine (50 mL), dried over Na$_2$SO$_4$ and concentrated. The crude compound was purified by column chromatography (100-200 silica) and washings with DCM and pentane to afford 1-12 (11 g, 75.8% yield) as an off-white solid. MS=403.5 [M+H]$^+$.

Example 2

1-(3-Bromomethyl-phenyl)-ethanone (2-2A)

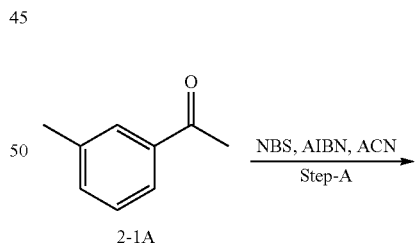

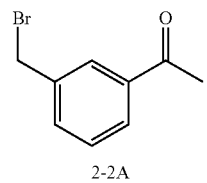

To a stirred solution of 1-m-tolylethanone 2-1A (25 g, 186.43 mmol) in ACN (ACN; 200 mL) was added NBS (36.4 g, 205.07 mmol) and azoisobutyronitrile (AIBN; 3.06 g, 18.64 mmol) at room temperature (ambient; RT). The reaction mixture was warmed to 90° C. for 6 hours (hr)

under N₂ atmosphere. The reaction mixture solvent was evaporated under reduced pressure and the crude residue washed with toluene (500 mL) and filtered the precipitate (NBS). Filtrate evaporated under reduced pressure and the crude residue was purified by flash column chromatography (100-200 silica) using 3% EtOAc (EtOAc) in petroleum ether (pet. ether) to afford 2-2A (27.6 g, 129.57 mmol, 70% yield) as an off-white solid. MS (ESI): m/z 213.0 (M+1)⁺.

Step-A above was adapted using 1-p-tolyl-ethanone 2-1B to prepare 2-2B.

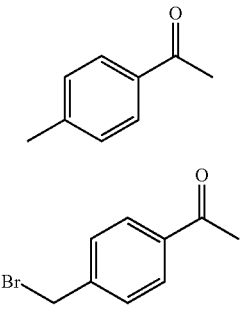

2-(2-(Tetrahydro-2H-pyran-2-yloxy)-ethoxy)-ethanol (2-4A)

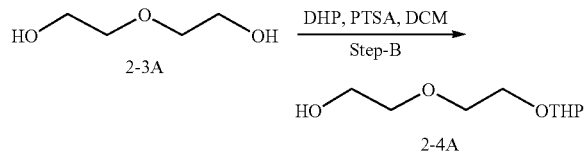

To a stirred solution of 2,2'-oxydiethanol 2-3A (30 g, 282.70 mmol) in DCM (900 mL) was added dihydropyran (DHP; 20.6 mL, 226.16 mmol) and pyridinium p-toluenesulfonate (PTSA; 5.3 g, 28.27 mmol) at 0° C., and stirred at RT for 4 hr. The reaction mixture was diluted with water (600 mL) extracted with CH₂Cl₂ (3×800 mL), the combined organic layers were washed with brine (2×100 mL) and dried over Na₂SO₄ and concentrated. The residue was purified by flash column chromatography (100-200 silica) using 2% MeOH (MeOH) in DCM to afford 2-4A (16 g, 84.21 mmol, 30% yield) as a yellow thick liquid.

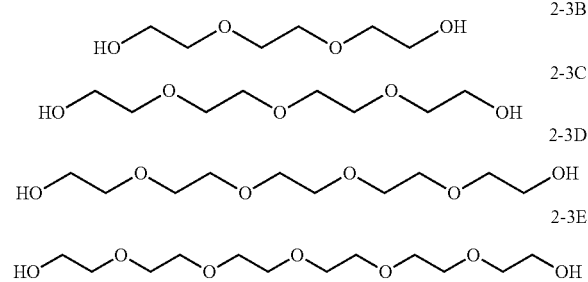

Step-B was adapted by substituting 2-3B through 2-3E for 2-3A, to prepare the following tetrahydro-2H-pyran (THP) compounds:

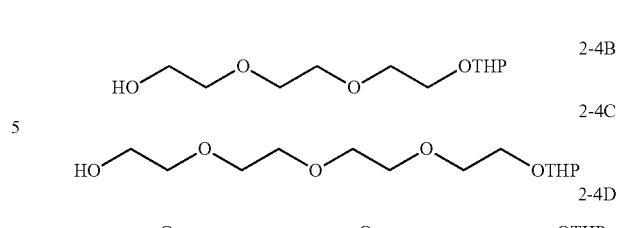

2-3B (30 g, 0.2 mmol) was used to prepare 2-4B (10 g, 21% yield).

2-3C (30 g, 0.15 mmol) was used to prepare 2-4C (7 g, 16% yield).

2-3D (10 g, 42.0 mmol) was used to prepare 2-4D (3.01 g, 22.2% yield).

2-3E (10 g, 35.0 mmol) was used to prepare 2-4E (4.02 g, 30.8% yield).

1-(3-(2-(2-Tetra-2H-pyran-2-yloxy)-ethoxy)-ethoxy)-methyl)-phenyl)-ethanone (2-5A)

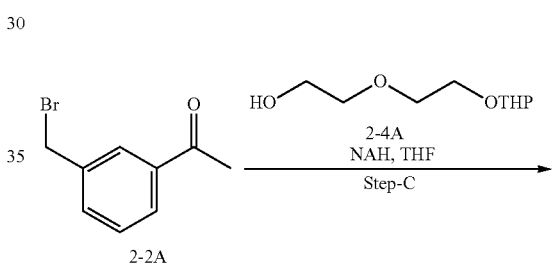

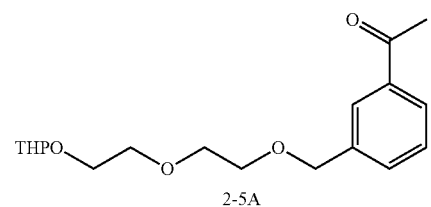

To a stirred solution of 1-(3-(bromomethyl)-phenyl)-ethanone 2-2A (8 g, 42.1 mmol) in THF (50 mL) was added NaH (1.6 g, 42.1 mmol) at 0° C., and reaction was continued at RT for 30 min. 2-4A (9.3 g, 44.2 mmol) in THF (30 mL) was added to reaction mixture at 0° C. for 5 min. and reaction was continued at RT for 16 hr. The reaction mixture was quenched with ice cold water (100 mL) and extracted with EtOAc (3×200 mL). The combined organic layers were washed with water (2×200 mL), brine (150 mL), dried over Na₂SO₄ and concentrated. The residue was purified by flash column chromatography (100-200 silica) using 20% EtOAc/hexanes to afford 2-5A (3.8 g, 11.80 mmol, 28% yield) as yellow thick liquid. MS (ESI): m/z 344.9 (M+23)⁺.

Step-C was adapted by substituting 2-4B through 2-4E for 2-4A, respectively, to prepare the following compounds:

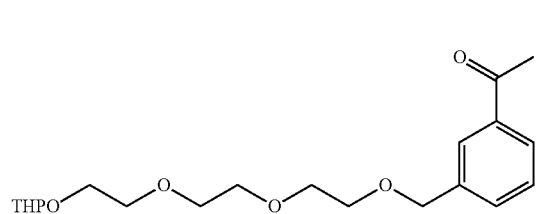
2-5B

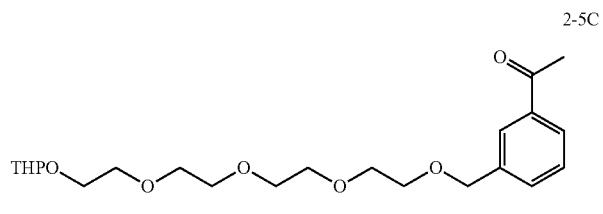
2-5C

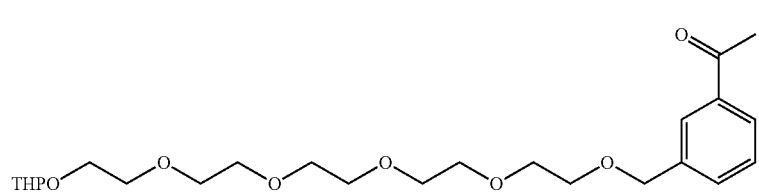
2-5D

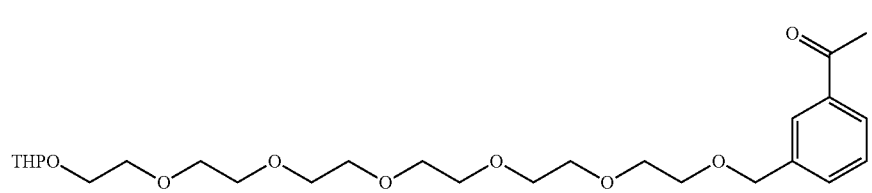
2-5E 2-4B (1.3 g, 5.0 mmol) was used to prepare 2-5B (3.8 g, 28% yield).

2-4C (2.5 g, 9.027 mmol) was used to prepare 2-5C (1.7 g, 46% yield). MS (ESI): m/z 428.2 (M+18)$^+$.

2-4D (3.0 g, 9.32 mmol) was used to prepare 2-5D (1.51 g, 35.7% yield). MS (ESI): m/z 477.2 (M+23)$^+$.

2-4E (3.0 g, 8.19 mmol) was used to prepare 2-5E (1.71 g, 41.2% yield).

Step-C was also adapted by substituting 2-2B for 2-2A, together with 2-4A through 2-4E, respectively, to prepare the following compounds:

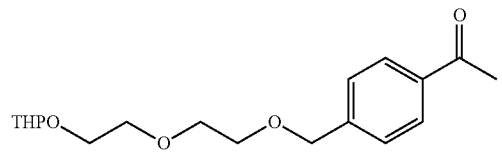
2-5F

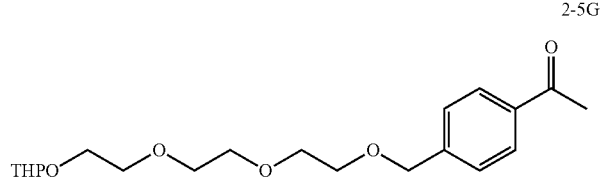
2-5G

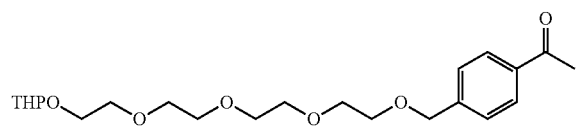
2-5H

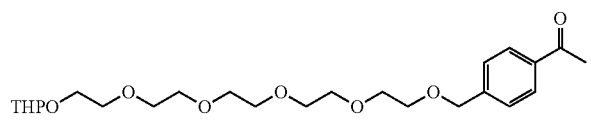
2-5I

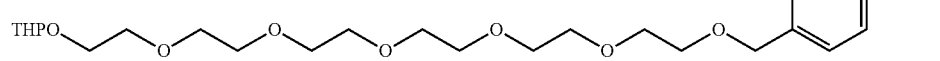
2-5J 2-4A (1.6 g, 8.4 mmol) was used to prepare 2-5F (910 mg, 32% yield). MS (ESI): m/z 340.2 (M+18)$^+$.

2-4B (1.4 g, 5.0 mmol) was used to prepare 2-5G (790 mg, 38% yield).

2-4C (1.3 g, 4.67 mmol) was used to prepare 2-5H (750 mg, 38% yield).

2-4D (1.5 g, 4.658 mmol) was used to prepare 2-5I (950 mg, 45% yield). MS (ESI): m/z 472.3 (M+18)$^+$.

2-4E (1.8 g, 4.92 mmol) was used to prepare 2-5J (1.02 g, 41% yield). MS (ESI): m/z 516.3 (M+18)⁺.

1-(3-(2-(2-Hydroxyethoxy)-ethoxy)-methyl)-phenyl)-ethanone (2-6A)

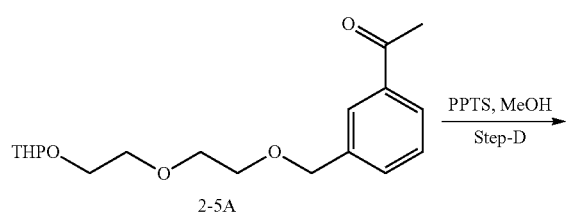

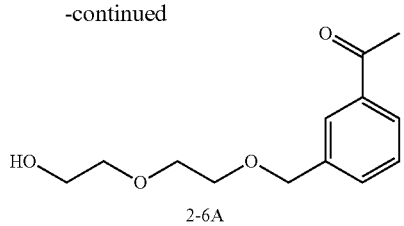

2-6A

To a stirred solution of 2-5A (3.8 g, 11.8 mmol) in MeOH (40 mL) was added pyridinium p-toluene sulfonate (PPTS; 0.59 g, 2.30 mmol) at 0° C. and stirred at RT for 16 hr. The solvents were distilled-off under reduced pressure. The residue obtained was extracted with EtOAc (3×150 mL). The combined organic layer washed with brine (100 mL), dried over Na₂SO₄ and concentrated. The residue was purified by flash column chromatography (100-200 silica) using 5% acetone in DCM to afford 2-6A (1.4 g, 5.88 mmol, 50% yield) as a gummy liquid. MS (ESI): m/z 239.0 (M+1)⁺.

The above procedure was adapted to prepare the following compounds:

2-6B 2-6C

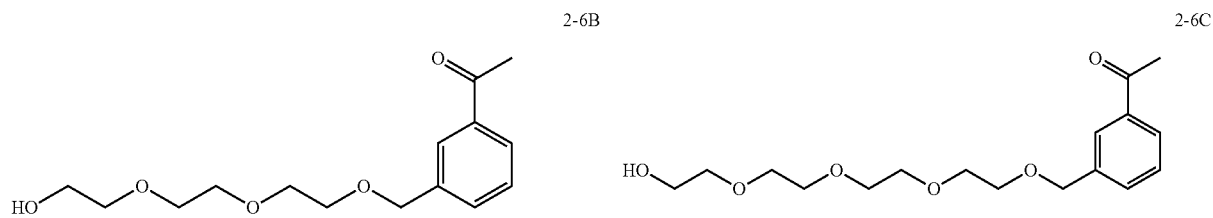

2-6D 2-6E

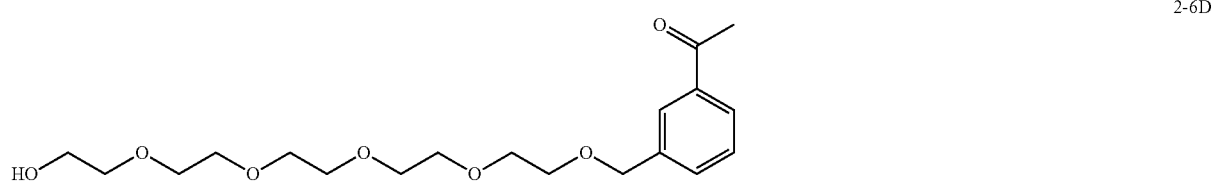

2-6F 2-6G

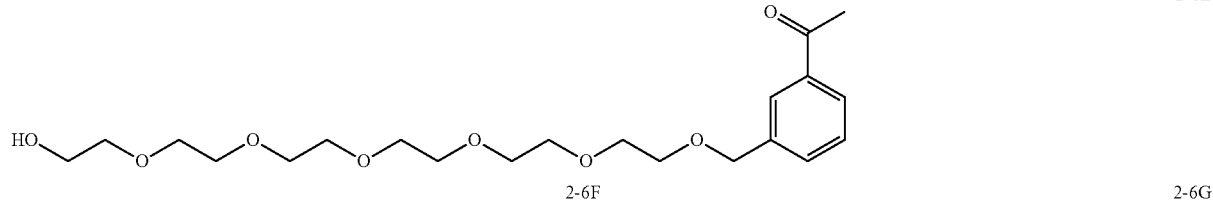

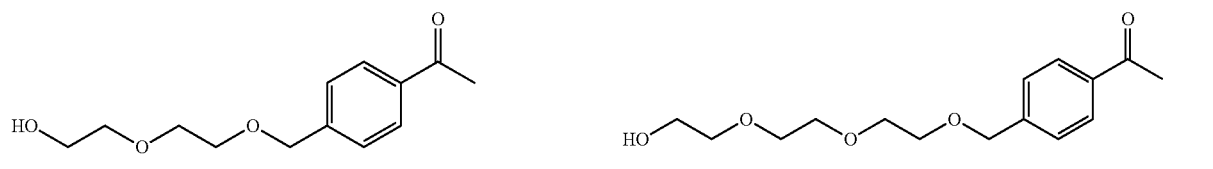

2-6H

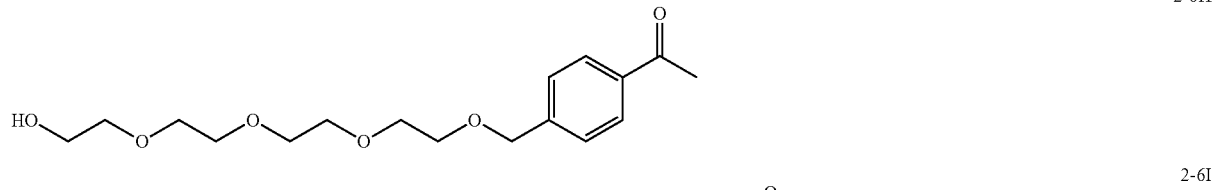

2-6I

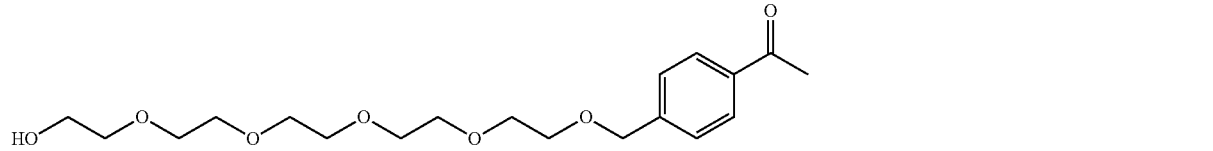

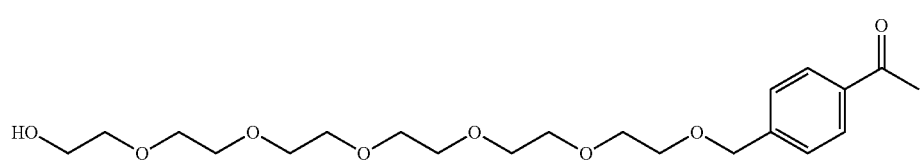
2-6J 2-5B (720 mg, 5.0 mmol) was used to prepare 2-6B (589 mg, 84% yield). MS not collected.
2-5C (1.7 g, 4.146 mmol) was used to prepare 2-6C (1.2 g, 89%). MS (ESI): m/z 327.1 (M+1)$^+$.
2-5D (1.5 g, 3.3 mmol) was used to prepare 2-6D (850 mg, 70%). MS (ESI): m/z 371.1 (M+1)$^+$.
2-5E (1.7 g, 3.4 mmol) was used to prepare 2-6E (1.1 g, 78%). MS (ESI): m/z 415.2 (M+1)$^+$.
2-5F (900 mg, 2.8 mmol) was used to prepare 2-6F (650 mg, 97%). MS (ESI): m/z 239.1 (M+1)$^+$.
2-5G (790 mg, 2.1 mmol) was used to prepare 2-6G (600 mg, 92%). MS (ESI): m/z 283.1 (M+1)$^+$.
2-5H (1.3 g, 4.67 mmol) was used to prepare 2-6H (750 mg, 38%). MS (ESI): m/z 412 (M+1)$^+$.
2-5I (950 mg, 2.092 mmol) was used to prepare 2-6I (560 mg, 72%). MS (ESI): m/z 369.3 (M+1)$^+$.
2-5J (1.02 g, 2 mmol) was used to prepare 2-6J (800 mg, 94%). MS (ESI): m/z 415.2 (M+1)$^+$.

2-(2-(3-Acetylbenzyloxy) ethoxy) Ethyl Methane Sulfonate (2-7A)

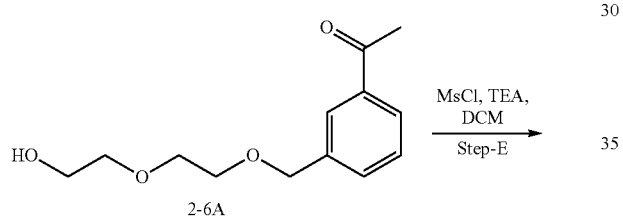

Methane sulfonyl chloride (0.7 mL, 8.80 mmol) was added to a solution of 2-6A (1.4 g, 5.88 mmol) in DCM (50 mL) and triethylamine (2.5 mL, 17.6 mmol) at 0° C. and stirred at RT for 1 hr. The reaction mixture was diluted with water (50 mL) extracted with DCM (3×100 mL). The combined organic layer was washed with brine (100 mL), dried over Na$_2$SO$_4$ and concentrated. The residue was purified by flash column chromatography (100-200 silica) using 30% EtOAc in hexanes to afford 2-7A (1.8 g, 5.69 mmol, 97% yield) as gummy liquid. MS (ESI): m/z 316.8 (M+1)$^+$.

The above procedure was adapted to prepare the following compounds:

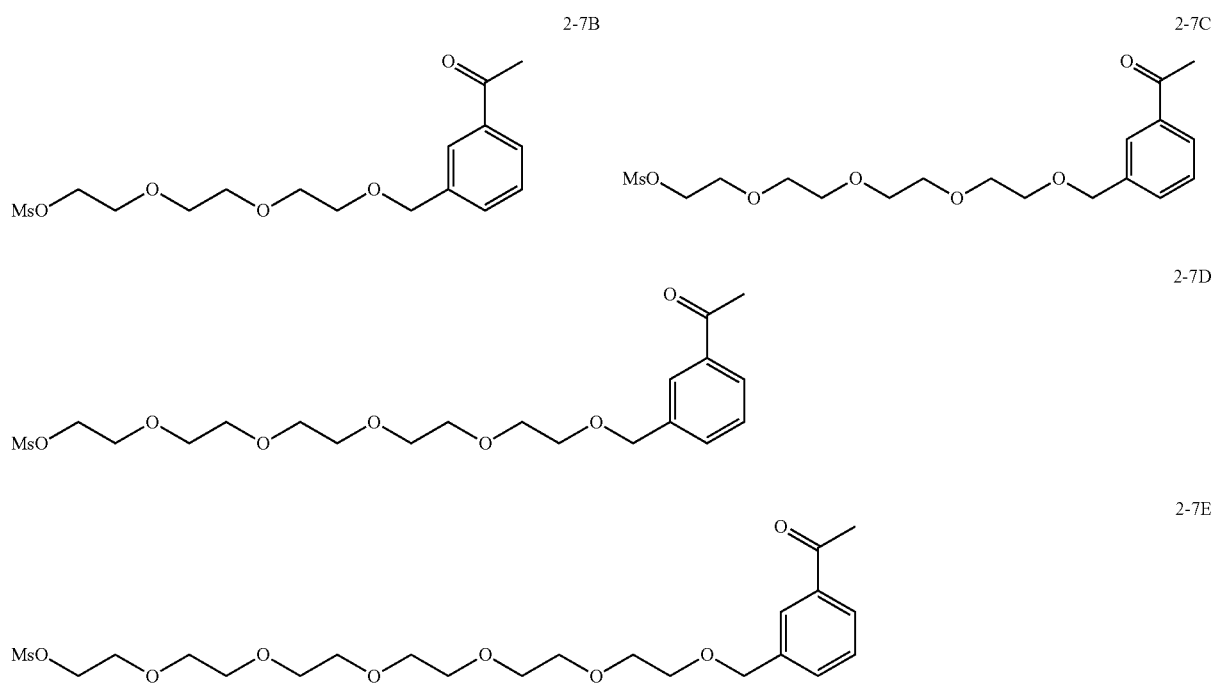

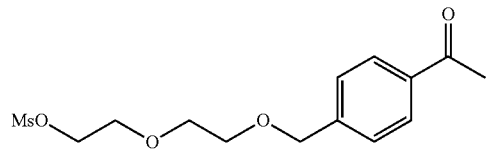
2-7F

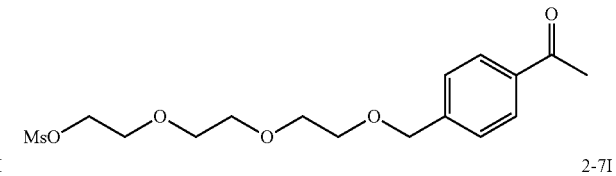
2-7G

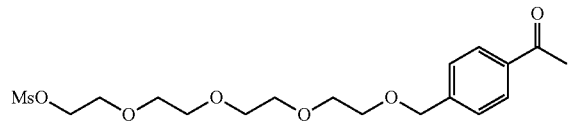
2-7H 2-7I

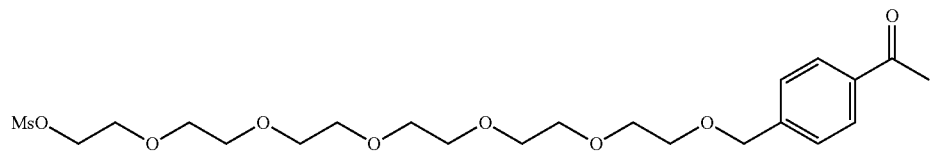
2-7J 2-6B (700 mg, 2.4 mmol) was used to prepare 2-7B (650 mg, 68%). MS (ESI): m/z 361.1 (M+1)⁺.
2-6C (400 mg, 1.226 mmol) was used to prepare 2-7C (420 mg, 85%). MS not collected.
2-6D (850 mg, 2.29 mmol) was used to prepare 2-7D (800 mg, 78%). MS (ESI): m/z 466.2 (M+18)⁺.
2-6E (500 mg, 2.29 mmol) was used to prepare 2-7E (460 mg, 70%). MS not collected.
2-6F (650 mg, 2.7 mmol) was used to prepare 2-7F (660 mg, 76%). MS (ESI): m/z 317 (M+1)⁺.
2-6G (600 mg, 2.1 mmol) was used to prepare 2-7G (540 mg, 72%). MS (ESI): m/z 361.0 (M+1)⁺.
2-6H (600 mg, 1.46 mmol) was used to prepare 2-7H (460 mg, 78%). MS not collected.
2-6I (560 mg, 1.513 mmol) was used to prepare 2-71 (600 mg, 88%). MS (ESI): m/z 466.3 (M+18)⁺.
2-6J (800 mg, 1.92 mmol) was used to prepare 2-7J (610 mg, 64%). MS (ESI): m/z 493.1 (M+1)⁺.

6-(N-(2-(2-(3-Acetylbenzyloxy)-ethoxy)-ethyl)-methylsulfonamido)-5-cyclopropyl-2-(4-fluorophenyl)-N-methylbenzofuran-3-carboxamide (2-8A)

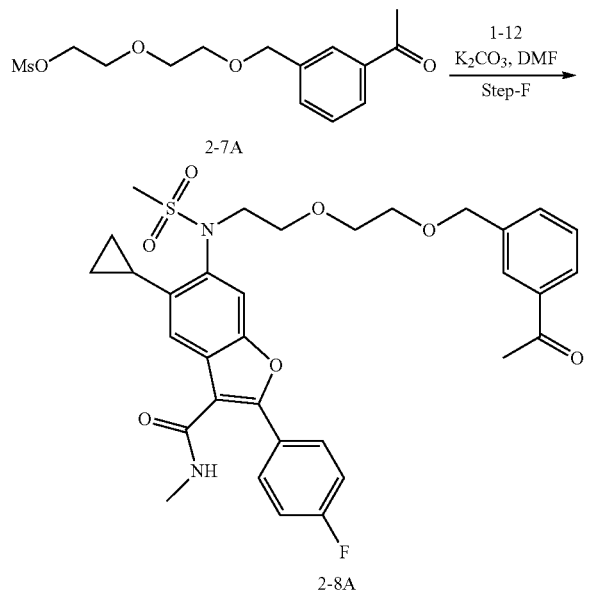

To a stirred solution of [1-12] (1.6 g, 4.00 mmol) in DMF (40 mL) was added potassium carbonate (1.6 g, 11.90 mmol) followed by 2-7A (1.8 g, 5.60 mmol), catalytic amount of tetrabutyl ammonium iodide at 80° C. for 16 hr. The reaction mixture was cooled to RT and diluted with EtOAc (75 mL) washed with water (2×40 mL), brine (25 mL) and dried over Na₂SO₄ and concentrated. The residue was purified by flash column chromatography (100-200 silica) using 2% MeOH-DCM to afford 2-8A (1.3 g, 2.09 mmol, 42% yield) as an off-white solid. MS (ESI): m/z 622.9 (M+1)⁺.

The above procedure was adapted to prepare the following compounds:

6-[(2-{2-[2-(3-Acetyl-benzyloxy)-ethoxy]-ethoxy}-ethyl)-methanesulfonyl-amino]-5-cyclopropyl-2-(4-fluoro-phenyl)-benzofuran-3-carboxylic Acid Methylamide (2-8B)

2-7B (535 mg, 1.4 mmol) was used to prepare 2-8B (518 mg, 63%). MS (ESI): m/z 667.2 (M+1)⁺.

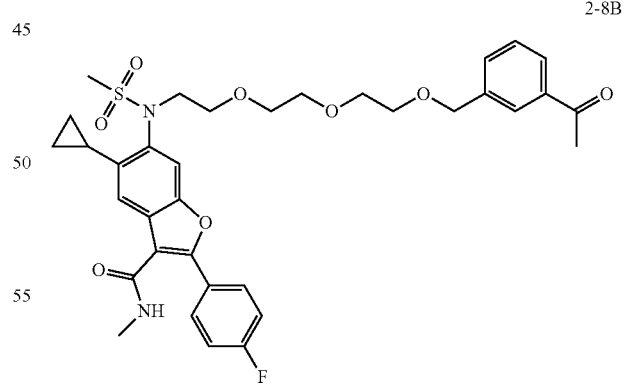

6-{[2-(2-{2-[2-(3-Acetyl-benzyloxy)-ethoxy]-ethoxy}-ethoxy)-ethyl]-methanesulfonyl-amino}-5-cyclopropyl-2-(4-fluoro-phenyl)-benzofuran-3-carboxylic Acid Methylamide (2-8C)

2-7C (380 mg, 0.940 mmol) was used to prepare 2-8C (320 mg, 57%). MS (ESI): m/z 711.1 (M+1)⁺.

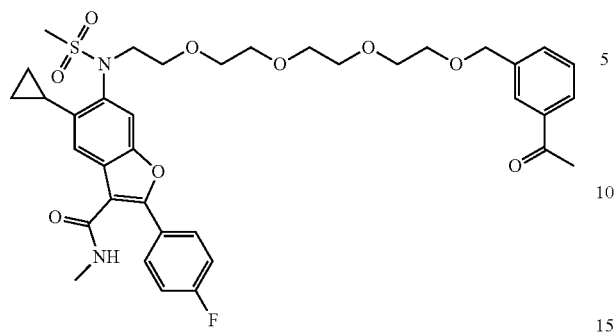

6-({2-[2-(2-{2-[2-(3-Acetyl-benzyloxy)-ethoxy]-ethoxy}-ethoxy)-ethoxy]-ethyl}-methanesulfonyl-amino)-5-cyclopropyl-2-(4-fluoro-phenyl)-benzo-furan-3-carboxylic Acid Methylamide (2-8D)

2-7D (536 mg, 1.19 mmol) was used to prepare 2-8D (550 mg, 73%). MS (ESI): m/z 755.2 (M+1)⁺.

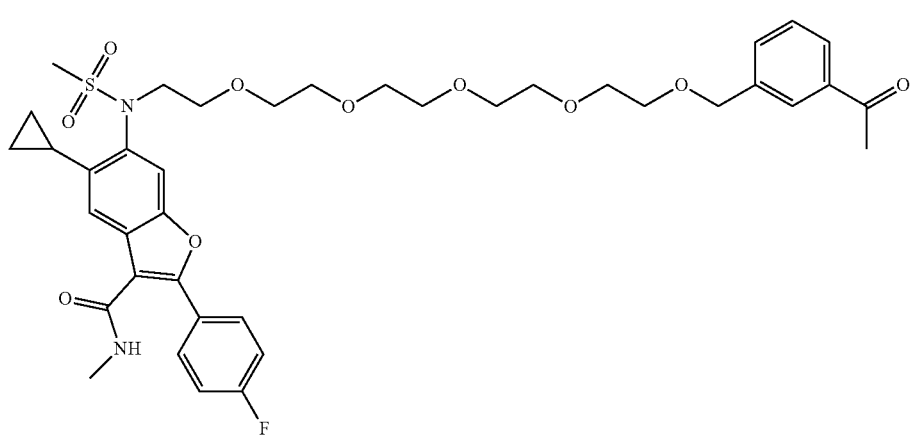

6-[(2-{2-[2-(2-{2-[2-(3-Acetyl-benzyloxy)-ethoxy]-ethoxy}-ethoxy)-ethoxy]-ethoxy}-ethyl)-methane-sulfonyl-amino]-5-cyclopropyl-2-(4-fluoro-phenyl)-benzofuran-3-carboxylic Acid Methylamide (2-8E)

2-7E (411 mg, 0.83 mmol) was used to prepare 2-8E (402 mg, 64%). MS (ESI): m/z 799.2 (M+1)⁺.

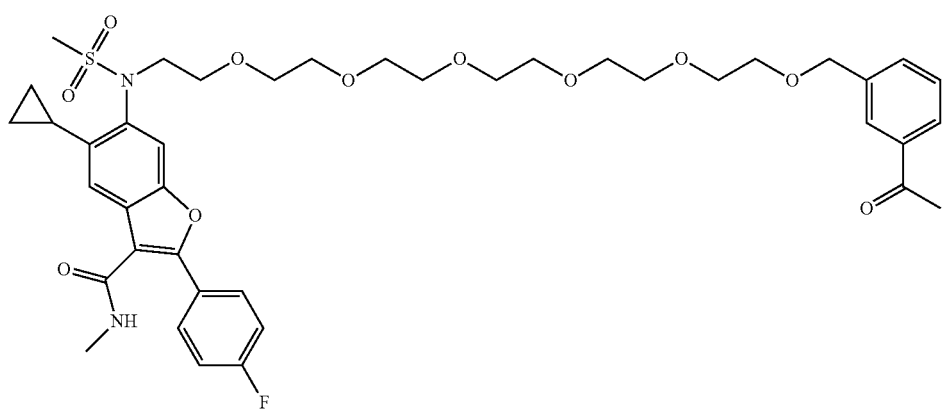

6-({2-[2-(4-Acetyl-benzyloxy)-ethoxy]-ethyl}-methanesulfonyl-amino)-5-cyclopropyl-2-(4-fluoro-phenyl)-benzofuran-3-carboxylic Acid Methylamide (2-8F)

2-7F (377 mg, 1.19 mmol) was used to prepare 2-8F (460 mg, 75%). MS (ESI): m/z 623.2 (M+1)⁺.

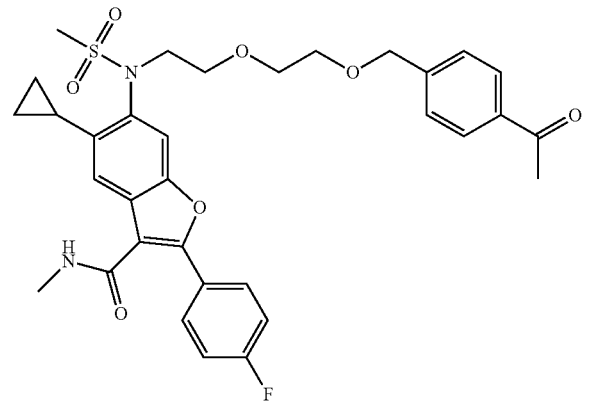

6-[(2-{2-[2-(4-Acetyl-benzyloxy)-ethoxy]-ethoxy}-ethyl)-methanesulfonyl-amino]-5-cyclopropyl-2-(4-fluoro-phenyl)-benzofuran-3-carboxylic Acid Methylamide (2-9G)

2-7G (429 mg, 1.1 mmol) was used to prepare 2-8G (420 mg, 65%). MS (ESI): m/z 665.6 (M+1)⁺.

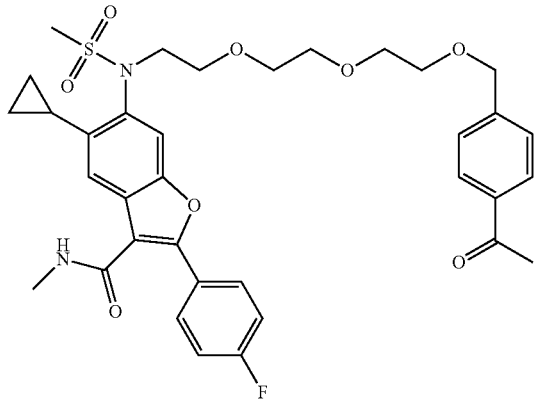

6-{[2-(2-{2-[2-(4-Acetyl-benzyloxy)-ethoxy]-ethoxy}-ethoxy)-ethyl]-methanesulfonyl-amino}-5-cyclopropyl-2-(4-fluoro-phenyl)-benzofuran-3-carboxylic Acid Methylamide (2-8H)

2-7H (1.18 g, 3.61 mmol) was used to prepare 2-8H (1.4 g, quantitative). MS (ESI): m/z 711.3 (M+1)⁺.

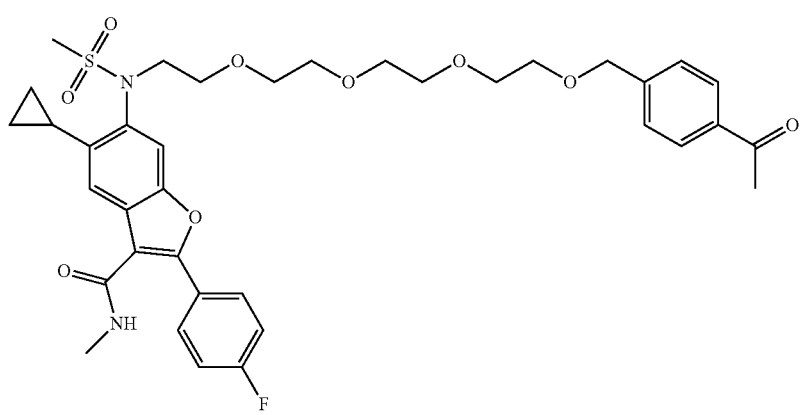

6-({2-[2-(2-{2-[2-(4-Acetyl-benzyloxy)-ethoxy]-ethoxy}-ethoxy)-ethoxy]-ethyl}-methanesulfonyl-amino)-5-cyclopropyl-2-(4-fluoro-phenyl)-benzofuran-3-carboxylic Acid Methylamide (2-8I)

2-7I (434 mg, 0.970 mmol) was used to prepare 2-8I (300 mg, 53%). MS (ESI): m/z 755.3 (M+1)⁺.

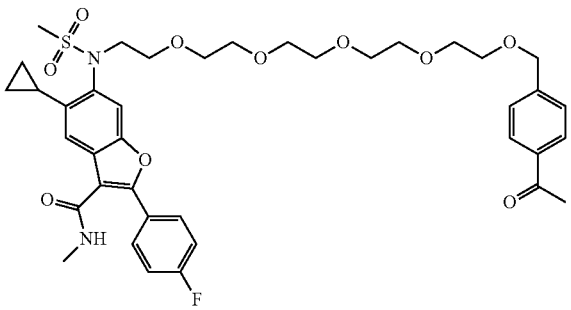

6-[(2-{2-[2-(2-{2-[2-(4-Acetyl-benzyloxy)-ethoxy]-ethoxy}-ethoxy)-ethoxy]-ethoxy}-ethyl)-methane-sulfonyl-amino]-5-cyclopropyl-2-(4-fluoro-phenyl)-benzofuran-3-carboxylic Acid Methylamide (2-8J)

2-7J (440 mg, 0.89 mmol) was used to prepare 2-8J (350 mg, 58%). MS (ESI): m/z 799.3 (M+1)$^+$.

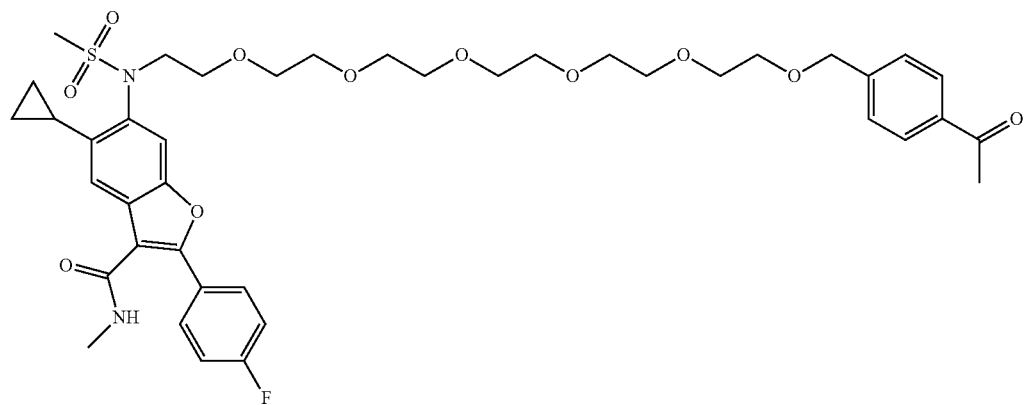

2-8J

To a stirred solution of 2-8A (0.35 g, 0.56 mmol) in THF (5 mL) was added potassium hexamethyldisilazane at −78° C., and the reaction mixture was warmed to −55° C. for 1 hr. Diethyl oxalate was added to the reaction mixture at −78° C. and the reaction mixture was warmed to −55° C. for 2 hr under nitrogen atmosphere. The reaction was quenched with ammonium chloride solution, and extracted with EtOAc (3×40 mL). The combined organic layers were washed with brine (2×20 mL), dried over Na$_2$SO$_4$ and concentrated. The residue was purified by flash column chromatography using neutral silica (100-200 silica) 2% MeOH-DCM to afford (0.7 g, crude) 2-9A, as a brownish gummy solid. MS (ESI): m/z 721.1 (M−1)$^+$.

The above procedure was adapted to prepare the following compounds:

4-{3-2-(2-{[5-Cyclopropyl-2-(4-fluoro-phenyl)-3-methylcarbamoyl-benzofuran-6-yl]-methanesulfonyl-amino}-ethoxy)-ethoxymethyl]-phenyl}-2-hydroxy-4-oxo-but-2-enoic Acid Ethyl Ester (2-9A)

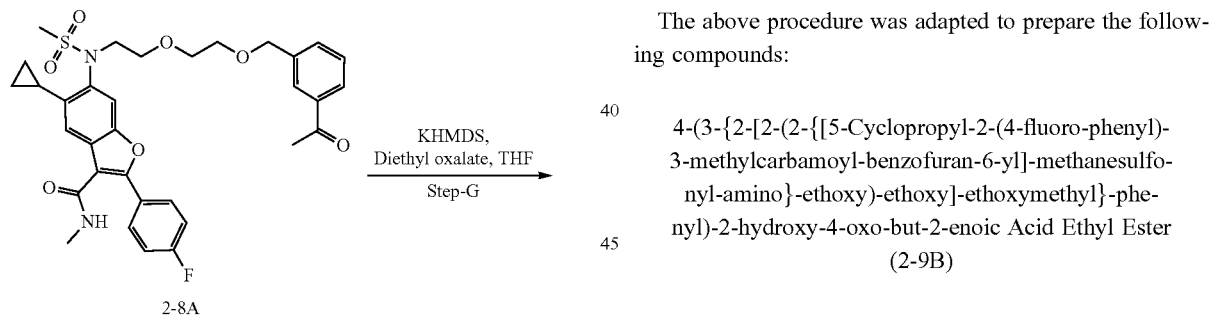

2-8A 4-(3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-phenyl)-2-hydroxy-4-oxo-but-2-enoic Acid Ethyl Ester (2-9B)

2-8B (100 mg, 0.15 mmol) was used to prepare 2-9B (60 mg, crude). MS (ESI): m/z 767.2 (M+1)$^+$.

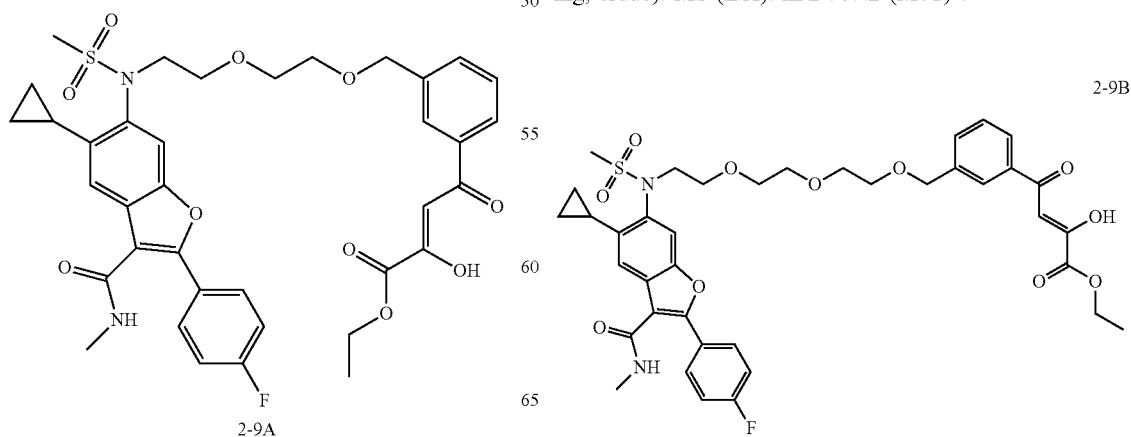

2-9A 2-9B

4-[3-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxymethyl)-phenyl]-2-hydroxy-4-oxo-but-2-enoic Acid Ethyl Ester (2-9C)

2-8C (160 mg, 0.225 mmol) was used to prepare 2-9C (110 mg, crude). MS (ESI): m/z 811.2 (M+1)+.

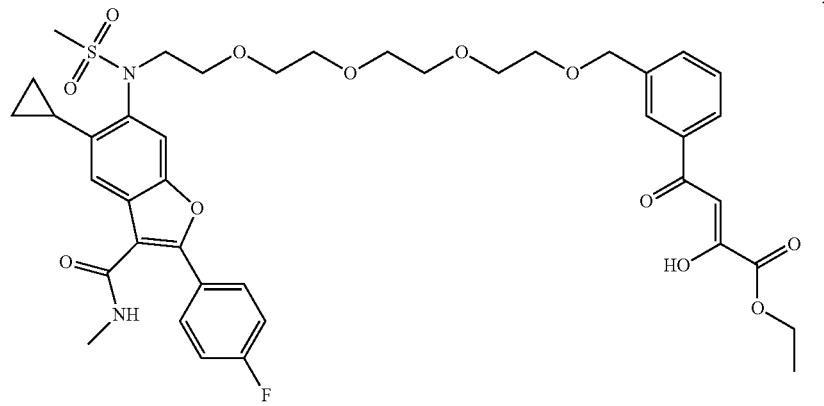

2-9C

4-{3-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxymethyl]-phenyl}-2-hydroxy-4-oxo-but-2-enoic Acid Ethyl Ester (2-9D)

2-8D (100 mg, 0.13 mmol) was used to prepare 2-9D (50 mg, 44%). MS (ESI): m/z 855.3 (M+1)+.

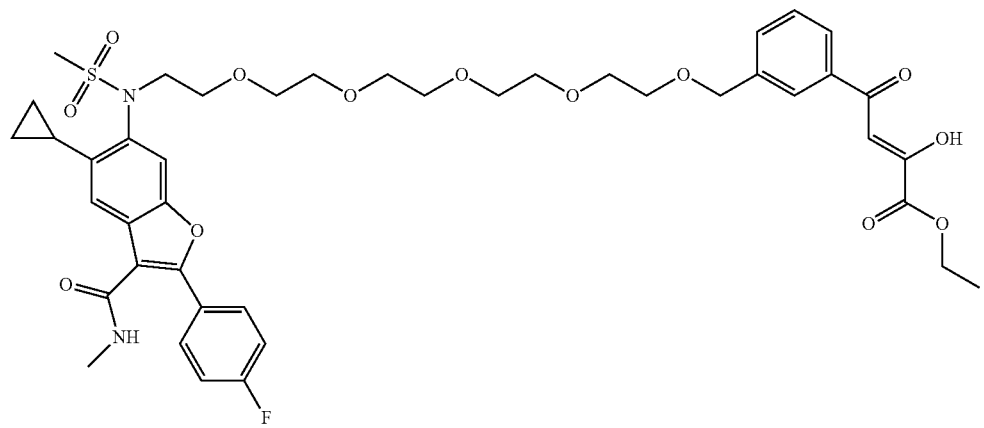

2-9D

4-(3-{2-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxy]-ethoxymethyl}-phenyl)-2-hydroxy-4-oxo-but-2-enoic Acid Ethyl Ester (2-9E)

2-8E (100 mg, 0.12 mmol) was used to prepare 2-9E (75 mg, 66%). MS (ESI): m/z 899.3 (M+1)+.

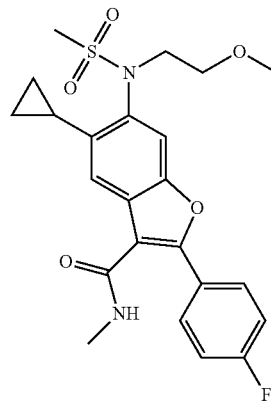

4-{4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-phenyl}-2-hydroxy-4-oxo-but-2-enoic Acid Ethyl Ester (2-9F)

2-8F (100 mg, 0.16 mmol) was used to prepare 2-9F (150 mg). MS (ESI): m/z 723.1 (M+1)⁺.

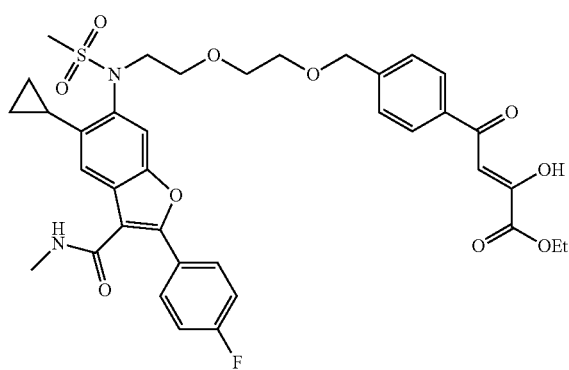

4-(4-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-phenyl)-2-hydroxy-4-oxo-but-2-enoic Acid Ethyl Ester (2-9G)

2-8G (100 mg, 0.15 mmol) was used to prepare 2-9G (115 mg, crude). MS (ESI): m/z 767.0 (M+1)⁺.

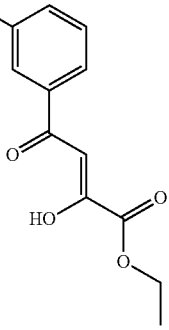

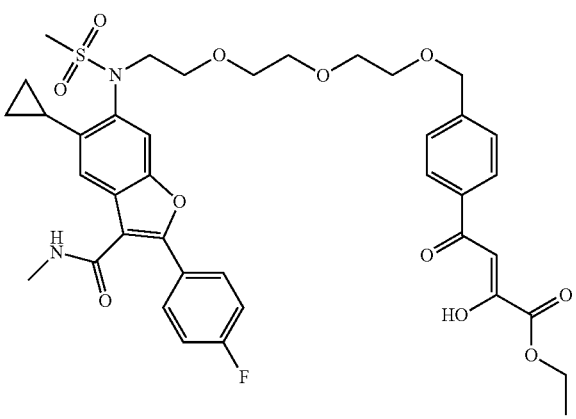

4-[4-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxymethyl)-phenyl]-2-hydroxy-4-oxo-but-2-enoic Acid Ethyl Ester (2-9H)

2-8H (100 mg, 0.14 mmol) was used to prepare 2-9H (80 mg, crude). MS (ESI): m/z 811.6 (M+1)⁺.

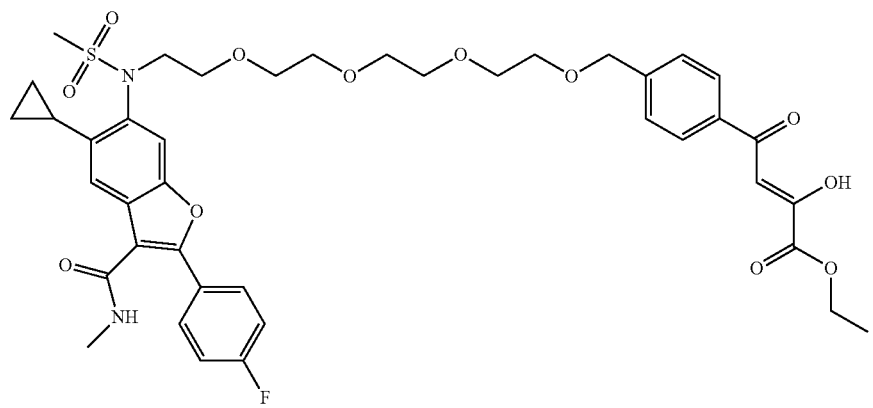

4-{4-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxymethyl]-phenyl}-2-hydroxy-4-oxo-but-2-enoic Acid Ethyl Ester (2-9I)

2-8I (100 mg, 0.132 mmol) was used to prepare 2-9I (90 mg, crude). MS (ESI): m/z 855.3 (M+1)$^+$.

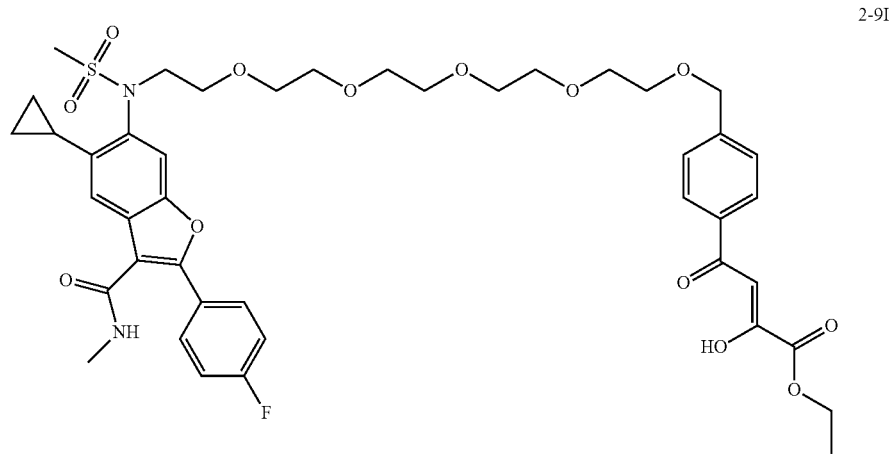 [SMILES: CCOC(=O)/C(O)=C/C(=O)c1ccc(COCCOCCOCCOCCOCCN(c2cc3oc(-c4ccc(F)cc4)c(C(=O)NC)c3cc2C2CC2)S(C)(=O)=O)cc1]

4-(4-{2-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxy]-ethoxymethyl}-phenyl)-2-hydroxy-4-oxo-but-2-enoic Acid Ethyl Ester (2-9J)

2-8J (150 mg, 0.19 mmol) was used to prepare 2-9J (120 mg, 71%). MS (ESI): m/z 899.4 (M+1)$^+$.

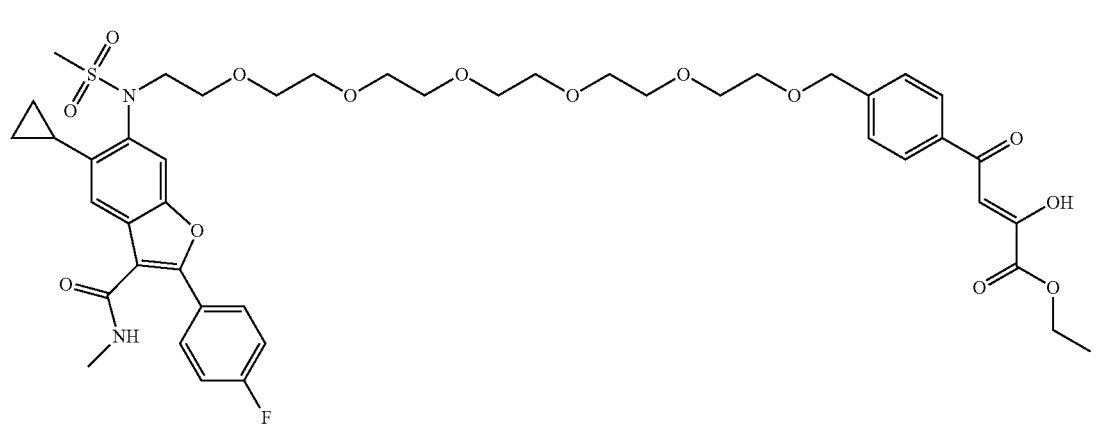

4-{3-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-phenyl}-2-hydroxy-4-oxo-but-2-enoic Acid (2-10A)

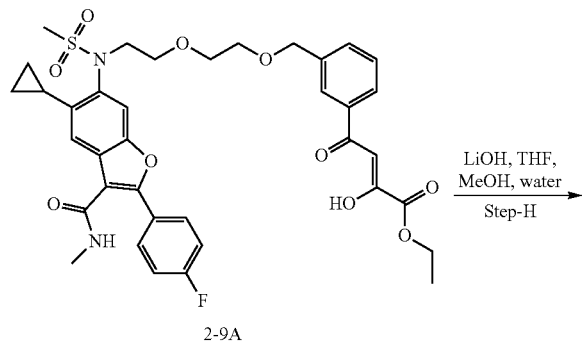

To a stirred solution of 2-8A crude mixture (0.7 g, 0.97 mmol) in THF and water (8 mL; 4:1) was added LiOH (0.14 g, 5.82 mmol) at 0° C. and reaction was continued at RT for 2 hr. After completion of the reaction (TLC), solvents were evaporated via rotary evaporator (Hiedolph rotavapour), residue extracted with pet. ether (50 mL). Then aqueous layer was neutralized with 1N HCl (10 mL) followed by extracted with EtOAc (3×100 mL). The combined organic layers were washed with brine (2×50 mL), dried Na$_2$SO$_4$ and concentrated. The residue was purified by preparative HPLC to afford 2-10A (50 mg) as an off-white solid. MS (ESI): m/z 693.7 (M−1)$^+$.

The above procedure was adapted to prepare the following compounds:

4-(3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-phenyl)-2-hydroxy-4-oxo-but-2-enoic Acid (2-10B)

2-9B (60 mg, crude) was used to prepare 2-10B (5.0 mg). MS (ESI): m/z 739.3 (M+1)$^+$.

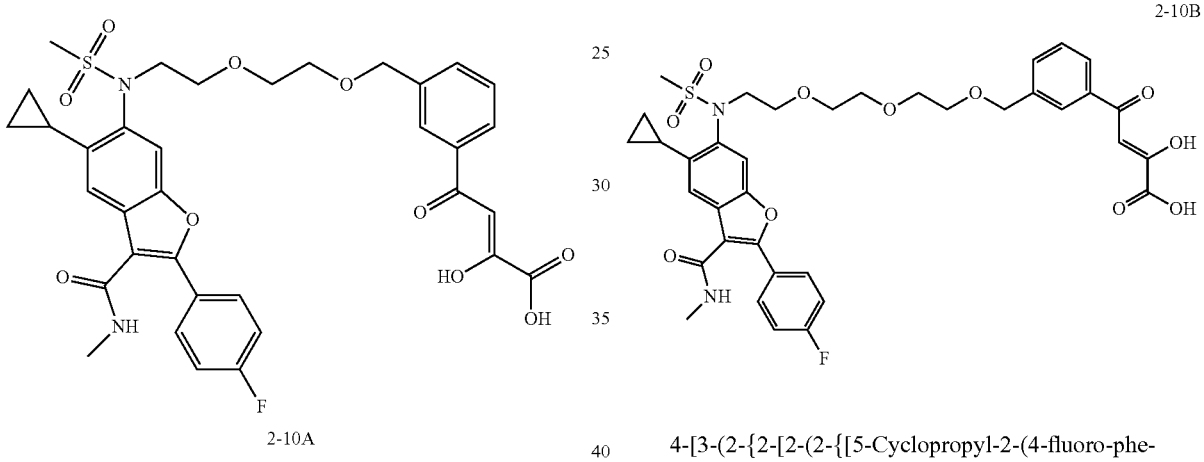

4-[3-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxymethyl)-phenyl]-2-hydroxy-4-oxo-but-2-enoic Acid (2-10C)

2-9C (120 mg, 0.148 mmol) was used to prepare 2-10C (4 mg, 4%). MS (ESI): m/z 781.6 (M−1)$^+$.

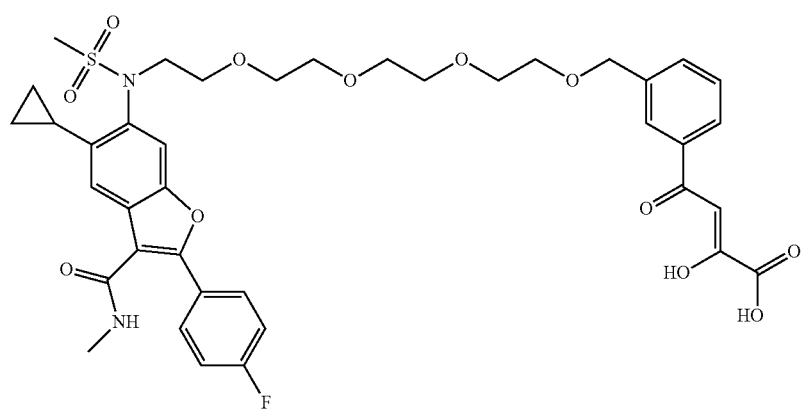

4-{3-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxymethyl]-phenyl}-2-hydroxy-4-oxo-but-2-enoic Acid (2-10D)

2-9D (50 mg, 0.06 mmol) was used to prepare 2-10D (5 mg, 10%). MS (ESI): m/z 827.2 (M+1)⁺.

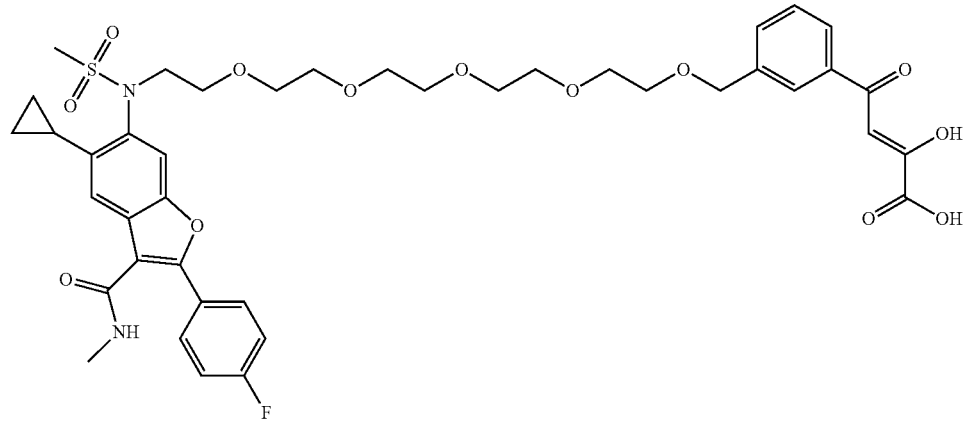

2-10D 4-(3-{2-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxy]-ethoxymethyl}-phenyl)-2-hydroxy-4-oxo-but-2-enoic Acid (2-10E)

2-9E (40 mg, 0.05 mmol) was used to prepare 2-10E (5 mg, 11%). MS (ESI): m/z 870.6 (M+1)⁺.

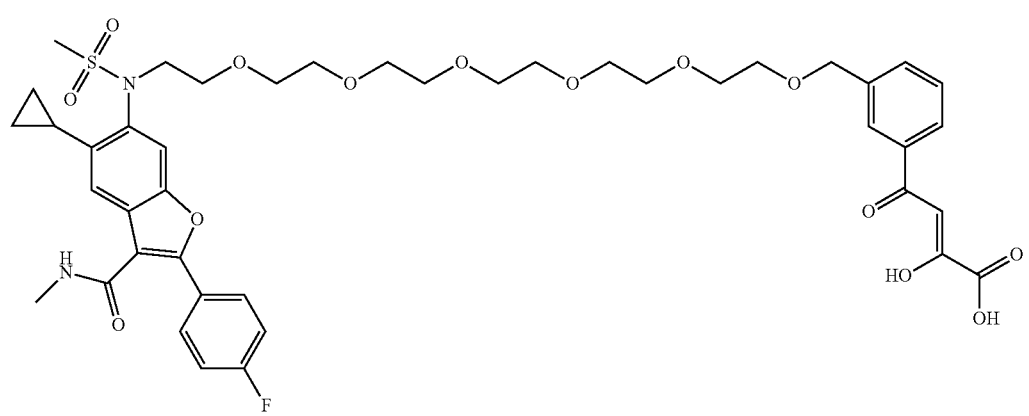

2-10E

4-{4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-phenyl}-2-hydroxy-4-oxo-but-2-enoic Acid (2-10F)

2-9F (90 mg, crude) was used to prepare 2-10F (8.6 mg). MS (ESI): m/z 692.9 (M−1)⁻.

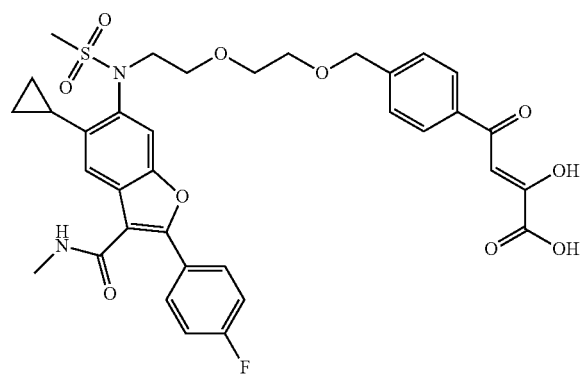

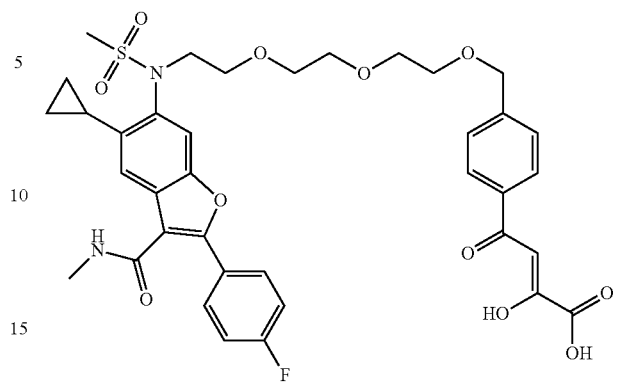

4-(4-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-phenyl)-2-hydroxy-4-oxo-but-2-enoic Acid (2-10G)

2-9G (50 mg, crude) was used to prepare 2-10G (3.6 mg). MS (ESI): m/z 739.3 (M+1)$^+$.

4-[4-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxymethyl)-phenyl]-2-hydroxy-4-oxo-but-2-enoic Acid (2-10H)

2-9H (60 mg, 0.074 mmol) was used to prepare 2-10H (11.5 mg, 19%). MS (ESI): m/z 783.3 (M+1)$^+$.

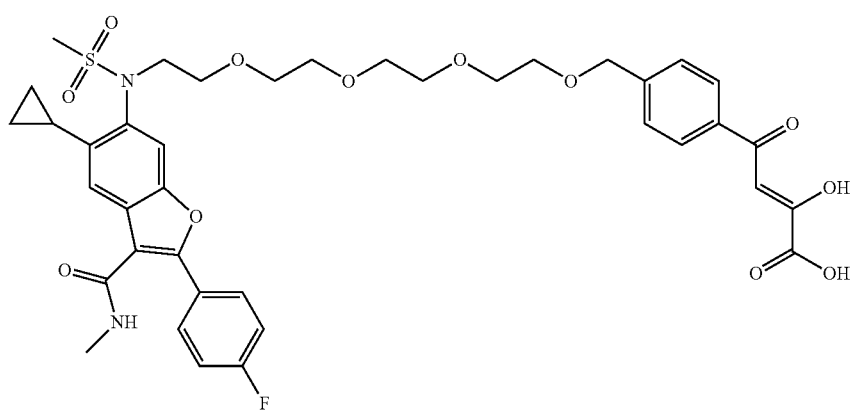

4-{4-[2-(2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-ethoxy)-ethoxymethyl]-phenyl}-2-hydroxy-4-oxo-but-2-enoic Acid (2-10I)

2-9I (60 mg, 0.0705 mmol) was used to prepare 2-10I (6 mg, 10%). MS not collected.

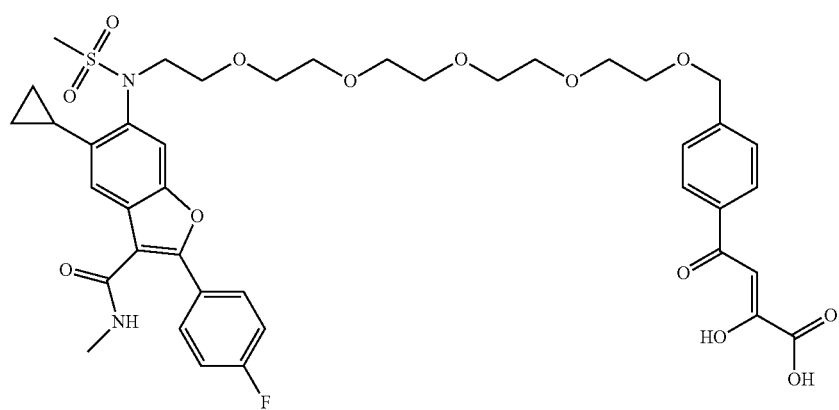

4-(4-{2-[2-(2-{2-[2-(2-{[5-Cyclopropyl-2-(4-fluoro-phenyl)-3-methylcarbamoyl-benzofuran-6-yl]-meth-anesulfonyl-amino}-ethoxy)-ethoxy]-ethoxy}-ethoxy)-ethoxy]-ethoxymethyl}-phenyl)-2-hydroxy-4-oxo-but-2-enoic Acid (2-10J)

2-9J (70 mg, 0.08 mmol) was used to prepare 2-10J (10 mg, 14%). MS (ESI): m/z 871.8 (M+1)$^+$.

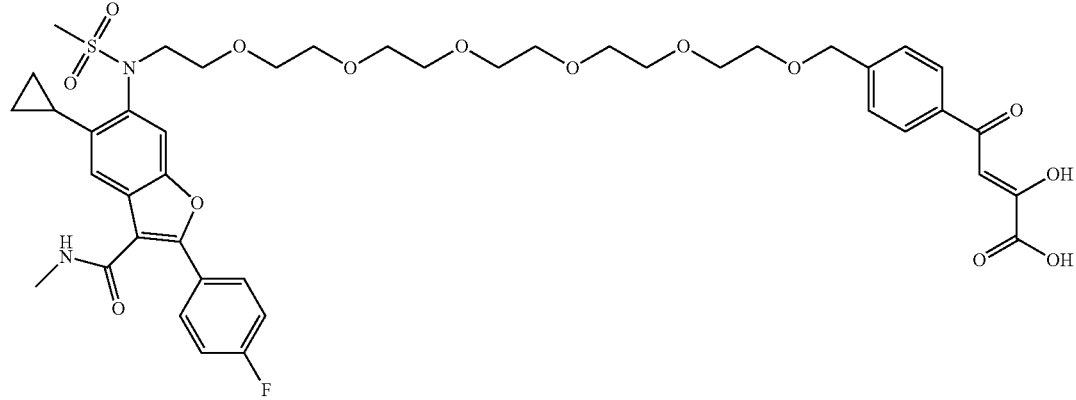

2-10J

Example 3

1-(3-((2-Hydroxyethoxy)-methyl)-phenyl)-ethanone (3-2A)

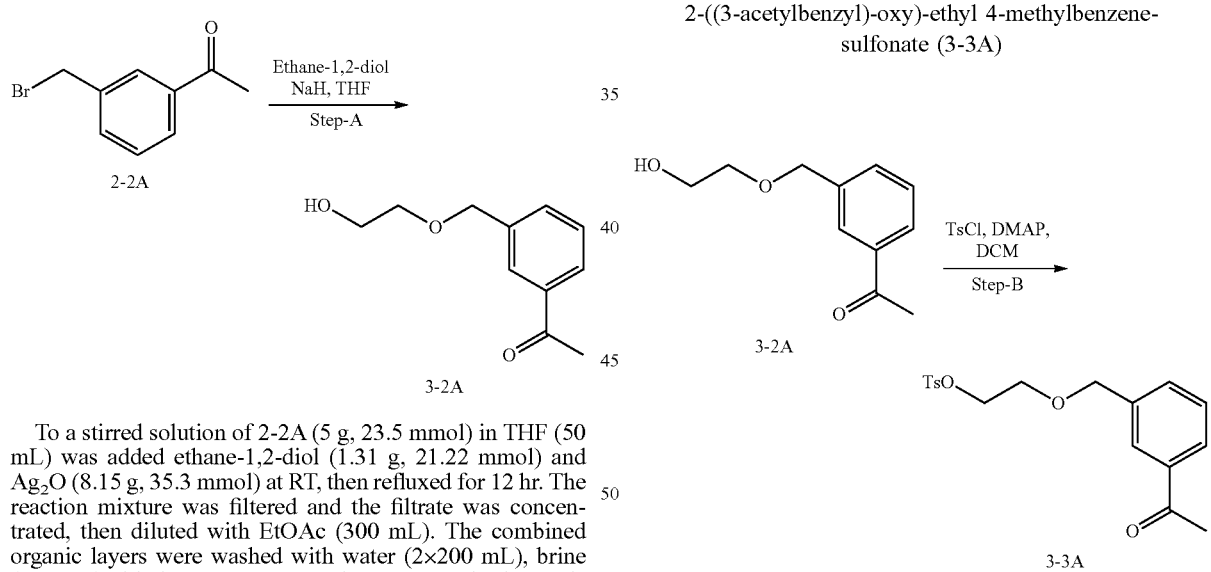

To a stirred solution of 2-2A (5 g, 23.5 mmol) in THF (50 mL) was added ethane-1,2-diol (1.31 g, 21.22 mmol) and Ag$_2$O (8.15 g, 35.3 mmol) at RT, then refluxed for 12 hr. The reaction mixture was filtered and the filtrate was concentrated, then diluted with EtOAc (300 mL). The combined organic layers were washed with water (2×200 mL), brine (150 mL), dried over Na$_2$SO$_4$, and concentrated. The crude residue was purified by flash column chromatography (100-200 silica) using 30% EtOAc/hexanes to afford 3-2A (2.01 g, 10.3 mmol, 44.6% yield) as a colorless thick liquid. MS (ESI): m/z 195.06 (M+1)$^+$.

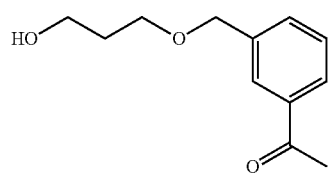

3-2B

Adapting the above procedure (Step-A), propane-1,2-diol (1 g, 4.73 mmol) was substituted for ethane-1,2-diol to prepare 3-2B (670 mg, 68%). MS (ESI): m/z 209.0 (M+1)$^+$.

2-((3-acetylbenzyl)-oxy)-ethyl 4-methylbenzene-sulfonate (3-3A)

p-Toluene sulfonyl chloride (740 mg, 3.91 mmol) was added to a solution of 3-2A (630 mg, 3.01 mmol) in DCM (15 mL) and triethylamine (1.45 mL, 9.6 mmol) at 0° C. and DMAP (cat. amount), stirred at RT for 1 hr. The reaction mixture was diluted with water (100 mL), and extracted with DCM (3×100 mL). The combined organic layers were washed with brine (100 mL), dried over Na$_2$SO$_4$, and concentrated. The crude residue was purified by flash column chromatography (100-200 silica) using 30% EtOAc in hexanes to afford 3-3A (710 mg, 2.06 mmol, 64.2% yield) as a brown gummy liquid. MS (ESI): m/z 348.9 (M+1)$^+$.

1-(3-((2-(3-hydroxypropoxy)-ethoxy)-methyl)-phenyl)-ethanone (3-4A)

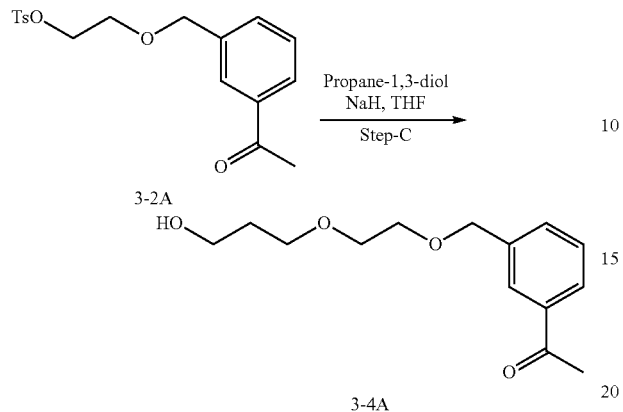

To a stirred solution of 1,3-propanediol (0.73 mL, 10.1 mmol) in THF (10 mL) was added NaH (37 mg, 2.2 mmol) at 0° C., and reaction was continued at RT for 30 min. 3-3A (710 mg, 2.01 mmol) in THF (5 mL) was added to the reaction mixture at 0° C. over 5 min. and reaction was refluxed for 4 hr. The reaction mixture was quenched with ice cold water (100 mL) and extracted with EtOAc (3×100 mL), The combined organic layers were washed with water (2×100 mL), brine (150 mL), dried over Na$_2$SO$_4$ and concentrated. The residue was purified by flash column chromatography (100-200 silica) using 30% EtOAc/hexanes to afford 3-4A (260 mg, 1.08 mmol, 50% yield) as a colorless thick liquid. MS (ESI): m/z 253.1 (M+1)$^+$.

3-(2-((3-acetylbenzyl)-oxy)-ethoxy)-propyl Methanesulfonate (3-5A)

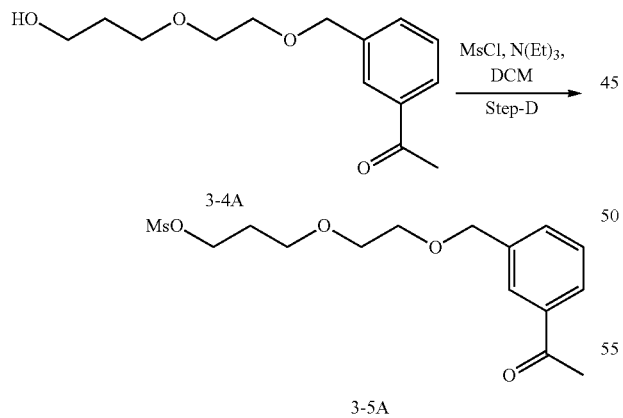

Methane sulfonylchloride (0.11 mL, 1.4 mmol) was added to a solution of 3-4A (300 mg, 1.10 mmol) in DCM (10 mL) and triethylamine (0.51 mL, 3.5 mmol) at 0° C. and stirred at RT for 2 hr. The reaction mixture was diluted with water (50 mL) and extracted with DCM (3×50 mL). The combined organic layers were washed with brine (50 mL), dried over Na$_2$SO$_4$ and concentrated. The residue was purified by flash column chromatography (100-200 silica) using 25% EtOAc in hexanes to afford 3-5A (355 mg, 0.81 mmol, 90% yield) as a brown liquid. MS (ESI): m/z 331.1 (M+1)$^+$.

6-(N-(3-(2-((3-acetylbenzyl)-oxy)-ethoxy)-propyl)-methylsulfonamido)-5-cyclopropyl-2-(4-fluorophenyl)-N-methylbenzofuran-3-carboxamide (3-6A)

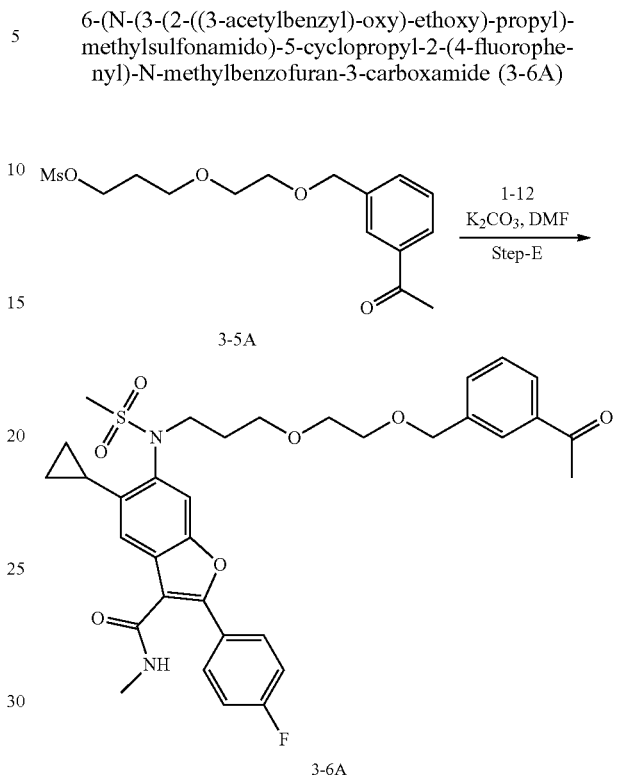

To a stirred solution of 1-12 (350 mg, 0.80 mmol) in DMF (10 mL) was added potassium carbonate (360 mg, 2.60 mmol) followed by 3-5A (345 mg, 1.01 mmol), catalytic amount of TBAI at 80° C. for 16 hr. The reaction mixture was cooled to RT and diluted with EtOAc (100 mL), then washed with water (2×50 mL), brine (50 mL) and dried over Na$_2$SO$_4$ and concentrated. The residue was purified by flash column chromatography (100-200 silica) using 45% EtOAc/pet. ether to afford 3-6A (380 mg, 0.59 mmol, 69% yield) as an off-white solid. MS (ESI): m/z 636.9 (M+1)$^+$.

4-{3-[2-(3-{[5-Cyclopropyl-2-(4-fluoro-phenyl)-3-methylcarbamoyl-benzofuran-6-yl]-methanesulfonyl-amino}-propoxy)-ethoxymethyl]-phenyl}-2-hydroxy-4-oxo-but-2-enoic Acid Ethyl Ester (3-7A)

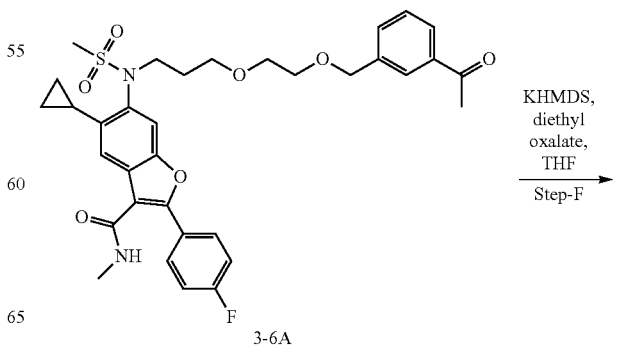

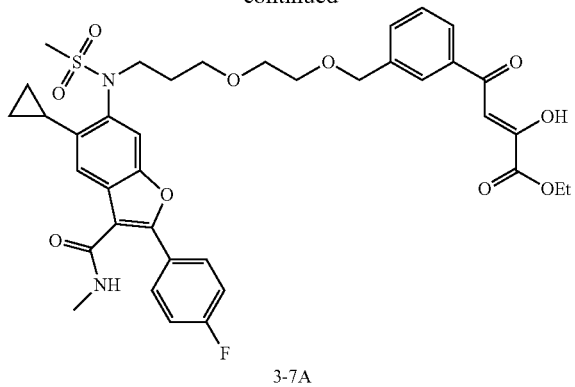

3-7A

To a stirred solution of 3-6A (100 mg, 0.12 mmol) in THF (5 mL) was added potassium bis(trimethylsilyl)amide (KHMDS; 0.39 mL, 0.31 mmol) at −78° C., and the reaction mixture was warmed to −55° C. for 1 hr. Then, diethyl oxalate (0.03 mL, 0.21 mmol) added to the reaction mixture at −78° C. and the reaction mixture warmed to −55° C. for 2 hr, under nitrogen atmosphere. The reaction mixture was quenched with ammonium chloride solution, extracted into EtOAc (3×40 mL). The combined organic layers were washed with brine (2×20 mL), dried over $Na_2SO_4$ and concentrated. The residue was purified by flash column chromatography using neutral silica (100-200 silica) 5% acetone-DCM to afford (90 mg, crude) 3-7A, as a brownish gummy liquid. MS (ESI): m/z 737.2 $(M+1)^+$.

4-{3-[2-(3-{[5-Cyclopropyl-2-(4-fluoro-phenyl)-3-methylcarbamoyl-benzofuran-6-yl]-methanesulfonyl-amino}-propoxy)-ethoxymethyl]-phenyl}-2-hydroxy-4-oxo-but-2-enoic Acid (3-8A)

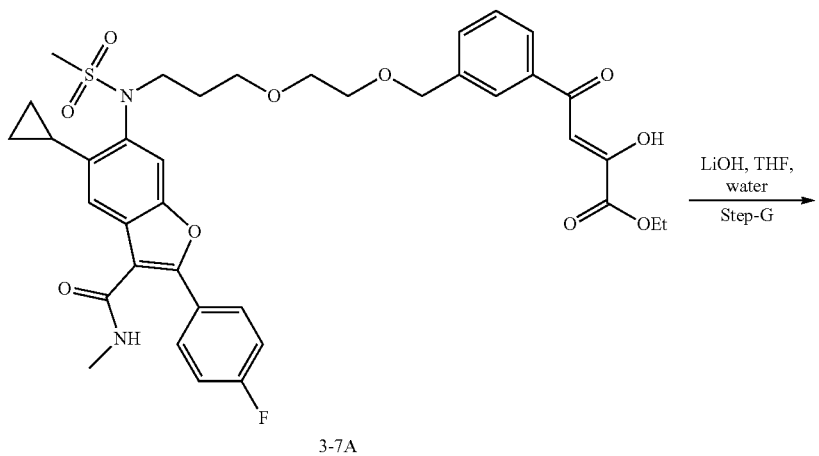

3-7A

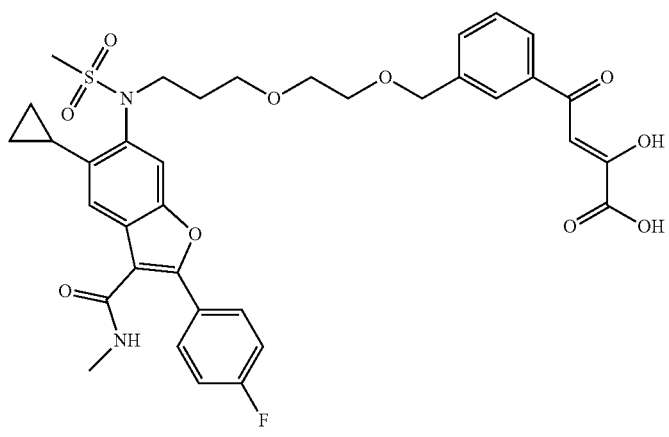

3-8A

To a stirred solution of 3-7A (90 mg, 0.10 mmol) in THF and water (5 mL, (1:1)) was added LiOH (20 mg, 0.70 mmol) at 0° C., and the reaction was continued at RT for 5 hr. After completion of the reaction (by TLC), solvents were evaporated with a rotary evaporator, and the residue extracted with ether (50 mL). The aqueous layer was neutralized with 1N HCl (5 mL) followed by extraction with EtOAc (3×50 mL). The combined organic layers were washed with brine (2×50 mL), dried over $Na_2SO_4$ and concentrated. The residue was purified by preparative HPLC to afford 3-8A (3.5 mg, 3% yield) as pale brown solid. MS (ESI): m/z 709.2 $(M+1)^+$.

4-{3-[3-(2-{[5-Cyclopropyl-2-(4-fluoro-phenyl)-3-methylcarbamoyl-benzofuran-6-yl]-methanesulfonyl-amino}-ethoxy)-propoxymethyl]-phenyl}-2-hydroxy-4-oxo-but-2-enoic Acid (3-8B)

The procedure given above was adapted by substituting 3-2B for 3-2A in Step-B, followed by appropriate modification of the succeeding Steps C-F, to prepare 3-8B. MS (ESI): m/z 709.6 $(M+1)^+$. 6-({2-[3-(3-Acetyl-benzyloxy)-propoxy]-ethyl}-methanesulfonyl-amino)-5-cyclopropyl-2-(4-fluoro-phenyl)-benzofuran-3-carboxylic acid methylamide (3-6B) was prepared during Step-E of this procedure.

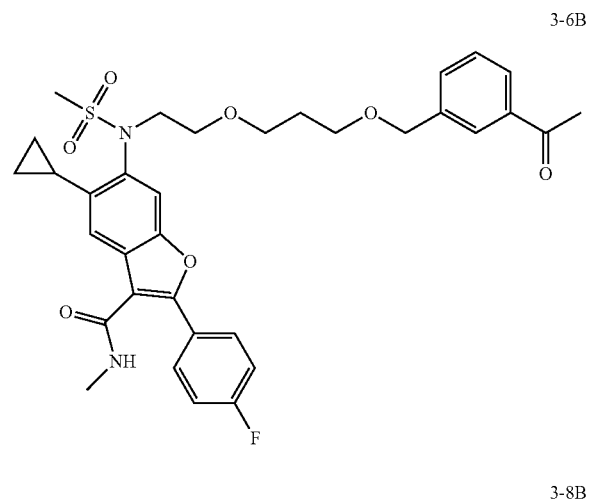

Example 4

2,2,3,3-Tetramethyl-4,7,10,13-tetraoxa-3-silapentadecan-15-ol (4-2)

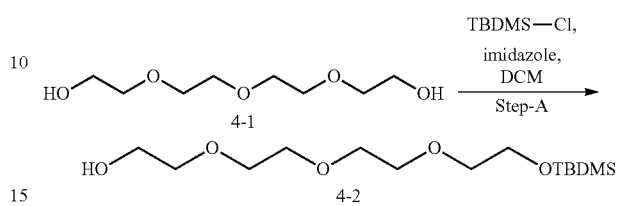

To a stirred solution of 2,2'-(2,2'-oxybis(ethane-2,1-diyl)bis(oxy))diethanol 4-1 (5 g, 25.7 mmol) in DCM (100 mL) was added imidazole (2.1 g, 30.9 mmol) and tert-butyldimethylsilyl chloride (TBDMSCl; 3.48 g, 23.1 mmol) at 0° C. and stirred to RT for 6 hr. The reaction mixture was diluted with DCM (100 mL) and washed with water (2×100 mL) and brine (50 mL). The organic layer was concentrated under reduced pressure and the crude residue was purified by flash column chromatography (100-200 silica) using 30% EtOAc/pet. ether gave 4-2 (1.8 g, 5.8 mmol, 22% yield) as an off-white solid.

2,2,3,3-Tetramethyl-4,7,10,13-tetraoxa-3-silapentadecan-15-yl methanesulfonate (4-3)

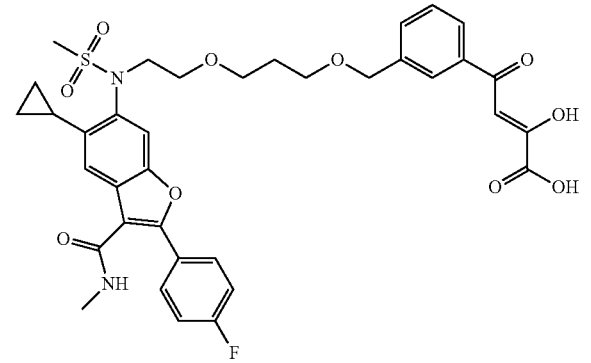

To a stirred solution of 4-2 (0.2 g, 0.65 mmol) in DCM (10 mL) was added methane sulfonylchloride (0.1 mL, 0.78 mmol) and triethylamine (0.13 mL, 0.9741 mmol) at 0° C., and stirred at RT for 4 hr. The reaction mixture was diluted with water (20 mL), extracted with DCM (3×20 mL), the combined organic layers were washed with brine (2×10 mL) and dried over $Na_2SO_4$ and concentrated. The crude residue was purified by flash column chromatography (100-200 silica) using 20% EtOAc/pet. ether to afford 4-3 (0.1 g, 0.26 mmol, 40% yield) as a yellow liquid.

5-Cyclopropyl-2-(4-fluorophenyl)-N-methyl-6-(N-(2,2,3,3-tetramethyl-4,7,10,13-tetraoxa-3-silapentadecan-15-yl)-methylsulfonamido)benzofuran-3-carboxamide (4-4)

-continued

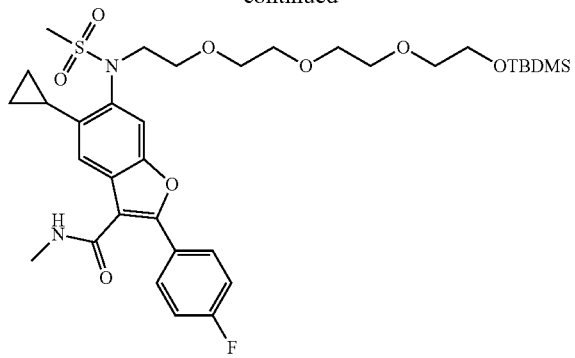

4-4

To a stirred solution of 1-12 (0.05 g, 0.12 mmol) in DMF (10 mL) was added K$_2$CO$_3$ (0.052 g, 0.37 mmol) followed by 4-3 (0.072 g, 0.18 mmol), catalytic amount of TBAI at 80° C. for 16 hr. The reaction mixture was cooled to RT and diluted with EtOAc (15 mL) washed with water (2×10 mL), brine (15 mL) and dried over Na$_2$SO$_4$ and concentrated. The crude residue was purified by flash column chromatography (100-200 silica) using 2% MeOH-DCM to afford 4-4 (0.02 g, 0.03 mmol, 23% yield) as an off-white solid. MS (ESI): m/z 710.2 (M+18)$^+$.

5-Cyclopropyl-2-(4-fluorophenyl)-6-(N-(2-(2-(2-(2-hydroxyethoxy)-ethoxy)-ethoxy)-ethyl) Methyl-sulfonamido)-N-methylbenzofuran-3-carboxamide (4-5)

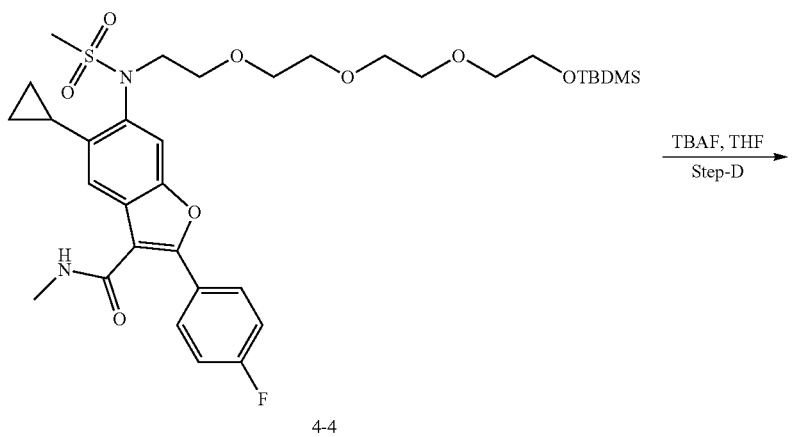

4-4

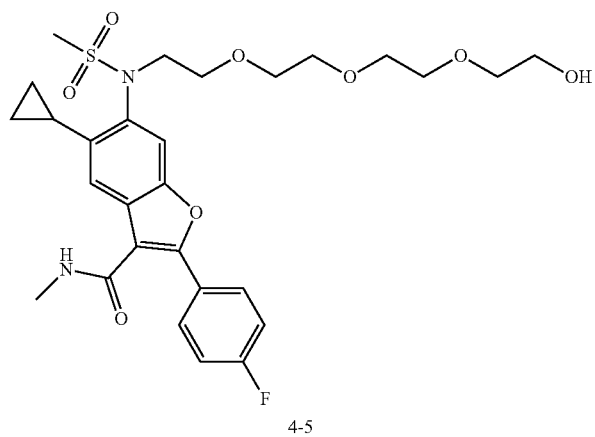

4-5

To a stirred solution of 4-4 (0.1 g, 0.14 mmol) in THF (5 mL) was added tetrabutylammonium fluoride (0.2 mL, 0.16 mmol) at 0° C. and stirred at RT for 4 hr. The reaction mixture was quenched with the satd. aq. ammonium chloride solution. The quenched solution was extracted with EtOAc (3×10 mL). The combined organic layer washed with brine (20 mL), dried over $Na_2SO_4$ and concentrated. The crude residue was purified by flash column chromatography (100-200 silica) using 5% MeOH-DCM to afford 4-5 (0.05 g, 0.08 mmol, 60% yield) as an off-white solid. MS (ESI): m/z 601.1 (M+23)$^+$.

15-Azido-2,2,3,3-tetramethyl-4,7,10,13-tetraoxa-3-silapentadecane (4-6)

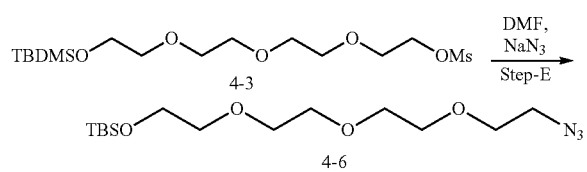

To a stirred solution of 4-3 (1.5 g, 3.88 mmol) in DMF (30 mL) was added sodium azide (303 mg, 4.6 mmol) at RT and stirred at 60° C. for 20 hr. After consumption of starting material (by TLC), reaction was diluted with water (90 mL) and extracted with EtOAc (3×40 mL). The combined organic layer was washed with brine (80 mL), dried over $Na_2SO_4$ and concentrated. The crude residue was purified by flash column chromatography (100-200 silica) using 20% EtOAc in hexanes to afford 4-6 (750 mg, 2.25 mmol, 58% yield) as a yellowish liquid.

2-(2-(2-(2-Azidoethoxy)-ethoxy)-ethoxy)-ethanol (4-7)

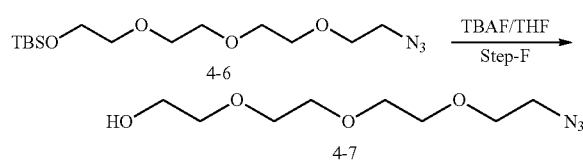

To a stirred solution of 4-6 (750 mg, 2.25 mmol) in THF (20 mL) was added tetra-n-butylammonium fluoride (TBAF; 2.7 mL, 2.7 mmol) at 0° C., and warmed the reaction mixture to RT and stirring continued for 2 hr. The reaction mixture was diluted with water and extracted with EtOAc (2×30 mL) washed with water (30 mL), brine (30 mL) and dried over $Na_2SO_4$ and concentrated. The crude residue was purified by flash column chromatography (100-200 silica) using 40% EtOAc in pet. ether to afford 4-7 (400 mg, 1.82 mmol, 81% yield) as a yellow liquid.

2-(2-(2-(2-Azidoethoxy)-ethoxy)-ethoxy)-ethyl methanesulfonate (4-8)

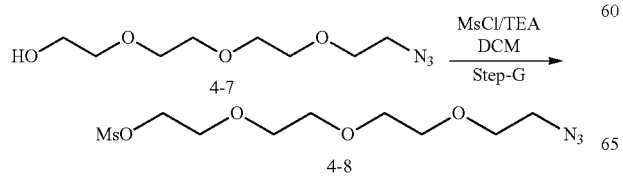

To a stirred solution of 4-7 (400 mg, 1.82 mmol) in DCM (10 mL) was added methane sulfonylchloride (0.17 mL, 2.19 mmol) and triethylamine (0.6 mL, 4.38 mmol) at 0° C., and stirred at RT for 4 hr. The reaction mixture was diluted with water (10 mL), extracted with DCM (3×15 mL). The combined organic layers were washed with brine (2×10 mL), dried over $Na_2SO_4$ and concentrated. The crude residue was purified by flash column chromatography (100-200 silica) using 30% EtOAc/pet. ether to afford 4-8 (390 g, 1.31 mmol, 72% yield) as a yellow liquid.

6-(N-(2-(2-(2-(2-Azidoethoxy)-ethoxy)-ethoxy)-ethyl)-methylsulfonamido)-5-cyclopropyl-2-(4-fluorophenyl)-N-methylbenzofuran-3-carboxamide (4-9)

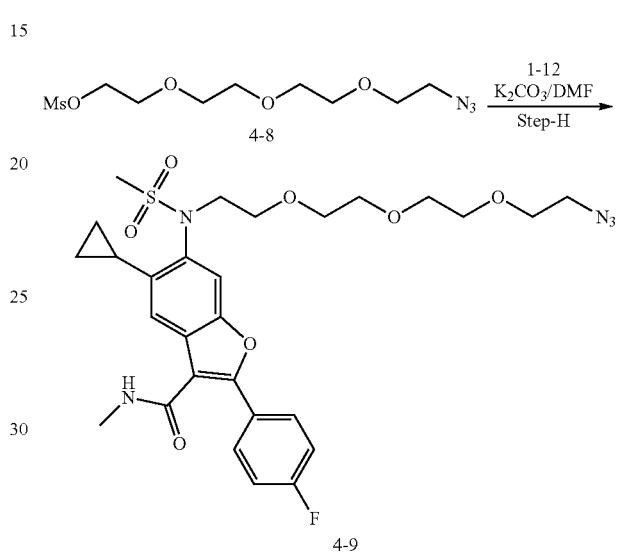

To a stirred solution of 1-12 (439 mg, 1.09 mmol) in DMF (10 mL) was added potassium carbonate (451 g, 3.27 mmol) followed by 4-8 (390 mg, 1.31 mmol), and catalytic amount of tetrabutylammonium iodide at 80° C. for 16 hr. The reaction mixture was cooled to RT and diluted with EtOAc (30 mL), washed with water (2×15 mL), brine (25 mL), dried over $Na_2SO_4$ and concentrated. The crude residue was purified by flash column chromatography (100-200 silica) using 20% EtOAc in hexane to afford 4-9 (320 g, 0.53 mmol, 48% yield) as an off-white solid. MS (ESI): m/z 648.3 (M+45)$^+$.

6-(N-(2-(2-(2-(2-Aminoethoxy)-ethoxy)-ethoxy)-ethyl)-methylsulfonamido)-5-cyclopropyl-2-(4-fluorophenyl)-N-methylbenzofuran-3-carboxamide (4-10)

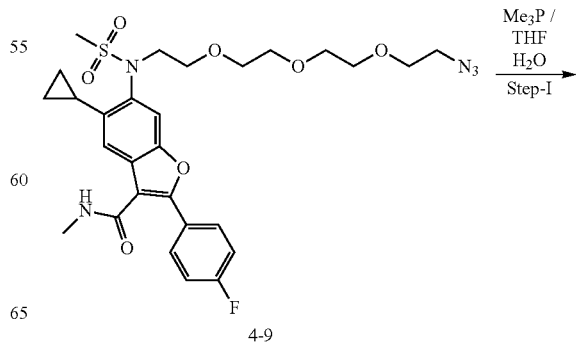

-continued

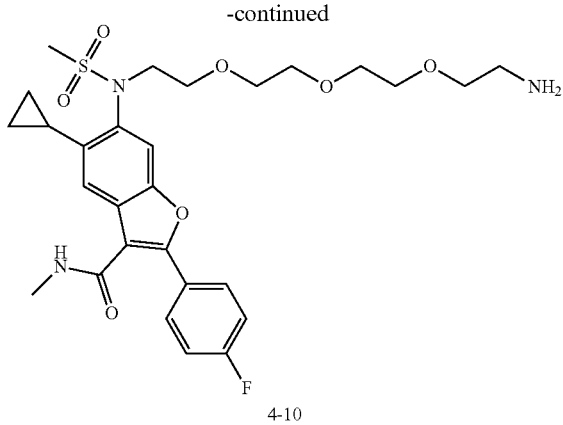

4-10

To a stirred solution of 4-9 (320 g, 0.530 mmol) in THF:H$_2$O (1:1, 10 mL). was added trimethyl phospine at 0° C., and the reaction mixture was warmed to 50° C. and stirred for 16 hr. After completion of the reaction (by TLC), the mixture was diluted with water, extracted with EtOAc (3×10 mL). The combined organic layers were washed with brine (2×10 mL), dried over Na$_2$SO$_4$ and concentrated. The crude residue was purified by flash column chromatography using neutral silica (100-200 silica) 5% MeOH-DCM to afford 4-10 (0.15 g, 0.26 mmol, 49% yield), as a brownish gummy solid. MS (ESI): m/z 578 (M+1)$^+$.

Example 5

2-(2,5,8,11-Tetraoxatridecan-13-yloxy)tetrahydro-2H-pyran (5-1A)

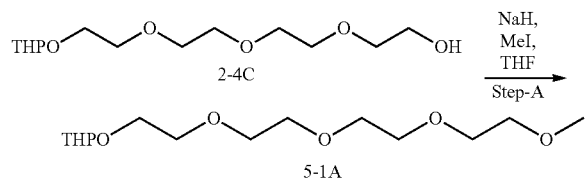

To a stirred suspension of NaH in THF was added a solution of 2-4C (500 mg, 1.8 mmol) in THF (5 mL) at 0° C. and the mixture was stirred at RT for 30 min. The mixture was cooled to 0° C., MeI was added, and the mixture allowed to stir at RT for 2 hr under nitrogen atmosphere. The reaction mixture was quenched with ice cold water, extracted with EtOAc (3×80 mL). The organic layer washed with water (50 mL), brine (50 mL), dried over Na$_2$SO$_4$ and concentrated. The crude residue was purified by flash column chromatography (100-200 silica) using 30% EtOAc in hexanes to afford 5-1A (280 mg, 0.95 mmol, 52% yield) as a yellow liquid.

Substituting butyl iodide for methyl iodide in Step-A, 2-4B (1 g, 4.27 mmol) was used to prepare 5-1B (718 mg, 58% yield).

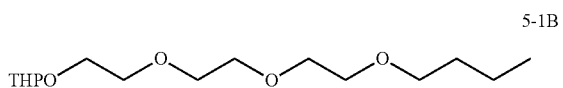

2,5,8,11-Tetraoxatridecan-13-ol (5-2A)

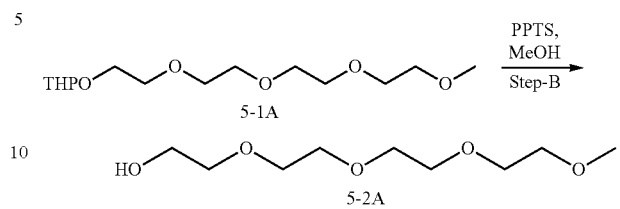

To a solution of 2-(2,5,8,11-tetraoxatridecan-13-yloxy)tetrahydro-2H-pyran 5-1A (280 mg, 0.96 mmol) in MeOH (5 mL) was added PPTS (24 mg, 0.096 mmol) and stirred at 0° C. to RT for 16 hr. The reaction mixture was concentrated under reduced pressure to get crude compound. Obtained crude was purified using silica gel column chromatography 5% MeOH in DCM to afford 5-2A (180 mg, 0.87 mmol, 90% yield) as a pale yellow liquid.

Adapting the above procedure, 5-1B (710 mg, 2.44 mmol) was used to prepare 5-2B (406 mg, 78%).

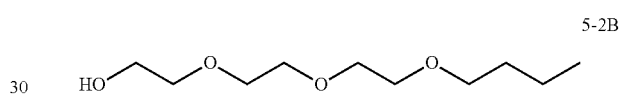

2,5,8,11-Tetraoxatridecan-13-yl Methanesulfonate (5-3A)

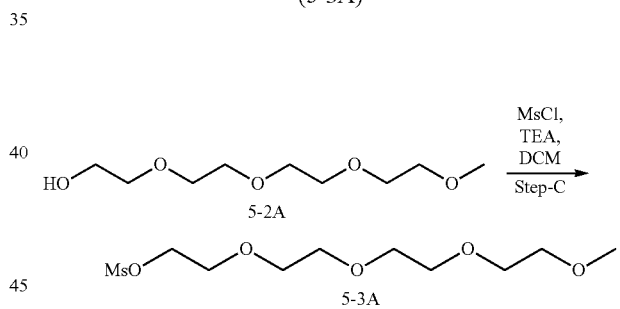

To a stirred solution of 5-2A (180 mg, 0.87 mmol) in DCM (5 mL) was added triethylamine (0.18 mL, 1.3 mmol) and methane sulfonyl chloride (0.1 mL, 1.13 mmol) at 0° C. and stirred at RT for 1 hr. The reaction mixture was diluted with excess DCM (40 mL) and washed with water (2×10 mL), brine (10 mL) and dried over Na$_2$SO$_4$, organic phase concentrated under reduced pressure to get crude compound. This was purified using 100-200 silica gel column chromatography using 2% MeOH in DCM to afford 5-3A (200 mg, 0.699 mmol, 80% yield) as a yellow liquid.

Adapting the above procedure, 5-2B (406 mg, 1.91 mmol) was used to prepare 5-3B (440 mg, 78%).

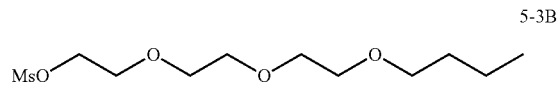 [SMILES: CCCCOCCOCCOCCOS(C)(=O)=O]

6-(N-(2,5,8,11-Tetraoxatridecan-13-yl)-methylsulfo-namido)-5-cyclopropyl-2-(4-fluorophenyl)-N-methylbenzofuran-3-carboxamide (5-4A)

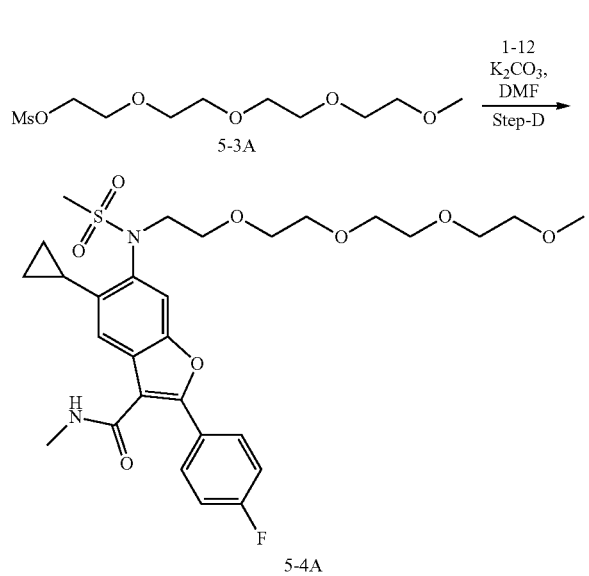 [SMILES: COCCOCCOCCOCCOS(C)(=O)=O ; CNC(=O)c1c(-c2ccc(F)cc2)oc2cc(N(CCOCCOCCOCCOC)S(C)(=O)=O)c(C3CC3)cc12]

To a solution of 1-12 (110 mg, 0.29 mmol) in DMF (3 mL) was added potassium carbonate (120 mg, 0.9 mmol) followed by 5-3A (102 mg, 0.35 mmol), catalytic amount of TBAI, then stirred at 70° C. for 16 hr. The reaction was cooled to RT and diluted with EtOAc (30 mL) washed with water (20 mL), brine (15 mL) and dried over $Na_2SO_4$, organic phase was concentrated under reduced pressure to get crude compound. Obtained crude was purified using 230-400 silica gel column chromatography using 15% acetone in DCM to afford 5-4A (67 mg, 0.11 mmol, 45% yield) as a white solid. MS (ESI): m/z 592.8 $(M+1)^+$.

6-({2-[2-(2-Butoxy-ethoxy)-ethoxy]-ethyl}-methanesulfonyl-amino)-5-cyclopropyl-2-(4-fluoro-phenyl)-benzofuran-3-carboxylic Acid Methylamide (5-4B)

Adapting the above procedure, 5-3B (150 mg, 0.52 mmol) was used to prepare 5-4B (13 mg, 4.2%). MS=590.85 $[M+1]^+$.

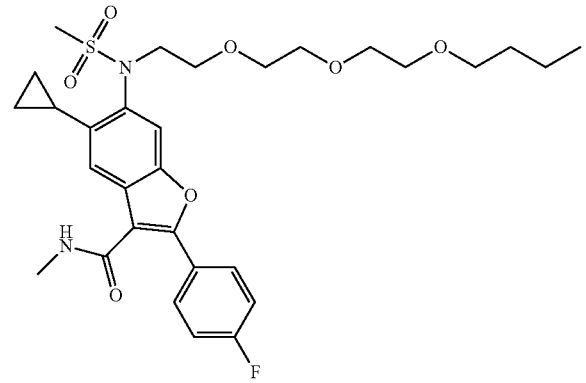

Example 6

Methyl 2-(bromomethyl)-benzoate (6-2A)

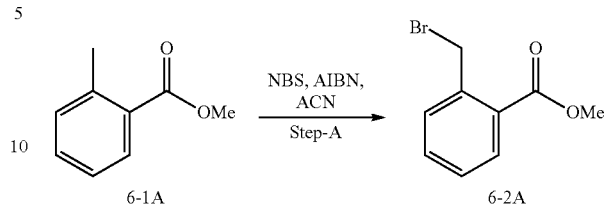

To a stirred solution of methyl 2-methylbenzoate 6-1A (5 g, 33.3 mmol) in ACN (200 mL) was added NBS (5.3 g, 30 mmol) and AIBN (547 mg, 3.33 mmol) at RT. The reaction mixture was warmed to 90° C. for 6 hr under nitrogen atmosphere. The reaction mixture solvent was evaporated under reduced pressure and the crude residue washed with toluene (500 mL) and filtered the precipitate (NBS). Filtrate evaporated under reduced pressure and the crude residue was purified by flash column chromatography (100-200 silica) using 2% EtOAc/pet. ether to afford 6-2A (5 g, 22.1 mmol, 65.7% yield) as a yellow thick liquid.

Adapting the above procedure, methyl 4-methylbenzoate 6-1B (5 g, 33.3 mmol) was used to prepare 6-2B (4.5 g, 60%). MS (ESI): m/z 231.0 $(M+1)^+$.

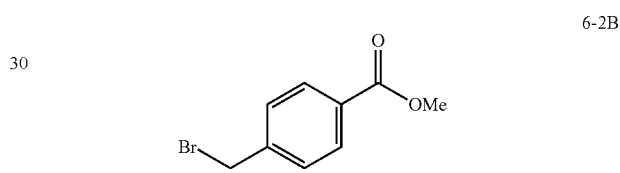

Methyl-2-((2-2(tetrahydro-2H-pyran-2-yloxy)-ethoxy)-methyl)benzoate (6-3A)

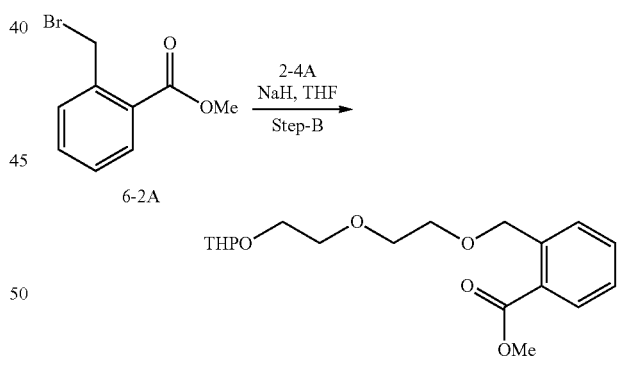

To a solution of NaH (116 mg, 2.6 mmol) in THF (20 mL) was added 2-4A (552 mg, 2.9 mmol) at 0° C. and stirred at RT for 1 hr. The reaction mixture was again cooled to 0° C., 6-2A (600 mg, 2.6 mmol) was added and stirred for RT for 16 hr. The reaction mixture was quenched with ice cold water and diluted with EtOAc (50 mL) washed with water (50 mL), brine (25 mL) and dried over $Na_2SO_4$, organic phase was concentrated under reduced pressure. The crude compound was purified using silica gel chromatography (15% EtOAc in hexane) to afford 6-3A (350 mg, 1.03 mmol, 40.4% yield). MS (ESI): m/z 339 $(M+1)^+$.

The above procedure was adapted to prepare the following compounds:

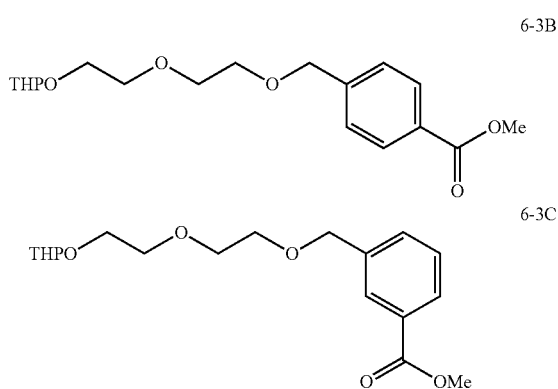

6-2B (7.28 g, 31.8 mmol) was used to prepare 6-3B (4 g, 41%). MS (ESI): m/z 255.0 (M-THP+1)⁺.

Methyl 3-methylbenzoate 6-2C (1.2 g, 5.113 mmol; TCI) was used to prepare 6-3C (0.3 g, 25%). MS (ESI): m/z 369.0 (M+1)⁺.

The above procedure was adapted, replacing 2-4A with 2-4B, to prepare the following compounds:

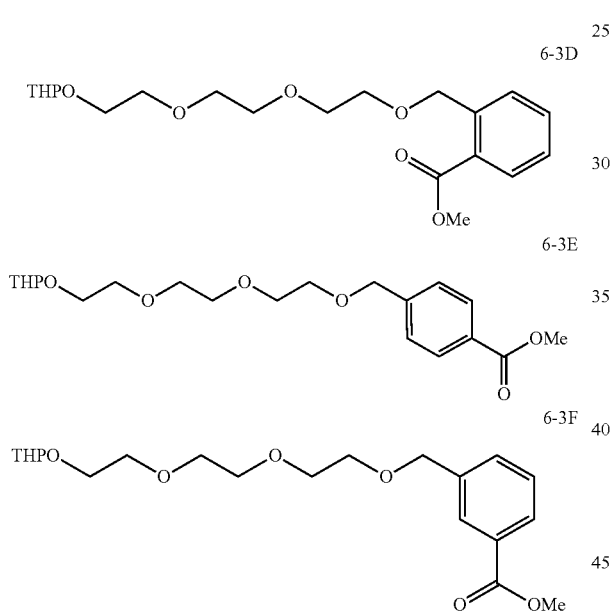

6-2A (1 g, 4.04 mmol) was used to prepare 6-3D (450 mg, 21%). MS (ESI): m/z 383.0 (M+1)⁺.

6-2B (820 mg, 3.5 mmol) was used to prepare 6-3E (450 mg, 41%). MS (ESI): m/z 299 [M-THP+1]⁺.

6-2C (0.753 g, 3.29 mmol) was used to prepare 6-3F (550 mg, 50%). MS (ESI): m/z 299 [M-THP+1]⁺.

Methyl 2-((2-(2-hydroxyethoxy)-ethoxy)-methyl) benzoate (6-4A)

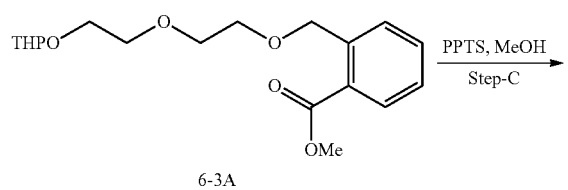

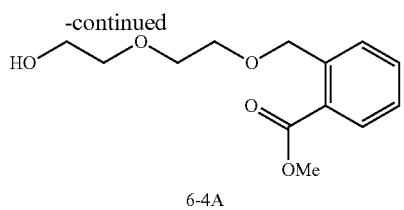

To a solution of 6-3A (310 mg, 0.916 mmol) in MeOH (5 mL) was added PPTS (46 mg, 0.18 mmol) and stirred at 0° C. to RT for 16 hr. The reaction mixture was distilled off and diluted with excess EtOAc (100 mL), washed with water (100 mL), brine (50 mL) and dried over Na₂SO₄, and the organic phase was concentrated under reduced pressure. The crude compound was purified using combi-flash column chromatography (30% EtOAc in hexane) to afford 6-4A (150 mg, 0.59 mmol, 65% yield). MS (ESI): m/z 315 (M+1)⁺.

Adapting the above procedure, the following compounds were made:

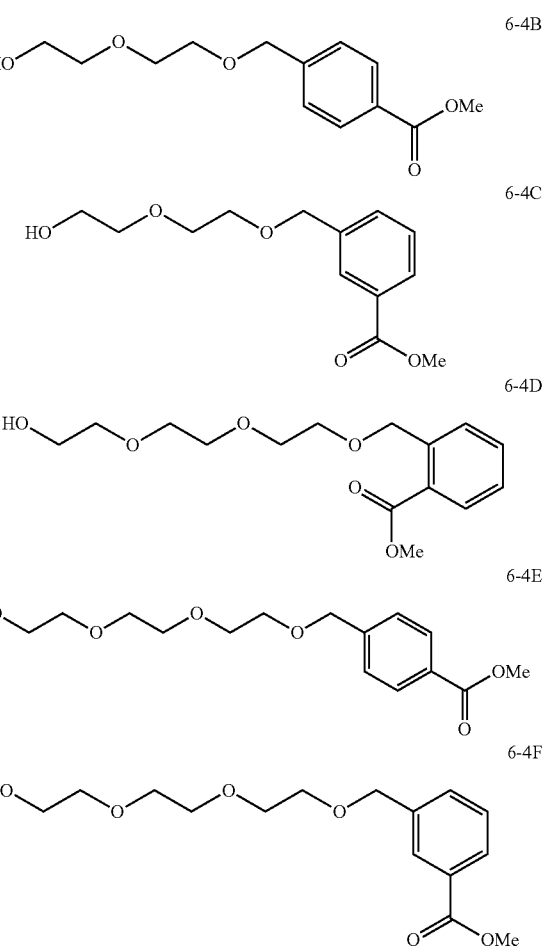

6-3B (4 g, 12.12 mmol) was used to prepare 6-4B (2.7 g, 90%). MS (ESI): m/z 240 (M-CH₃+1)⁺.

6-3C (0.3 g, 0.88 mmol) was used to prepare 6-4C (300 mg, 100%). MS (ESI): m/z 255 (M+1)⁺.

6-3D (260 mg, 0.65 mmol) was used to prepare 6-4D (140 mg, 70%). MS (ESI): m/z 299.0 (M+1)⁺.

6-3E (450 mg, 1.178 mmol) was used to prepare 6-4E (210 mg, 60%). MS (ESI): m/z 299.3 (M+1)⁺.

6-3F (550 mg, 1.43 mmol) was used to prepare 6-4F (280 mg, 65%). MS (ESI): m/z 299.3 (M+1)⁺.

2-[2-(2-Methanesulfonyloxy-ethoxy)-ethoxymethyl]-benzoic Acid Methyl Ester (6-5A)

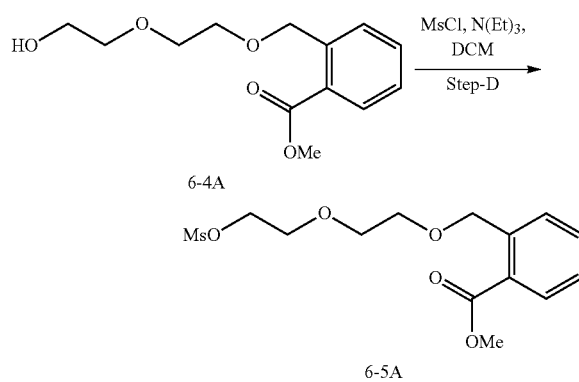

Methane sulfonylchloride (0.05 mL, 0.7 mmol) at 0° C. was added to a solution of 6-4A (150 mg, 0.5 mmol) in DCM (5 mL) and triethylamine (0.13 mL, 0.7 mmol) and stirred at RT for 1 hr. The reaction mixture was diluted with excess DCM (50 mL) and washed with water (50 mL), brine (20 mL) and dried over Na$_2$SO$_4$, organic phase concentrated under reduced pressure to get 6-5A (170 mg, 0.51 mmol, 87% yield) as a yellow color liquid.

The above procedure was adapted to prepare the following compounds:

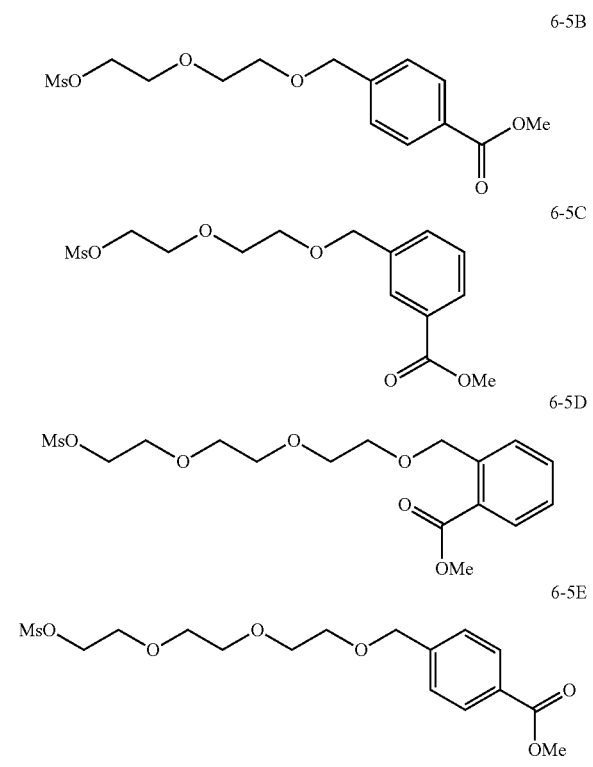

6-4B (2.7 g, 8.49 mmol) was used to prepare 6-5B (2.7 g, 77%). MS (ESI): m/z 333.5 (M+1)⁺.

6-4C (0.3 g, 1.181 mmol) was used to prepare 6-5C (280 mg, 46%). MS (ESI): m/z 350.1 (M+18)⁺.

6-4D (300 mg, 1 mmol) was used to prepare 6-5D (370 mg, 97%). MS (ESI): m/z 377.0 (M+1)⁺.

6-4E (200 mg, 0.671 mmol) was used to prepare 6-5E (220 mg, 87%). MS (ESI): m/z 377.3 (M+1)⁺.

6-4F (280 mg, 0.939 mmol) was used to prepare 6-5F (340 mg, 95%). MS (ESI): m/z 377.3 (M+1)⁺.

2-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic Acid Methyl Ester (6-6A)

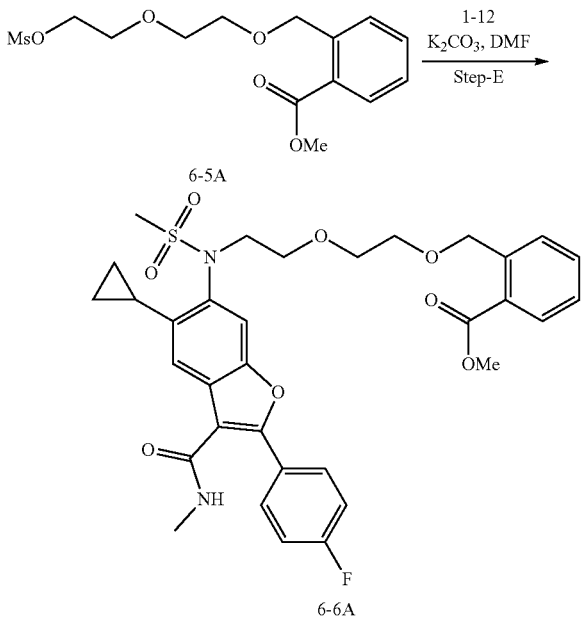

To a solution of 1-12 (141 mg, 0.350 mmol) in DMF (5 mL) was added potassium carbonate (144 mg, 1.04 mmol) followed by 6-5A (140 mg, 0.4 mmol), and catalytic amount of TBAI then stirred at 70° C. for 16 hr. The reaction mixture was cooled to RT and diluted with EtOAc (50 mL) washed with water (50 mL), brine (25 mL) and dried over Na$_2$SO$_4$, organic phase was concentrated under reduced pressure. The crude compound was purified using combi flash column chromatography (20% EtOAc in hexane) to afford 6-6A (120 mg, 0.188 mmol, 46.9% yield). MS (ESI): m/z 639.4 (M+1)⁺.

The above procedure was adapted to prepare the following compounds:

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic Acid Methyl Ester (6-6B)

6-5B (2.7 g, 8.13 mmol) was used to prepare 6-6B (2.5 g, 48%). MS (ESI): m/z 638.8 (M+1)$^+$.

3-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic acid methyl ester (6-6C)

6-5C (0.15 g, 0.45 mmol) was used to prepare 6-6C (0.08 g, 39.4%). MS (ESI): m/z 639.0 (M+1)$^+$.

2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-benzoic acid methyl ester (6-6D)

6-5D (170 mg, 0.45 mmol) was used to prepare 6-6D (115 mg, 51.8%). MS (ESI): m/z 683.6 (M+1)$^+$.

4-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-benzoic acid methyl ester (6-6E)

6-5E (210 mg, 0.55 mmol) was used to prepare 6-6E (180 mg, 53%). MS (ESI): m/z 683.5 (M+1)$^+$.

3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-benzoic acid methyl ester (6-6F)

6-5F ((340 mg, 0.90 mmol) was used to prepare 6-6F (240 mg, 47%). MS (ESI): m/z 682.7 (M+1)$^+$.

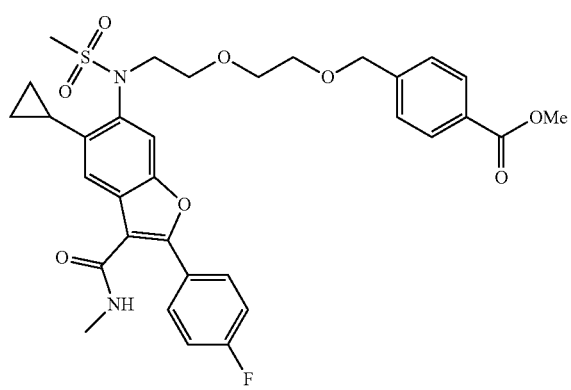
6-6B

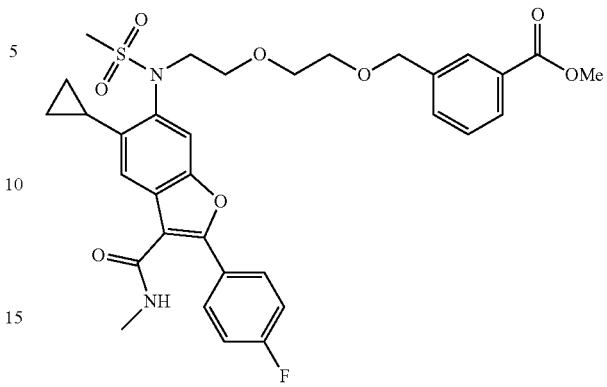
6-6C

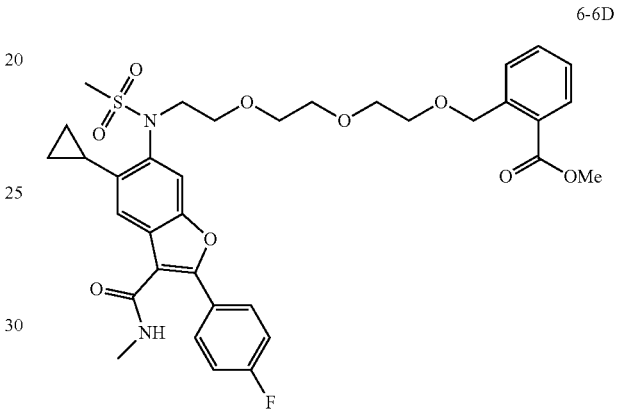
6-6D

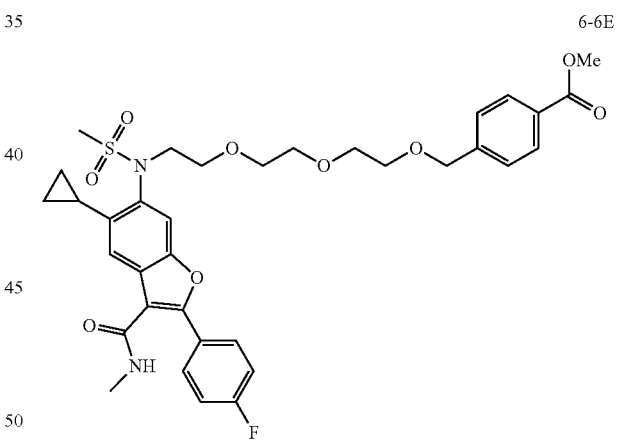
6-6E

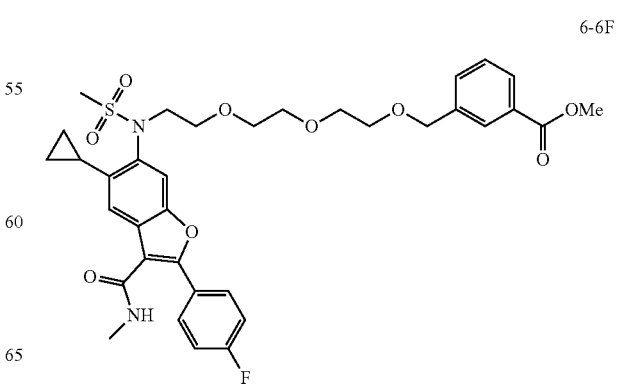
6-6F

2-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic Acid (6-7A)

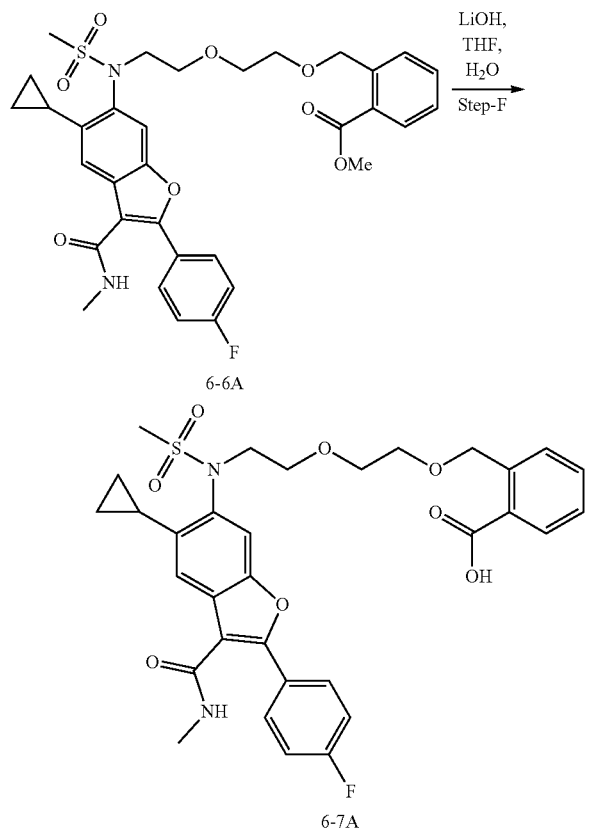

To a solution of 6-6A (50 mg, 0.07 mmol) in THF, MeOH and water (4:1:1) was added LiOH (11 mg, 0.47 mmol) and stirred at RT for 16 hr. After completion of the reaction as indicated by TLC, the reaction mixture was neutralized with 1N HCl and then extracted with EtOAc (2×50 mL). The combined organic layer was washed with brine (25 mL), dried over $Na_2SO_4$, and concentrated. The crude compound was purified by pentane washings to obtain 6-7A (25.5 mg, 0.04 mmol, 51.8% yield) as an off-white solid. MS (ESI): m/z 623.3 (M+1)$^+$.

The above procedure was adapted to prepare the following compounds:

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic Acid (6-7B)

6-6B (2.4 g, 3.761 mmol) was used to prepare 6-7B (1.2 g, 52%). MS (ESI): m/z 625.5 (M+1)$^+$.

3-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic Acid (6-7C)

6-6C (0.05 g, 0.073 mmol) was used to prepare 6-7C (0.03 g, 66%). MS (ESI): m/z 625.0. (M+1)$^+$.

2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-benzoic Acid (6-7D)

6-6D (80 mg, 0.11 mmol) was used to prepare 6-7D (35 mg, 44%). MS (ESI): m/z 669.3 (M+1)$^+$.

4-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-benzoic Acid (6-7E)

6-6E (100 mg, 0.14 mmol) was used to prepare 6-7E (45 mg, 46%). MS (ESI): m/z 667.0. (M−1)$^+$.

3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxymethyl}-benzoic Acid (6-7F)

6-6F (100 mg, 0.14 mmol) was used to prepare 6-7F (50 mg, 51%). MS (ESI): m/z 691.5 (M+23)$^+$.

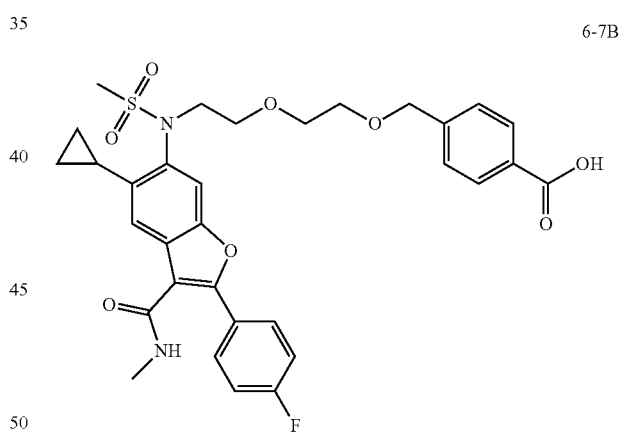

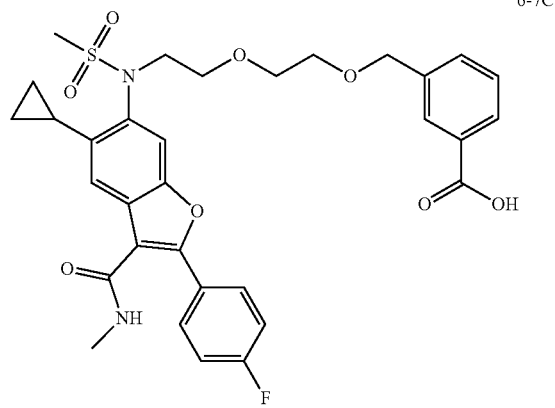

-continued

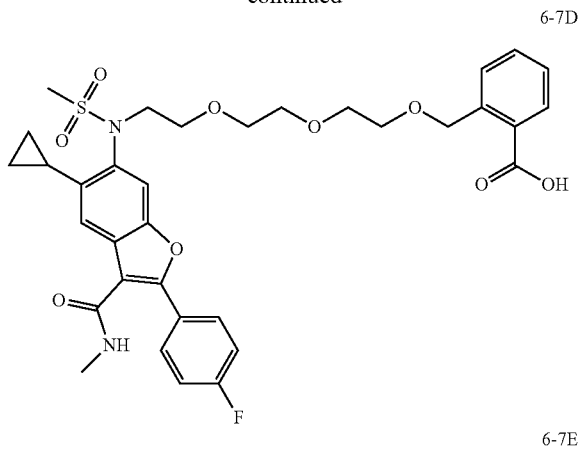

6-7D

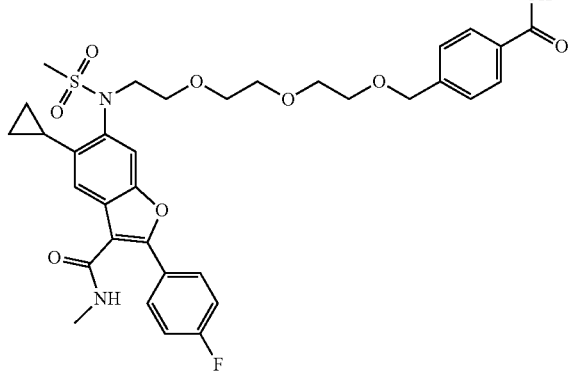

6-7E

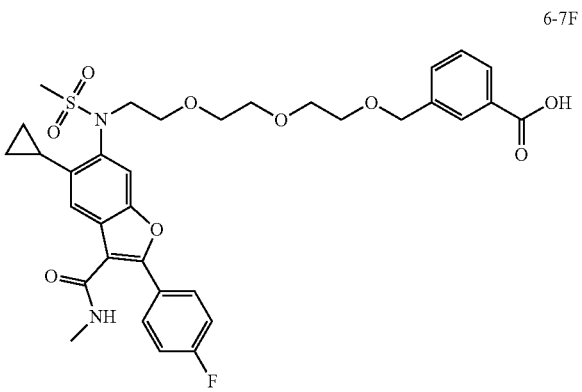 [SMILES: CNC(=O)c1c(-c2ccc(F)cc2)oc2cc(N(CCOCCOCCOCc3cccc(C(=O)O)c3)S(C)(=O)=O)c(C3CC3)cc12]

6-7F

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic Acid Ethyl Ester (6-8B1)

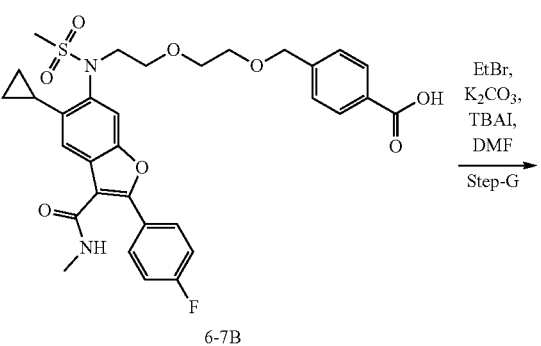

6-7B

-continued

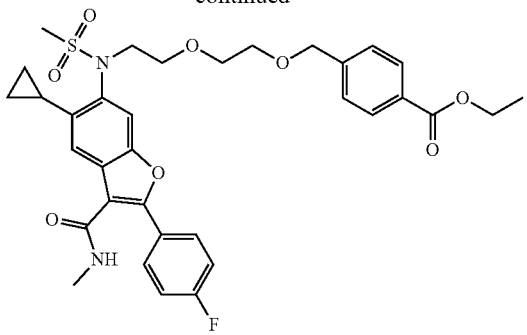

6-8B1

To a solution of 6-7B (50 mg, 0.08 mmol) in DMF (5 mL), was added potassium carbonate (13 mg, 0.09 mmol) followed by ethyl bromide (1-bromo ethane; 0.9 mL, 0.08 mmol), catalytic amount of TBAI then stirred at RT for 16 hr. The reaction was diluted with EtOAc (50 mL) washed with water (50 mL), brine (10 mL) and dried over $Na_2SO_4$, and the organic phase was concentrated under reduced pressure. The crude compound was purified by giving pentane washings to afford 6-8B1 (10.21 mg, 0.15 mmol, 20% yield). MS (ESI): m/z 653.2 $(M+1)^+$.

The above procedure was adapted to prepare the following compounds:

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic Acid Propyl Ester (6-8B2)

1-Bromo propane (13 mg, 0.09 mmol) was used to prepare 6-8B2 (32 mg, 66%). MS (ESI): m/z 695.6 $(M+1)^+$.

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic Acid Butyl Ester (6-8B3)

1-Bromo butane (6 mg, 0.04 mmol) was used to prepare 6-8B3 (15 mg, 55%). MS (ESI): m/z 681.6 $(M+1)^+$.

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic Acid Pentyl Ester (6-8B4)

1-Bromo pentane (18.1 g, 0.12 mmol) was used to prepare 6-8B4 (22 mg, 40%). MS (ESI): m/z 716.7 $(M+23)^+$.

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic Acid Carbamoylmethyl Ester (6-8B5)

2-Chloro acetamide (50 mg, 0.08 mmol) was used to prepare 6-8B5 (3.7 mg, 6.2%). MS (ESI): m/z 682.0 $(M+1)^+$.

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic Acid Methylsulfanylmethyl Ester (6-8B6)

Chloro-methylsulfanyl-methane (50 mg, 0.08 mmol) was used to prepare 6-8B6 (40 mg, 72%). MS (ESI): m/z 685.0 $(M+1)^+$.

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic Acid Benzyl Ester (6-8B7)

Bromo benzene (50 mg, 0.08 mmol) was used to prepare 6-8B7 (30 mg, 52%). MS (ESI): m/z 715.0 (M+1)$^+$.

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-benzoic Acid Ethoxycarbonylmethyl Ester (6-8B8)

Ethyl 2-bromoacetate (11.7 mg, 0.071 mmol) was used to prepare 6-8B8 (32 mg, 71%). MS (ESI): m/z 711.6 (M+1)$^+$.

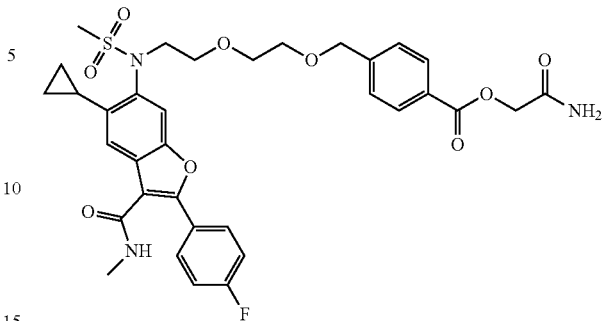
6-8B5

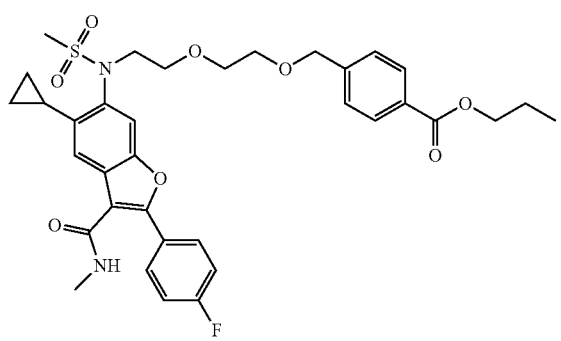
6-8B2

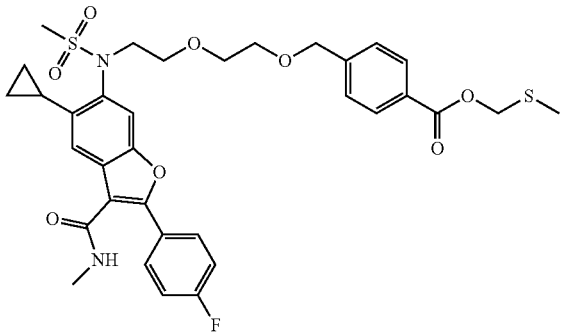
6-8B6

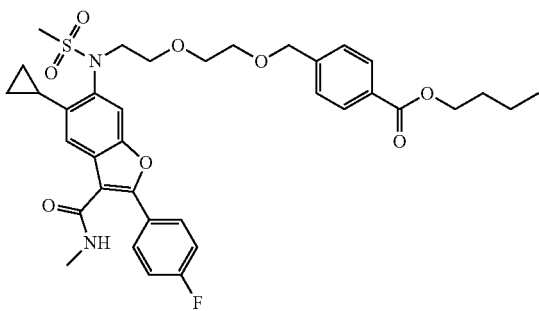
6-8B3

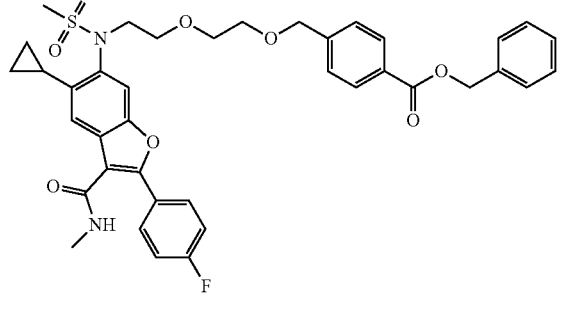
6-8B7

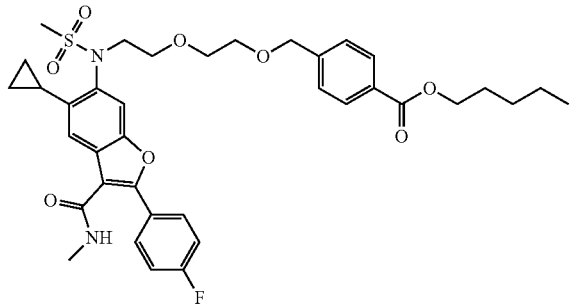
6-8B4

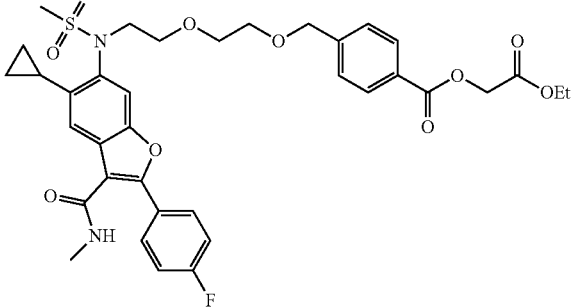
6-8B8

Example 7

2-(tert-Butoxycarbonylamino) Ethyl Methanesulfonate (7-2)

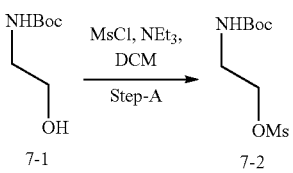 [SMILES: CC(C)(C)OC(=O)NCCO ; CC(C)(C)OC(=O)NCCOS(C)(=O)=O]

Methane sulfonylchloride (2.4 mL, 31.25 mmol) was added to a solution tert-butyl 2-hydroxy ethylcarbamate 7-1 (5 g, 31.25 mmol) in DCM (40 mL) and triethylamine (6.5 mL, 46.87 mmol) at 0° C. and stirred at RT for 4 hr. The reaction mixture was diluted with water (100 mL) extracted with DCM (3×150 mL). The combined organic layers were washed with brine (100 mL), dried over $Na_2SO_4$ and concentrated. The crude residue was purified by flash column chromatography (100-200 silica) using 10% EtOAc in hexanes to afford 7-2 (3.5 g, 14.64 mmol, 47% yield) as gummy liquid.

Tert-Butyl 2-(N-(5-cyclopropyl-2-(4-fluorophenyl)-3-(methylcarbamoyl) benzofuran-6-yl) Methylsulfonamido)-ethylcarbamate (7-3)

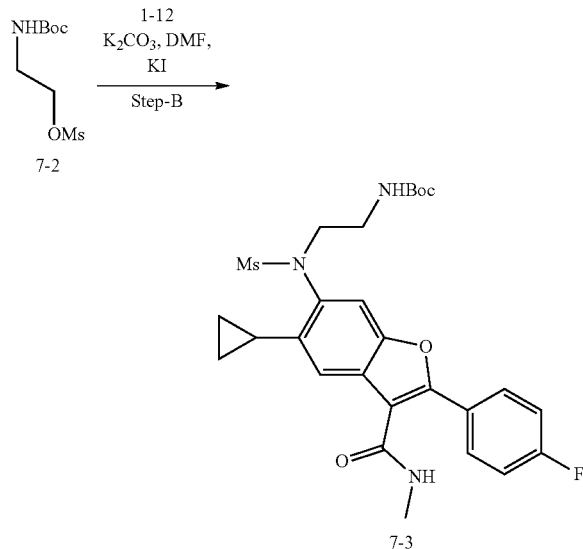

To a stirred solution of 1-12 (0.06 g, 0.15 mmol) in DMF (5 mL) was added potassium carbonate (0.062 g, 0.44 mmol) followed by 7-2 (0.053 g, 0.22 mmol), and a catalytic amount of TBAI at 80° C. for 10 hr. The reaction mixture was cooled to RT and diluted with EtOAc (25 mL) washed with water (2×15 mL), brine (15 mL), dried over $Na_2SO_4$ and concentrated. The crude residue was purified by flash column chromatography (100-200 silica) using 30% EtOAc in hexanes to afford 7-3 (0.02 g, 2.09 mmol, 24% yield) as an off-white solid.

6-(N-(2-Aminoethyl)-methylsulfonamido)-5-cyclopropyl-2-(4-fluorophenyl)-N-methyl Benzofuran-3-carboxamide (7-4)

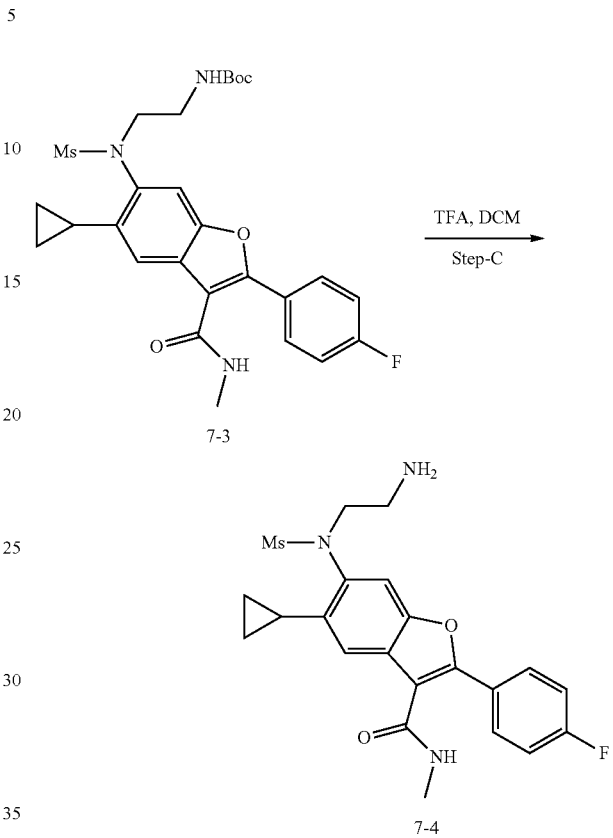

To a stirred solution of 7-3 (0.1 g, 0.18 mmol) in DCM (5 mL) was added TFA (0.06 mL) at 0° C. and stirred at RT for 2 hr. The solvents were evaporated under reduced pressure and the crude residue was purified by washings with pentane to afford 7-4 (0.04 g, 0.09 mmol, 50% yield) as a gummy liquid.

Tert-Butyl 2-(2-(N-(5-cyclopropyl-2-(4-fluorophenyl)-3-(methylcarbamoyl)benzofuran-6-yl) methylsulfonamido)-ethylamino)-2-oxoethylcarbamate (7-5)

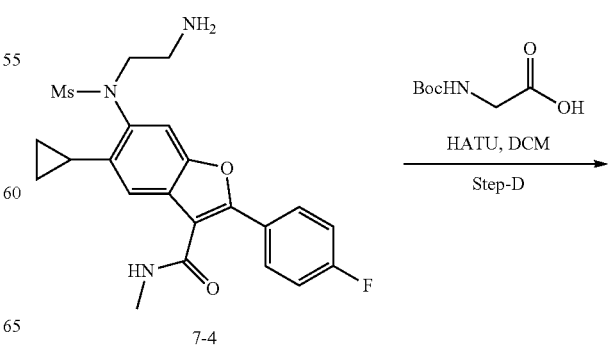

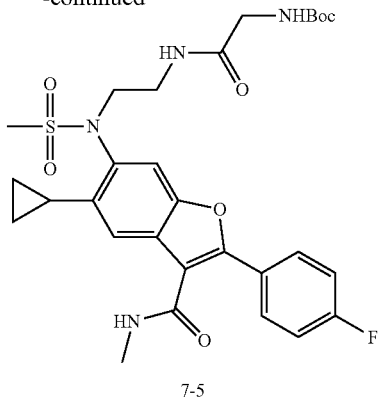

7-5

To a stirred solution of 7-4 (15 mg, 0.03 mmol) in DCM (5 mL) was added 1-ethyl-3-(3-dimethylaminopropyl)carbodiimide (EDCI; 0.08 g, 0.042 mmol), hydroxybenzotriazole (HOBT; 0.06 g, 0.04 mmol), and triethylamine (0.01 mL, 0.01 mmol), followed by the addition of 2-(tert-butoxycarbonylamino)acetic acid (0.05 g, 0.04 mmol) at 0° C. and continued stirring at RT for 10 hr. The reaction mixture was diluted with ice cold water (20 mL) and extracted with EtOAc (3×10 mL). The combined organic layers were washed with water (2×25 mL), brine (30 mL), dried over Na₂SO₄ and concentrated. The crude residue was purified by prep-TLC to afford 7-5 (0.01 g, 0.01 mmol, 50% yield) as a yellow thick liquid. MS (ESI): m/z 503.3 (M-Boc)⁺.

6-(N-(2-(2-Aminoacetamido)-ethyl)-methylsulfonamido)-5-cyclopropyl-2-(4-fluorophenyl)-N-methyl-benzofuran-3-carboxamide (7-6)

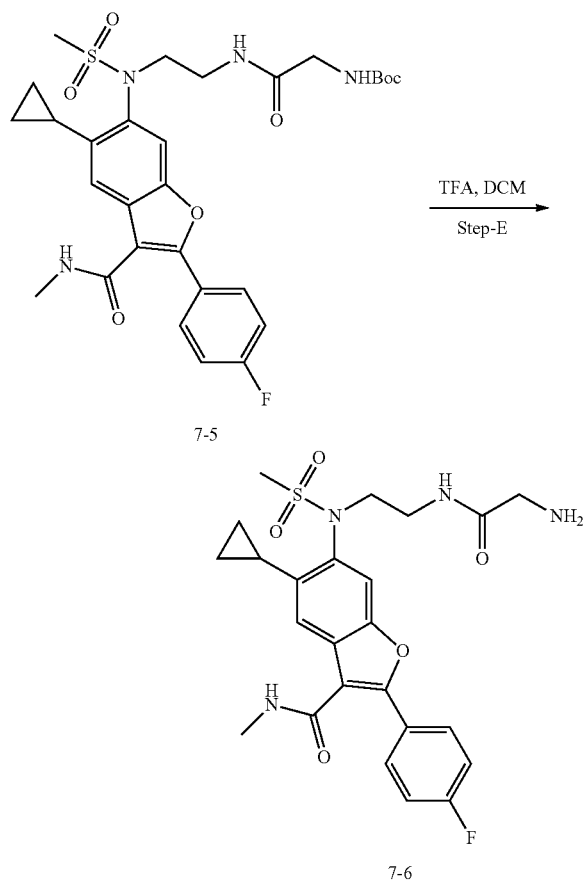

To a stirred solution of 7-5 (0.05 g, 0.07 mmol) in DCM (5 mL) was added TFA (0.3 mL) at 0° C. The reaction mixture was stirred at RT for 1 hr. The solvents were evaporated under reduced pressure and the crude residue was purified by washings with pentane to afford 7-6 (0.01 g, 0.02 mmol, 25% yield) as gummy liquid. MS (ESI): m/z: 503.2 (M+1)⁺.

4-{[(2-{[5-Cyclopropyl-2-(4-fluoro-phenyl)-3-methylcarbamoyl-benzofuran-6-yl]-methanesulfonylamino}-ethylcarbamoyl)-methyl]-carbamoyl}-butyric Acid (7-7)

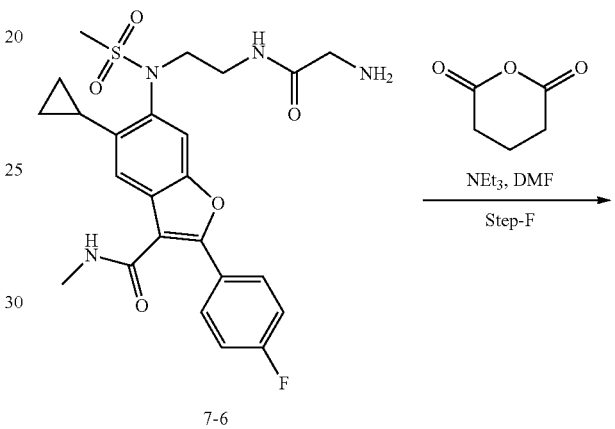

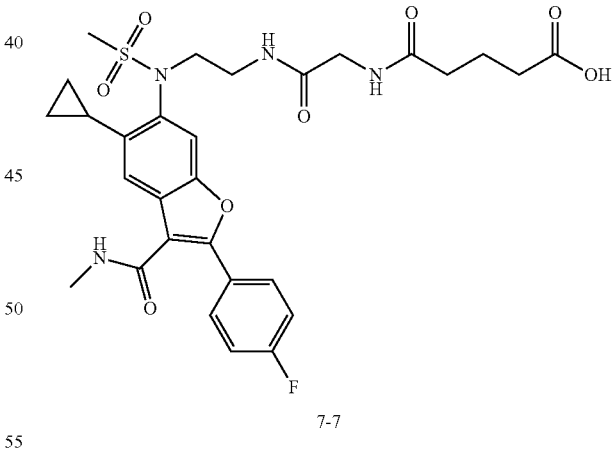

7-7

To a stirred solution of 7-6 (0.02 g, 0.04 mmol) in DMF (5 mL) was added triethylamine (0.02 g, 0.19 mmol) followed by dihydro-pyran-2,6-dione (0.01 g, 0.09 mmol), and catalytic amount of TBAI at RT for 16 hr. The reaction mixture was diluted with water (15 mL) and extracted with EtOAc (3×20 mL) washed with water (2×50 mL), brine (50 mL), dried over Na₂SO₄ and concentrated. The residue was purified by prep-TLC to afford 7-7 (5 mg, 0.008 mmol, 21% yield) as an off-white solid. MS (ESI): m/z 617.2 (M+1)⁺.

111

4-(3-{[(2-{[5-Cyclopropyl-2-(4-fluoro-phenyl)-3-methylcarbamoyl-benzofuran-6-yl]-methanesulfonyl-amino}-ethylcarbamoyl)-methyl]-carbamoyl}-phenyl)-butyric Acid Ethyl Ester (7-9)

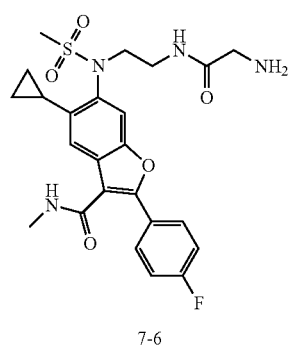

7-6

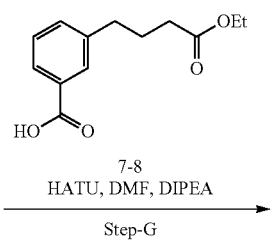

7-8
HATU, DMF, DIPEA
Step-G

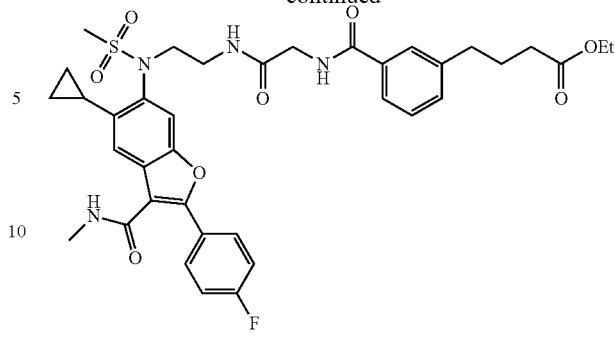

7-9

To a stirred solution of 7-6 (50 mg, 0.09 mmol) in DCM (5 mL) was added HATU (75 mg, 0.19 mmol), DIPEA (0.05 mL, 0.29 mmol) and 7-8 at 0° C. and the reaction was continued for 12 hr at RT. The reaction mixture was diluted with water (50 mL), extracted with EtOAc (3×50 mL). The combined organic layers were washed with brine (50 mL), dried over $Na_2SO_4$ and concentrated to afford 7-9 (60 mg, crude) as a brown thick mass. MS (ESI): m/z 721.3 $(M+1)^+$.

112

4-(3-{[(2-{[5-Cyclopropyl-2-(4-fluoro-phenyl)-3-methylcarbamoyl-benzofuran-6-yl]-methanesulfonyl-amino}-ethylcarbamoyl)-methyl]-carbamoyl}-phenyl)-butyric Acid (7-10)

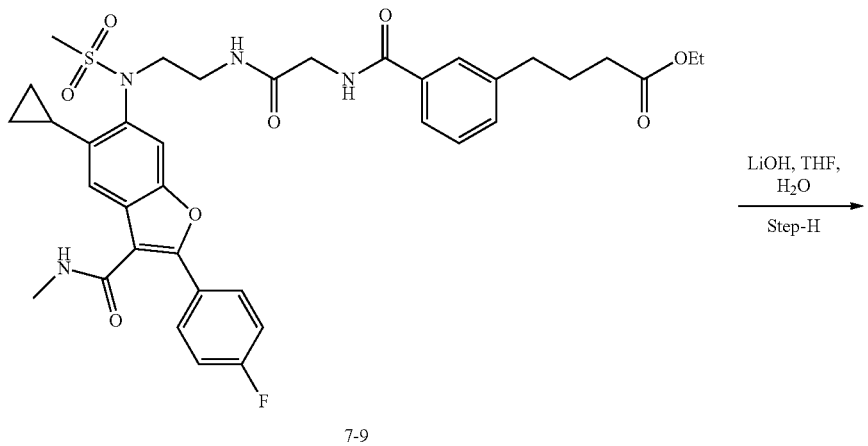

7-9

LiOH, THF, $H_2O$
Step-H

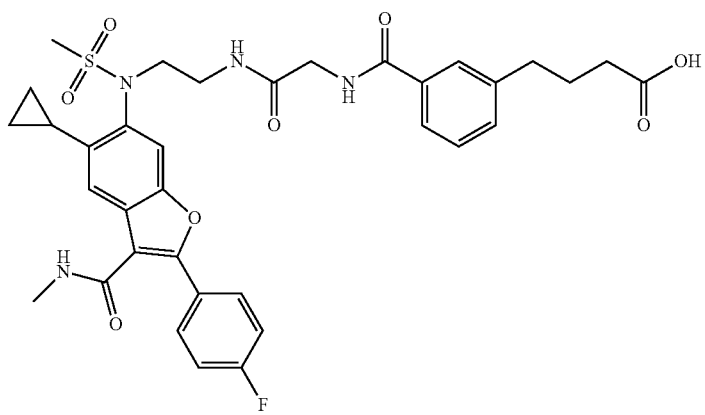

7-10

To a stirred solution of 7-9 (40 mg, 0.05 mmol) in THF and water (3 mL; 1:1) was added LiOH (5 mg, 0.16 mmol) at 0° C. and reaction was continued at RT for 5 hr. After completion of the reaction, solvents were evaporated under reduced pressure. The residue extracted with ether (20 mL). The aqueous layer was neutralized with 1N HCl (5 mL) followed by extracted with EtOAc (3×20 mL). The combined organic layers were washed with brine (2×20 mL), dried over Na$_2$SO$_4$ and concentrated. The crude residue was purified by preparative HPLC to afford 7-10 (3.5 mg, 7.3%) as light thick mass.

Example 8

2-Bromoethyl 2-aminoacetate (8-2)

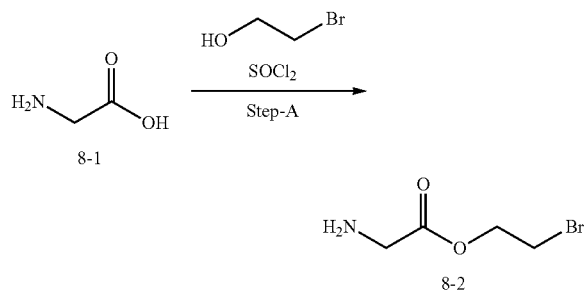

To a stirred solution of 2-aminoacetic acid 8-1 (1 g, 13.33 mmol) in DCM (25 mL) was added thionyl chloride (1.47 mL, 19.99 mmol) and 2-bromoethanol (1.65 g, 13.33 mmol) at 0° C., and stirred at RT for 10 hr. The reaction mixture was diluted with water (50 mL) and extracted with DCM (3×75 mL). The combined organic layers were concentrated and dried at reduced pressure. The crude residue was purified by washings with pentane/ether to afford 8-2 (0.5 g, 2.77 mmol, 20% yield) as an off-white solid.

2-Bromoethyl 2-(tert-butoxycarbonylamino)acetate (8-3)

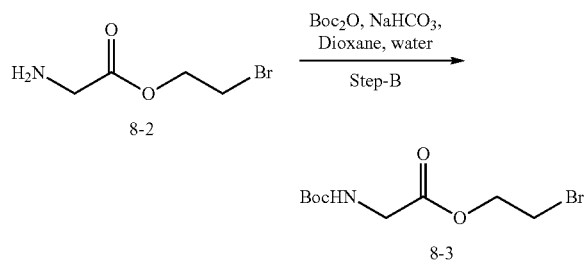

To a stirred solution of 8-2 (0.5 g, 2.77 mmol) in dioxane (5 mL) and water (5 mL) was added Boc anhydride (0.69 mL, 3.02 mmol) and sodium bicarbonate (0.23 g, 2.77 mmol) at 0° C., and stirring continued at RT for 16 hr. The reaction mixture was quenched with water (20 mL) and extracted with EtOAc (3×25 mL). The combined organic layers were washed with water (2×20 mL), brine (30 mL), dried over Na$_2$SO$_4$ and concentrated. The crude residue was purified by washings with pentane and ether to afford 8-3 (0.3 g, 1.06 mmol, 52% yield) as a yellow thick liquid.

2-(N-(5-Cyclopropyl-2-(4-fluorophenyl)-3-(methylcarbamoyl)benzofuran-6-yl)-methylsulfonamido)-ethyl 2-(tert-butoxycarbonylamino)acetate (8-3)

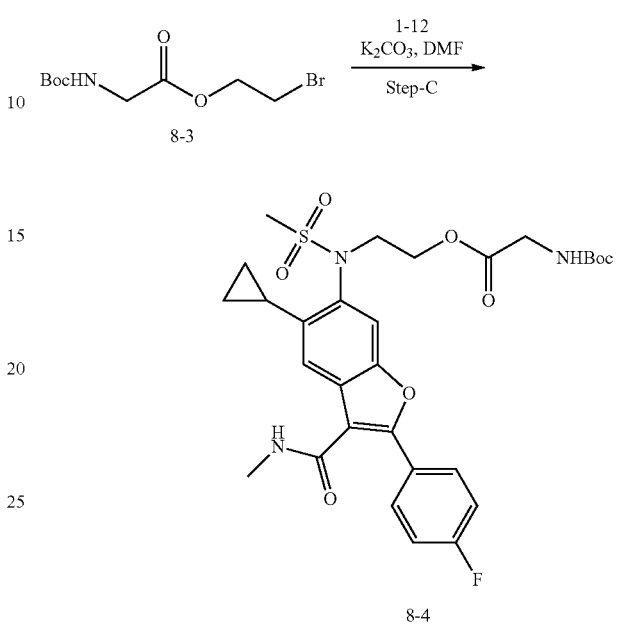

To a stirred solution of 1-12 (0.25 g, 0.62 mmol) in DMF (10 mL) was added potassium carbonate (0.25 g, 1.86 mmol) followed by 8-3 (0.23 g, 0.82 mmol) and catalytic amount of TBAI at 80° C. for 10 hr. The reaction mixture was cooled to RT and diluted with EtOAc (40 mL) washed with water (2×25 mL), brine (30 mL) and dried over Na$_2$SO$_4$ and concentrated. The crude residue was purified by flash column chromatography (100-200 silica) using 30% EtOAc in hexanes to afford 8-4 (0.26 g, 0.43 mmol, 50% yield) as a brown solid.

2-(N-(5-Cyclopropyl-2-(4-fluorophenyl)-3-(methylcarbamoyl)benzofuran-6-yl)-methylsulfonamido)-ethyl 2-aminoacetate (8-5)

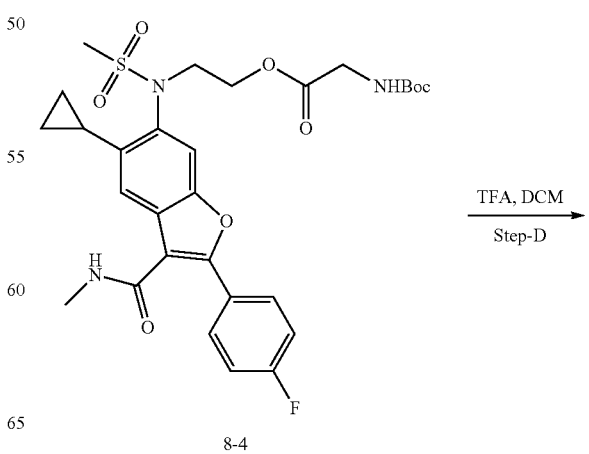

-continued

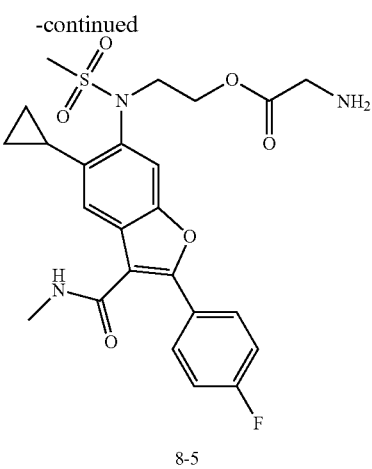

8-5

To a stirred solution of 8-4 (0.05 g, 0.08 mmol) in DCM (5 mL) was added trifluoroacetic acid (1 mL) at 0° C., and stirred at RT for 1 hr. The solvents were evaporated under reduced pressure and the crude residue was purified by washings with pentane and ether to afford 8-5 (0.02 g, 0.05 mmol, 47% yield) as a gummy liquid. MS (ESI): m/z 503.8 (M+1)$^+$.

4-[(2-{[5-Cyclopropyl-2-(4-fluoro-phenyl)-3-methylcarbamoyl-benzofuran-6-yl]-methanesulfonyl-amino}-ethoxycarbonylmethyl)-carbamoyl]-butyric Acid (8-6)

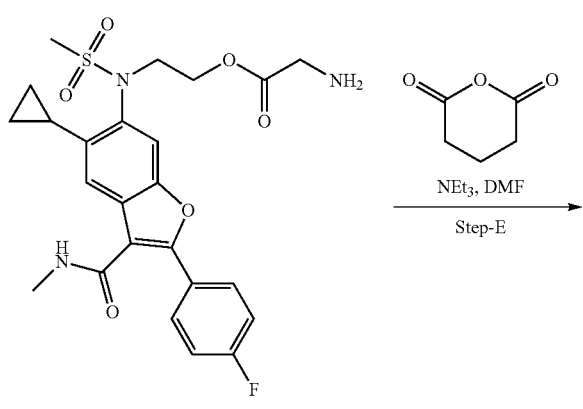

8-5

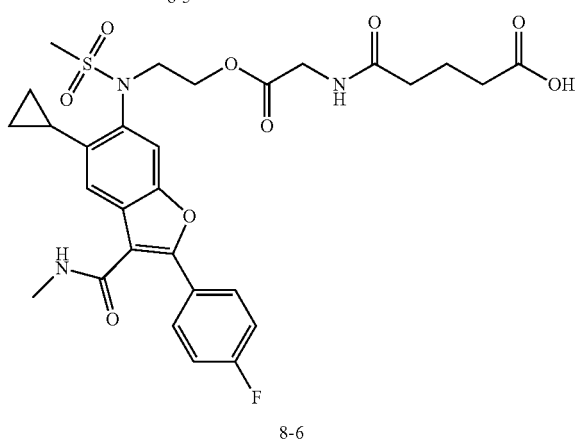

8-6

To a stirred solution of 8-5 (0.025 g, 0.05 mmol) in DMF (5 mL) was added triethylamine (0.03 mL, 0.25 mmol) followed by dihydro-pyran-2,6-dione (0.014 g, 0.12 mmol) and catalytic amount of TBAI at RT for 10 hr. The reaction mixture was diluted with water (15 mL) and extracted with EtOAc (3×20 mL), washed with water (2×50 mL), brine (50 mL), dried over Na$_2$SO$_4$ and concentrated. The crude residue was purified by prep-TLC to afford 8-6 (5 mg, 0.008 mmol, 16% yield) as an off-white solid. MS (ESI): m/z 615.8 (M−1)$^-$.

Example 9

1-(3-(Azidomethyl) Phenyl) Ethanone (9-2)

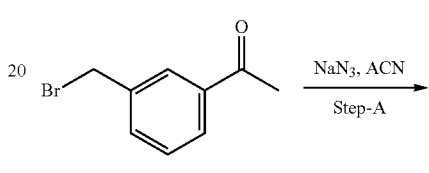

9-1

9-2

To a stirred solution of 1-(3-(bromomethyl) phenyl) ethanone 9-1 (3 g, 14.08 mmol) in ACN (42 mL) was added sodium azide (1.38 g, 21.32 mmol) at 0° C. The reaction mixture was warmed to reflux for 10 hr under nitrogen atmosphere. The solvents were evaporated under reduced pressure and the crude residue was diluted with water (50 mL) and extracted with EtOAc (3×50 mL). The combined organic layers were washed with brine (2×30 mL), dried over Na$_2$SO$_4$ and concentrated. The crude residue was purified by flash column chromatography (100-200 silica) using 10% EtOAc/pet. ether to afford 9-2 (2.23 g, 13.09 mmol, 93% yield) as a colorless liquid.

1-(3-(Aminomethyl)-phenyl)-ethanone (9-3)

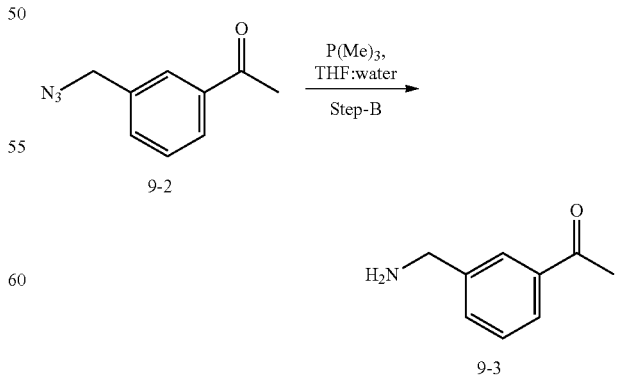

9-2

9-3

To a stirred solution of 9-2 (2 g, 11.42 mmol) in THF:H$_2$O (20 mL) was added trimethyl phosphine (57 mL, 57.15 mmol) at 0° C., and the reaction mixture was stirred at RT for 10 hr. The reaction mixture was diluted with water (60 mL), extracted with EtOAc (3×60 mL). The combined organic layers were washed with brine (2×30 mL), dried over $Na_2SO_4$ and concentrated. The crude residue was purified by washings with ether and pentane to afford 9-3 (1.36 g, 9.14 mmol, 77% yield) as a yellow thick liquid.

Tert-Butyl 3-acetylbenzylcarbamate (9-4)

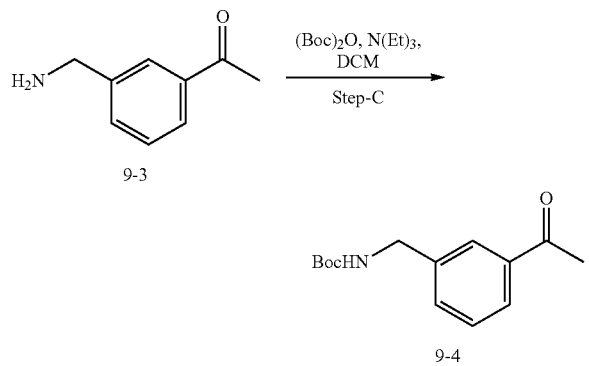

To a stirred solution of 9-3 (0.3 g, 2.013 mmol) in DCM (10 mL) was added Boc anhydride (0.5 mL, 2.19 mmol) and triethylamine (0.7 mL, 5.03 mmol) at 0° C., and the stirring was continued at RT for 20 hr. The reaction mixture was quenched with water (30 mL) and extracted with DCM (3×50 mL). The combined organic layers were washed with water (2×40 mL), brine (30 mL), dried over $Na_2SO_4$ and concentrated. The crude residue was purified by flash column chromatography (100-200 silica) using 12% EtOAc/hexanes to afford 9-4 (0.26 g, 1.06 mmol, 53% yield) as a thick yellow liquid. MS (ESI): m/z 267.1 $(M+18)^+$.

1(Z)-Ethyl 4-(3-((tert-butoxycarbonylamino)-methyl)-phenyl)-2-hydroxy-4-oxobut-2-enoate (9-5)

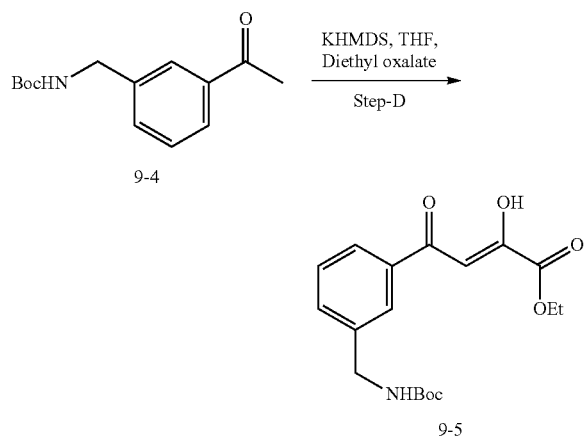

To a stirred solution of 9-4 (0.6 g, 2.41 mmol) in THF (20 mL) was added KHMDS at –78° C., and stirred the reaction mixture at –78° C. for 1 hr. Then, diethyl oxalate (0.49 mL, 3.61 mmol) was added to the reaction mixture at –78° C. and warm the reaction mixture to –60° C. for 30 min. The reaction mixture was quenched with ammonium chloride solution, extracted into EtOAc (3×40 mL). The combined organic layers were washed with brine (2×20 mL), dried over $Na_2SO_4$ and concentrated. The crude residue was purified by flash column chromatography using neutral silica (100-200 silica) 15% EtOAc/hexanes to afford 9-5 (0.55 g, 1.57 mmol, 65% yield) as a brownish gummy solid. MS (ESI): m/z 348.1 $(M-1)^-$.

4-(3-Aminomethyl-phenyl)-2-hydroxy-4-oxo-but-2-enoic Acid Ethyl Ester (9-6)

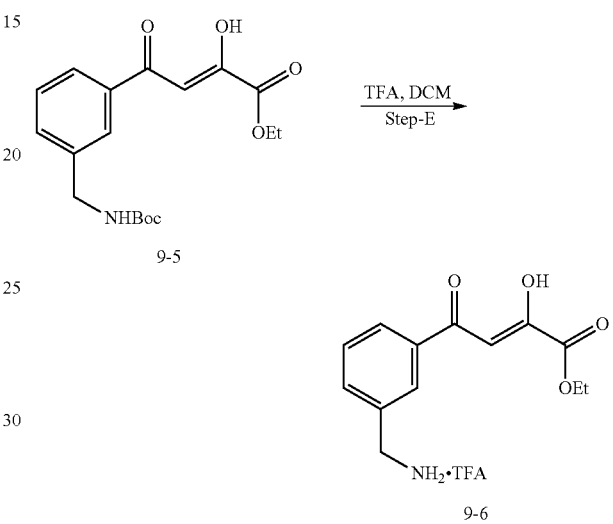

To a stirred solution of 9-5 (0.55 g, 1.57 mmol) in dioxane (20 mL) was added dioxane.HCl (10 mL) at 0° C., and stirring continued at RT for 6 hr. The solvents were evaporated under reduced pressure and the crude residue was purified by washings with pentane to afford 9-6 (0.3 g, 1.05 mmol, 66% yield) as a brown solid. MS (ESI): m/z 250.3 $(M+1)^+$.

Ethyl 2-(N-(5-cyclopropyl-2-(4-fluorophenyl)-3-(methylcarbamoyl)benzofuran-6-yl)-methylsulfona-mido)acetate (9-7)

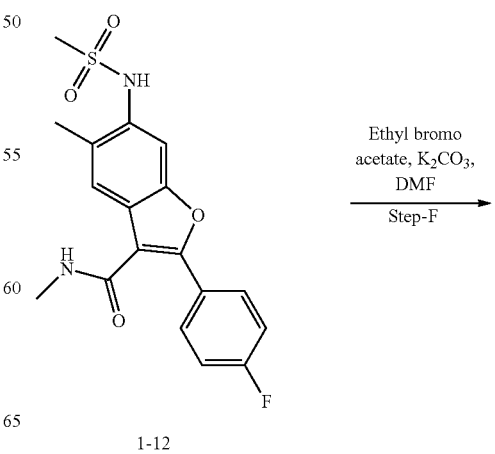

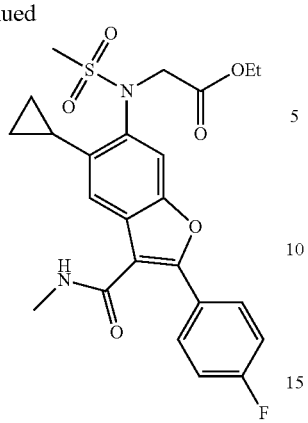

9-7

To a stirred solution of 1-12 (1 g, 2.48 mmol) in DMF (20 mL) was added potassium carbonate (1.03 g, 7.46 mmol) followed by ethyl bromoacetate (500 mg, 2.99 mmol), catalytic amount of tetrabutyl ammonium iodide at 80° C. for 16 hr. The reaction mixture was cooled to RT and diluted with EtOAc (75 mL) washed with water (2×50 mL), brine (25 mL) and dried over $Na_2SO_4$ and concentrated. The residue was purified by flash column chromatography (100-200 silica) using 2% MeOH-DCM to afford 9-7 (980 mg, 2 mmol, 80% yield) as an off-white solid. MS (ESI): m/z 489.1 $[M+H]^+$.

2-(N-(5-cyclopropyl-2-(4-fluorophenyl)-3-(methyl-carbamoyl)benzofuran-6-yl)-methyl Sulfonamide) acetic Acid (9-8)

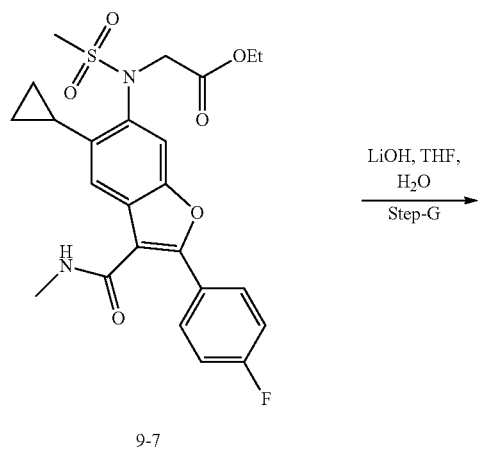

9-7

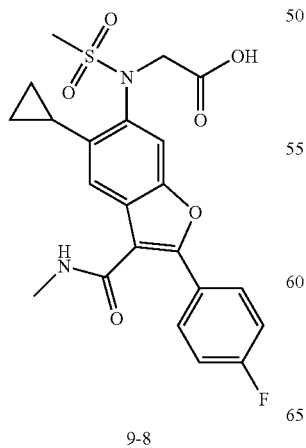

9-8

To a stirred solution of 9-7 (980 mg, 2 mmol) in THF and water (10 mL; 4:1) was added LiOH (289 mg, 12 mmol) at 0° C., and the reaction was continued at RT for 6 hr. After completion of the reaction (by TLC), solvents evaporated at rotary evaporator, residue extracted with ether (15 mL). Then aqueous layer was neutralized with 1N HCl (10 mL) followed by extracted with EtOAc (3×25 mL). The combined organic layers were washed with brine (2×15 mL), dried over $Na_2SO_4$ and concentrated. The residue was purified by washed with pentane to afford 9-8 (900 mg, 1.96 mmol, 97% yield) as a brown solid. MS (ESI): m/z 459.0 $[M-H]^+$.

Methyl 2-aminoacetate (9-10A)

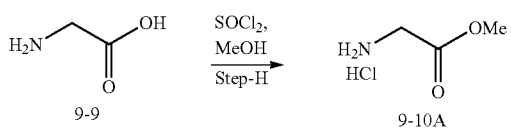 [SMILES: NCC(=O)O ; Cl ; COC(=O)CN]

To a stirred solution of 2-aminoacetic acid 8-1 (2 g, 26.64 mmol) in MeOH (20 mL) was added thionyl chloride (5.8 mL, 79.92 mmol) at 0° C., and stirred at RT for 16 hr. The solvents were evaporated under reduced pressure and the crude residue was purified by washings with pentane/ether to afford 9-10A (2.7 g, 21.6 mmol, 81% yield) as a brown solid.

The above procedure (Step-H) was adapted to prepare the following compounds:

Methylamino-acetic acid (1 g, 11.2 mmol) was used to prepare 9-10B (3 g, quantitative).

2-Amino-2-methyl-propionic acid (2 g, 29.12 mmol) was used to prepare 9-10C (4 g, quantitative).

1-Amino-cyclopropanecarboxylic acid (1 g, 9.89 mmol) was used to prepare 9-10D (1.4 g, 94%).

1-Amino-cyclopentanecarboxylic acid (1 g, 7.75 mmol) was used to prepare 9-10E (1.4 g, 94%).

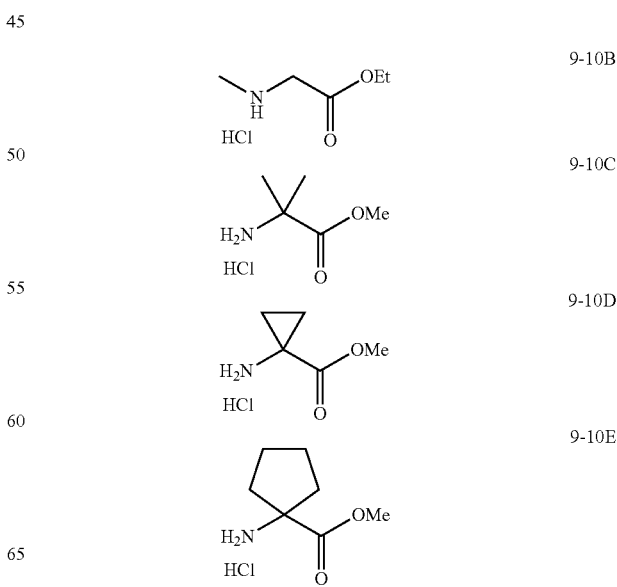

Methyl 2-(2-(N-(5-cyclopropyl-2-(4-fluorophenyl)-3-(methylcarbamoyl) benzofuran-6-yl) methylsulfonamido)acetamido)acetate (9-11A)

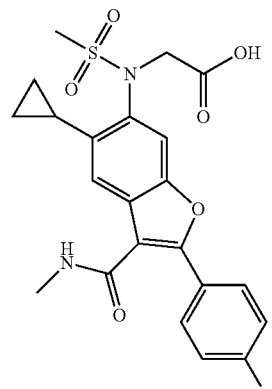

9-8

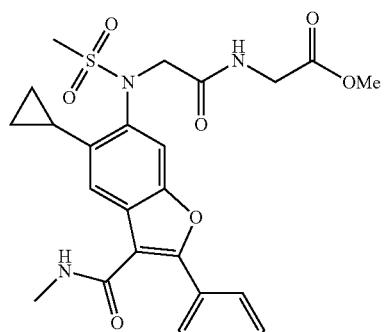

9-11A

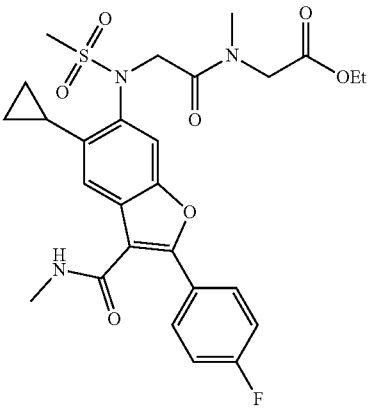

9-11B

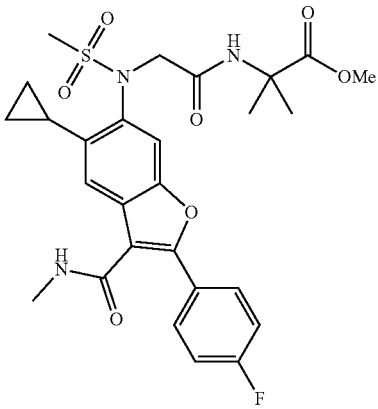

9-11C

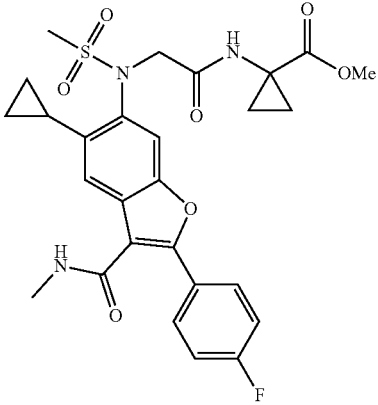

9-11D

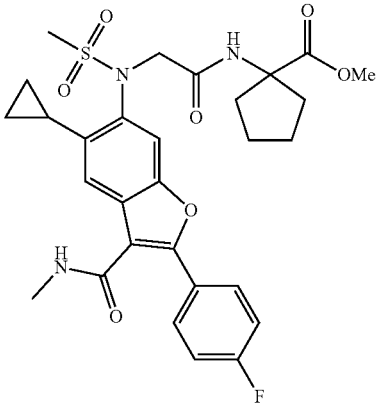

9-11E

To a stirred solution of 9-8 (0.2 g, 0.43 mmol) in DMF (10 mL) was added EDCI (0.17 g, 0.91 mmol), HOBT (0.06 g, 0.48 mmol), DIPEA (0.37 mL 2.17 mmol), followed by addition of 9-10A (0.08 g, 0.65 mmol) at 0° C. The reaction was stirred at RT for 10 hr. The reaction mixture was diluted with ice cold water (20 mL) and extracted with EtOAc (3×30 mL). The combined organic layers were washed with water (2×25 mL), brine (30 mL), dried over $Na_2SO_4$ and concentrated. The crude residue was purified by flash column chromatography (100-200 silica) using 30% EtOAc/hexanes to afford 9-11A (0.17 g, 0.32 mmol, 74% yield) as a yellow thick liquid. MS (ESI): m/z 532.1 $(M+1)^+$.

The above procedure (Step-I) was adapted to prepare the following compounds:

9-10B (63 mg, 0.54 mmol) was used to prepare 9-11B (250 mg, 83%).

9-10C (0.2 g, 0.43 mmol) was used to prepare 9-11C (0.14 g, 80%). MS (ESI): m/z 560.1 $(M+1)^+$.

9-10D (150 mg, 0.33 mmol) was used to prepare 9-11D (160 mg, 88%). MS (ESI): m/z 602.1 $[M-1]^+$.

9-10E (150 mg, 0.33 mmol) was used to prepare 9-11E (162 mg, 88%).

2-Amino-propionic acid methyl ester hydrochloride 9-10F (200 mg, 0.43 mmol; Sigma Aldrich) was used to prepare 9-11F (230 mg, 98%).

9-11F

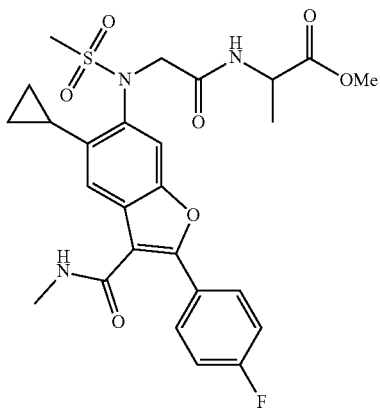

2-(2-(N-(5-Cyclopropyl-2-(4-fluorophenyl)-3-(methylcarbamoyl)benzofuran-6-yl) Methyl sulfonamido) acetamido) Acetic Acid (9-12A)

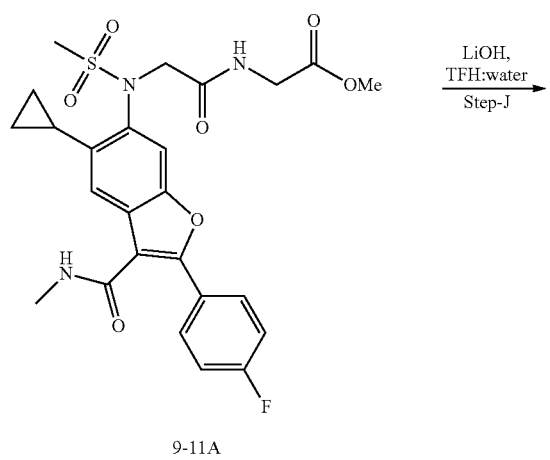

9-11A

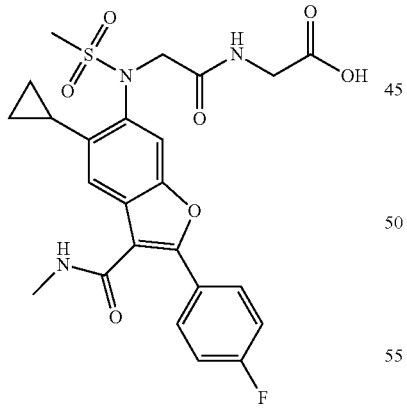

9-12A

To a stirred solution of 9-11A (0.24 g, 0.45 mmol) in THF and water (10 mL; 4:1) was added LiOH (0.04 g, 1.80 mmol) at 0° C. and reaction was continued at RT for 2 hr. After completion of the reaction (TLC), solvents evaporated at rotary evaporator, residue extracted with ether (50 mL). Then aqueous layer was neutralized with 1N HCl (10 mL) followed by extracted with EtOAc (3×50 mL). The combined organic layers were washed with brine (2×30 mL), dried over $Na_2SO_4$ and concentrated. The crude residue was purified by washed with pentane to afford 9-12A (0.107 g, 0.20 mmol, 65% yield) as a gummy liquid. MS (ESI): m/z 516.0 (M−1)⁻.

The above procedure was adapted to prepare the following compounds:

9-11B (95 mg, 0.16 mmol) was used to prepare 9-12B (60 mg, 66%). MS (ESI): m/z 530.0 (M−1).

9-11C (0.17 g, 0.32 mmol) was used to prepare 9-12C (0.12 g, 88%). MS (ESI): m/z 544.1 (M−1).

9-11D (150 mg, 0.2 mmol) was used to prepare 9-12D (110 mg, 78%). MS (ESI): m/z 542.0 [M−1].

9-11E (160 mg, 0.27 mmol) was used to prepare 9-12E (113 mg, 72%).

9-11F (190 mg, 0.39 mmol) was used to prepare 9-12F (134 mg, 73%). MS (ESI): m/z 529.9 [M−1]⁻.

9-12B

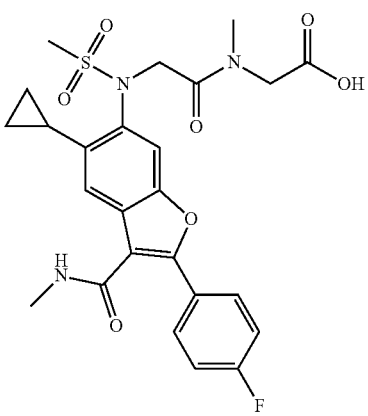

9-12C

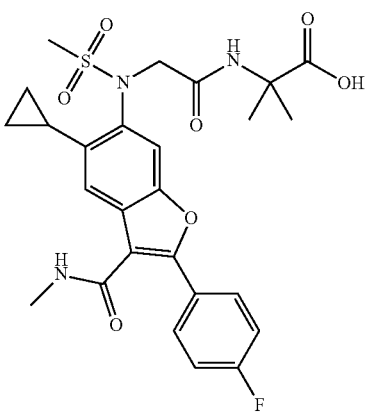

9-12D

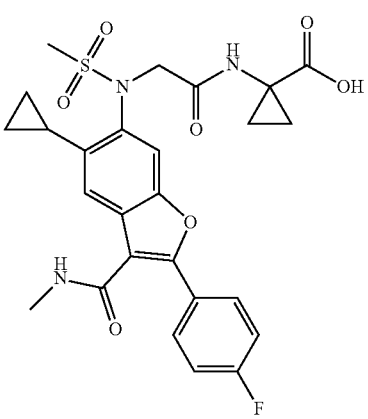

-continued

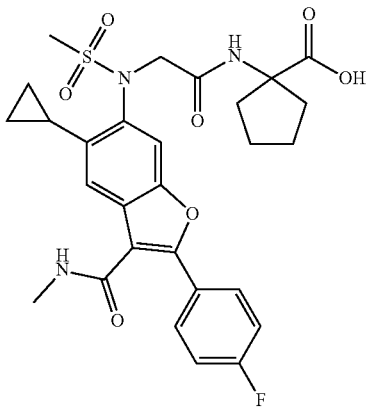

9-12E

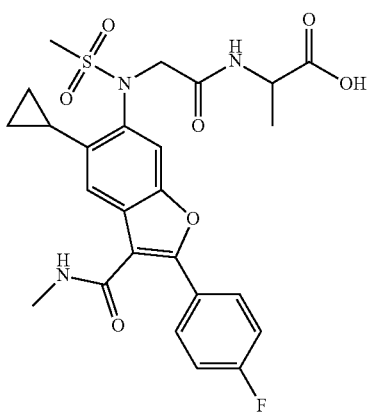

9-12F 4-(3-{[2-(2-{[5-Cyclopropyl-2-(4-fluoro-phenyl)-3-
methylcarbamoyl-benzofuran-6-yl]-methanesulfo-
nyl-amino}-acetylamino)-acetylamino]-methyl}-
phenyl)-2-hydroxy-4-oxo-but-2-enoic Acid Ethyl
Ester (9-13A)

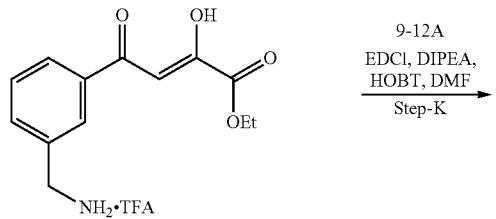

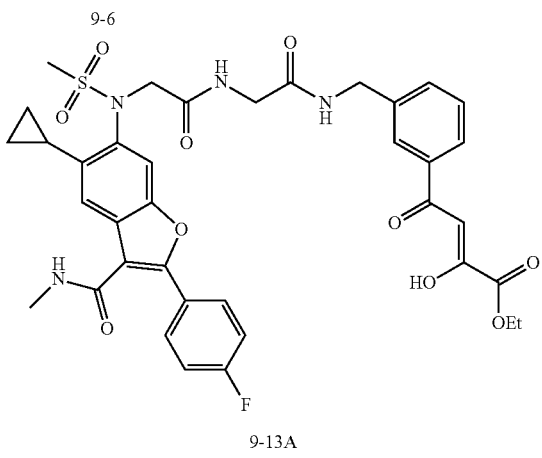

9-13A

To a stirred solution of 9-6 (0.15 g, 0.43 mmol) in DMF (8 mL) was added EDCI (0.16 g, 0.61 mmol), HOBT (0.043 g, 0.32 mmol) and DIPEA (0.25 mL, 1.45 mmol), followed by addition of 9-12A (0.12 g, 0.43 mmol) at 0° C., and reaction was continued at RT for 12 hr. The reaction mixture was diluted with ice cold water (20 mL) and extracted with EtOAc (3×30 mL). The combined organic layers were washed with water (2×25 mL), brine (30 mL), dried over $Na_2SO_4$ and concentrated. The crude residue was purified by flash column chromatography (100-200 silica) using 60% EtOAc/hexanes to afford 9-13A (0.23 g, crude) as an off-white solid. MS (ESI): m/z 749.6 $(M+1)^+$.

The above procedure was adapted to prepare the following compounds:

4-[3-({2-[(2-{[5-Cyclopropyl-2-(4-fluoro-phenyl)-3-
methylcarbamoyl-benzofuran-6-yl]-methanesulfo-
nyl-amino}-acetyl)-methyl-amino]-acetylamino}-
methyl)-phenyl]-2-hydroxy-4-oxo-but-2-enoic Acid
Ethyl Ester (9-13B)

9-12B (130 mg, 0.24 mmol) was used to prepare 9-13B (150 mg, crude). MS (ESI): m/z 761.0 $(M-1)^-$.

4-(3-{[2-(2-{[5-Cyclopropyl-2-(4-fluoro-phenyl)-3-
methylcarbamoyl-benzofuran-6-yl]-methanesulfo-
nyl-amino}-acetylamino)-2-methyl-propio-
nylamino]-methyl}-phenyl)-2-hydroxy-4-oxo-but-2-
enoic Acid Ethyl Ester (9-13C)

9-12C (0.13 g, 0.238 mmol) was used to prepare 9-13C (0.12 g crude). MS (ESI): m/z 775.2 $(M+1)^+$.

4-[3-({[1-(2-{[5-Cyclopropyl-2-(4-fluoro-phenyl)-3-
methylcarbamoyl-benzofuran-6-yl]-methanesulfo-
nyl-amino}-acetylamino)-cyclopropanecarbonyl]-
amino}-methyl)-phenyl]-2-hydroxy-4-oxo-but-2-
enoic Acid Ethyl Ester (9-13D)

9-12D (90 mg, 0.16 mmol) was used to prepare 9-13D (152 mg, 83%). MS (ESI): m/z 775.4 $[M+1]^+$.

4-[3-({[1-(2-{[5-Cyclopropyl-2-(4-fluoro-phenyl)-3-
methylcarbamoyl-benzofuran-6-yl]-methanesulfo-
nyl-amino}-acetylamino)-cyclopentanecarbonyl]-
amino}-methyl)-phenyl]-2-hydroxy-4-oxo-but-2-
enoic Acid Ethyl Ester (9-13E)

9-12E (80 mg, 0.14 mmol) was used to prepare 9-13E (150 mg, 84%). MS (ESI): m/z 801.3 [M-1].

4-(3-{[2-(2-{[5-Cyclopropyl-2-(4-fluoro-phenyl)-3-
methylcarbamoyl-benzofuran-6-yl]-methanesulfo-
nyl-amino}-acetylamino)-propionylamino]-methyl}-
phenyl)-2-hydroxy-4-oxo-but-2-enoic Acid Ethyl
Ester (9-13F)

9-12F (120 mg, 0.23 mmol) was used to prepare 9-13F (164 mg, 94%). MS (ESI): m/z 761.3 $[M-1]^-$.

9-13B
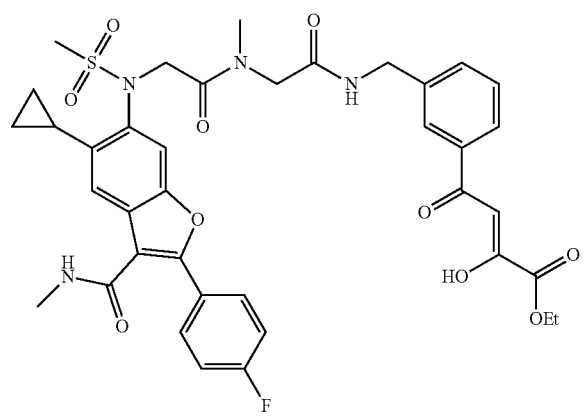
9-13E
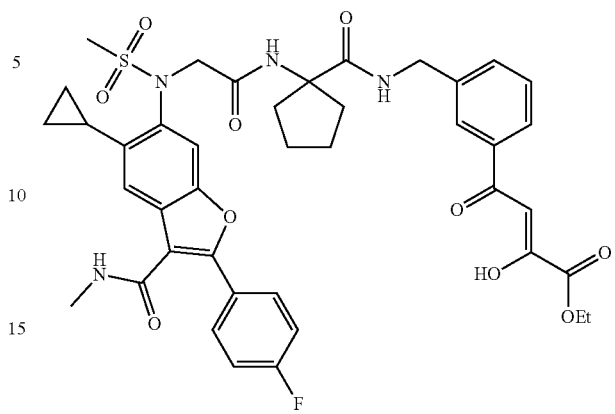
9-13C
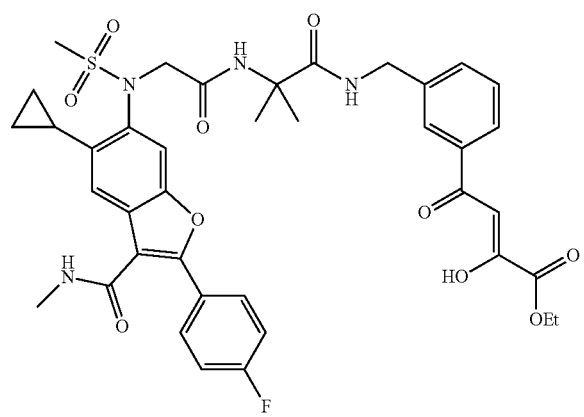
9-13F
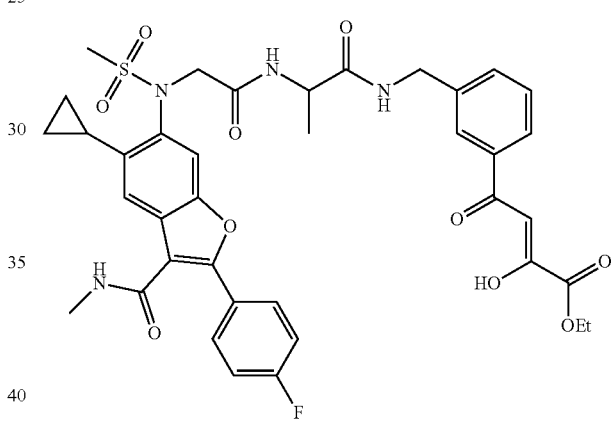
4-(3-{[2-(2-{[5-Cyclopropyl-2-(4-fluoro-phenyl)-3-methylcarbamoyl-benzofuran-6-yl]-methanesulfonyl-amino}-acetylamino)-acetylamino]-methyl}-phenyl)-2-hydroxy-4-oxo-but-2-enoic Acid (9-14A)
9-13D
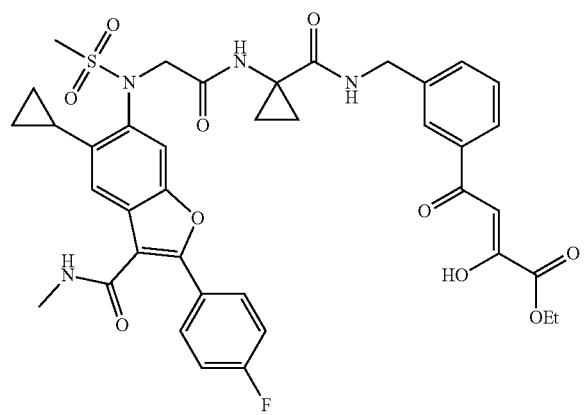
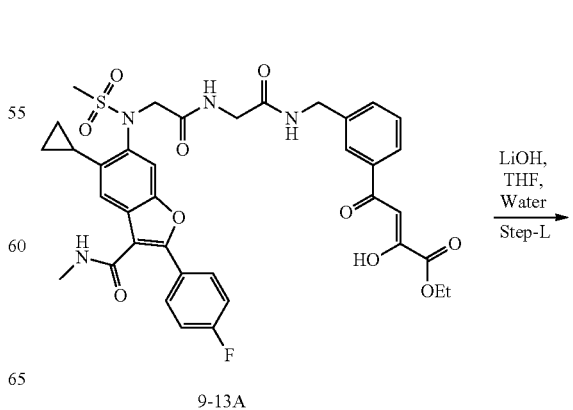
9-13A -continued

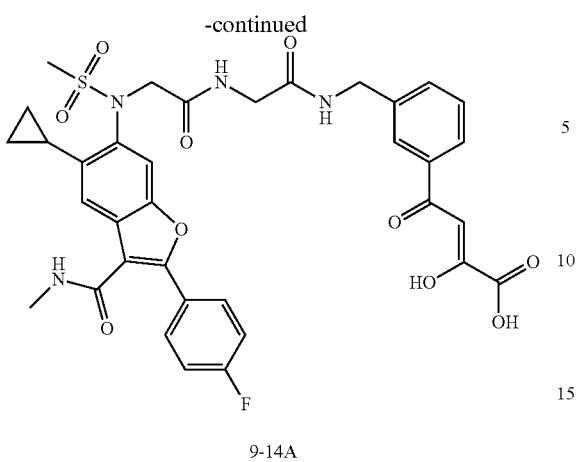

9-14A

To a stirred solution of 9-13A (0.1 g, 0.13 mmol) in THF and water (10 mL; 4:1) was added LiOH (0.01 g, 0.53 mmol) at 0° C. and reaction was continued at RT for 2 hr. After completion of the reaction (TLC), solvents evaporated at rotary evaporator, residue extracted with ether (15 mL). Then aqueous layer was neutralized with 1N HCl (10 mL) followed by extracted with EtOAc (3×25 mL). The combined organic layers were washed with brine (2×15 mL), dried over $Na_2SO_4$ and concentrated. The crude residue was purified by washed with pentane and prep-HPLC to afford 9-14A (0.017 g, 0.02 mmol, 17% yield) as a brown solid. MS (ESI): m/z 718.8 (M−1)⁻.

The above procedure was adapted to prepare the following compounds:

4-[3-({2-[(2-{[5-Cyclopropyl-2-(4-fluoro-phenyl)-3-methylcarbamoyl-benzofuran-6-yl]-methanesulfonyl-amino}-acetyl)-methyl-amino]-acetylamino}-methyl)-phenyl]-2-hydroxy-4-oxo-but-2-enoic acid (9-14B)

9-13B (150 mg, 0.19 mmol) was used to prepare 9-14B (5 mg, 2.8%). MS (ESI): m/z 732.9 (M−1)⁻.

4-(3-{[2-(2-{[5-Cyclopropyl-2-(4-fluoro-phenyl)-3-methylcarbamoyl-benzofuran-6-yl]-methanesulfonyl-amino}-acetylamino)-2-methyl-propionylamino]-methyl}-phenyl)-2-hydroxy-4-oxo-but-2-enoic Acid (9-14C)

9-13C (0.13 g, 0.16 mmol) was used to prepare 9-14C (0.035 g, 36%). MS (ESI): m/z 749.2 (M+1)⁺.

4-[3-({[1-(2-{[5-Cyclopropyl-2-(4-fluoro-phenyl)-3-methylcarbamoyl-benzofuran-6-yl]-methanesulfonyl-amino}-acetylamino)-cyclopropanecarbonyl]-amino}-methyl)-phenyl]-2-hydroxy-4-oxo-but-2-enoic Acid (9-14D)

9-13D (150 mg, 0.19 mmol) was used to prepare 9-14D (35 mg, 20%). MS (ESI): m/z 745.9 [M−1].

4-[3-({[1-(2-{[5-Cyclopropyl-2-(4-fluoro-phenyl)-3-methylcarbamoyl-benzofuran-6-yl]-methanesulfonyl-amino}-acetylamino)-cyclopentanecarbonyl]-amino}-methyl)-phenyl]-2-hydroxy-4-oxo-but-2-enoic Acid (9-14E)

9-13E (150 mg, 0.19 mmol) was used to prepare 9-14E (30 mg, 22%). MS (ESI): m/z 774.8 [M+1]⁺.

4-(3-{[2-(2-{[5-Cyclopropyl-2-(4-fluoro-phenyl)-3-methylcarbamoyl-benzofuran-6-yl]-methanesulfonyl-amino}-acetylamino)-propionylamino]-methyl}-phenyl)-2-hydroxy-4-oxo-but-2-enoic Acid (9-14F)

9-13F (80 mg, 0.1 mmol) was used to prepare 9-14F (3 mg, 3.8%). MS (ESI): m/z 732.8 [M−1]⁻.

9-14B

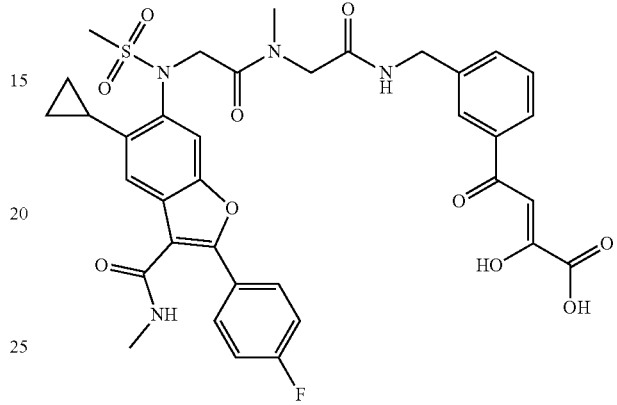

9-14C

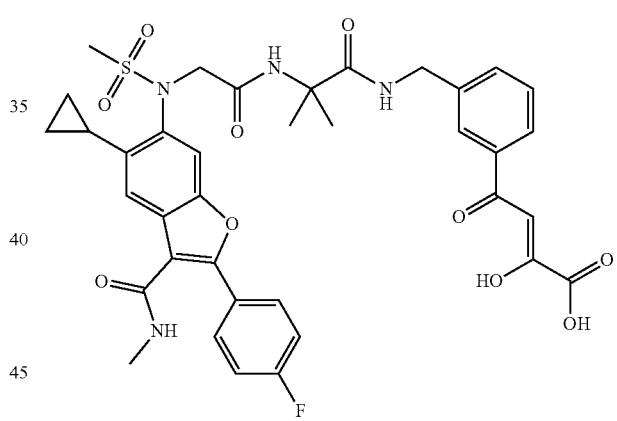

9-14D

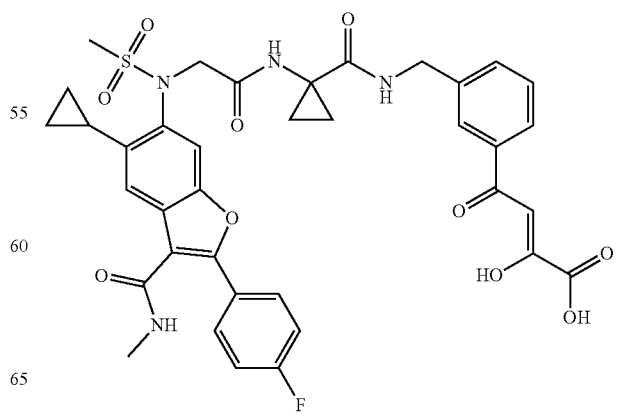

131

-continued 9-14E

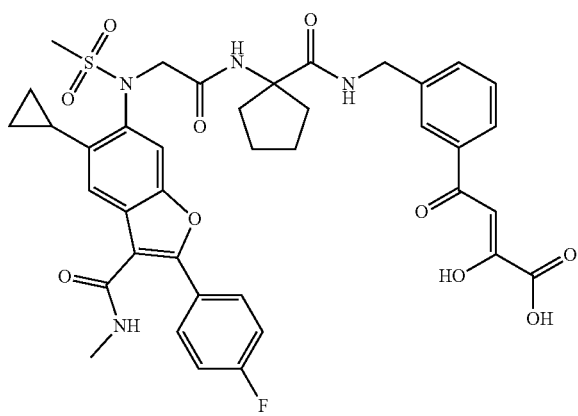

9-14F

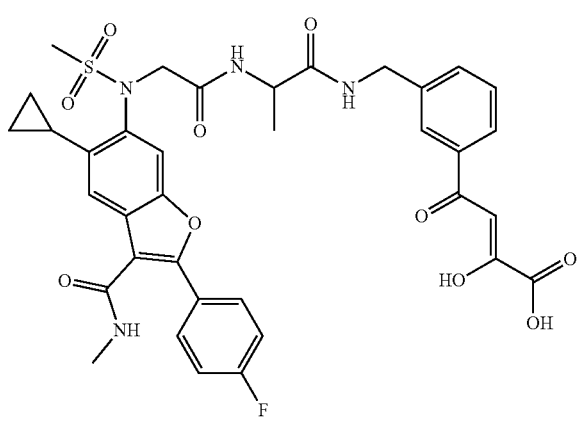

Example 10

Methyl 5-aminopentanoate Hydrochloride (10-2A)

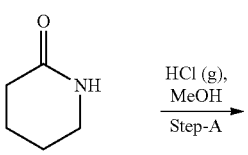

To a stirred solution of piperidin-2-one 10-1A (500 mg, 5.05 mmol) in MeOH (10 mL) was passed HCl gas. The reaction mixture was stirred at RT for 4 hr under N₂ atmosphere. Then reaction mixture warmed to 55° C. and stirring continued for 16 hr. Reaction solvents were evaporated under reduced pressure and the crude residue was washed with diethyl ether to afford 10-2A (608 mg, 129.57 mmol, 72% yield) as an off-white solid.

Step-A above was adapted using 3-methyl-piperidin-2-one 10-1B (250 mg, 2.2 mmol) to prepare 10-2B (300 mg, 80%).

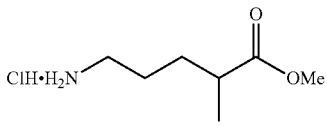

5-[2-(2-{[5-Cyclopropyl-2-(4-fluoro-phenyl)-3-methylcarbamoyl-benzofuran-6-yl]-methanesulfonyl-amino}-acetylamino)-acetylamino]-pentanoic Acid Methyl Ester (10-3A)

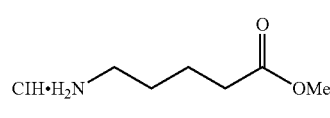

To a solution of 9-12A (125 mg, 0.24 mmol) in DMF (4 mL) was added HOBT (48 mg, 0.36 mmol), DIPEA (0.15 mL, 0.84 mmol) and EDC.HCl (100 mg, 0.53 mmol) at 0° C. After 15 min, 10-2A (51 mg, 0.26 mmol) was added at 0° C. and the reaction was continued to stir at RT for 16 hr. After completion of the reaction as indicated by TLC, the mixture was poured in to ice cold water (10 mL), extracted with EtOAc (25 mL). The organic layer was washed with water (20 mL), brine (10 mL), dried over Na₂SO₄ and concentrated. The crude compound was purified by column chromatography (100-200) silica to afford 10-3A (110 mg, 72% yield) as an off-white solid. MS (ESI): m/z 632.0 [M+1]⁺.

5-[2-(2-{[5-Cyclopropyl-2-(4-fluoro-phenyl)-3-methylcarbamoyl-benzofuran-6-yl]-methanesulfonyl-amino}-acetylamino)-acetylamino]-2-methyl-pentanoic Acid Methyl Ester (10-3B)

Step-B above was adapted using 10-2B (27 mg, 0.17 mmol) to prepare 10-3B (70 mg, 95.4%). MS (ESI): m/z 644.9 [M+1]⁺.

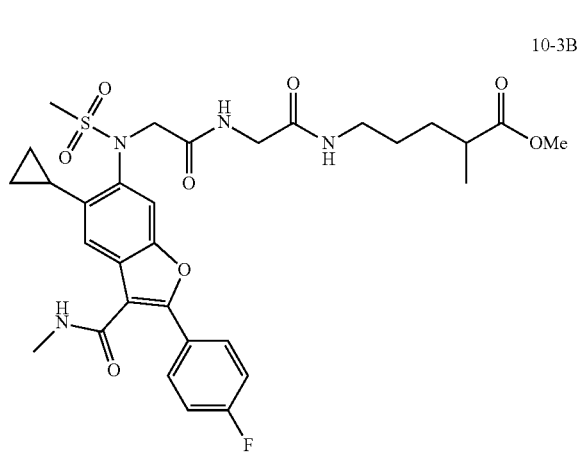 [SMILES: CNC(=O)c1c(-c2ccc(F)cc2)oc2cc(N(CC(=O)NCC(=O)NCCCC(C)C(=O)OC)S(C)(=O)=O)c(C3CC3)cc12]

5-[2-(2-{[5-Cyclopropyl-2-(4-fluoro-phenyl)-3-methylcarbamoyl-benzofuran-6-yl]-methanesulfonyl-amino}-acetylamino)-acetylamino]-pentanoic Acid (10-4A)

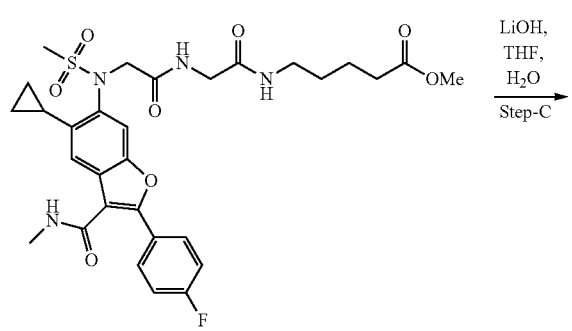

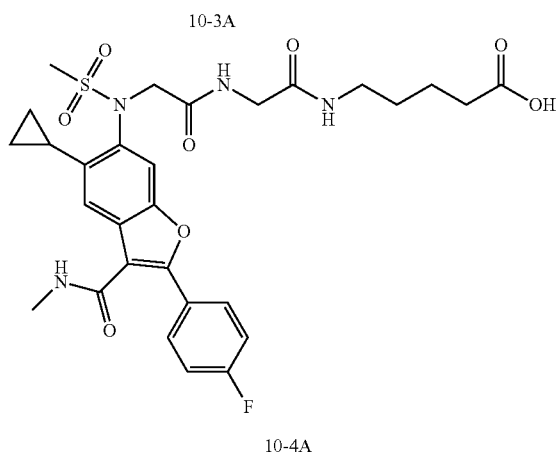

To a stirred solution of 10-3A (100 mg, 1.59 mmol) in THF (4 mL) and water (1 mL) was added LiOH (229 mg, 9.54 mmol) at 0° C. and reaction was continued at RT for 16 hr. After completion of the reaction (TLC), solvents were concentrated under reduced pressure, residue extracted with ether (10 mL). Aqueous layer was neutralized with 1N HCl (1 mL) followed by extracted with EtOAc (3×10 mL). The combined organic layers were washed with brine (2×10 mL), dried over $Na_2SO_4$ and concentrated. The crude residue was purified by washings with pentane to afford 10-4A (22 mg, 0.035 mmol 22.6% yield) as an off-white solid. MS (ESI): m/z 616.8 [M+1]$^+$.

5-[2-(2-{[5-Cyclopropyl-2-(4-fluoro-phenyl)-3-methylcarbamoyl-benzofuran-6-yl]-methanesulfonyl-amino}-acetylamino)-acetylamino]-2-methyl-pentanoic Acid (10-4B)

Step-C above was adapted using 10-3B (60 mg, 0.09 mmol) to prepare 10-4B (45 mg, 78% yield). MS (ESI): m/z 629.5 [M+1]$^+$.

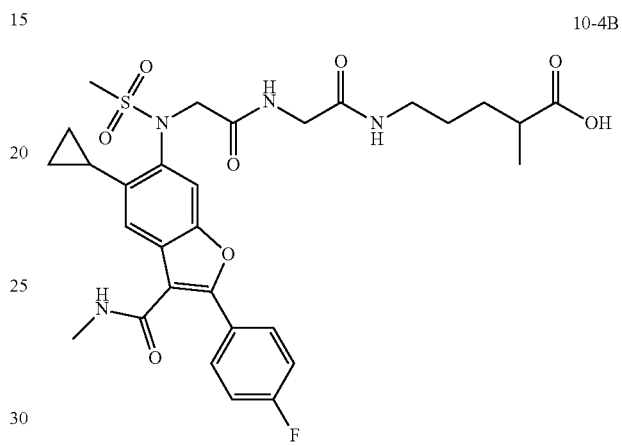

Example 11

(E)-Methyl 2-(2-(2-(2-hydroxyethoxy)-ethoxy)vinyl)benzoate (11-2A)

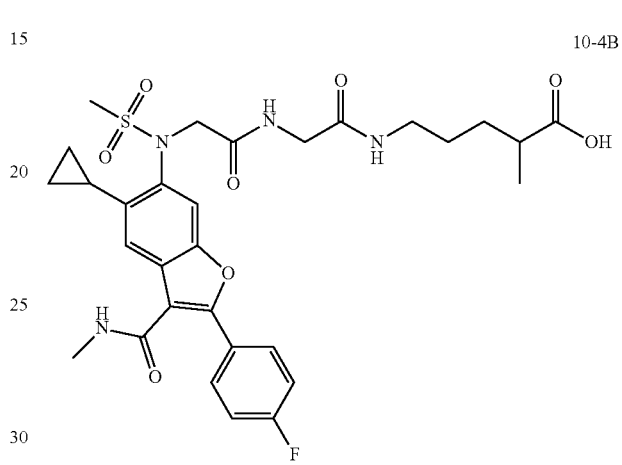

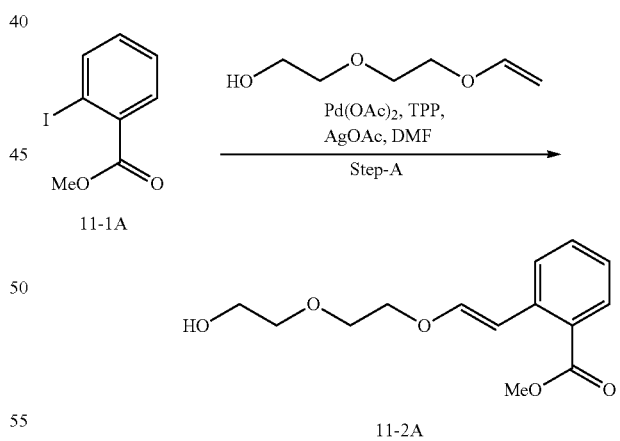

To a stirred solution of 2-(2-vinyloxy)ethoxy)ethanol (2.03 g, 15.33 mmol; Sigma-Aldrich) in DMF, silver acetate was added at RT. After 5 min, 11-1A (800 mg, 3.06 mmol) and triphenyl phosphine (80 mg, 0.30 mmol) were added to the reaction mixture, which was then degassed with $N_2$ for 15 min. Palladium acetate (38.62 mg, 0.0575) was added and the mixture was heated to 70° C. for 16 hr. After completion of the reaction, the mixture was diluted with water and extracted with EtOAc. The organic layer was washed with water, brine, dried ($Na_2SO_4$) and concentrated.

The crude compound was purified by column chromatography to afford 11-3A (0.365 g, 1.37 mmol, 45% yield) as a brown thick liquid. MS (ESI): m/z 267.17 [M+1]⁺.

The above procedure was adapted to prepare the following compounds:

3-Iodo-benzoic acid ethyl ester 11-1B (800 mg, 2.89 mmol) was used to prepare 11-2B (700 mg, 86%). MS (ESI): m/z 281.28 [M+1]⁺.

4-Iodo-benzoic acid methyl ester 11-1C (800 mg, 3.06 mmol) was used to prepare 11-2C (350 mg, 43%). MS (ESI): m/z 267.14 [M+1]⁺.

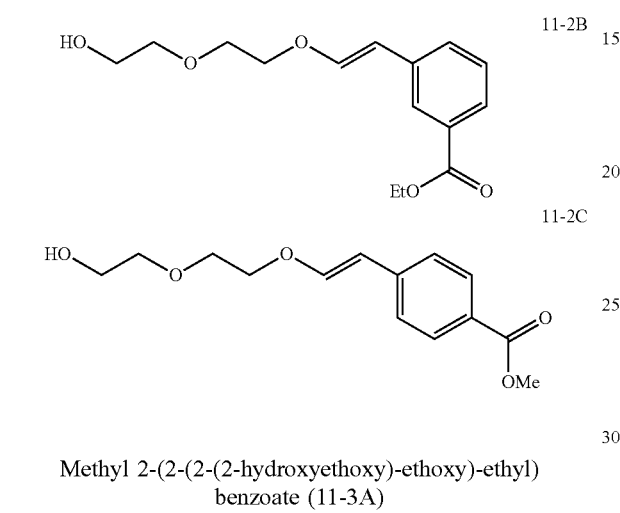

Methyl 2-(2-(2-(2-hydroxyethoxy)-ethoxy)-ethyl) benzoate (11-3A)

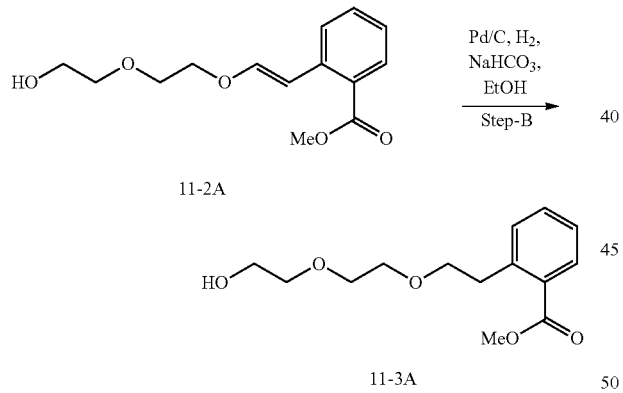

To a stirred solution of 11-2A (0.36 g, 1.37 mmol) in ethanol was added Pd in carbon (0.036 mg, 10% w/w) at RT for 4 hr under hydrogen atmosphere (balloon). After completion of the reaction, the mixture was filtered through celite pad and washed with EtOAc. The combined organic layer was dried over Na₂SO₄ and concentrated. The crude residue was purified by column chromatography to get 11-3A (0.32 g, 1.19 mmol, 86% yield) as a dark brown thick liquid. MS (ESI): m/z 269.22 [M+1]⁺.

The above procedure was adapted to prepare the following compounds:

11-2B (700 mg, 2.5 mmol) was used to prepare 11-3B (563 mg, 80%). MS (ESI): m/z 283.19 [M+1]⁺.

11-2B (200 mg, 0.75 mmol) was used to prepare 11-3B (190 mg, 84%). MS (ESI): m/z 269.18 [M+1]⁺.

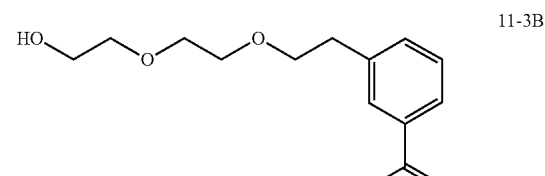

2-{2-[2-(2-Methanesulfonyloxy-ethoxy)-ethoxy]-ethyl}-benzoic Acid Methyl Ester (11-4A)

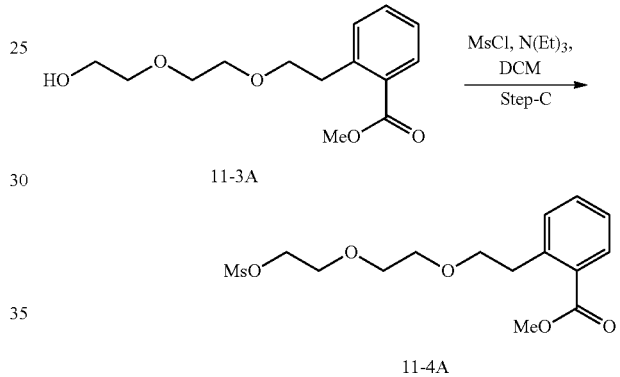

To a stirred solution of 11-3A (308 mg, 1.15 mmol) in DCM was added triethylamine (0.32 mL, 2.3 mmol) at 0° C. After 5 min, mesyl chloride (0.13 mL, 1.73 mmol) was added to the reaction mixture at the same temperature. The mixture was allowed to stir at RT for 2 hr. Then, the mixture was diluted with water, extracted with DCM. The organic layer was washed with brine, dried over Na₂SO₄ and concentrated to get crude compound. This was purified by column chromatography to afford 11-4A (338 mg, 0.98 mmol, 85% yield) as a colorless liquid. MS (ESI): m/z 347.26 [M+1]⁺.

The above procedure was adapted to prepare the following compounds:

11-3B (415 mg, 1.47 mmol) was used to prepare 11-4B (420 mg, 84%).

11-3C (190 mg, 0.71 mmol) was used to prepare 11-4C (230 mg, 93.8%). MS (ESI): m/z 347.1 [M+1]⁺.

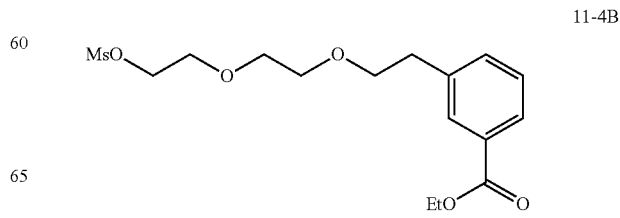

4-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethyl}-benzoic Acid Methyl Ester (11-5C)

11-4C (225 mg, 0.56 mmol) was used to prepare 11-5C (145 mg, 40%). MS (ESI): m/z 653.37 [M+1]⁺.

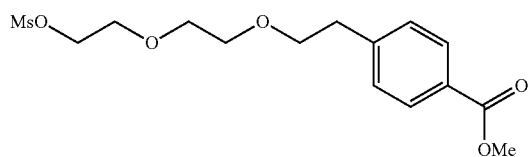

11-4C

2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethyl}-benzoic Acid Methyl Ester (11-5A)

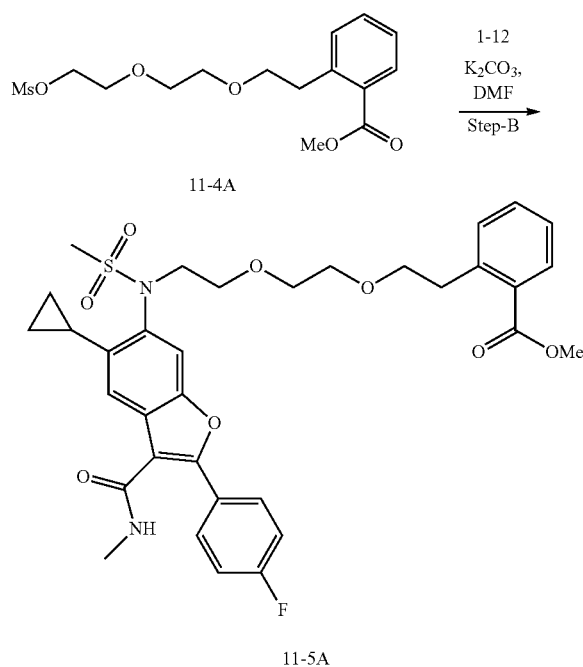

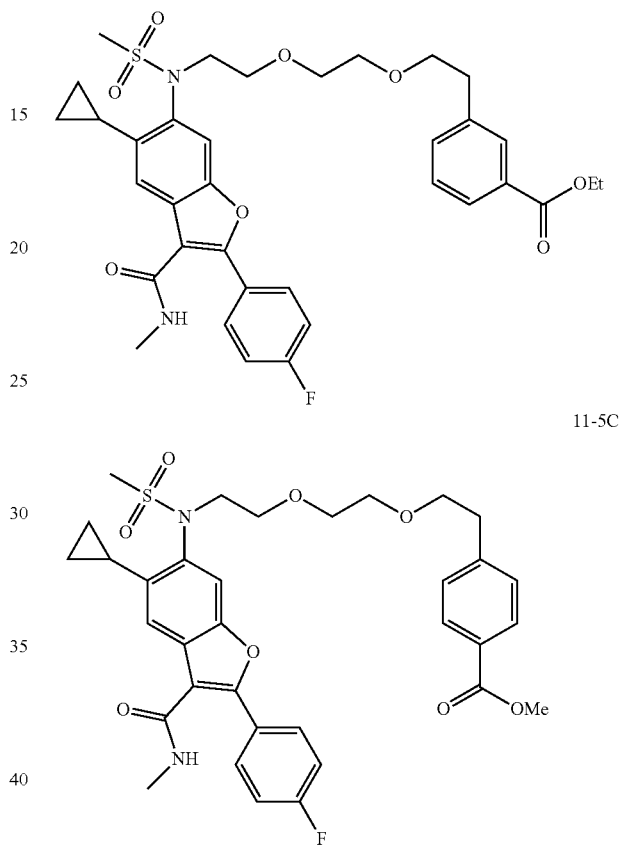

To a stirred solution of [1-12] (160 mg, 0.39 mmol) in DMF potassium carbonate (109 mg, 0.76 mmol) was added at RT. After 5 min, 11-4A (165 mg, 0.47 mmol), catalytic amount of TBAI were added to the reaction and heated to 70° C. The reaction was maintained at 70-75° C. for 16 hr. After completion of the reaction indicated by TLC, the mixture was diluted with ice water, extracted with EtOAc. The organic layer was washed with water, brine, dried over Na₂SO₄ and concentrated. The crude compound was purified by column chromatography to get 11-5A (132 mg, 0.2 mmol, 50.9% yield) as an off-white semi solid. MS (ESI): m/z 653.41 [M+1]⁺.

The above procedure was adapted to prepare the following compounds:

3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethyl}-benzoic Acid Ethyl Ester (11-5B)

11-4B (253 mg, 0.744 mmol) was used to prepare 11-5B (168 mg, 39%). MS (ESI): m/z 667.34 [M+1]⁺.

2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethyl}-benzoic Acid (11-6A)

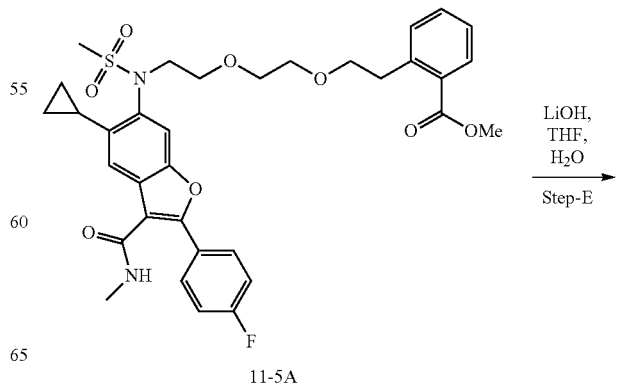

-continued

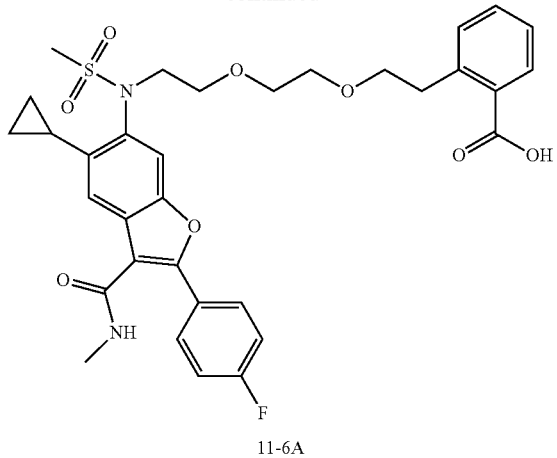

11-6A

To a stirred solution of 11-5A (100 mg, 0.15 mmol) in THF and water (4 mL, 4:1) was added LiOH (21 mg, 0.9 mmol) at 0° C. and reaction was continued at RT for 16 hr. After completion of the reaction (TLC), solvents were evaporated at rotary evaporator. The crude residue extracted with ether (2×20 mL). The aqueous layer was neutralized with 1N HCl (10 mL), then extracted with EtOAc (3×30 mL). The combined organic layers were washed with brine (20 mL), dried over Na$_2$SO$_4$ and concentrated. The crude residue was purified by washings with diethyl ether and pentane to afford 11-6A (32 mg, 0.05 mmol, 33% yield) as a white solid. MS (ESI): m/z 639.39 [M+1]$^+$.

The above procedure was adapted to prepare the following compounds:

3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethyl}-benzoic Acid (11-6B)

11-5B (60 mg, 0.09 mmol) was used to prepare 11-6B (17 mg, 29%). MS (ESI): m/z 639.3 [M+1]$^+$.

4-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethyl}-benzoic Acid (11-6C)

11-5C (100 mg, 0.15 mmol) was used to prepare 11-6C (25 mg, 25%). MS (ESI): m/z 639.3 [M+1]$^+$.

11-6B

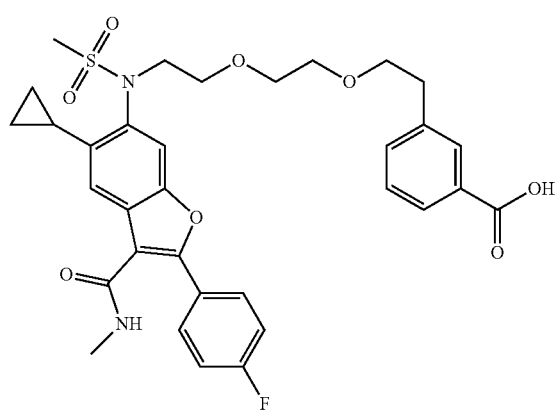

-continued 11-6C

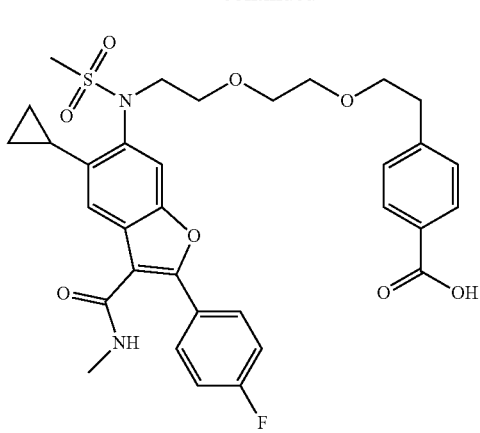

Example 12

2-(2-(2-(Allyloxy)-ethoxy)-ethoxy)tetrahydro-2H-pyran (12-1)

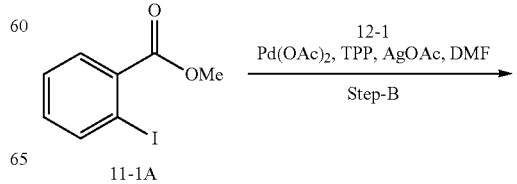

To a stirred suspension of NaH in THF (80 mL) was added a solution of 2-4A (8 g, 42 mmol) in THF (20 mL) at 0° C. and the mixture was stirred at RT for 30 min. Then the mixture was cooled to 0° C., added allyl bromide (5.6 g, 44 mmol) and allowed to stir at RT for 16 hr under nitrogen atmosphere. The reaction mixture was quenched with ice cold water, and extracted with EtOAc (3×100 mL). The organic layer washed with water (80 mL), brine (80 mL), dried over Na$_2$SO$_4$ and concentrated. The crude residue was purified by flash column chromatography (100-200 silica) using 30% EtOAc in hexanes to afford 12-1 (9 g, 39 mmol, 92% yield) as a pale yellow liquid.

(E)-Methyl 2-(3-(2-(2-(tetrahydro-2H-pyran-2-yloxy)-ethoxy)-ethoxy)-prop-1-enyl)benzoate (12-2A)

11-1A

-continued

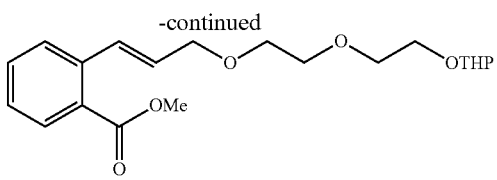

12-2A

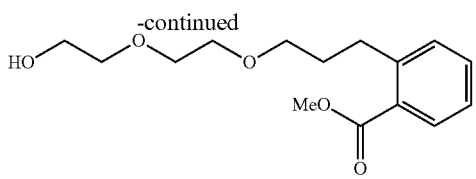

12-4A

To a stirred solution of methyl 2-iodobenzoate 11-1A (1 g, 3.8 mmol) in DMF (8 mL) was added 12-1 (2.2 g, 11.4 mmol), triphenyl phosphine, and silver acetate (639 mg, 3.8 mmol) at RT. The reaction mixture degassed for 15 min with argon, palladium acetate (128 mg, 0.19 mmol) was added, and the mixture heated to 80° C. for 18 hr. The reaction mixture was filtered through a celite pad, washed with EtOAc thoroughly. The filtrate washed with water and brine, dried over $Na_2SO_4$ and concentrated under reduced pressure. The crude residue was purified by flash column chromatography (100-200 silica) using 20% EtOAc/pet. ether to afford 12-4A (300 mg, 0.82 mmol, 23% yield) as a yellow liquid. MS (ESI): m/z 364.0 $(M+1)^+$.

Methyl 2-(3-(2-(2-(tetrahydro-2H-pyran-2-yloxy)-ethoxy)-propyl)benzoate (12-3A)

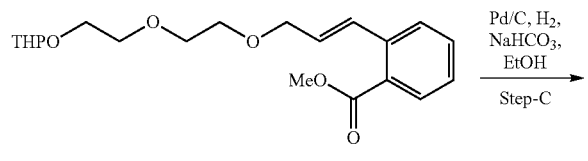

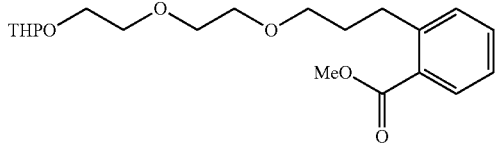

12-3A

To a solution of 12-2A (300 mg, 0.82 mmol) in EtOH (5 mL) was added 10% Pd/C (90 mg) and stirred at RT for 3 hr under $H_2$ atmosphere. The reaction mixture was filtered on a Celite bed and washed with 10% MeOH-EtOAc. The filtrate was distilled under reduced pressure to get 12-3A (300 mg, 0.81 mmol, quantitative yield).

Methyl 2-(3-(2-(2-hydroxyethoxy)-ethoxy)-propyl) benzoate (12-4A)

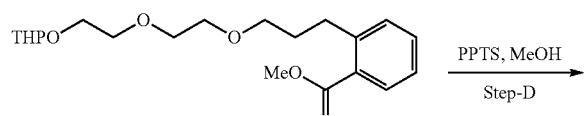

To a solution of 12-3A (300 mg, 0.81 mmol) in MeOH (5 mL) was added PPTS (41 mg, 0.16 mmol) and stirred at 0° C. to RT for 16 hr. The reaction mixture was distilled off and diluted with excess (100 mL), washed with water (100 mL), brine (50 mL) and dried over $Na_2SO_4$, and the organic phase was concentrated under reduced pressure. The crude compound was purified using CombiFlash® (Teledyne Isco) column chromatography (40% EtOAc in hexane) to afford 12-4A (160 mg, 0.56 mmol, 69% yield). MS (ESI): m/z 305.2 $(M+23)^+$.

2-{3-[2-(2-Methanesulfonyloxy-ethoxy)-ethoxy]-propyl}-benzoic Acid Methyl Ester (12-5A)

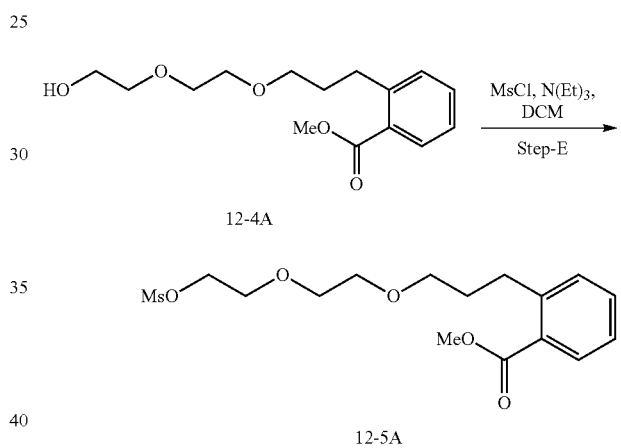

Methane sulfonylchloride (0.07 mL, 0.85 mmol) at 0° C. was added to a solution of 12-4A (160 mg, 410.56 mmol) in DCM (5 mL) and triethylamine (0.13 mL, 0.9 mmol) and stirred at RT for 1 hr. The reaction mixture was diluted with excess DCM (50 mL) and washed with water (50 mL) and brine (20 mL), and dried over $Na_2SO_4$. The organic phase was concentrated under reduced pressure to give 12-5A (130 mg, 0.34 mmol, 61% yield) as a yellow liquid. MS (ESI): m/z 375.0 $(M+1)^+$.

2-{3-[2-(2-{[5-Cyclopropyl-2-(4-fluoro-phenyl)-3-methylcarbamoyl-benzofuran-6-yl]-methanesulfonyl-amino}-ethoxy)-ethoxy]-propyl}-benzoic Acid Methyl Ester (12-6A)

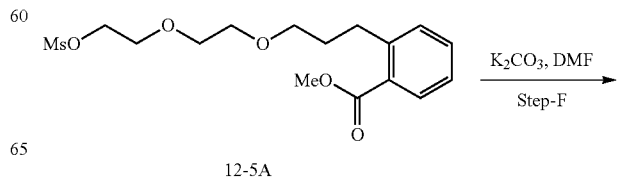

12-5A

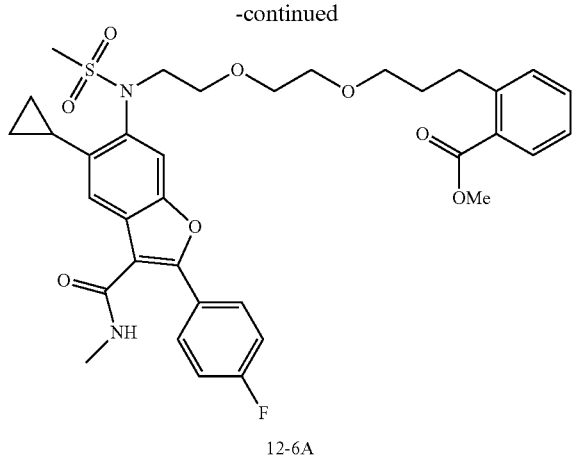

12-6A

To a solution of 1-12 (116 mg, 0.28 mmol) in DMF (5 mL) was added potassium carbonate (120 mg, 0.86 mmol) followed by 12-7A (130 mg, 0.34 mmol), catalytic amount of TBAI then stirred at 70° C. for 16 hr. The reaction was cooled to RT and diluted with EtOAc (50 mL), washed with water (50 mL), brine (25 mL), and dried over Na$_2$SO$_4$, and the organic phase was concentrated under reduced pressure. Obtained crude was purified using Combi-flash column chromatography (30% EtOAc in hexane) to afford 12-6A (129 mg, 0.19 mmol, 69% yield) as an off-white solid. MS (ESI): m/z 666.7 (M+1)$^+$.

2-{3-[2-(2-{[5-Cyclopropyl-2-(4-fluoro-phenyl)-3-methylcarbamoyl-benzofuran-6-yl]-methanesulfonyl-amino}-ethoxy)-ethoxy]-propyl}-benzoic Acid (12-7A)

To a solution of 12-6A (80 mg, 0.12 mmol) in THF, MeOH and water (4:1:1) was added LiOH (15 mg, 0.6 mmol) and stirred at RT for 16 hr. After completion as indicated by TLC, the reaction mixture was neutralized with 1N HCl and then extracted with EtOAc. The organic layer was washed with brine, dried over Na$_2$SO$_4$ and concentrated. The crude compound was purified by giving pentane washings to afford 12-7A (25 mg, 0.038 mmol, 32% yield) as an off-white solid. MS (ESI): m/z 653.4 (M+1)$^+$.

The above procedure was adapted to prepare the following compounds:

3-{3-[2-(2-{[5-Cyclopropyl-2-(4-fluoro-phenyl)-3-methylcarbamoyl-benzofuran-6-yl]-methanesulfonyl-amino}-ethoxy)-ethoxy]-propyl}-benzoic Acid (12-7B)

Ethyl 3-iodobenzoate 11-1B was substituted for methyl 2-iodobenzoate 11-1A in Step-A, with appropriate modification of subsequent steps, to prepare 12-7B. MS (ESI): m/z 653.4 (M+1)$^+$.

4-{3-[2-(2-{[5-Cyclopropyl-2-(4-fluoro-phenyl)-3-methylcarbamoyl-benzofuran-6-yl]-methanesulfonyl-amino}-ethoxy)-ethoxy]-propyl}-benzoic Acid (12-7C)

Methyl 4-iodobenzoate 11-1C was substituted for methyl 2-iodobenzoate 11-1A in Step-A, with appropriate modification of subsequent steps, to prepare 12-7C. MS (ESI): m/z 653.4 (M+1)$^+$.

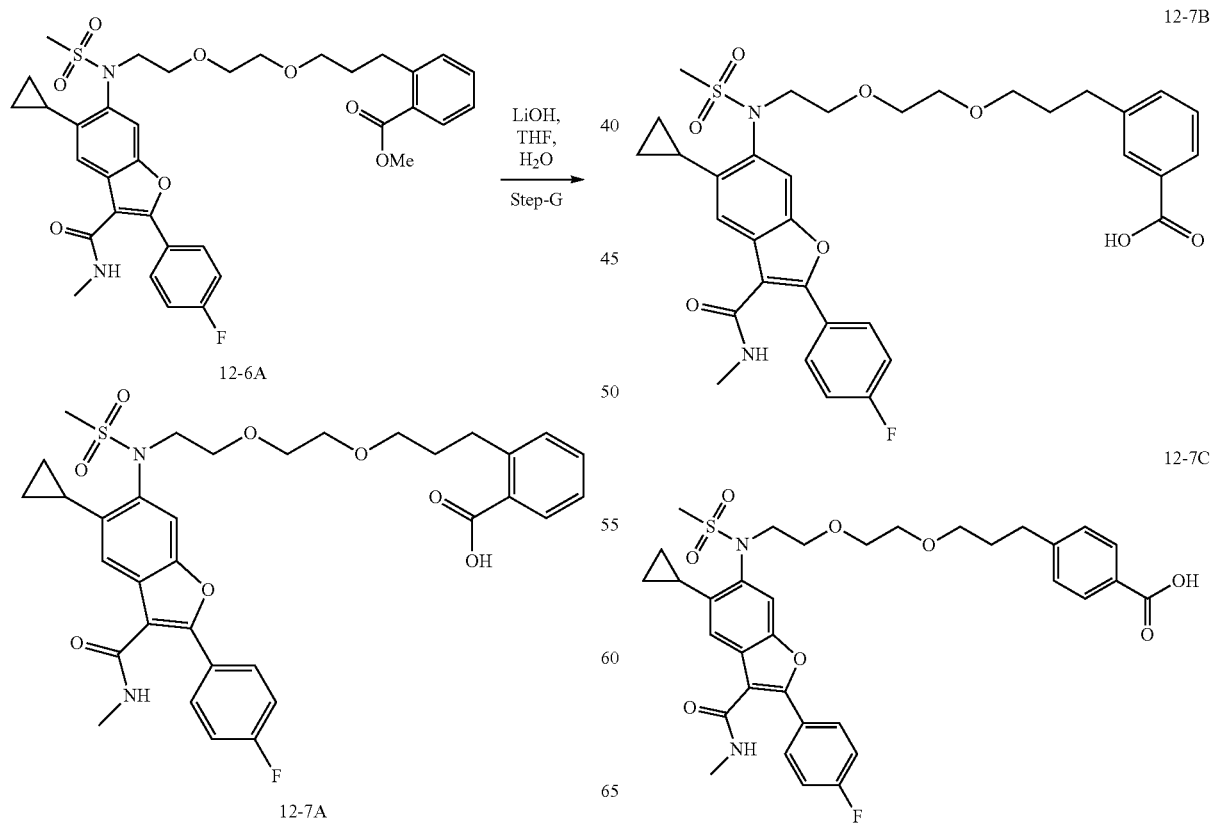

Example 13

(2-Bromoethoxy)tetrahydro-2H-pyran (13-2)

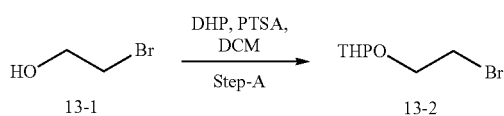

To a solution of 2-bromo ethanol 13-1 (5 g, 40 mmol) in DCM (250 mL) was added p-toluenesulfonic acid (760 mg, 4 mmol) followed by dihydropyran (4.3 mL, 48 mmol) at 0° C. and stirred at RT for 5 hr. The reaction mixture was diluted with EtOAc (100 mL) washed with water (100 mL), brine (10 mL) and dried over $Na_2SO_4$, and concentrated under reduced pressure at 25° C. The crude compound was purified using silica gel chromatography (5% EtOAc in hexanes) to afford 13-2 (5 g, 24 mmol, 60% yield) as a pale yellow color liquid.

2-(2-(But-3-enyloxy)-ethoxy)tetrahydro-2H-pyran (13-3AT)

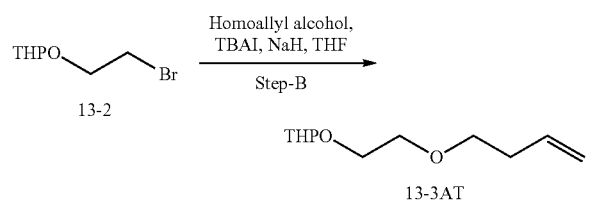

To a solution of NaH (885 mg, 24 mmol) in THF (50 mL) was added 13-2 (5 g, 24 mmol) at 0° C. and stirred at RT for 1 hr. The reaction mixture was again cooled to 0° C., homoallyl alcohol (1.9 mL, 22.8 mmol) was added and stirred for RT for 16 hr. The reaction mixture was quenched with ice cold water and diluted with EtOAc (50 mL) washed with water (50 mL), brine (10 mL) dried over $Na_2SO_4$, and concentrated under reduced pressure. The crude compound was purified using silica gel chromatography (5% EtOAc in hexanes) to afford 13-3AT (1.5 g, 7.5 mmol, 31% yield) as a pale yellow color liquid.

(E)-Methyl 4-(2-(4-hydroxybutoxy)vinyl)benzoate (13-5C)

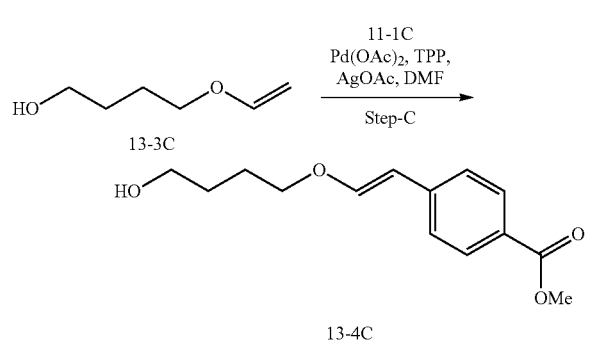

To a solution of 4-iodo-benzoic acid methyl ester 11-1C (1.2 g, 4.5 mmol) in DMF (5 mL) was added 4-vinyloxy-butan-1-ol 13-3C (2.65 g, 22.9 mmol; TCI), $Ag(OAc)_2$ (751 mg, 4.5 mmol) and TPP (117 mg, 0.45 mmol) sequentially and degassed for 15 min, followed by addition of $Pd(OAc)_2$ (100 mg, 0.14 mmol) and again degassed for 5 min, and stirred at 70° C. for 16 hr. The reaction was cooled to RT and diluted with EtOAc (200 mL) washed with water (200 mL), brine (50 mL), dried over $Na_2SO_4$, and concentrated under reduced pressure. The crude compound was purified by silica gel chromatography (100-200 silica) using 30% EtOAc in hexanes to afford 13-4C (520 mg, 2.08 mmol, 43% yield) as a brown thick liquid. MS (ESI): m/z 251.2 $[M+1]^+$.

The above procedure was adapted to prepare the following compounds:

13-3A (783 mg, 3 mmol) was used to prepare 13-4A (600 mg, 46%). MS (ESI): m/z 357.3 $(M+1)^+$.

3-Allyloxy-propan-1-ol 13-3B (1.7 g, 14.65 mmol) was used to prepare 13-4B (300 mg, 39%). MS (ESI): m/z 251.2 $[M+1]^+$.

Hept-6-en-1-ol 13-3D (1 g, 8.77 mmol) was used to prepare 13-4D (800 mg, 80%). MS (ESI): m/z=249.2 $[M+H]^+$.

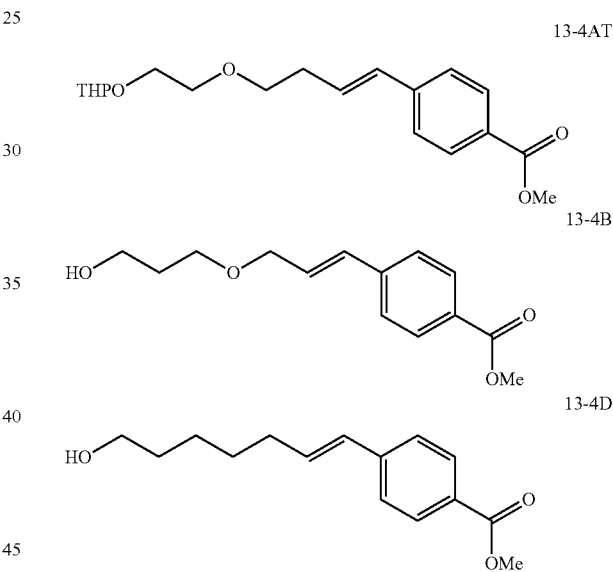

Methyl 4-(2-(4-hydroxybutoxy)-ethyl)benzoate (13-5C)

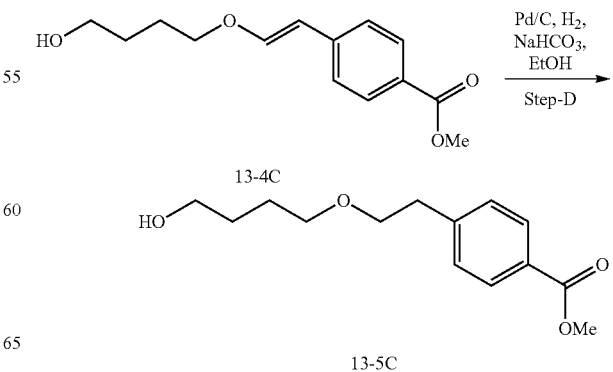

To a solution 13-4C (520 mg, 2.08 mmol) in ethanol (5 mL) was added 20% Pd(OH)$_2$/C (30 mg) and stirred at RT for 3 hr under H$_2$ atmosphere. The reaction mixture was filtered on ciliate bed and washed with 10% MeOH-EtOAc. Filtrate was distilled under reduced pressure, the crude compound was purified by column chromatography (100-200 silica) using 30% EtOAc in hexanes to afford 13-5C (400 mg, 1.58 mmol, 76% yield). MS (ESI): m/z 253.0 (M+1)$^+$.

The above procedure was adapted to prepare the following compounds:

13-4A (600 mg, 1.79 mmol) was used to prepare 13-5A (530 mg, 87%).

13-4B (300 mg, 1.2 mmol) was used to prepare 13-5B (160 mg, 52%). MS (ESI): m/z 253.2 (M+1)$^+$.

13-4D (800 mg, 3.22 mmol) was used to prepare 13-5D (600 mg, 74.4%).

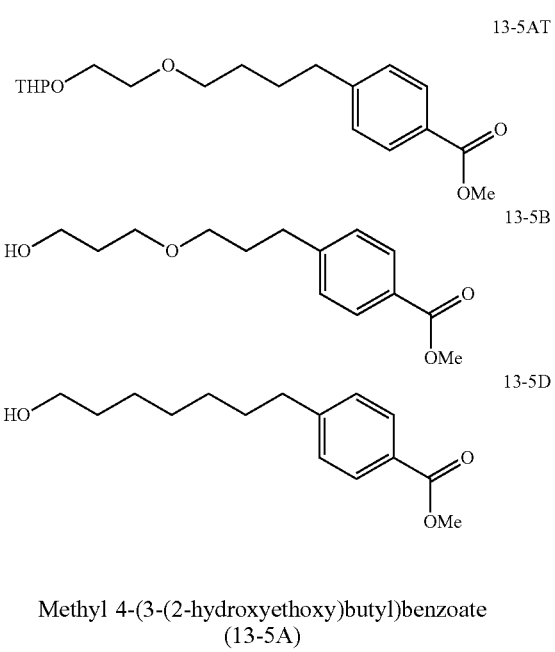

Methyl 4-(3-(2-hydroxyethoxy)butyl)benzoate (13-5A)

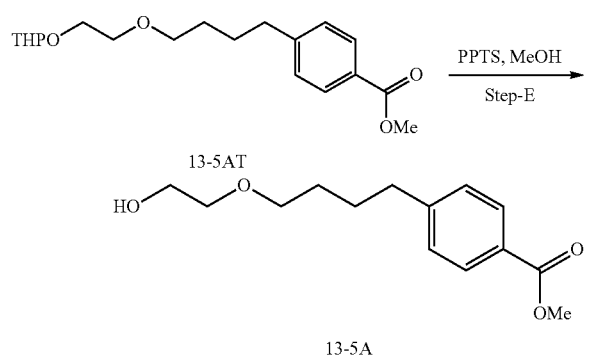

To a solution of 13-5AT (530 mg, 1.5 mmol) in MeOH (5 mL) was added PPTS (79 mg, 0.3 mmol) and stirred at 0° C. to RT for 16 hr. The reaction mixture was distilled off and diluted with excess EtOAc (100 mL), washed with water (100 mL), brine (50 mL), dried over Na$_2$SO$_4$, and concentrated under reduced pressure. The crude compound was purified using combi-flash column chromatography (18% EtOAc in hexanes) to afford 13-5A (250 mg, 0.99 mmol, 66% yield). MS (ESI): m/z 253.2 (M+1)$^+$.

Methyl 4-(2-(4-(methylsulfonyloxy)butoxy)-ethyl)benzoate (13-6C)

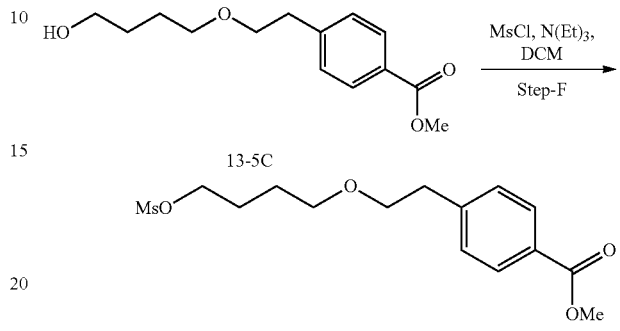

Methane sulfonylchloride (0.15 mL, 1.90 mmol) at 0° C. was added to a solution of 13-5C (400 mg, 1.58 mmol) in DCM (5 mL) and triethylamine (0.53 mL, 3.79 mmol) and stirred at RT for 1 hr. The reaction mixture was diluted with excess DCM (50 mL) and washed with water (50 mL), brine (20 mL), dried over Na$_2$SO$_4$, and concentrated under reduced pressure. The crude compound was purified by column chromatography (100-200 silica) using 30% EtOAc in hexanes to afford 13-6C (400 mg, 1.21 mmol, 75% yield) as a color less liquid. MS (ESI): m/z 331.3 (M+1)$^+$.

The above procedure was adapted to prepare the following compounds:

13-5A (250 mg, 0.99 mmol) was used to prepare 13-6A (300 mg, 93%). MS (ESI): m/z 331.2 (M+1)$^+$.

13-5B (160 mg, 0.63 mmol) was used to prepare 13-6B (165 mg, 78%). MS (ESI): m/z 331.2 (M+1)$^+$.

13-5D (600 mg, 2.4 mmol) was used to prepare 13-6D (700 mg, 93.3%). Confirmed by $^1$H NMR.

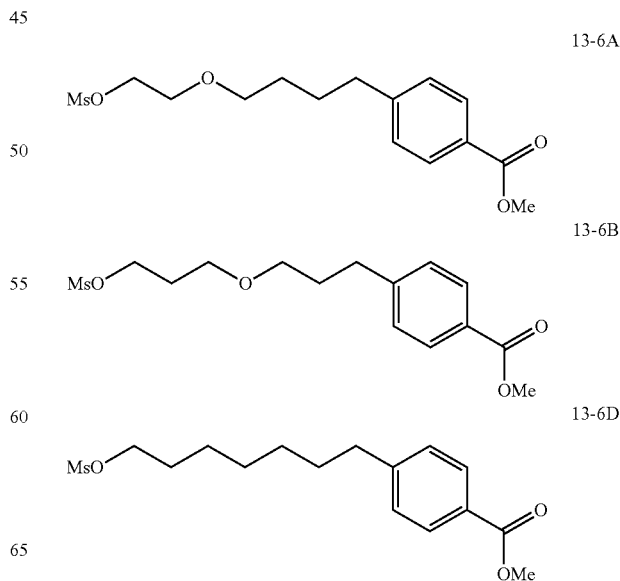

4-[2-(4-{[5-Cyclopropyl-2-(4-fluoro-phenyl)-3-methylcarbamoyl-benzofuran-6-yl]-methanesulfonyl-amino}-butoxy)-ethyl]-benzoic Acid Methyl Ester (13-7C)

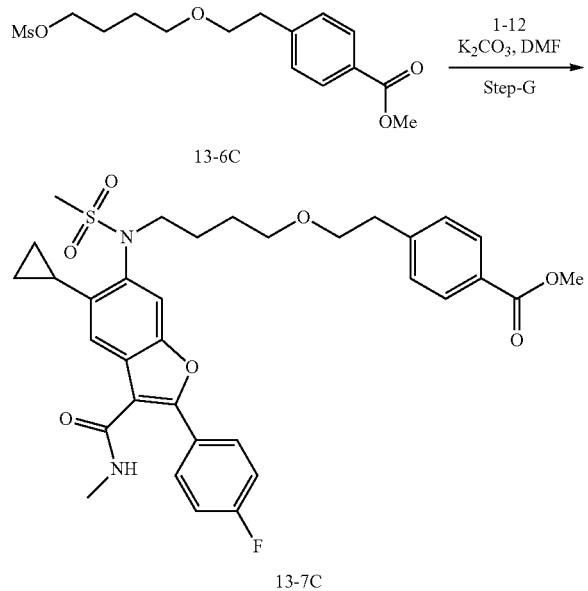

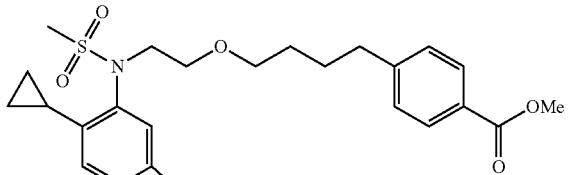

To a stirred solution of 1-12 (304 mg, 0.75 mmol) in DMF (5 mL) was added potassium carbonate (313 mg, 2.27 mmol) followed by 13-6C (300 mg, 0.91 mmol), catalytic amount of TBAI then stirred at 70° C. for 16 hr. The reaction mixture was cooled to RT and diluted with EtOAc (50 mL) washed with water (50 mL), brine (25 mL), dried over $Na_2SO_4$, and concentrated under reduced pressure. The crude compound was purified using column chromatography (100-200 silica) using 30% EtOAc in hexanes to afford 13-7C (280 mg, 0.44 mmol, 59% yield) as an off-white solid. MS (ESI): m/z 637.4 $(M+1)^+$.

The above procedure was adapted to prepare the following compounds:

4-[4-(2-{[5-Cyclopropyl-2-(4-fluoro-phenyl)-3-methylcarbamoyl-benzofuran-6-yl]-methanesulfonyl-amino}-ethoxy)-butyl]-benzoic Acid Methyl Ester (13-7A)

13-6A (197 mg, 0.59 mmol) was used to prepare 13-7A (130 mg, 34%). MS (ESI): m/z 637.3 $(M+1)^+$.

4-[3-(3-{[5-Cyclopropyl-2-(4-fluoro-phenyl)-3-methylcarbamoyl-benzofuran-6-yl]-methanesulfonyl-amino}-propoxy)-propyl]-benzoic Acid Methyl Ester (13-7B)

13-6B (160 mg, 0.48 mmol) was used to prepare 13-7B (130 mg, 42%). MS (ESI): m/z 637.0 $(M+1)^+$.

4-(7-{[5-Cyclopropyl-2-(4-fluoro-phenyl)-3-methylcarbamoyl-benzofuran-6-yl]-methanesulfonyl-amino}-heptyl)-benzoic Acid Methyl Ester (13-7D)

13-6D (195 mg, 0.62 mmol) was used to prepare 13-7D (110 mg, 28%). MS (ESI): m/z 635.6 $(M+1)^+$.

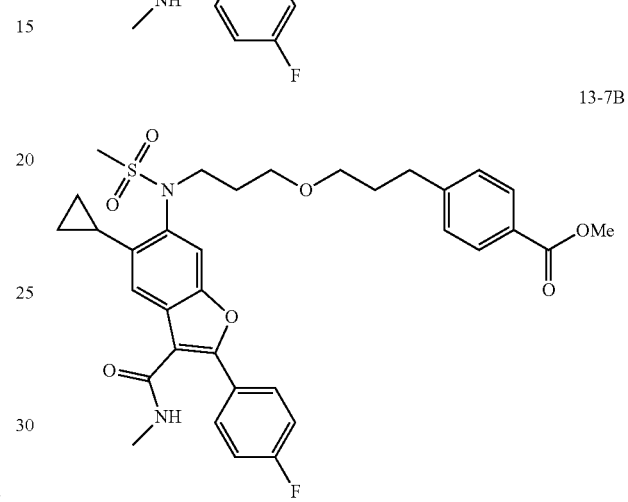

4-(2-(4-(N-(5-cyclopropyl-2-(4-fluorophenyl)-3-(methylcarbamoyl)benzofuran-6-yl)-methylsulfonamido)butoxy)-ethyl)benzoic Acid (13-8C)

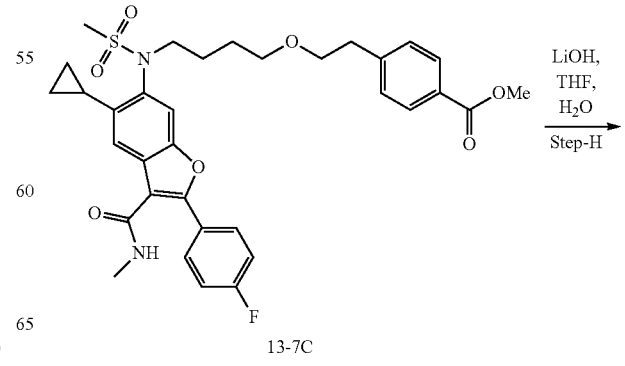

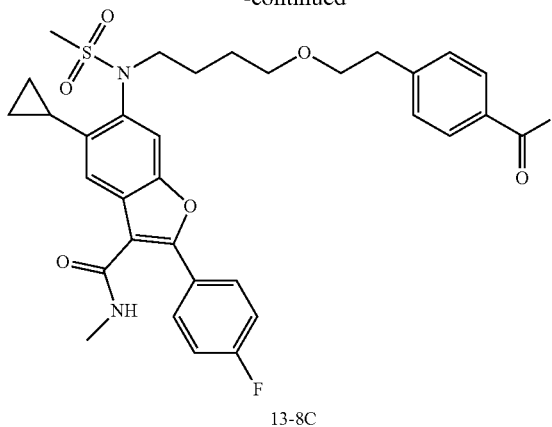

13-8C

To a stirred solution of 13-7C (100 mg, 0.157 mmol) in THF, MeOH & water (4:1:1; 6 mL) was added LiOH (19 mg, 0.785 mmol) and stirred at RT for 16 hr. After completion of the reaction as indicated by TLC, the reaction mixture was neutralized with 1N HCl and extracted with EtOAc. The organic layer was washed with brine, dried ($Na_2SO_4$), and concentrated. The crude compound was purified by washings with DCM and pentane to afford 13-8C (40 mg, 0.064 mmol, 41% yield) as an off-white solid. MS (ESI): m/z 621.5 $(M-1)^+$.

The above procedure was adapted to prepare the following compounds:

4-[4-(2-{[5-Cyclopropyl-2-(4-fluoro-phenyl)-3-methylcarbamoyl-benzofuran-6-yl]-methanesulfonyl-amino}-ethoxy)-butyl]-benzoic Acid (13-8A)

13-7A (50 mg, 0.07 mmol) was used to prepare 13-8A (16 mg, 35%). MS (ESI): m/z 623.3 $(M+1)^+$.

4-[3-(3-{[5-Cyclopropyl-2-(4-fluoro-phenyl)-3-methylcarbamoyl-benzofuran-6-yl]-methanesulfonyl-amino}-propoxy)-propyl]-benzoic Acid (13-8B)

13-7B (90 mg, 0.14 mmol) was used to prepare 13-8B (40 mg, 45%). MS (ESI): m/z 623.1 $(M+1)^+$.

4-(7-{[5-Cyclopropyl-2-(4-fluoro-phenyl)-3-methylcarbamoyl-benzofuran-6-yl]-methanesulfonyl-amino}-heptyl)-benzoic Acid (13-8D)

13-7D (60 mg, 0.09 mmol) was used to prepare 13-8D (27 mg, 46%). MS (ESI): m/z 621.3 $(M+1)^+$.

13-8A

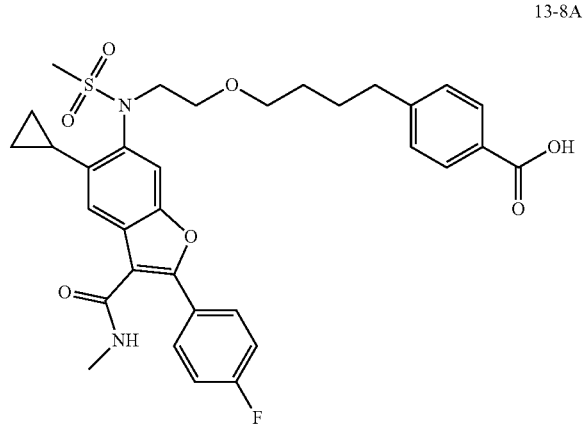

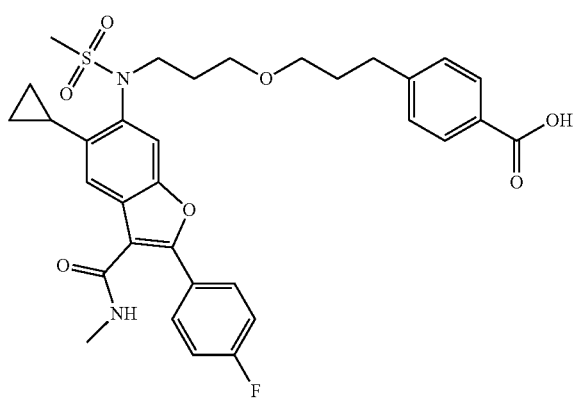

Example 14

2-(2-(2-(Tetrahydro-2H-pyran-2-yloxy)-ethoxy)-ethylmethanesulfonate (14-1)

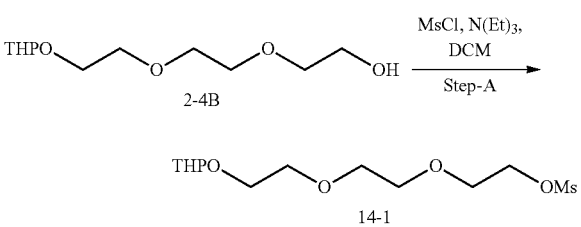

Methanesulfonyl chloride (1.1 mL, 13.88 mmol) at 0° C. was added to a solution of 2-4B (2.5 g, 10.68 mmol) in THF (22 mL) and triethylamine (3 mL, 21.36 mmol) and stirred at RT for 1 hr. The reaction mixture was diluted with excess DCM (150 mL) and washed with water (100 mL), brine (100 mL) and dried over $Na_2SO_4$, and the organic phase concentrated under reduced pressure. The crude compound was purified using 100-200 silica gel column chromatography (3% MeOH in DCM) to afford 14-1 (3 g, 9.61 mmol, 91% yield) as a pale yellowish oily liquid.

Ethyl 2-(2-(2-(2-(tetrahydro-2H-pyran-2-yloxy)-ethoxy)-ethoxy)-ethoxy)benzoate (14-3A)

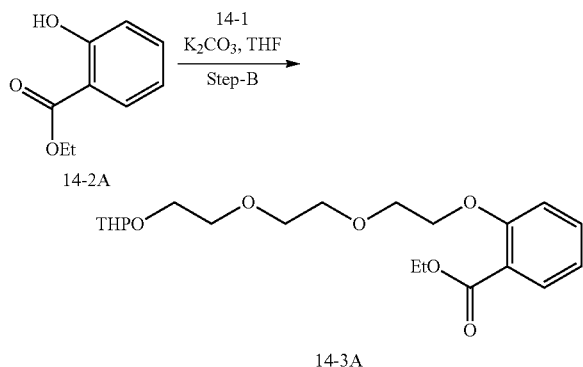

To a solution of 14-1 (800 mg, 2.56 mmol) in DMF (10 mL) was added potassium carbonate (353 mg, 2.56 mmol) followed by ethyl 2-hydroxybenzoate 14-2A (553 mg, 3.33 mmol) and stirred at 70° C. for 16 hr. The reaction was cooled to RT and diluted with EtOAc (100 mL), washed with water (100 mL), and brine (50 mL) and dried over $Na_2SO_4$; and the organic phase was concentrated under reduced pressure. Obtained crude compound was purified using silica gel chromatography (40% EtOAc in hexanes) to afford 14-4A (700 mg, 1.83 mmol, 71% yield). MS (ESI): m/z 382.73 $(M+1)^+$.

The above procedure was adapted to prepare the following compounds:

Ethyl 3-hydroxy-benzoate 14-2B (553 mg, 3.33 mmol) was used to prepare 14-3B (700 mg, 73%). MS (ESI): m/z 399.8 $(M+18)^+$.

Ethyl 4-hydroxy-benzoate 14-2C (553 mg, 3.33 mmol) was used to prepare 14-3C (800 mg, 81%). MS (ESI): m/z 405.4 $(M+23)^+$.

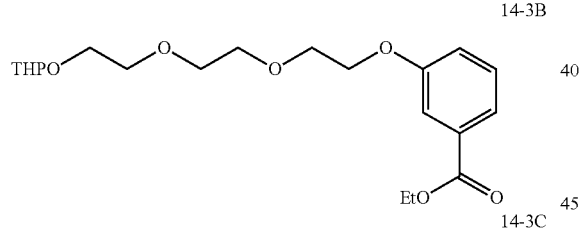

Ethyl 2-(2-(2-(2-hydroxyethoxy)-ethoxy)-ethoxy)benzoate (14-4A)

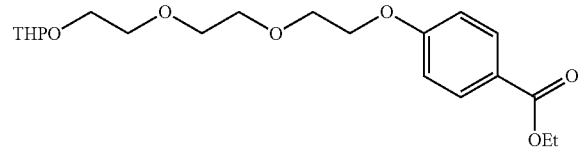

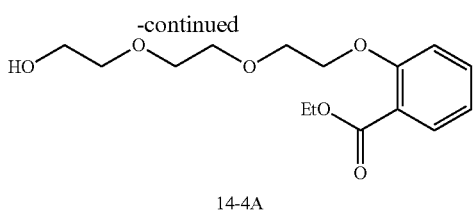

To a stirred solution of 14-3A (700 mg, 1.83 mmol) in DCM (10 mL) was added pyridinium p-toluenesulfonate (353 mg, 2.56 mmol) at 0° C., and stirred at RT for 4 hr. The reaction mixture was diluted with water (100 mL) extracted with DCM (3×50 mL), the combined organic layers were washed with brine (2×50 mL) and dried over $Na_2SO_4$ and concentrated. The residue was purified by flash column chromatography (100-200 silica) using (40% EtOAc in hexanes) to afford 14-4A (400 mg, 1.34 mmol, 74% yield) as a colorless oily liquid. MS (ESI): m/z 252.9 $(M+1)^+$.

The above procedure was adapted to prepare the following compounds:

14-3B (720 mg, 1.83 mmol) was used to prepare 14-4B (450 mg, 80%). MS (ESI): m/z 252.9 $(M+1)^+$.

14-3C (800 mg, 2.09 mmol) was used to prepare 14-4C (520 mg, 83%). MS (ESI): m/z 252.9 $(M+1)^+$.

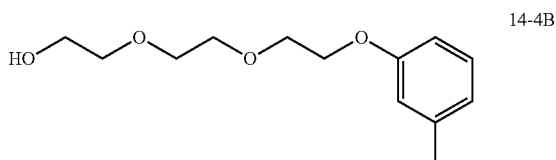

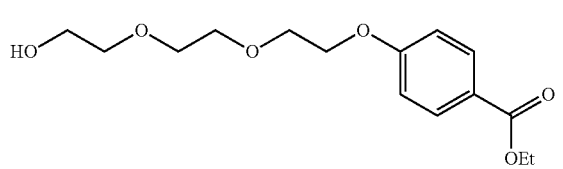

2-{2-[2-(2-Methanesulfonyloxy-ethoxy)-ethoxy]-ethoxy}-benzoic Acid Ethyl Ester (14-5A)

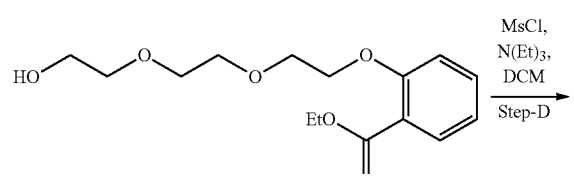

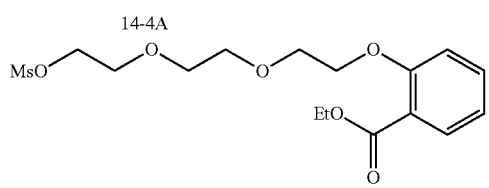

Methane sulfonyl chloride (229 mg, 2.01 mmol) at 0° C. was added to a solution of 14-4A (400 mg, 1.34 mmol) in DCM (6 mL) and triethylamine (339 mg, 3.35 mmol) and stirred at RT for 1 hr. The reaction mixture was diluted with excess DCM (50 mL) and washed with water (50 mL), then brine (20 mL), dried over Na$_2$SO$_4$, and the organic phase concentrated under reduced pressure to get crude compound. Obtained compound was purified using 100-200 silica gel column chromatography (50% EtOAc in hexanes) to afford 14-5A (440 mg, 1.17 mmol, 87% yield) as a pale brownish gummy liquid. MS (ESI): m/z 377.3 (M+1)$^+$.

The above procedure was adapted to prepare the following compounds:

14-4B (300 mg, 1 mmol) was used to prepare 14-5B (280 mg, 74%). MS (ESI): m/z 376.7 (M+1)$^+$.

14-4C (300 mg, 1 mmol) was used to prepare 14-5C (305 mg, 80%). MS (ESI): m/z 376.7 (M+1)$^+$.

To a solution of 1-12 (250 mg, 0.62 mmol) in DMF (3 mL) was added potassium carbonate (257 mg, 1.86 mmol) followed by 14-5A (280 mg, 0.74 mmol), catalytic amount of TBAI, then stirred at 70° C. for 16 hr. The reaction was cooled to RT and diluted with EtOAc (50 mL), washed with water (50 mL), brine (25 mL), and dried over Na$_2$SO$_4$, and the organic phase was concentrated under reduced pressure to get crude compound. Obtained crude was purified using silica gel chromatography (50% EtOAc in hexanes) to afford 14-6A (200 mg, 0.29 mmol, 47% yield). MS (ESI): m/z 681.5 (M−1)$^−$.

The above procedure was adapted to prepare the following compounds:

3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-benzoic Acid Ethyl Ester (14-6C)

14-5B (280 mg, 0.74 mmol) was used to prepare 14-6B (150 mg, 29%). MS (ESI): m/z 682.7 (M+1)$^+$.

4-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-benzoic Acid Ethyl Ester (14-6C)

14-5C (280 mg, 0.74 mmol) was used to prepare 14-6C (180 mg, 35%). MS (ESI): m/z 683.3 (M+1)$^+$.

2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-benzoic Acid Ethyl Ester (14-6A)

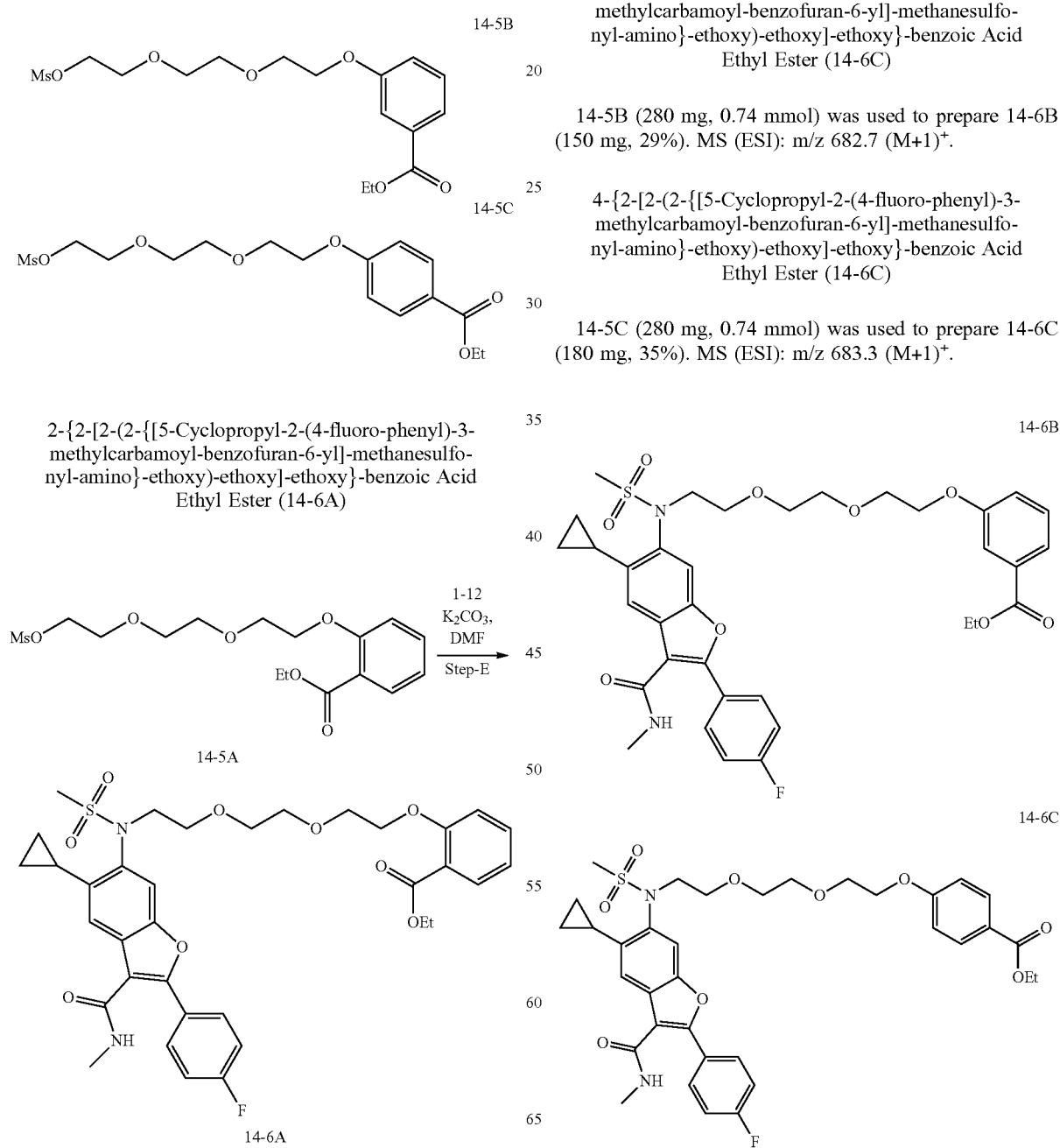

2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-benzoic Acid (14-7A)

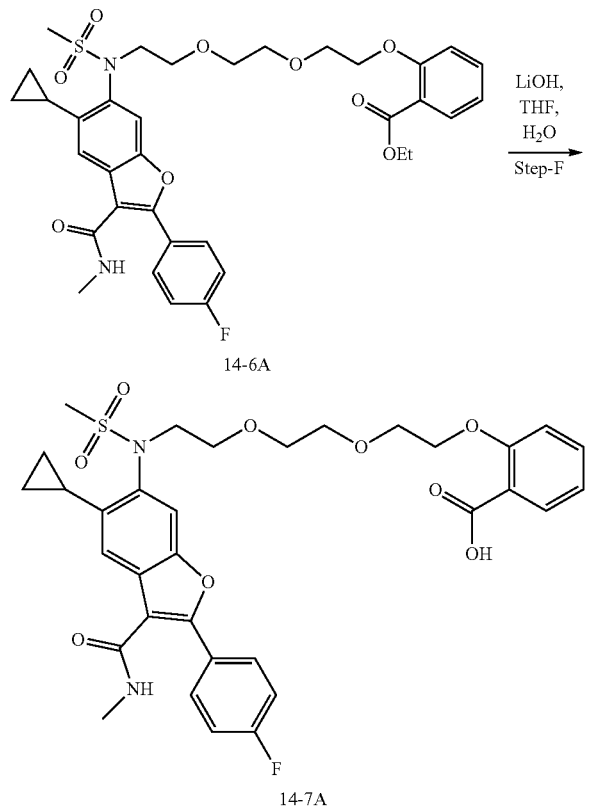

14-6A 14-7A

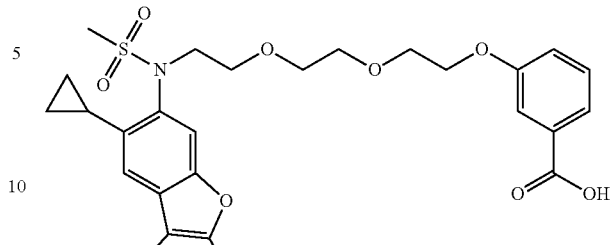

14-7B

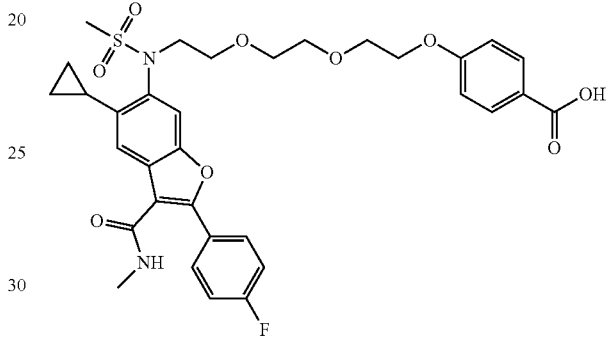

14-7C

To a solution of 14-6A (50 mg, 0.073 mmol) in THF and water (4:1; 4 mL) was added LiOH (8 mg, 0.36 mmol) and stirred at RT for 16 hr. After completion as indicated by TLC, the reaction mixture was neutralized with 1N HCl and then extracted with EtOAc. The organic layer was washed with brine, dried ($Na_2SO_4$), and concentrated to get crude compound. Obtained crude was purified by Prep TLC to give 14-7A (20 mg, 0.030 mmol, 41% yield) as an off-white solid. MS (ESI): m/z 655.5 (M+1)$^+$.

The above procedure was adapted to prepare the following compounds:

3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-benzoic Acid (14-7B)

14-6B (75 mg, 0.11 mmol) was used to prepare 14-7B (20 mg, 27%). MS (ESI): m/z 654.8 (M+1)$^+$.

4-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-benzoic Acid (14-7C)

14-6C (100 mg, 0.14 mmol) was used to prepare 14-7C (30 mg, 31%). MS (ESI): m/z 655.3 (M+1)$^+$.

Example 15

6-(Tetrahydro-2H-pyran-2-yloxy)hexan-1-ol (15-2)

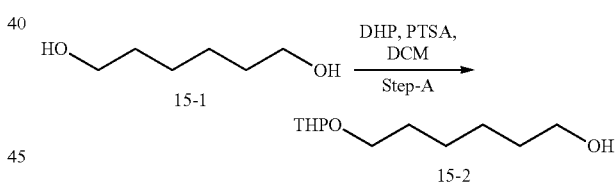

To a stirred solution of 15-1 (4 g, 33.8 mmol) in DCM (200 mL) was added dihydropyran (2.78 mL, 30.5 mmol) and PPTS (1.2 g, 6.8 mmol) at 0° C., and stirred at RT for 4 hr. The reaction mixture was diluted with water (300 mL), extracted with DCM (3×250 mL). The combined organic layers were washed with brine (2×100 mL) and dried over $Na_2SO_4$ and concentrated. The residue was purified by flash column chromatography (100-200 silica) using 2% MeOH/DCM to afford 15-2 (2 g, 9.9 mmol, 30% yield) as a colorless thick liquid.

6-(Tetrahydro-2H-pyran-2-yloxy)hexyl methanesulfonate (15-3)

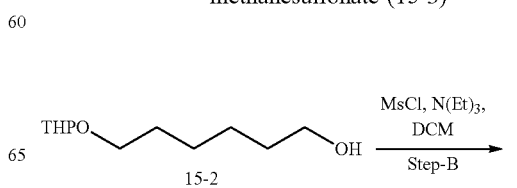

-continued

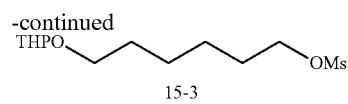
15-3

Methane sulfonylchloride (0.8 g, 3.96 mmol)) was added to a solution of 15-2 (0.33 mL, 4.4 mmol) in DCM (10 mL) and triethylamine (1.15 mL, 8.6 mmol) at 0° C. and stirred at RT for 2 hr. The reaction mixture was diluted with water (25 mL) extracted with DCM (3×50 mL). The combined organic layers were washed with brine (100 mL), dried over Na$_2$SO$_4$, and concentrated. The crude residue was purified by flash column chromatography (100-200 silica) using 30% EtOAc in hexanes to afford 15-3 (850 mg, 3.04 mmol, 78% yield) as a colorless thick liquid.

Ethyl 4-(7-(tetrahydro-2H-pyran-2-yloxy)heptyl)benzoate (15-4)

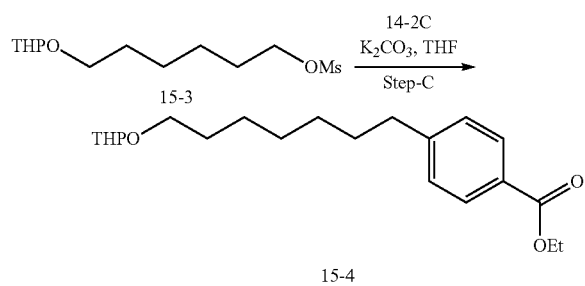

To a stirred solution of 14-2C (400 mg, 2.4 mmol) in DMF (10 mL) was added potassium carbonate (332.5 mg, 2.65 mmol), 15-3 (742 mg, 2.65 mmol) at RT and reaction was continued to stirring at 70° C. for 16 hr. The reaction mixture was quenched with ice cold water (20 mL) and extracted with EtOAc (3×50 mL). The combined organic layers were washed with water (2×20 mL), brine (15 mL), dried over Na$_2$SO$_4$ and concentrated. The residue was purified by flash column chromatography (100-200 silica) using 20% EtOAc/hexanes to afford 15-4 (600 mg, 1.72 mmol, 71% yield) as light pink solid. MS (ESI): m/z 373.47 [M+23]$^+$.

Ethyl 4-(6-hydroxyhexyloxy)benzoate (15-5)

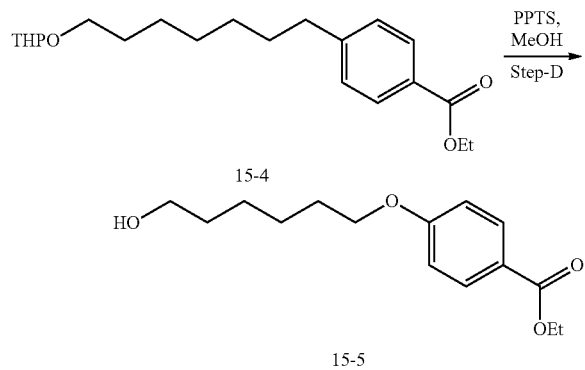

To a stirred solution of 15-4 (570 g, 1.63 mmol) in MeOH (5 mL) was added pyridinium p-toluenesulfonate (91 mg, 0.33 mmol) at 0° C. and stirred at RT for 16 hr. The solvents were distilled-off under reduced pressure. The residue obtained was extracted with EtOAc (3×50 mL). The combined organic layers were washed with brine (100 mL), dried over Na$_2$SO$_4$ and concentrated. The residue was purified by flash column chromatography (100-200 silica) using 5% acetone:DCM to afford 15-5 (348 mg, 1.31 mmol, 80% yield) as gummy liquid. MS (ESI): m/z 266.97 [M+1]$^+$.

Ethyl 4-(6-(methylsulfonyloxy)hexyloxy)benzoate (15-6)

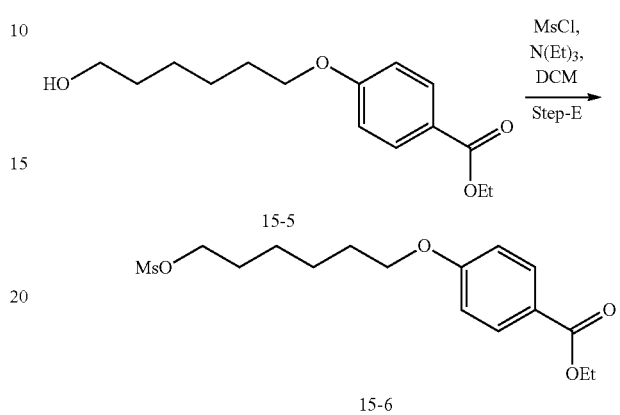

Methanesulfonyl chloride (0.12 mL, 1.56 mmol)) was added to a solution of 15-5 (345 mg, 1.29 mmol) in DCM (10 mL) and triethylamine (0.4 mL, 3.1 mmol) at 0° C. and stirred at RT for 2 hr. The reaction mixture was diluted with water (25 mL) extracted with DCM (3×20 mL). The combined organic layers were washed with brine (25 mL), dried over Na$_2$SO$_4$ and concentrated. The crude residue was purified by flash column chromatography (100-200 silica) using 20% EtOAc in hexanes to afford 15-6 (385 mg, 1.12 mmol, 86.8% yield) as a colorless thick liquid. MS (ESI): m/z 344.7 [M+1]$^+$.

4-(6-{[5-Cyclopropyl-2-(4-fluoro-phenyl)-3-methyl-carbamoyl-benzofuran-6-yl]-methanesulfonyl-amino}-hexyloxy)-benzoic Acid Ethyl Ester (15-7)

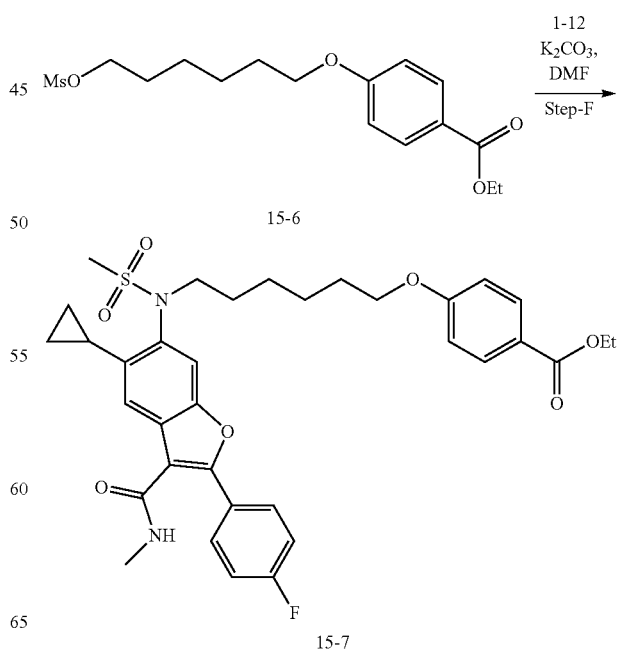

To a stirred solution of 1-12 (250 mg, 0.62 mmol) in DMF (10 mL) was added potassium carbonate (257 mg, 1.86 mmol) followed by [15-6] (256 mg, 0.74 mmol), catalytic amount of tetra-butyl ammonium iodide at 80° C. for 16 hr. The reaction mixture was cooled to RT and diluted with EtOAc (50 mL) washed with water (2×50 mL), brine (25 mL) and dried over Na$_2$SO$_4$ and concentrated. The residue was purified by flash column chromatography (100-200 silica) using 2% MeOH: DCM to afford 15-7 (252 mg, 0.39 mmol, 60% yield) as an off-white solid. MS (ESI): m/z 651.4 [M+1]$^+$.

4-(6-{[5-Cyclopropyl-2-(4-fluoro-phenyl)-3-methyl-carbamoyl-benzofuran-6-yl]-methanesulfonyl-amino}-hexyloxy)-benzoic Acid (15-8)

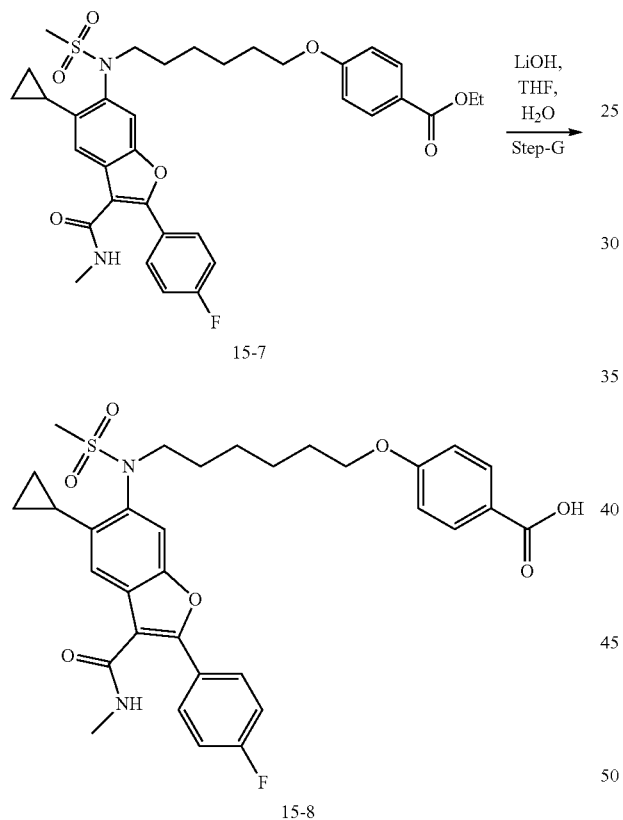

To a stirred solution of 15-7 (80 mg, 0.12 mmol) in THF and water (4 mL, 4:1) was added LiOH (17.7 mg, 0.73 mmol) at 0° C. and reaction was continued at RT for 16 hr. After completion of the reaction (TLC), solvents were evaporated at rotary evaporator, residue extracted with ether (25 mL). Then aqueous layer was neutralized with 1N HCl (2 mL) followed by extracted with EtOAc (3×20 mL). The combined organic layers were washed with brine (2×15 mL), dried over Na$_2$SO$_4$ and concentrated. The crude residue was purified by preparative HPLC to give 15-8 (18 mg, 0.03 mmol, 24% yield) as an off-white solid. MS (ESI): m/z 622.74 [M+H]$^+$.

Example 16

5-(Tetrahydro-2H-pyran-2-yloxy)-pentan-1-ol (16-2)

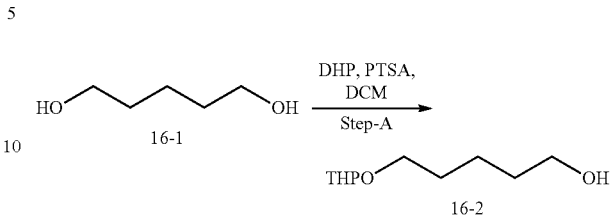

To a stirred solution of 16-1 (20 g, 192 mmol) in DCM (400 mL) was added dihydropyran (14 g, 163.4 mmol) and pyridinium p-toluenesulfonate (3.6 g, 19.2 mmol) at 0° C., and stirred at RT for 4 hr. The reaction mixture was diluted with water (500 mL) extracted with DCM (3×350 mL). The combined organic layers were washed with brine (2×100 mL) and dried over Na$_2$SO$_4$ and concentrated. The crude residue was purified by flash column chromatography (100-200 silica) using 2% MeOH/DCM to afford 16-2 (5.6 g, 30 mmol, 15% yield) as a colorless thick liquid.

Methyl 4-((5-(tetrahydro-2H-pyran-2-yloxy)-pentyloxy)-methyl)benzoate (16-3)

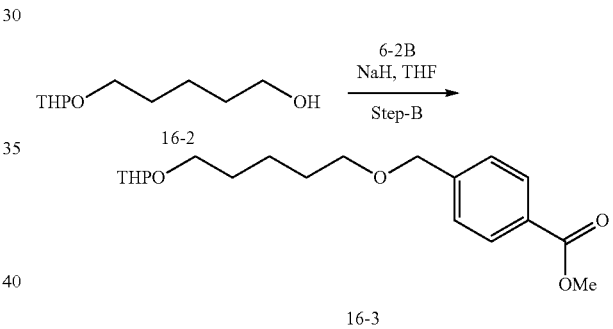

To a solution of NaH (536 mg, 22.3 mmol) in THF (40 mL) was added 16-2 (2.8 g, 14.89 mmol) at 0° C. and stirred at RT for 1 hr. The reaction mixture was again cooled to 0° C., methyl 4-(bromomethyl)benzoate 6-2B (3.58 g, 15.63 mmol) was added, and stirred for RT for 6 hr. The reaction mixture was quenched with ice cold water and diluted with EtOAc (100 mL) washed with water (50 mL), brine (25 mL), dried over Na$_2$SO$_4$, and concentrated under reduced pressure. The crude compound was purified using silica gel chromatography (15% EtOAc in hexane) to afford 16-3 (1 g, 2.97 mmol, 20% yield). MS (ESI): m/z 359.3 [M+23]$^+$.

Methyl 4-((5-hydroxypentyloxy)-methyl)benzoate (16-4)

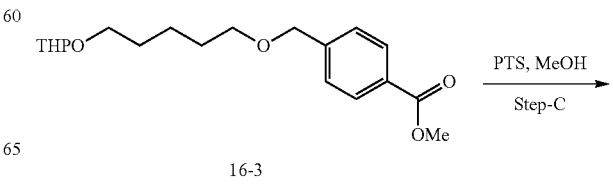

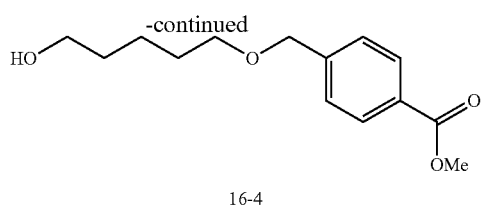

16-4

To a stirred solution of 16-3 (1 g, 2.97 mmol) in MeOH (5 mL) was added pyridinium p-toluenesulfonate (75 mg, 0.29 mmol) at 0° C. and stirred at RT for 16 hr. The solvents were distilled-off under reduced pressure. The residue obtained was extracted with EtOAc (3×50 mL). The combined organic layer washed with brine (100 mL), dried over $Na_2SO_4$ and concentrated. The residue was purified by flash column chromatography (100-200 silica) using 5% acetone-DCM to afford methyl 16-4 (720 mg, 2.85 mmol, 96% yield) as gummy liquid. MS (ESI): m/z 253.2 [M+1]$^+$.

Methyl 4-((5-(methylsulfonyloxy)-pentyloxy)-methyl)benzoate (16-5)

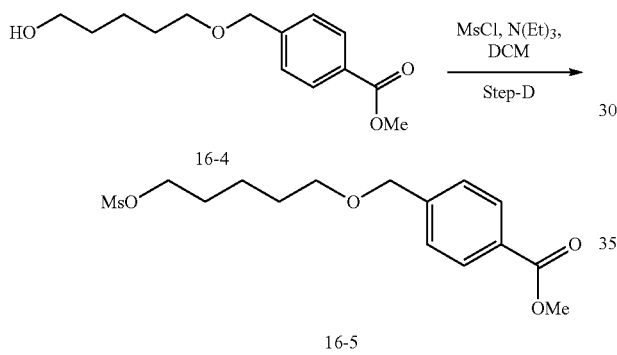

Methane sulfonylchloride (0.28 mL, 3.4 mmol) was added to a solution of 16-4 (850 mg, 3.37 mmol) in DCM (10 mL) and triethylamine (0.4 mL, 3.1 mmol) at 0° C. and stirred at RT for 2 hr. The reaction mixture was diluted with water (25 mL) extracted with DCM (3×20 mL). The combined organic layers were washed with brine (25 mL), dried over $Na_2SO_4$ and concentrated. The crude residue was purified by flash column chromatography (100-200 silica) using 20% EtOAc in hexanes to afford 16-5 (600 mg, 1.8 mmol, 63% yield) as a colorless thick liquid. MS (ESI): m/z 331.2 [M+1]$^+$.

4-(5-{[5-Cyclopropyl-2-(4-fluoro-phenyl)-3-methyl-carbamoyl-benzofuran-6-yl]-methanesulfonyl-amino}-pentyloxymethyl)-benzoic Acid Methyl Ester (16-6)

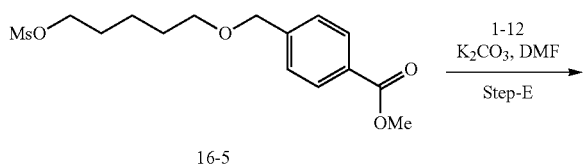

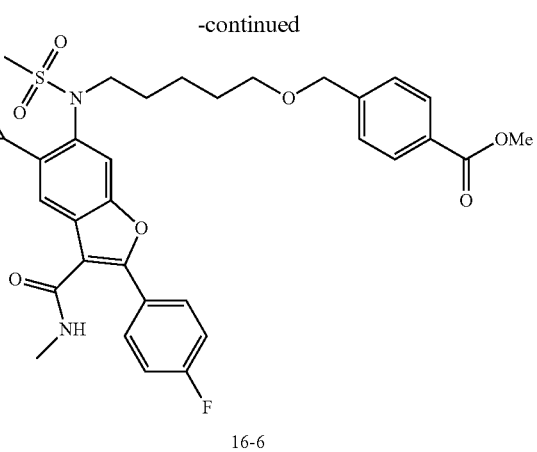

16-6

To a stirred solution of 1-12 (600 mg, 1.52 mmol) in DMF (10 mL) was added potassium carbonate (627 mg, 4.54 mmol) followed by 16-5 (600 mg, 1.82 mmol), catalytic amount of tetrabutyl ammonium iodide at 80° C. for 16 hr. The reaction mixture was cooled to RT and diluted with EtOAc (50 mL) washed with water (2×50 mL), brine (25 mL) and dried over $Na_2SO_4$ and concentrated. The residue was purified by flash column chromatography (100-200 silica) using 2% MeOH-DCM to afford 16-6 (850 mg, 1.33 mmol, 89% yield) as an off-white solid. MS (ESI): m/z 637.33 [M+H]$^+$.

4-(5-{[5-Cyclopropyl-2-(4-fluoro-phenyl)-3-methyl-carbamoyl-benzofuran-6-yl]-methanesulfonyl-amino}-pentyloxymethyl)-benzoic Acid (16-7)

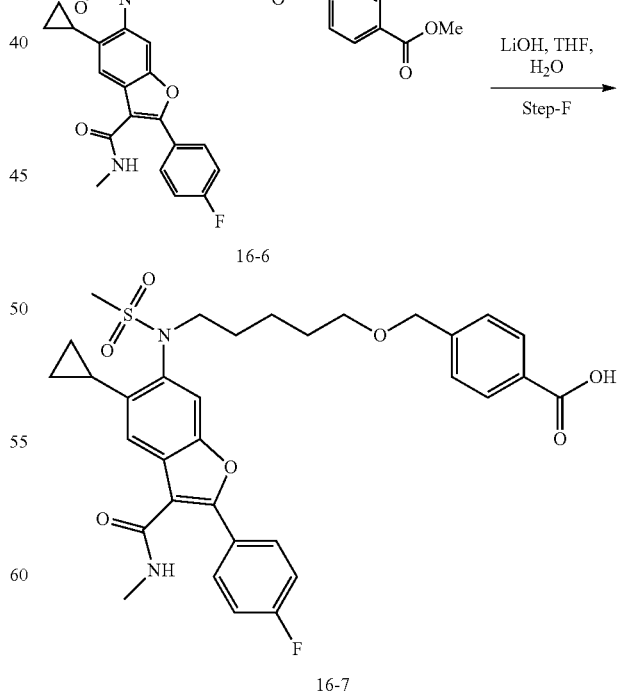

To a stirred solution of 16-6 (850 mg, 1.34 mmol) in THF and water (10 mL; 4:1) was added LiOH (192 mg, 8.02 mmol) at 0° C. and reaction was continued at RT for 16 hr. After completion of the reaction (TLC), solvents were evaporated via rotary evaporator, and residue was extracted with ether (25 mL). The aqueous layer was neutralized with 1N HCl (2 mL), and extracted with EtOAc (3×20 mL). The combined organic layers were washed with brine (2×15 mL), dried over $Na_2SO_4$ and concentrated. The crude residue was purified by preparative HPLC to give 16-7 (72 mg, 0.12 mmol, 8.6% yield) as an off-white solid. MS (ESI): m/z 623.3 $[M+1]^+$.

Example 17A

Ethyl 2-fluoro-5-methylbenzoate (17A-2)

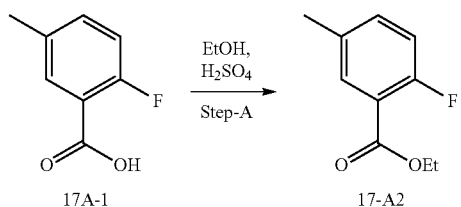

To a stirred solution of 2-fluoro-5-methylbenzoic acid 17A-1 (2 g, 12.9 mmol) in EtOH (20 mL) was added $H_2SO_4$ (0.1 mL, catalytic) at 0° C. and the reaction was refluxed for 2 hr. The reaction mixture was concentrated, and to the residue was added ice cold water (100 mL) and extracted with EtOAc (3×200 mL), The combined organic layers were washed with water (2×200 mL), brine (150 mL), dried over $Na_2SO_4$ and concentrated. The residue was purified by flash column chromatography (100-200 silica) using 15% EtOAc/hexanes to afford 17A-2 (2.2 g, 12.08 mmol, 95% yield) as a colorless thick liquid. MS=183.1 $[M+H]^+$.

Ethyl 5-(bromomethyl)-2-fluorobenzoate (17-3A)

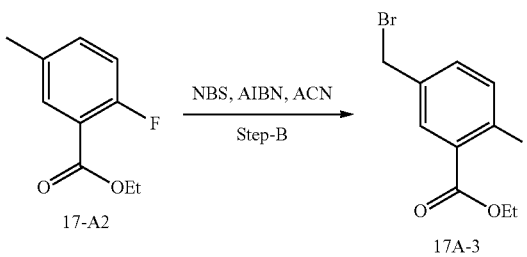

To a stirred solution of 17-2A (2.2 g, 12.09 mmol) in ACN (20 mL) was added NBS (2.32 g, 13.1 mmol) and AIBN (198 mg, 1.21 mmol) at RT. The reaction mixture was warmed to 90° C. for 6 h under nitrogen atmosphere. The reaction mixture solvent was evaporated under reduced pressure and the crude residue washed with toluene (100 mL) and filtered the precipitate (NBS). The filtrate was evaporated under reduced pressure and the crude residue was purified by flash column chromatography (100-200 silica) using 5% EtOAc/pet. ether to afford 17-3A (2.51 g, 19.61 mmol, 81% yield) as a colorless liquid.

Ethyl 2-fluoro-5-((2-(2-((tetrahydro-2H-pyran-2-yl)-oxy)-ethoxy)-ethoxy)-methyl)benzoate (17A-4)

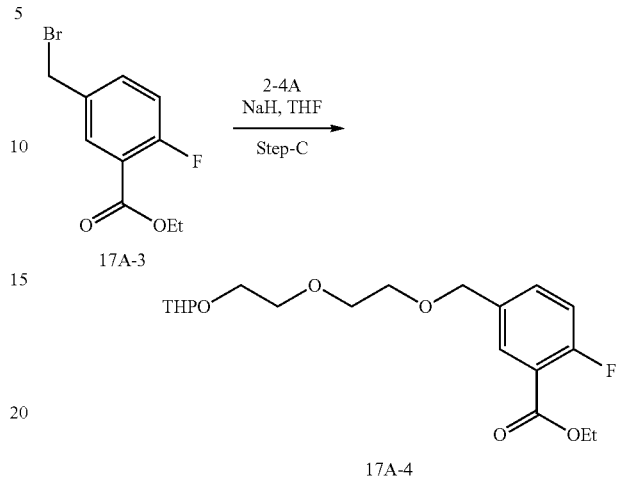

To a stirred solution of 2-4A (656 mg, 3.40 mmol) in THF (5 mL) was added NaH (165 mg, 3.40 mmol) at 0° C., and reaction was continued at RT for 30 min. 17A-3 (1.0 g, 3.8 mmol) in THF (10 mL) was added to reaction mixture at 0° C. for 5 min. and reaction was continued at RT for 16 hr. The reaction mixture was quenched with ice cold water (100 mL) and extracted with EtOAc (3×100 mL), the combined organic layers were washed with water (2×100 mL), brine (100 mL), dried over $Na_2SO_4$ and concentrated. The residue was purified by flash column chromatography (100-200 silica) using 20% EtOAc/hexanes to afford 17A-4 (270 mg, 0.729 mmol, 8.9% yield) as a thick yellow liquid. MS=283.1 $[M-THP]^+$.

Ethyl 2-fluoro-5-((2-(2-hydroxyethoxy)-ethoxy)-methyl)benzoate (17A-5)

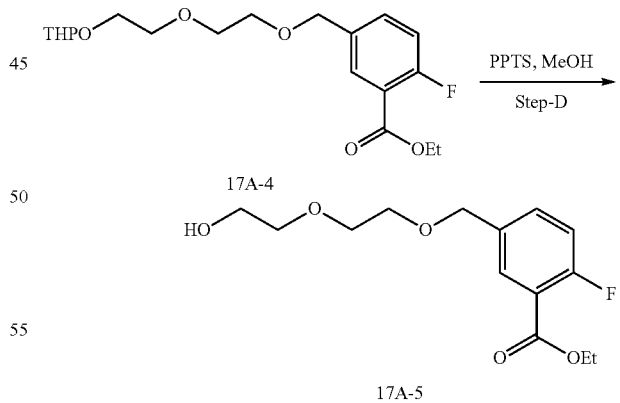

To a stirred solution of 17A-4 (270 mg, 0.72 mmol) in MeOH (5 mL) was added PPTS (37 mg, 0.014 mmol) at 0° C. and stirred at RT for 12 hr. The solvents were distilled off under reduced pressure. The residue obtained was extracted with EtOAc (3×50 mL), the combined organic layers were washed with brine (50 mL), dried over $Na_2SO_4$ and concentrated to afford 17A-5 (190 mg, 0.61 mmol, 91% yield) as a brown gummy liquid. MS=283.09 $[M-1]$.

2-Fluoro-5-[2-(2-methanesulfonyloxy-ethoxy)-ethoxymethyl]-benzoic Acid Ethyl Ester (17A-6)

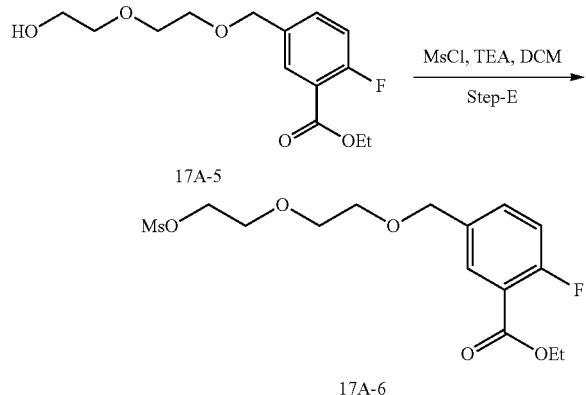

Methane sulfonyl chloride (0.06 mL, 0.79 mmol) was added to a solution of 17A-5 (190 mg, 0.61 mmol) in DCM (5 mL) and triethylamine (0.28 mL, 1.91 mmol) at 0° C. and stirred at RT for 2 hr. The reaction mixture was diluted with water (50 mL) extracted with DCM (3×50 mL), the combined organic layers were washed with brine (50 mL), dried over $Na_2SO_4$ and concentrated. The residue was purified by flash column chromatography (100-200 silica) using 25% EtOAc in hexane to afford 17A-6 (108 mg, 0.32 mmol, 44.8% yield) as a colorless gummy liquid. MS=382.09 $[M+18]^+$.

5-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-2-fluoro-benzoic Acid Ethyl Ester (17A-7)

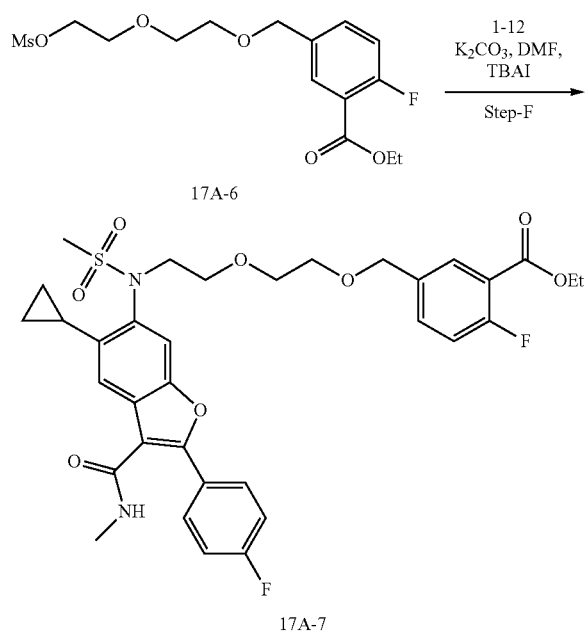

To a stirred solution of 1-12 (100 mg, 0.24 mmol) in DMF (5 mL) was added potassium carbonate (103 mg, 0.74 mmol) followed by 17A-6 (108 mg, 0.29 mmol), a catalytic amount of TBAI at 80° C. for 16 hr. The reaction mixture was cooled to RT and diluted with EtOAc (50 mL) washed with water (2×40 mL), brine (25 mL) and dried over $Na_2SO_4$ and concentrated. The residue was purified by flash column chromatography (100-200 silica) using 25% EtOAc:pet. ether to afford 17A-7 (59 mg, 0.088 mmol, 35.2% yield) as an off-white solid. MS=670.9 $[M+1]^+$.

5-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-2-fluoro-benzoic Acid (17A-8A)

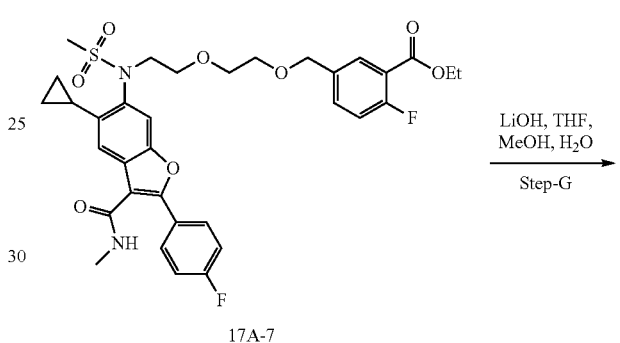

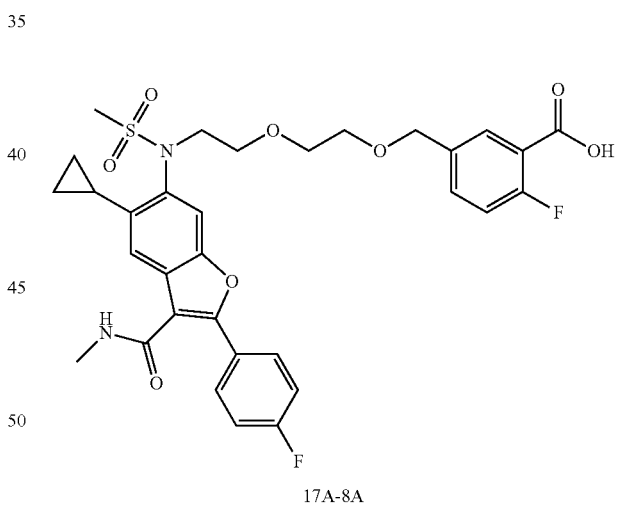

To a stirred solution of 17A-7 (50 mg, 0.07 mmol) in THF and water (3 mL; 1:1) was added LiOH (18 mg, 0.74 mmol) at 0° C. and reaction was continued at RT for 5 hr. After completion of the reaction (TLC), solvents evaporated under reduced pressure, residue extracted with ether (50 mL). Then aqueous layer was neutralized with 1N HCl (5 mL) followed by extracted with EtOAc (3×20 mL). The combined organic layers were washed with brine (2×20 mL), dried over $Na_2SO_4$ and concentrated. The residue was washed with ether pentene to afford 17A-8A (14.2 mg, 30.1% yield) as an off-white solid. MS=641.29 $[M-1]$.

5-Cyclopropyl-6-({2-[2-(4-fluoro-3-hydroxycarbamoyl-benzyloxy)-ethoxy]-ethyl}-methanesulfonylamino)-2-(4-fluoro-phenyl)-benzofuran-3-carboxylic Acid Methylamide (17A-8B)

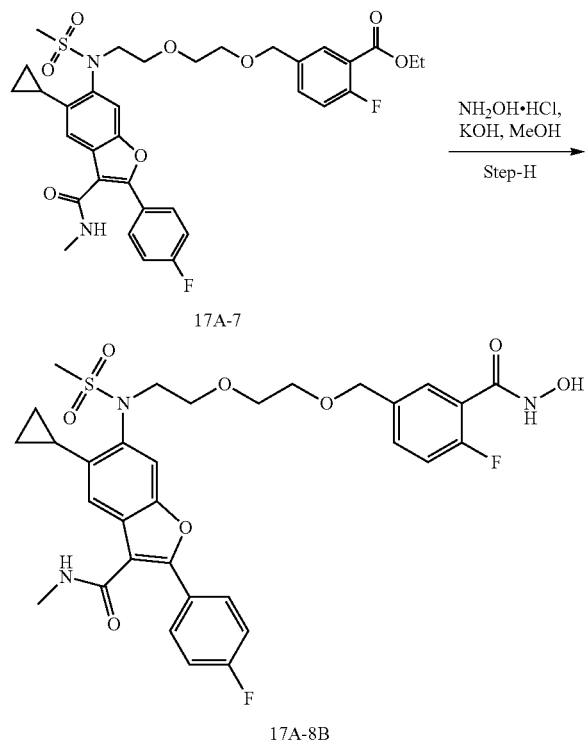

To a stirred solution of hydroxylamine hydrochloride (1 g, 14.34 mmol) in MeOH (1.5 mL) was added KOH (1.2 g, 21.51 mmol) in MeOH at 0° C. One mL of this solution was added to a solution of 17A-7 (50 mg, 0.07 mmol) in MeOH at 0° C., and the reaction was continued at RT for 1 hr. After completion of the reaction (TLC), solvents were evaporated under reduced pressure, then water was added and the solution was neutralized with 1N HCl (5 mL), followed by extraction with EtOAc (3×20 mL). The combined organic layers were washed with brine (2×20 mL), dried over Na₂SO₄ and concentrated. The residue was purified with preparative HPLC to afford 17A-8B (5 mg, 10% yield) as a brown solid. MS=658.2 [M+1]⁺.

Example 17B

Methyl 2-methoxy-5-methylbenzoate (17B-2)

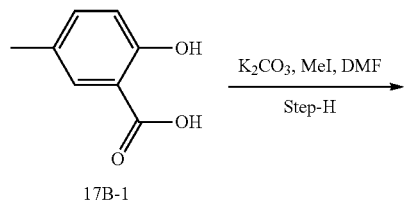

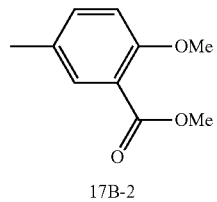

To a stirred solution of 2-hydroxy-5-methylbenzoic acid 17B-1 (3 g, 19.73 mmol) in DMF (50 mL) was added K₂CO₃ (8.2 g, 59.21 mmol) and methyl iodide (2.7 mL, 43.41 mmol) at 0° C. and reaction was stirred at RT for 6 hr. To the reaction mixture was added ice cold water (100 mL) and extracted with EtOAc (3×100 mL), the combined organic layers were washed with water (2×200 mL), brine (150 mL), dried over Na₂SO₄ and concentrated. The residue was purified by flash column chromatography (100-200 silica) using 15% EtOAc/hexanes to afford 17B-2 (3.4 g, 18.88 mmol, 85% yield) as a colorless thick liquid. MS (ESI): m/z 181.1 (M+1)⁺.

5-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-2-methoxy-benzoic Acid (17B-8)

Starting from 17B-2, substituted for 17A-2 in Step-B, the procedure given in Example 17A was adapted to prepare 17B-8. MS (ESI): m/z 654.8 (M+1)⁺.

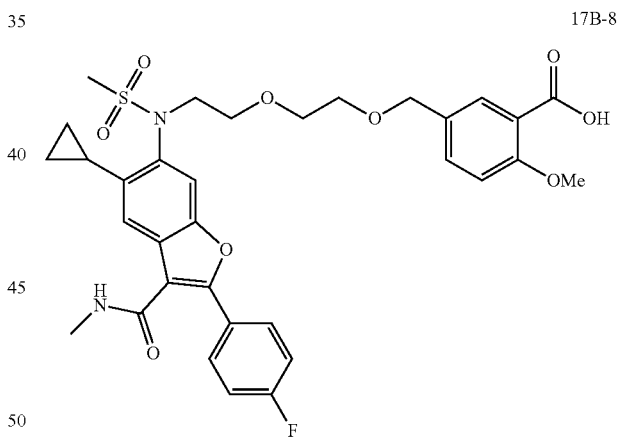

Example 18

Methyl 4-iodo-2-methylbenzoate (18-2A)

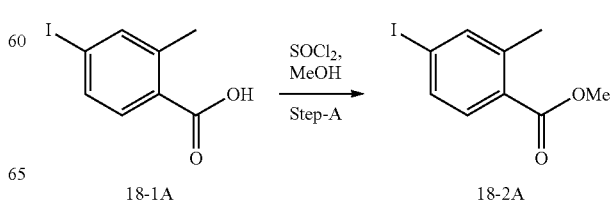

To a solution of 4-iodo-2-methyl-benzoic acid 18-1A (2 g, 7.62 mmol) in MeOH (20 mL) was added thionyl chloride (1.5 mL, 10.87 mmol) at 0° C. and stirred at reflux for 6 hr. The reaction mixture was distilled off and diluted with EtOAc (50 mL), washed with water (100 mL), NaHCO$_3$ solution (50 mL), dried over Na$_2$SO$_4$, and concentrated under reduced pressure. The crude compound was purified using silica gel chromatography (10% EtOAc in hexanes) to afford 18-2A (1.8 g, 6.55 mmol, 85.7% yield) as a brown oily liquid.

Methyl 4-formyl-3-methylbenzoate (18-3B)

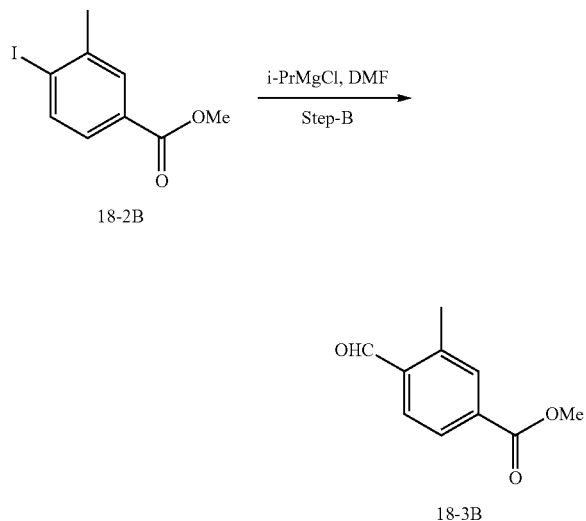

To a stirred solution of 18-2B (3.2 g, 11.5 mmol; TCI) in THF was treated with isopropyl magnesium chloride (i-PrMgCl) in THF (22.8 mL of 2.0 M in THF, 46 mmol) at −15° C. After 2 hr stirring at the same temperature, dry DMF (4.3 mL, 57.5 mmol) was added and the reaction was allowed to warm to 23° C. over 1 hr. After consumption of the starting material (by TLC), the reaction was quenched with aqueous 1M HCl (60 mL), followed by extracted with EtOAc, dried over Na$_2$SO$_4$ and concentrated. The crude compound was purified by flash column chromatography (100-200 silica) using 5% EtOAc in hexanes to afford 18-3B (1.4 g, 7.8 mmol, 70% yield) as an off-white solid. MS (ESI): m/z 179.2 (M+1)$^+$.

Step-B above was adapted using methyl 4-iodo-2-methyl-benzoate (18-2A) (1.8 g, 6.52 mmol) to prepare 18-3A (906 mg, 78%).

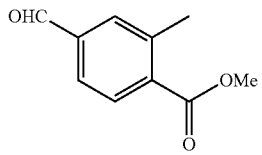

Methyl 4-(hydroxymethyl)-3-methylbenzoate (18-4B)

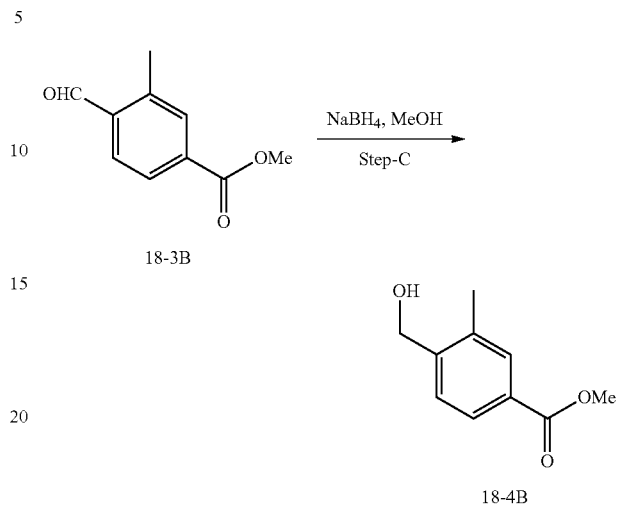

To a stirred solution of 18-3B (1.4 g, 7.8 mmol) in MeOH, was added NaBH$_4$ (0.29 g, 7.8 mmol) at 0° C. and stirred to RT for 30 min. After consumption of starting material (TLC), reaction mixture was quenched with saturated ammonium chloride solution, then MeOH was distilled off and aqueous layer was extracted with EtOAc, dried over Na$_2$SO$_4$ and concentrated at reduced pressure. The crude product was purified by flash column chromatography (100-200 silica) using 20% EtOAc in hexane to afford 18-4B (1.2 g, 6.6 mmol, 84% yield) as a colorless liquid. MS (ESI): m/z 181.0 (M+1)$^+$.

Step-C above was adapted using 18-3A (900 mg, 5.0 mmol) to prepare 18-4A (801 mg, 88%). MS (ESI): m/z 81.17 [M+1]$^+$.

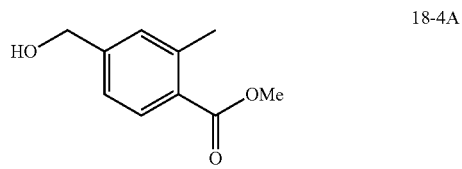

Methyl 4-(bromomethyl)-3-methylbenzoate (18-5B)

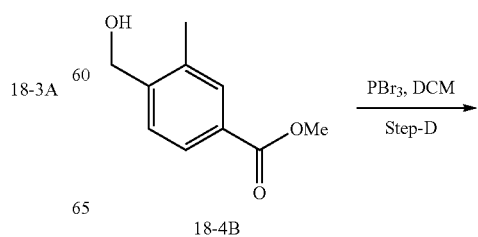

-continued

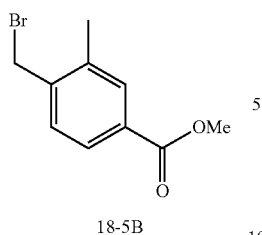

18-5B

To a stirred solution of 18-4B (1.2 g, 6.6 mmol) in DCM, was added phosphorous tribromide (0.64 mL, 6.6 mmol) at 0° C. and stirred to RT for 30 min. After consumption of the starting material (by TLC), reaction was quenched with saturated NaHCO$_3$ solution and extracted with DCM. The organic layer was dried over Na$_2$SO$_4$, and concentrated under reduced pressure. The crude compound was purified by flash column chromatography (100-200 silica) using 5% EtOAc in hexane to afford 18-5B (0.95 g, 3.9 mmol, 59% yield) as a colorless semi-solid.

Step-D above was adapted using 18-4A (1.42 g, 7.88 mmol) to prepare 18-5A (920 mg, 48%).

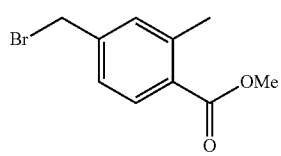

18-5A

Methyl 3-methyl-4-((2-(2-(tetrahydro-2H-pyran-2-yloxy)-ethoxy)-ethoxy)-methyl)benzoate (18-6B)

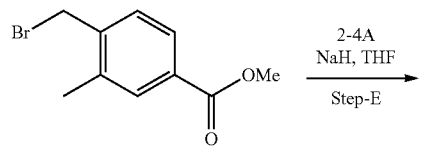

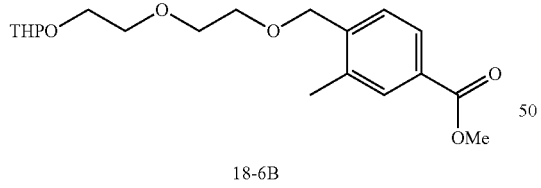

18-6B

To a stirred solution of 2-4A (0.745 g, 3.9 mmol) in THF (20 mL) was added NaH (102 mg, 4.29 mmol) portion wise at 0° C. and stirred at RT for 1 hr, then added the solution of 18-5B (950 mg, 3.9 mmol) in THF (10 mL) at the same temperature and stirred at RT for 4 hr. The reaction mixture was quenched with saturated ammonium chloride solution and diluted with EtOAc (100 mL) washed with water (100 mL), brine (50 mL) and dried over Na$_2$SO$_4$, and the organic phase was concentrated under reduced pressure. The crude compound was purified by flash column chromatography (100-200 silica) using 20% EtOAc in hexane to afford 18-6B (500 mg, 1.42 mmol, 36% yield) as a pale yellow liquid. MS (ESI): m/z 269.0 (M-THP+1)$^+$.

Step-E above was adapted using [18-5A (650 mg, 3.81 mmol) to prepare [18-6A (602 mg, 44%). MS (ESI): m/z 370.39 [M+18]$^+$.

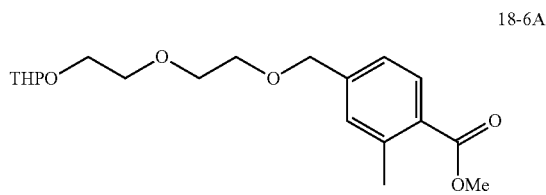

18-6A

Methyl 4-((2-(2-hydroxyethoxy)-ethoxy)-methyl)-3-methylbenzoate (18-7B)

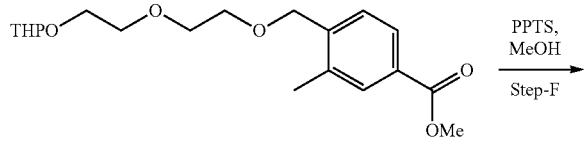

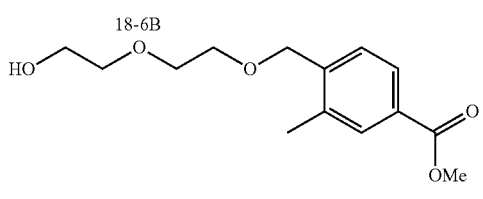

18-7B

To a solution of 18-6B (500 mg, 1.42 mmol) in MeOH (10 mL) was added PPTS (35.6 mg, 0.14 mmol) and stirred at 0° C. to RT for 16 hr. The reaction mixture was distilled off and diluted with excess EtOAc (50 mL), washed with water (50 mL), brine (20 mL), dried over Na$_2$SO$_4$, and concentrated under reduced pressure. The crude compound was purified by flash column chromatography (100-200 silica) using 30% EtOAc in hexane to afford to afford 18-7B (270 mg, 1.0 mmol, 71% yield) as a yellowish liquid. MS (ESI): m/z 269.0 (M+1)$^+$.

Step-F above was adapted using 18-6A (600 mg, 1.7 mmol) to prepare 18-7A (252 mg, 57%). MS (ESI): m/z 269.2 [M+1]$^+$.

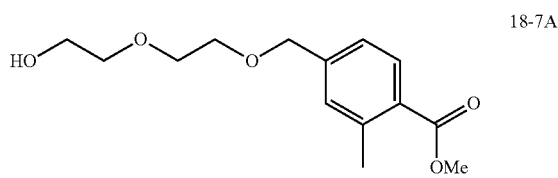 [SMILES: COC(=O)c1ccc(COCCOCCO)cc1C]

18-7A

4-[2-(2-Methanesulfonyloxy-ethoxy)-ethoxymethyl]-3-methyl-benzoic Acid Methyl Ester (18-8B)

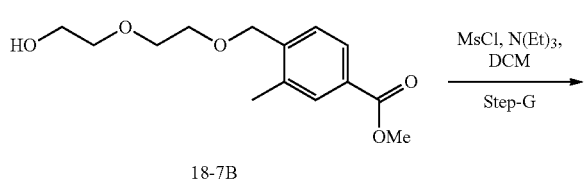

18-7B

-continued

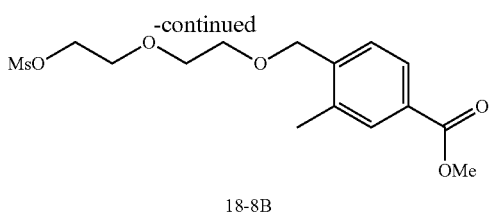

18-8B

To a stirred solution of 18-7B (0.270 g, 1.01 mmol) in DCM (6 mL) was added triethylamine (0.33 mL, 2.41 mmol) and methanesulfonyl chloride (0.097 mL, 1.2 mmol) at 0° C. and stirred at RT for 1 hr. The reaction mixture was diluted with excess DCM (50 mL) and washed with water (50 mL), brine (20 mL), dried over Na$_2$SO$_4$, and concentrated under reduced pressure. The crude compound was purified by flash column chromatography (100-200 silica) using 25% EtOAc in hexane to afford 18-8B (250 mg, 0.72 mmol, yield 71%) as a colorless liquid. MS (ESI): m/z 347.0 (M+1)$^+$.

Step-G was adapted using 18-7A (260 mg, 0.9 mmol) to prepare 18-8A (270 mg, 80.4%). MS (ESI): m/z 347.1 [M+1]$^+$.

To a solution of 1-12 (252 mg, 0.62 mmol) in DMF (5 mL) was added potassium carbonate (260 mg, 1.88 mmol) followed by 18-8B (250 mg, 0.72 mmol), catalytic amount of TBAI then stirred at 70° C. for 16 hr. The reaction was cooled to RT and diluted with EtOAc (50 mL) washed with water (50 mL), brine (15 mL) and dried over Na$_2$SO$_4$, and the organic phase was concentrated under reduced pressure. The crude compound was purified by flash column chromatography (100-200 silica) using 30% EtOAc in hexane to afford 18-9B 210 mg, 0.32 mmol, 51% yield) as an off-white solid. MS (ESI): m/z 653.3 (M+1)$^+$.

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-2-methyl-benzoic Acid Methyl Ester (18-9A)

Step-H was adapted using 18-8A (225 mg, 1.55 mmol) to prepare 18-9A (184 mg, 50%). MS (ESI): m/z 653.2 [M+1]$^+$.

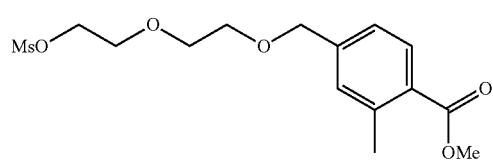

18-8A

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-3-methyl-benzoic Acid Methyl Ester (18-9B)

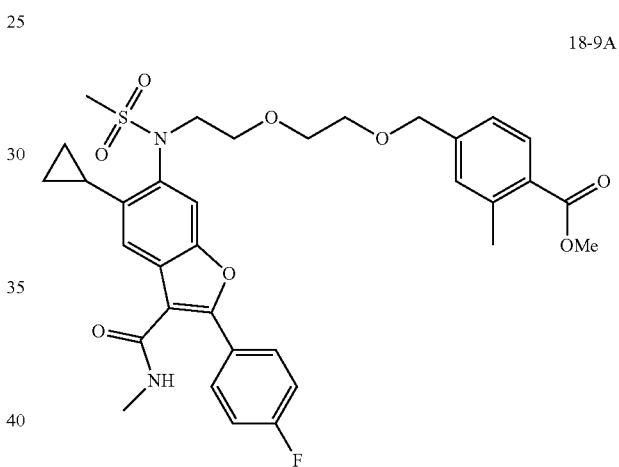

18-9A

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-3-methyl-benzoic Acid (18-10B)

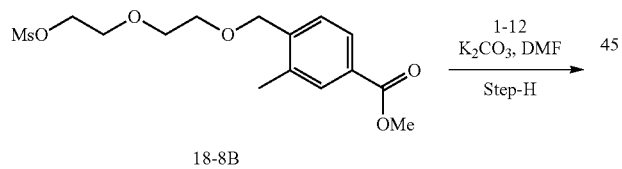

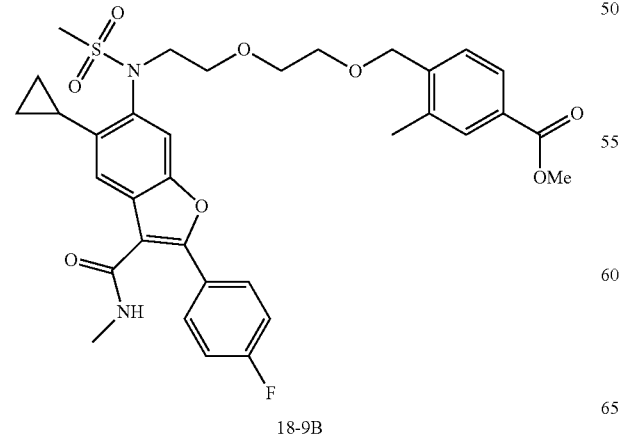

18-9B

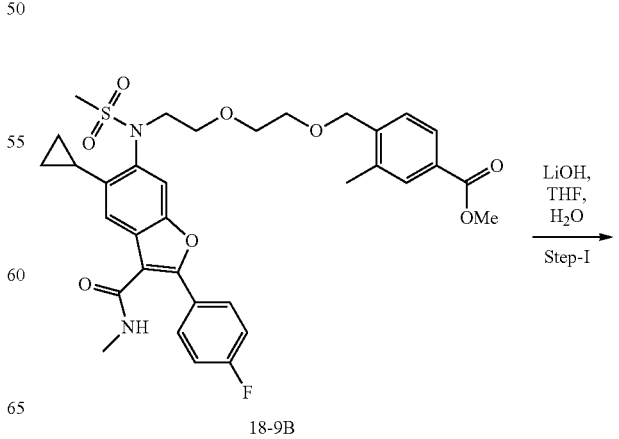

18-9B

-continued

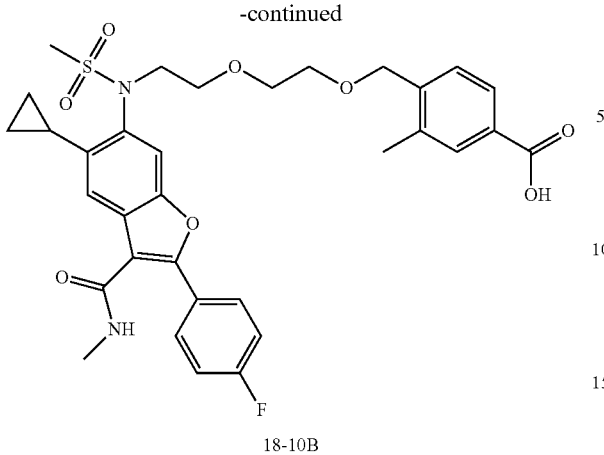

18-10B

To a solution of 18-9B (100 mg, 0.15 mmol) in THF and water (4:1; 6 mL) was added LiOH.H$_2$O (22 mg, 0.91 mmol) and stirred at RT for 16 hr. After completion of the reaction as indicated by TLC, the reaction mixture was neutralized with 1N HCl and then extracted with EtOAc (3×20 mL). The combined organic layer was washed with brine, dried (Na$_2$SO$_4$) and concentrated under reduced pressure. The crude compound was purified by column chromatography (100-200 silica) using 2% MeOH in DCM, followed by DCM and pentane washing to afford 18-10B (45 mg, 0.07 mmol, 46% yield) as an off-white solid. MS (ESI): m/z 639.0 (M+1)$^+$.

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-2-methyl-benzoic Acid (18-10A)

This procedure was adapted using 18-9A (100 mg, 0.1 mmol) to prepare 18-10A (37 mg, 38%). MS (ESI): m/z 639.3 [M+1]$^+$.

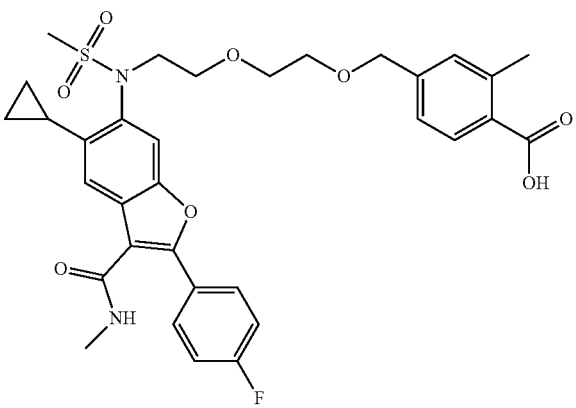

18-10A

Example 19

Methyl 2-chloroisonicotinate (19-2A)

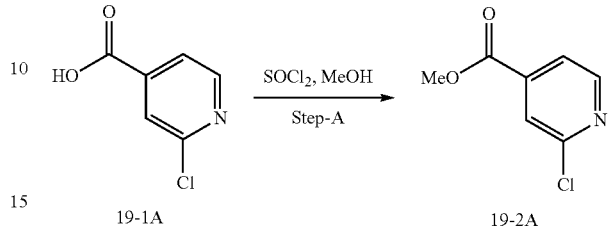

19-1A    19-2A

To a solution of 2-chloroisonicotinic acid 19-1A (5 g, 31.8 mmol) in MeOH (50 mL) was added SOCl$_2$ (2.7 mL, 38.2 mmol) portion-wise at 0° C., and the mixture was stirred at RT for 16 hr. Solvent was evaporated under reduced pressure. The reaction was quenched with saturated sodium carbonate and diluted with EtOAc (50 mL) washed with water (50 mL), brine (20 mL) and dried over Na$_2$SO$_4$, and the organic phase was concentrated under reduced pressure. Obtained crude compound was purified using silica gel chromatography (15% EtOAc in hexanes) to afford 19-2A (4.4 g, 25.7 mmol, 81% yield) as an off-white solid. MS (ESI): m/z 172.1 (M+1)$^+$.

Step-A was adapted using 6-chloronicotinic acid to prepare 19-2B.

(6-Chloropyridin-3-yl)-methanol (19-3B)

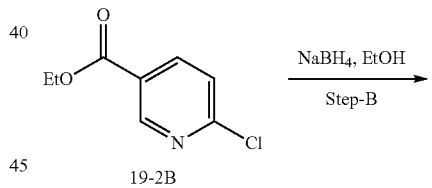

19-2B

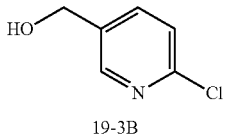

19-3B

To a solution of 19-2B (500 mg, 2.693 mmol) in MeOH (5 mL) was added sodium borohydride (153 mg, 4.04 mmol) portion wise at 0° C. and stirred at RT for 16 hr. The reaction was quenched with saturated ammonium chloride and diluted with EtOAc (50 mL) washed with water (50 mL), brine (20 mL) and dried over Na$_2$SO$_4$, and the organic phase was concentrated under reduced pressure to get crude compound. Obtained crude was purified using silica gel chromatography (30% EtOAc in hexanes) to afford 19-3B (230 mg, 1.60 mmol, 59% yield) as a pale yellow solid. MS (ESI): m/z 144.0 (M+1)$^+$.

Step-B was adapted using 19-2A (1 g, 5.8 mmol) to prepare 19-3A (800 mg, 95%). MS (ESI): m/z 144.0 (M+1)$^+$.

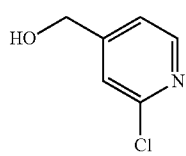

19-3A 5-(Bromomethyl)-2-chloropyridine (19-4B)

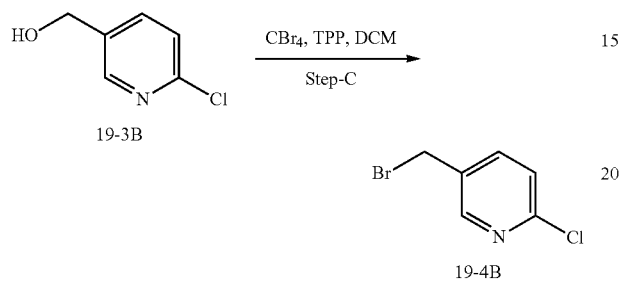

19-3B 19-4B

To a solution of 19-3B (115 mg, 0.804 mmol) in DCM (3 mL) was added carbon tetrabromide (320 mg, 0.965 mmol), triphenylphosphine (210 mg, 0.965 mmol), and stirred at 0° C. to RT for 16 hr. The reaction mixture was diluted with excess DCM (20 mL), washed with water (20 mL), brine (10 mL) and dried over $Na_2SO_4$, and the organic phase was concentrated under reduced pressure. Obtained crude compound was purified using silica gel chromatography (8% EtOAc in hexanes) to afford 19-4B (100 mg, 0.48 mmol, yield 60%). MS (ESI): m/z 206.0 (M−1)⁺.

Step-C was adapted using 19-3A (800 mg, 5.5 mmol) to prepare 19-4A (600 mg, 52%). MS (ESI): m/z 206.1 (M−1)⁺.

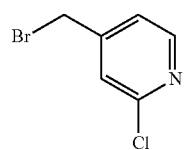

19-4A 2-(Chloro-5-((2-(2-((tetrahydro-2H-pyran-2-yl) oxy)-ethoxy)-ethoxy)-methyl)-pyridine) (19-5B)

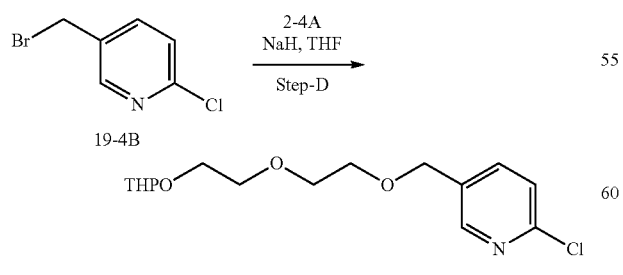

19-4B 19-5B

To a solution of 2-4A (77 mg, 0.40 mmol) in THF (2 mL) was added NaH (12 mg, 0.48 mmol) portion wise at 0° C. and stirred at RT for 1 hr and then added a solution of 19-4B in THF (100 mg, 0.40 mmol; 1 mL) at the same temperature and stirred at RT for 3 hr. The reaction was quenched with saturated ammonium chloride and diluted with EtOAc (50 mL) washed with water (50 mL), brine (20 mL) and dried over $Na_2SO_4$, and the organic phase was concentrated under reduced pressure to get crude compound. Obtained crude was purified using silica gel chromatography (35% EtOAc in hexanes) to afford 19-5B (70 mg, 0.22 mmol, 55% yield) as a brownish gummy liquid. MS (ESI): m/z 316.3 (M+1)⁺.

Step-D was adapted using 19-4A (600 mg, 2.9 mmol) to prepare 19-5A (300 mg, 30%). MS (ESI): m/z 316.3 (M+1)⁺.

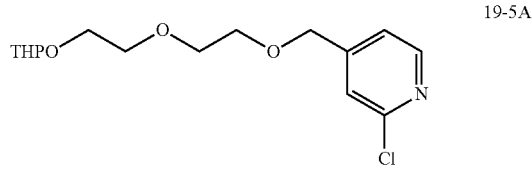

19-5A 2-(2-((6-Chloropyridine-3-yl)-methoxy)-ethoxy)-ethanol (19-6B)

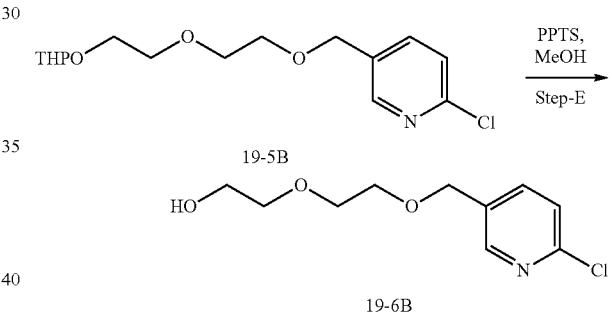

19-5B 19-6B

To a solution of 19-5B (70 mg, 0.22 mmol) in MeOH (1 mL) was added PPTS (11 mg, 0.04 mmol) and stirred at 0° C. to RT for 16 hr. The reaction mixture was distilled off and diluted with excess EtOAc (20 mL), washed with water (20 mL), brine (10 mL) and dried over $Na_2SO_4$, and the organic phase was concentrated under reduced pressure to get crude compound. Obtained crude was purified using silica gel chromatography (50% EtOAc in hexanes) to afford 19-6B (40 mg, 0.173 mmol, 78% yield) as a brownish gummy liquid. Confirmed by ¹H NMR.

Step-E was adapted using 19-5A (300 mg, 0.95 mmol) was used to prepare 19-6A (100 mg, 45%). MS (ESI): m/z 232.1 (M+1)⁺.

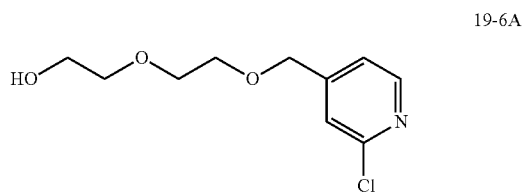 [SMILES: OCCOCCOCc1ccnc(Cl)c1]

19-6A

2-(2-((6-Chloropyridin-3-yl)-methoxy)-ethoxy)-ethyl methanesulfonate (19-7B)

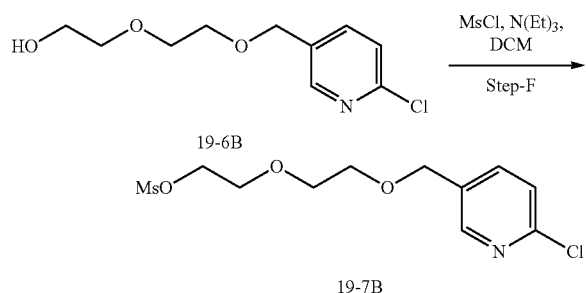

Methane sulfonyl chloride (29 mg, 0.26 mmol) was added to a solution of 19-6B (40 mg, 0.17 mmol) in DCM (1 mL) and triethylamine (43 mg, 0.4329 mmol) at 0° C. and stirred at RT for 2 hr. The reaction mixture was diluted with excess DCM (10 mL) and washed with water (10 mL), brine (10 mL) and dried over $Na_2SO_4$, and the organic phase concentrated under reduced pressure to get crude compound. Obtained compound was purified using 100-200 silica gel column chromatography (40% EtOAc in hexanes) to afford 19-7B (36 mg, 0.116 mmol, 67% yield) as a brownish oily liquid. MS (ESI): m/z 310.18 $(M+1)^+$.

Step-F was adapted using 19-6A (100 mg, 0.43 mmol) was used to prepare 19-7A (100 mg, 76%). MS (ESI): m/z 310.1 $(M+1)^+$.

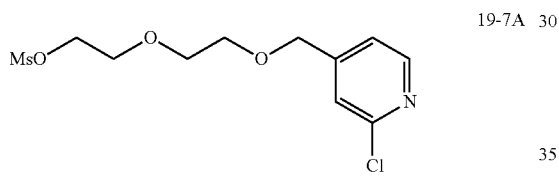

2-(2-((6-Chloropyridin-3-yl)-methoxy)-ethoxy)-ethyl)-methylsulfonamido)-5-cyclopropyl-2-(4-fluorophenyl)-N-methylbenzofuran-3-carboxamide (19-8B)

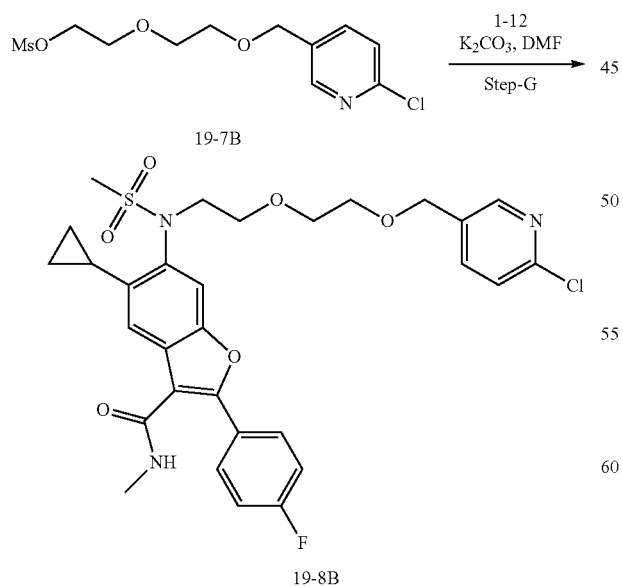

To a solution of 1-12 (39 mg, 0.097 mmol) in DMF (1 mL) was added potassium carbonate (40 mg, 0.291 mmol) followed by 19-7B (36 mg, 0.11 mmol), catalytic amount of TBAI then stirred at 70° C. for 16 hr. The reaction was cooled to RT and diluted with EtOAc (20 mL) washed with water (20 mL), brine (15 mL) and dried over $Na_2SO_4$, and the organic phase was concentrated under reduced pressure. Obtained crude product was purified using prep TLC method to afford 19-8B (25 mg, 0.04 mmol, 34% yield). MS (ESI): m/z 616.4 $(M+1)^+$.

6-({2-[2-(2-Chloro-pyridin-4-ylmethoxy)-ethoxy]-ethyl}-methanesulfonyl-amino)-5-cyclopropyl-2-(4-fluoro-phenyl)-benzofuran-3-carboxylic Acid Methylamide (19-8A)

Step-G was adapted using 19-7A (100 mg, 0.32 mmol) to prepare 19-8A (39 mg, 17%). MS (ESI): m/z 616.2 $(M+1)^+$.

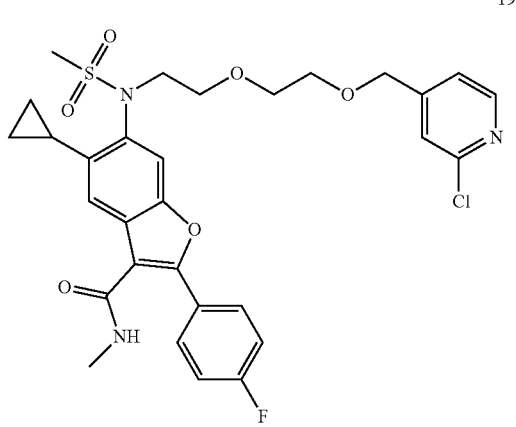

Example 20

Ethyl 4-methyl-1-naphthoate (20-2)

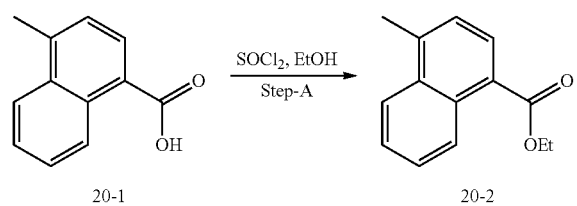

To a solution of 20-1 (5 g, 26.9 mmol) in ethanol (50 mL) was added thionyl chloride (4.8 g, 40.32 mmol) at 0° C. and stirred at reflux for 6 hr. The reaction mixture was distilled off and diluted with EtOAc (100 mL), washed with water (100 mL), $NaHCO_3$ solution (50 mL) and dried over $Na_2SO_4$, and concentrated under reduced pressure. The crude compound was purified using silica gel chromatography (10% EtOAc in hexanes) to afford 20-2 (5 g, 23.63 mmol, 87% yield) as a brown oily liquid. MS (ESI): m/z 215.1 $(M+1)^+$.

183

Ethyl 4-(bromomethyl)-1-naphthoate (20-3)

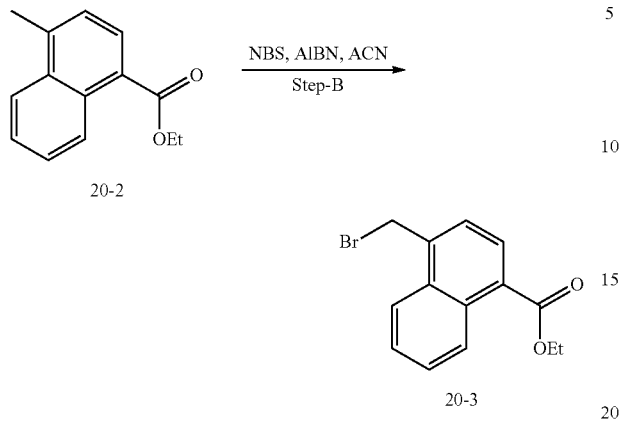

To a solution of 20-2 (1 g, 4.67 mmol) in ACN (40 mL) was added N-bromo succinimide (744 mg, 4.20 mmol), azo isobutyronitrile (76 mg, 0.46 mmol), and stirred at reflux for 6 hr. The reaction mixture was diluted with EtOAc (100 mL), washed with water (100 mL), brine (50 mL) and dried over $Na_2SO_4$, and concentrated under reduced pressure. The crude compound was purified using silica gel chromatography (3% EtOAc in hexanes) to afford 20-3 (600 mg, 2.05 mmol, 44% yield). MS (ESI): m/z 293.1 $(M+1)^+$.

Ethyl 4-((2-(2-((tetrahydro-2H-pyran-2-yl)-oxy)-ethoxy)-ethoxy)-methyl)-1-naphthoate (20-4)

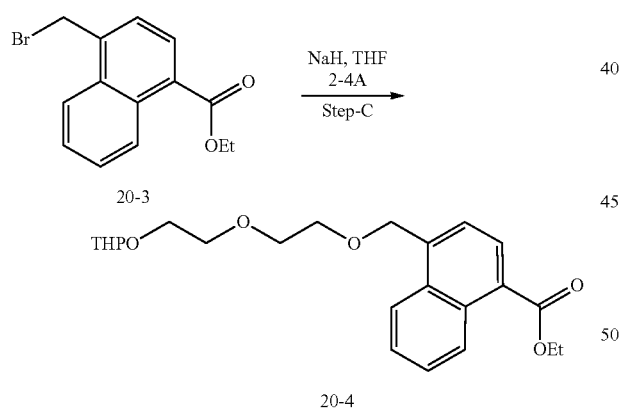

To a solution of 2-4A (800 mg, 4.21 mmol) in THF (20 mL) was added NaH (121 mg, 5.05 mmol) portion-wise at 0° C. and stirred at RT for 1 hr and added the solution of 20-3 (1.47 g, 5.05 mmol) in THF (10 mL) at the same temperature and stirred at RT for 3 hr. The reaction mixture was quenched with saturated ammonium chloride and diluted with EtOAc (100 mL), washed with water (100 mL), brine (50 mL), and dried over $Na_2SO_4$, and concentrated under reduced pressure. The crude compound was purified using silica gel chromatography (30% EtOAc in hexanes) to afford 20-4 (600 mg, 1.49 mmol, 35% yield) as a pale green gummy liquid. MS (ESI): m/z 420.4 $(M+18)^+$.

184

Ethyl 4-((2-(2-hydroxyethoxy)-ethoxy)-methyl)-1-naphthoate (20-5)

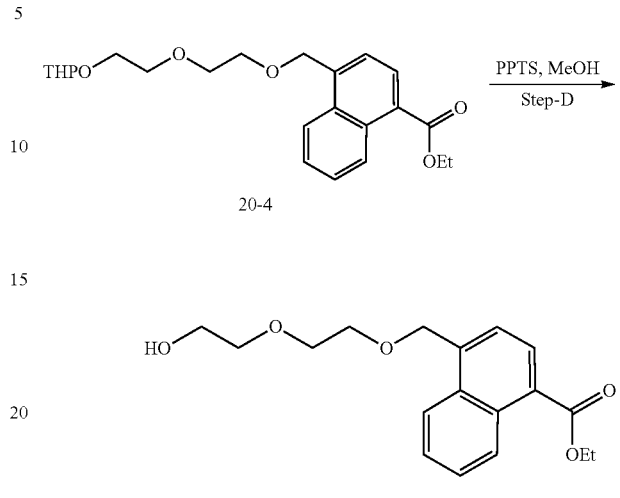

To a solution of 20-4 (600 mg, 1.49 mmol) in MeOH (10 mL) was added PPTS (37.7 mg, 0.15 mmol) and stirred at 0° C. to RT for 16 hr. The reaction mixture was distilled off and diluted with excess EtOAc (50 mL), washed with water (50 mL), brine (20 mL) and dried over $Na_2SO_4$, and concentrated under reduced pressure to get crude compound. Obtained crude was purified using silica gel chromatography (50% EtOAc in hexanes) to afford 20-5 (365 mg, 1.15 mmol, 77% yield) as a pale green gummy liquid. MS (ESI): m/z 319.3 $(M+1)^+$.

4-[2-(2-Methanesulfonyloxy-ethoxy)-ethoxymethyl]-naphthalene-1-carboxylic Acid Ethyl Ester (20-6)

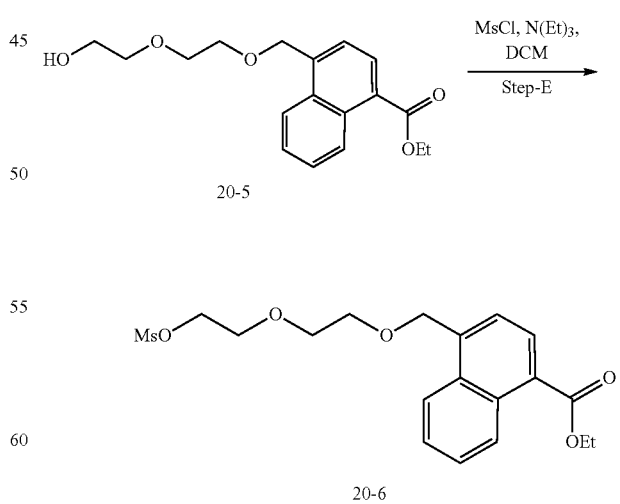

Methane sulfonylchloride (193 mg, 1.69 mmol) at 0° C. was added to a solution of 20-5 (360 mg, 1.13 mmol) in DCM (5 mL) and triethylamine (286 mg, 2.83 mmol) and stirred at RT for 2 hr. The reaction mixture was diluted with excess DCM (50 mL) and washed with water (50 mL), brine (20 mL), and dried over Na$_2$SO$_4$, and concentrated under reduced pressure. The crude compound was purified using 100-200 silica gel column chromatography (40% EtOAc in hexanes) to afford 20-6 (355 mg, 0.89 mmol, 79% yield) as a pale green oily liquid. MS (ESI): m/z 397.2 (M+1)$^+$.

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-naphthalene-1-carboxylic Acid Ethyl Ester (20-7)

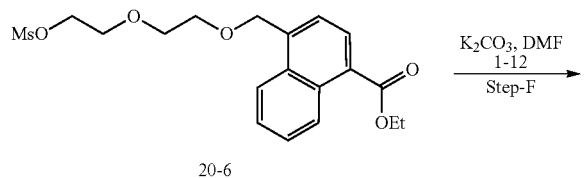

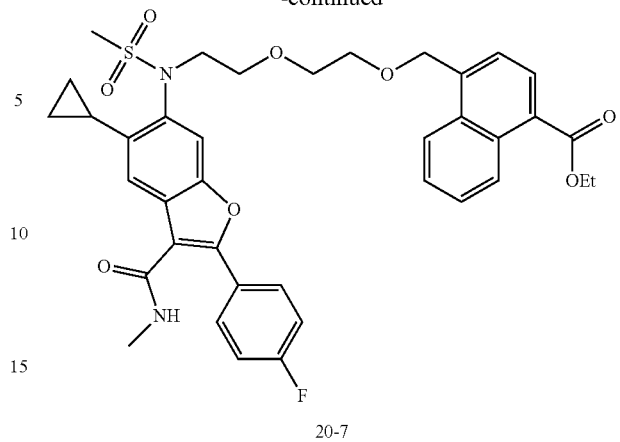

To a solution of 1-12 (250 mg, 0.62 mmol) in DMF (4 mL) was added potassium carbonate (257 mg, 1.86 mmol) followed by 20-6 (295 mg, 0.74 mmol), a catalytic amount of TBAI, then stirred at 70° C. for 16 hr. The reaction mixture was cooled to RT and diluted with EtOAc (50 mL) washed with water (50 mL), brine (15 mL) and dried over Na$_2$SO$_4$, and concentrated under reduced pressure. The crude compound was purified using 100-200 silica gel column chromatography (40% EtOAc in hexanes) to afford 20-7 (180 mg, 0.25 mmol, 39% yield) as an off-white solid. MS (ESI): m/z 703.3 (M+1)$^+$.

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-naphthalene-1-carboxylic Acid (20-8)

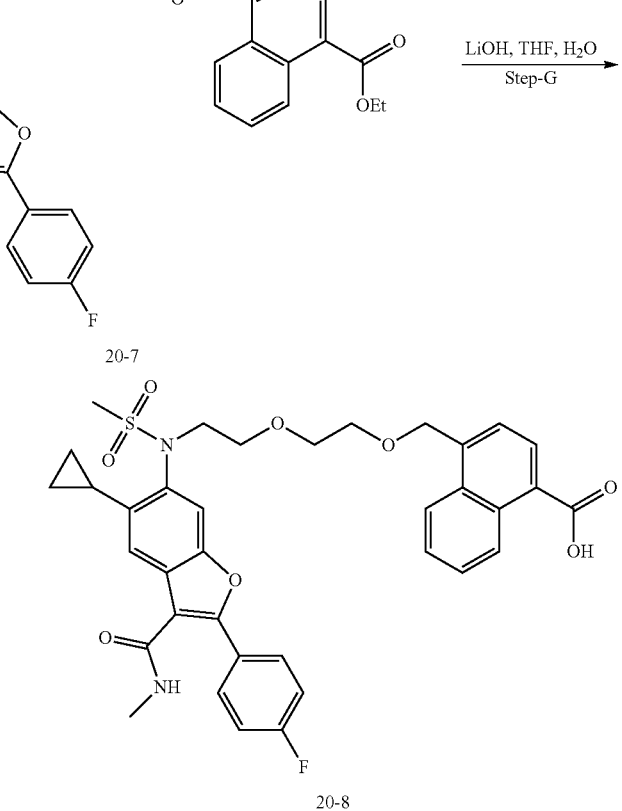

To a solution of 20-7 (100 mg, 0.14 mmol) in MeOH, THF and water (1:4:1; 6 mL) was added LiOH.H$_2$O (28 mg, 0.71 mmol) and stirred at RT for 16 hr. After completion of the reaction as indicated by TLC, the reaction mixture was neutralized with 1N HCl and then extracted with EtOAc (3×25 mL). The combined organic layer was washed with brine, dried over Na$_2$SO$_4$ and concentrated. The crude compound was purified by prep TLC to afford 20-8 (30 mg, 0.04 mmol, 31% yield) as an off-white solid. MS (ESI): m/z 673.5 (M+1)$^+$.

Example 21

2-(2-(Tetrahydro-2H-pyran-2-yloxy)-ethoxy)-ethyl Methanesulfonate (21-1)

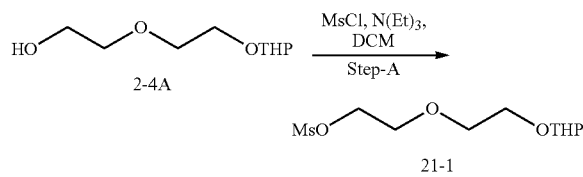

To a stirred solution of 2-4A (300 mg, 1.57 mmol) in DCM, was added triethylamine (0.3 mL, 1.88 mmol) at 0° C. After 5 min, mesyl chloride (0.15 mL, 1.88 mmol) was added to the reaction mixture at the same temperature then reaction warmed to stir at RT for 2 hr. The reaction mixture was diluted with water, and extracted with DCM (3×30 mL). The combined organic layer was washed with brine, dried over Na$_2$SO$_4$ and concentrated. The crude compound was purified by column chromatography to afford 21-1 (390 mg, 1.45 mmol, 92% yield) as an off-white solid.

5-Cyclopropyl-2-(4-fluorophenyl)-N-methyl-6-(N-(2-(2-(tetrahydro-2H-pyran-yloxy)ethoxy)ethyl)-methylsulfonamido)benzofuran-3-carboxamide (21-2)

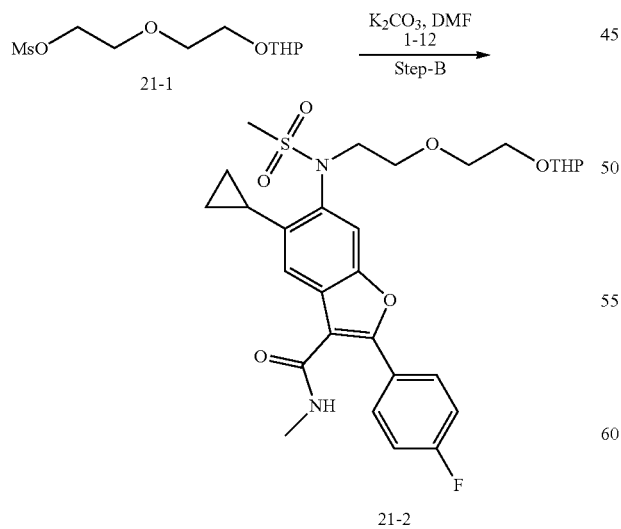

To a stirred solution of 1-12 (300 mg, 0.75 mmol) in DMF (10 mL) was added potassium carbonate (309 mg, 2.24 mmol) followed by 21-1 (237 mg, 0.89 mmol), catalytic amount of tetrabutylammonium iodide at 80° C. for 16 hr. The reaction mixture was cooled to RT and diluted with EtOAc (50 mL) washed with water (2×40 mL), brine (25 mL) and dried over Na$_2$SO$_4$ and concentrated at reduced pressure. The crude residue was purified by flash column chromatography (100-200 silica) using 2% MeOH-DCM to afford 21-2 (312 mg, 0.54 mmol, 73% yield) as an off-white solid. MS (ESI): m/z 572.8 (M−1).

5-Cyclopropyl-2-(4-fluorophenyl)-6-(N-(2-(2-hydroxyethoxy)-ethyl)-methylsulfonamido)-N-methyl-benzofuran-3-carboxamide (21-3)

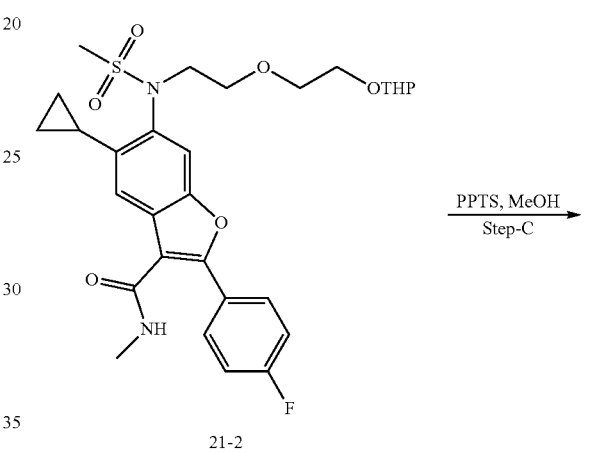

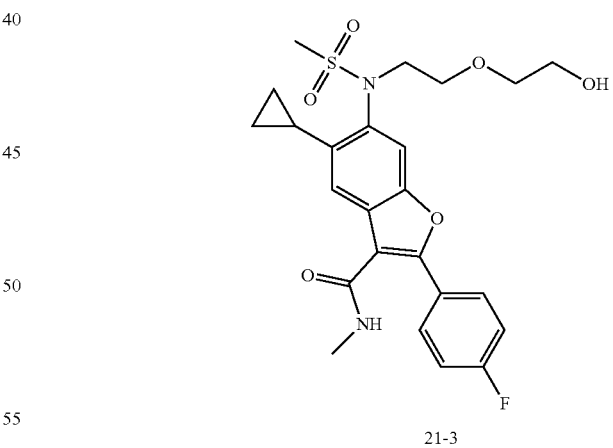

To a stirred solution of 21-2 (312 mg, 0.54 mmol) in MeOH (6 mL) was added pyridinium p-toluenesulfonate (30 mg, 0.11 mmol) at 0° C. and stirred at RT for 16 hr. The solvents were distilled-off under reduced pressure. The residue obtained was extracted with EtOAc (3×20 mL). The combined organic layer washed with brine (10 mL), dried over Na$_2$SO$_4$ and concentrated at reduced pressure. The crude residue was purified by flash column chromatography (100-200 silica) using 5% acetone-DCM to afford 21-3 (200 mg, 0.4 mmol, 76%) as gummy liquid. MS (ESI): m/z 491.4 (M+1)⁺.

Methanesulfonic Acid 2-(2-{[5-cyclopropyl-2-(4-fluoro-phenyl)-3-methylcarbamoyl-benzofuran-6-yl]-methanesulfonyl-amino}-ethoxy)-ethyl Ester (21-4)

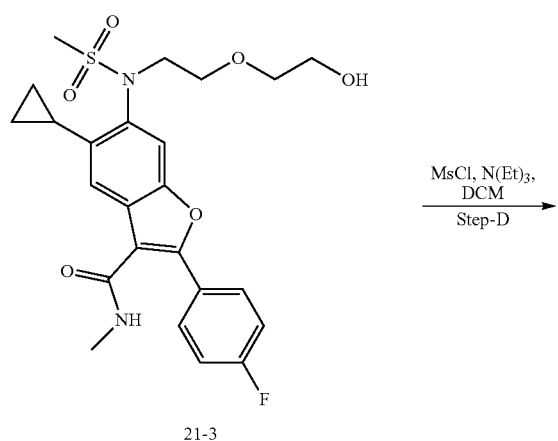

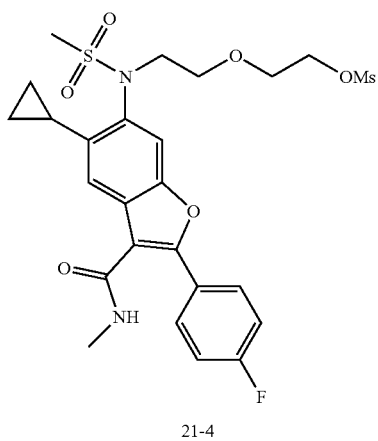

To a stirred solution of 21-3 (40 mg, 0.08 mmol) in DCM, was added triethylamine (0.02 mL, 0.19 mmol) at 0° C. After 5 min, mesyl chloride (0.007 mL, 0.09 mmol) was added to the reaction mixture at the same temperature. The reaction mixture was allowed to stir at RT for 2 hr. After, reaction mixture was diluted with water, and extracted with DCM (2×20 mL). The combined organic layer was washed with brine, dried over Na₂SO₄ and concentrated at reduced pressure. The crude compound was purified by column chromatography to get 21-4 (41 mg, 0.07 mmol, 90% yield) as an off-white solid. MS (ESI): m/z=569.4 (M+1)⁺.

Thioacetic Acid S-[2-(2-{[5-cyclopropyl-2-(4-fluoro-phenyl)-3-methylcarbamoyl-benzofuran-6-yl]-methanesulfonyl-amino}-ethoxy)-ethyl] Ester (21-5)

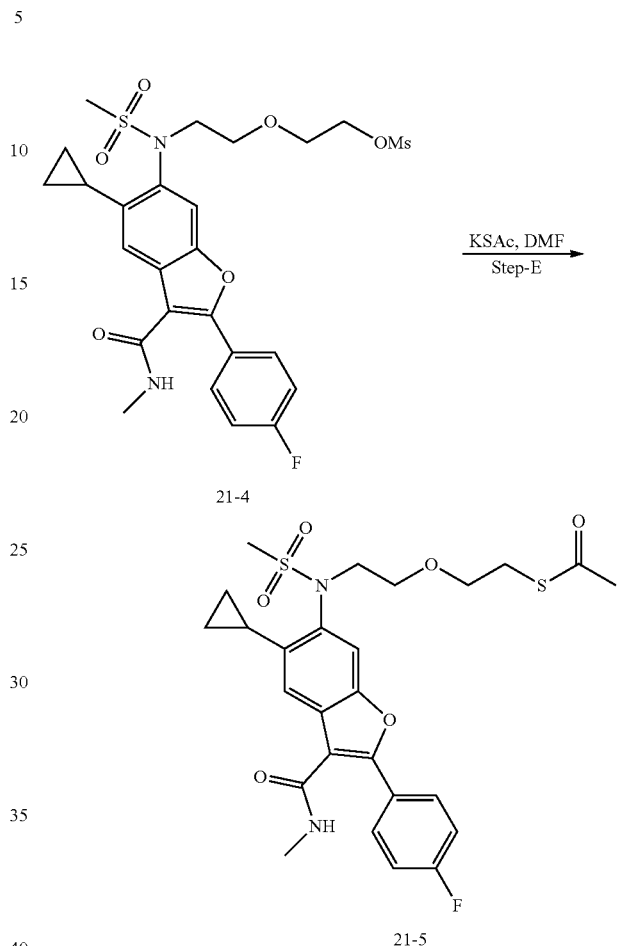

To a stirred solution of 21-4 (41 mg, 0.7 mmol) in DMF (2 mL), potassium thioacetate (KSAc; 8.15 mg, 0.072 mmol) was added slowly at 0° C. and stirred at RT for 16 hr. The reaction mixture was diluted with water (15 mL) extracted with EtOAc (3×25 mL). The combined organic layers were washed with brine (2×15 mL) and dried over Na₂SO₄ and concentrated at reduced pressure. The crude residue was purified by flash column chromatography (100-200 silica) using 10% EtOAc/hexane to afford 21-5 (16 mg, 0.029 mmol, 41% yield) as a colorless solid. MS (ESI): m/z 548.6 [M+1]⁺.

Example 22

1-(3-(3-Hydroxyprop-1-en-1-yl)-phenyl)-ethanone (22-2)

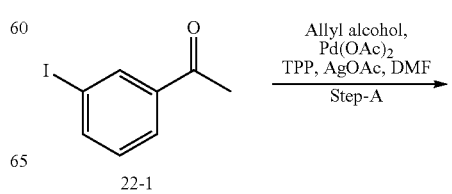

-continued

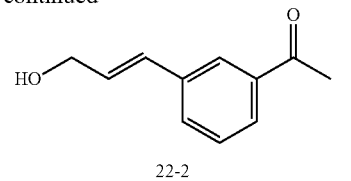

22-2

To a stirred solution of 1-(3-iodophenyl) ethanone 22-1 (200 mg, 0.81 mmol) in DMF (3 mL) was added allyl alcohol (252 mg, 4.06 mmol), AgOAc (137 mg, 0.81 mmol), TPP (21 mg, 0.081 mmol). The mixture was purged with argon for 15 min and Pd(OAc)$_2$ (27 mg, 0.04 mmol) was added at RT. The reaction mixture was warmed to 70° C. for 16 hr under nitrogen atmosphere. The reaction mixture was diluted with water (10 mL) extracted with EtOAc (3×50 mL), the combined organic layers were washed with brine (2×40 mL) and dried over Na$_2$SO$_4$ and concentrated. The residue was purified by column chromatography (100-200 silica) using 20-25% EtOAc/Pet. ether to afford 22-2 (100 mg, 0.56, 69.9% yield) as a colorless liquid. MS=177.1 [M+1]$^+$.

1-(3-(3-Hydroxypropyl)-phenyl)-ethanone (22-3)

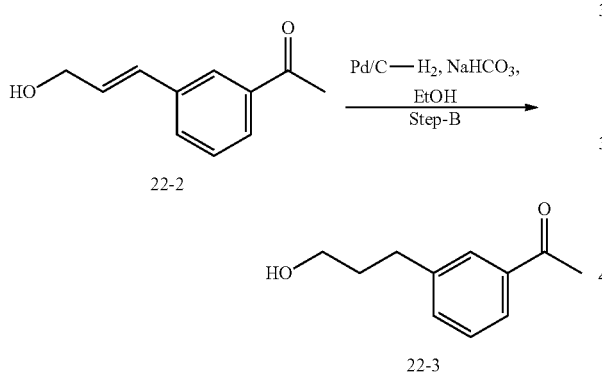

To a stirred solution of 22-2 (200 mg, 1.13 mmol) in EtOH (10 mL) was added NaHCO$_3$ (95 mg, 1.13 mmol), Pd/C (10% w/w) 15 mg, at RT. The reaction mixture was stirred for 3 hr under H$_2$ atmosphere (1 atm). The reaction mixture filtered through a celite bed, washed with EtOAc (50 mL), the combined organic layers were dried over Na$_2$SO$_4$ and concentrated under reduced pressure to afford 22-3 (190 mg, 0.94, 95% yield) as a colorless liquid.

3-(3-Acetylphenyl)-propyl methanesulfonate (22-4)

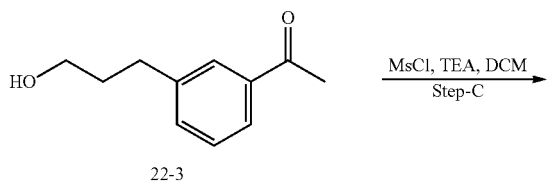

-continued

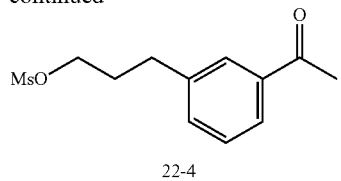

22-4

Methane sulfonyl chloride (0.137 mL, 1.68 mmol) was added to a solution of 22-3 (250 mg, 1.40 mmol) in DCM (10 mL) and triethylamine (0.591 mL, 4.21 mmol) at 0° C. and stirred at RT for 2 hr. The reaction mixture was diluted with water (50 mL) extracted with DCM (3×100 mL). The combined organic layers were washed with brine (100 mL), dried over Na$_2$SO$_4$ and concentrated. The residue was purified by flash column chromatography (100-200 silica) using 15% EtOAc in hexanes to afford 22-4 (180 mg, 0.703 mmol, 50.1% yield) as a colorless liquid. MS=257.1 [M+1]$^+$.

2-((Tetrahydro-2H-pyran-2-yl)-oxy)-ethanol (22-6)

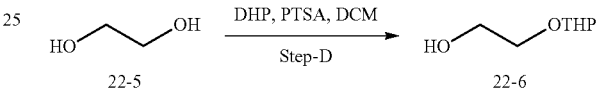

To a stirred solution of ethane-1,2-diol 22-5 (5 g, 80.6 mmol) in DCM (50 mL) was added DHP (6.4 g, 76.61 mmol) and PTSA (1.53 g, 8.06 mmol) at 0° C., and stirred at RT for 4 hr. The reaction mixture was diluted with water (150 mL) extracted with DCM (3×200 mL), the combined organic layers were washed with brine (2×100 mL) and dried over Na$_2$SO$_4$ and concentrated. The residue was purified by flash column chromatography (100-200 silica) using 20% EtOAc-Pet. ether to afford 22-6 (1.2 g, 8.21, 10.2% yield) as pale yellow liquid.

1-(3-(3-(2-((Tetrahydro-2H-pyran-2-yl)-oxy)-ethoxy)-propyl)-phenyl) Ethanone (22-7)

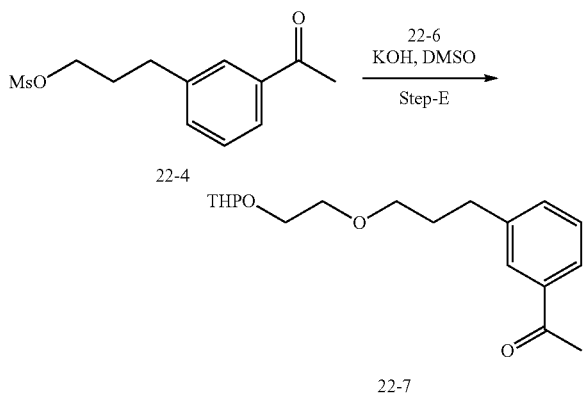

To a stirred solution of 22-6 (926 mg, 6.3 mmol) in DMSO (6 mL) was added NaOH (284 mg, 5.07 mmol) at 0° C., and reaction was continued at RT for 30 min. 22-4 (650 mg, 2.53 mmol) in DMSO (4 mL) was added to reaction mixture at 0° C. for 5 min. and reaction was continued at RT for 1 hr. The reaction mixture was quenched with ice cold water (100 mL) and extracted with EtOAc (3×100 mL). The combined organic layers were washed with water (2×200 mL), brine (150 mL), dried over Na₂SO₄ and concentrated. The residue was purified by flash column chromatography (100-200 silica) using 15% EtOAc/hexanes to afford 22-7 (420 mg, 1.37 mmol, 54.5% yield) as a colorless thick liquid. MS=324.1 [M+1]⁺.

1-(3-(3-(2-Hydroxyethoxy)-propyl)-phenyl) Ethanone (22-8)

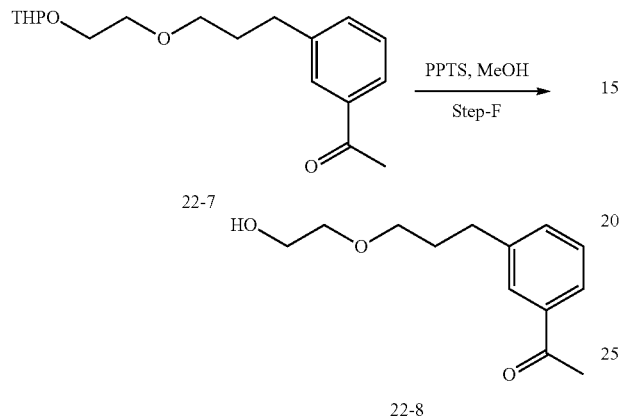

To a stirred solution of 22-7 (400 mg, 1.3 mmol) in MeOH (10 mL) was added PPTS (70 mg, 0.26 mmol) at 0° C. and stirred at RT for 16 hr. The solvents were distilled off under reduced pressure. The residue obtained was extracted with EtOAc (3×100 mL). The combined organic layers were washed with brine (100 mL), dried over Na₂SO₄ and concentrated to afford 22-8 (210 mg, 0.945 mmol, 72.4% yield) as a colorless gummy liquid.

2-(3-(3-Acetylphenyl)-propoxy)-ethyl Methanesulfonate (22-9)

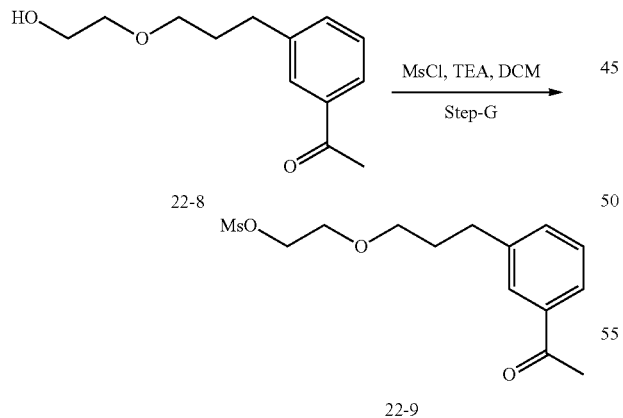

Methane sulfonyl chloride (0.1 mL, 1.29 mmol) was added to a solution of 22-8 (210 mg, 0.95 mmol) in DCM (50 mL) and triethylamine (0.4 mL, 2.8 mmol) at 0° C. and stirred at RT for 1 hr. The reaction mixture was diluted with water (50 mL) extracted with DCM (3×100 mL). The combined organic layers were washed with brine (100 mL), dried over Na₂SO₄ and concentrated. The residue was purified by flash column chromatography (100-200 silica) using 30% EtOAc in hexanes to afford 22-9 (220 mg, 0.733 mmol, 77.7% yield) as gummy liquid.

6-(N-(2-(3-(3-Acetylphenyl)-propoxy)-ethyl)-methylsulfonamido)-5-cyclopropyl-2-(4-fluorophenyl)-N-methylbenzofuran-3-carboxamide (22-10)

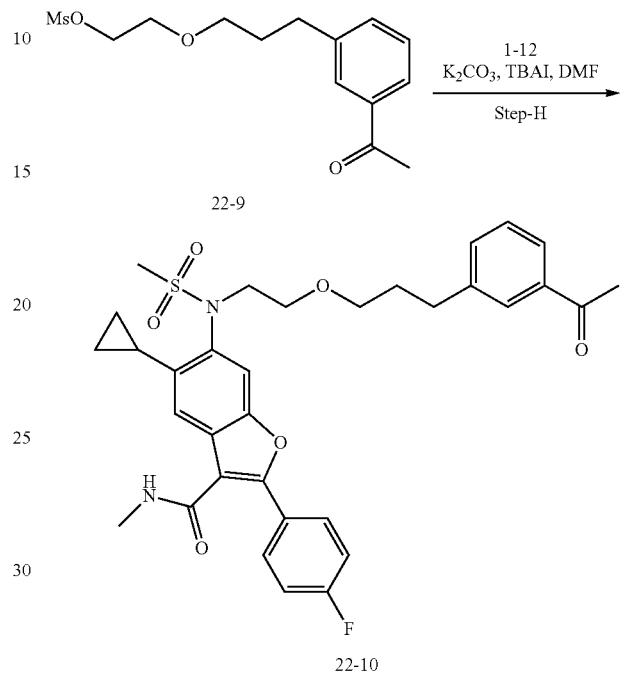

To a stirred solution of 1-12 (100 mg, 0.24 mmol) in DMF (5 mL) was added potassium carbonate (103 mg, 0.74 mmol) followed by 22-9 (110 mg, 0.37 mmol), catalytic amount of TBAI at 80° C. for 16 hr. The reaction mixture was cooled to RT and diluted with EtOAc (75 mL) washed with water (2×40 mL), brine (25 mL) and dried over Na₂SO₄ and concentrated. The residue was purified by flash column chromatography (100-200 silica) using 30% EtOAc:pet. ether to afford 22-10 (110 mg, 0.181 mmol, 73.3% yield) as an off-white solid. MS=607.11 [M+1]⁺.

4-{3-[3-(2-{[5-Cyclopropyl-2-(4-fluoro-phenyl)-3-methylcarbamoyl-benzofuran-6-yl]-methanesulfonyl-amino}-ethoxy)-propyl]-phenyl}-2-hydroxy-4-oxo-but-2-enoic Acid Ethyl Ester (22-11)

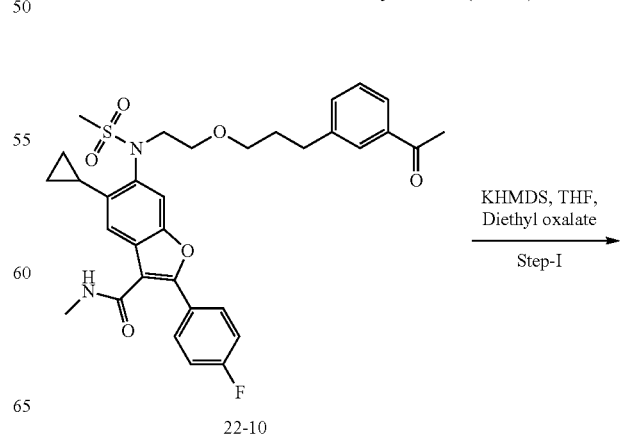

-continued

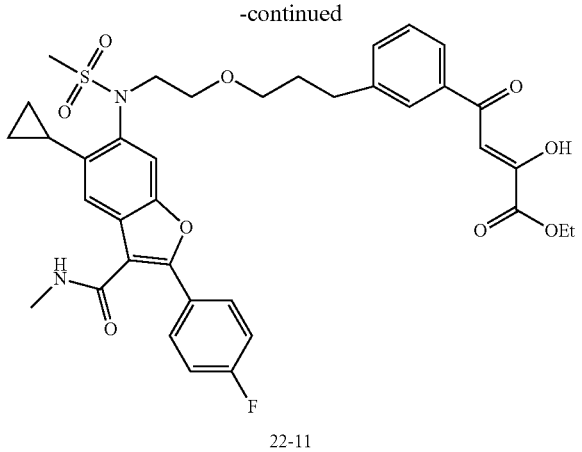

22-11

To a stirred solution of 22-10 (50 mg, 0.082 mmol) in THF (3 mL) was added KHMDS (0.247 mL, 0.24 mmol) at −78° C., and warm the reaction mixture to −55° C. for 1 hr. Then, diethyl oxalate (0.048 mL, 0.31 mmol) added to the reaction mixture at −78° C. and warm the reaction mixture to −55° C. for 2 hr, under nitrogen atmosphere. The reaction mixture was quenched with ammonium chloride solution, extracted into EtOAc (3×40 mL). The combined organic layers were washed with brine (2×20 mL), dried over Na$_2$SO$_4$ and concentrated. The residue was purified by flash column chromatography using neutral silica (100-200 silica) 2% MeOH-DCM to afford (40 mg, crude) 22-11, as a brownish gummy mass. MS=707.24 [M+1]$^+$.

4-(3-(3-(2-(N-(5-cyclopropyl-2-(4-fluorophenyl)-3-(methylcarbamoyl)benzofuran-6-yl) methyl sulfonamido)-ethoxy)-propyl)-phenyl)-2-hydroxy-4-oxobut-2-enoic Acid (22-12)

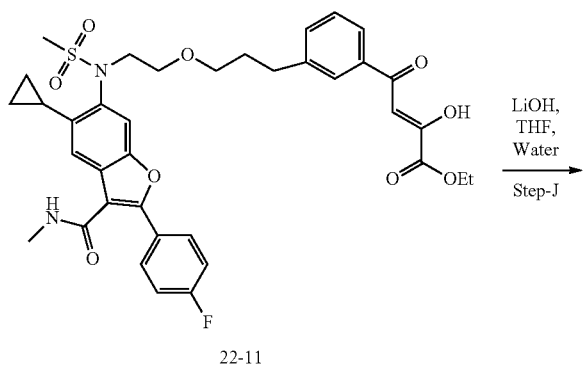

22-12

To a stirred solution of 22-11 (40 mg, 0.056 mmol) in THF and water (1 mL; (1:1)) was added LiOH (8 mg, 0.33 mmol) at 0° C. and reaction was continued at RT for 5 hr. After completion of the reaction (TLC), solvents evaporated under reduced pressure, residue extracted with ether (50 mL). Then aqueous layer was neutralized with 1N HCl (5 mL) followed by extracted with EtOAc (3×20 mL). The combined organic layers were washed with brine (2×20 mL), dried over Na$_2$SO$_4$ and concentrated. The residue was purified by preparative HPLC to obtain 22-12 (4 mg) as light thick mass. MS=679.1 [M+1]$^+$.

Example 23 t-Butyl 2-(2-(2-(2-hydroxyethoxy)-ethoxy)-ethoxy) acetate (23-3A)

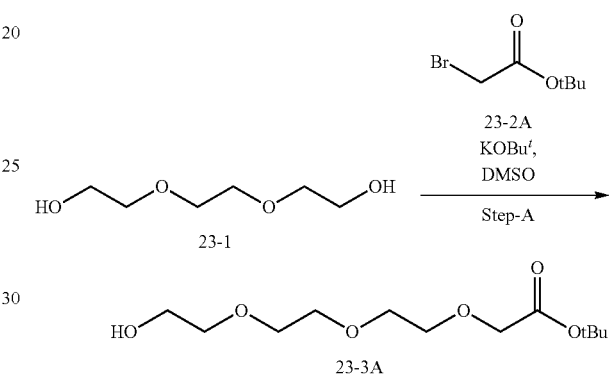

To a stirred solution of 2,2'-(ethane-1,2-diylbis(oxy))diethanol 23-1 (5 g, 33.33 mmol) in DMSO (50 mL) was added potassium tert-butoxide (2.2 g, 20 mmol) at 0° C., and tert-butyl 2-bromoacetate 23-2A (2.5 mL, 15.43 mmol) was added to reaction mixture at 0° C. Then reaction mixture was heated to 60° C. and continued stirring for 16 hr. The reaction mixture quenched with ice cold water (100 mL) and extracted with EtOAc (3×200 mL). The combined organic layers were washed with water (2×200 mL), brine (150 mL), dried over Na$_2$SO$_4$ and concentrated. The residue was purified by flash column chromatography (100-200 silica) using 40% EtOAc/hexanes to afford 23-3A (1.2 g, 4.87 mmol, 13.6% yield) as a yellow thick liquid. Confirmed by $^1$H NMR.

2,2,3,3-tetramethyl-4,7,10-trioxa-3-siladodecan-12-ol (23-2B1)

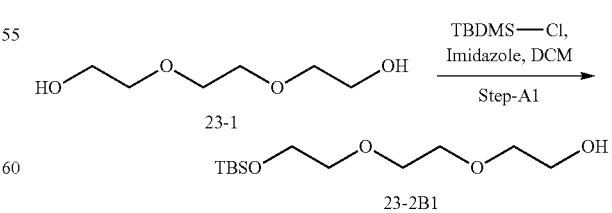

To a stirred solution of 23-1 (20 g, 133.33 mmol) in dichloromethane (100 mL) was added imidazole (5.4 g, 79.99 mmol) and TBDMSCl (10.0 g g, 66.66 mmol) at 0° C. and stirred to RT for 10 hr. The reaction mixture was diluted with DCM (200 mL) and washed with water (2×100 mL) and brine (50 mL). The organic layer was concentrated under reduced pressure and the crude residue was purified by flash column chromatography (100-200 silica) using 20% ethyl acetate/pet. ether gave 23-2B1 (10 g, 37.87 mmol, 28% yield) as a colorless liquid.

2,2,3,3-tetramethyl-4,7,10-trioxa-3-siladodecan-12-ylmethanesulfonate (23-2B2)

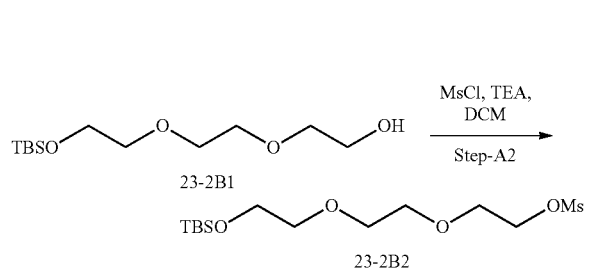

Methane sulfonyl chloride (1.5 mL, 18.93 mmol) and triethylamine (3.2 mL, 22.72 mmol) were added to a solution of 23-2B1 (5 g, 18.93 mmol) in DCM (100 mL) at 0° C. and stirred at RT for 2 hr. Reaction mixture diluted with water (25 mL), extracted with DCM (3×25 mL). The combined organic layers were washed with saturated $NaHCO_3$ solution (10 mL), brine (25 mL), dried over sodium $Na_2SO_4$ and concentrated. This crude compound was purified flash column chromatography (100-200 silica) using 15% EtOAc/ hexanes to afford 23-2B2 (1.1 g, 3.21 mmol, 85% yield) as a colorless liquid.

Ethyl 2,2,3,3,14-pentamethyl-4,7,10,13-tetraoxa-3-silapentadecan-15-oate (23-2B3)

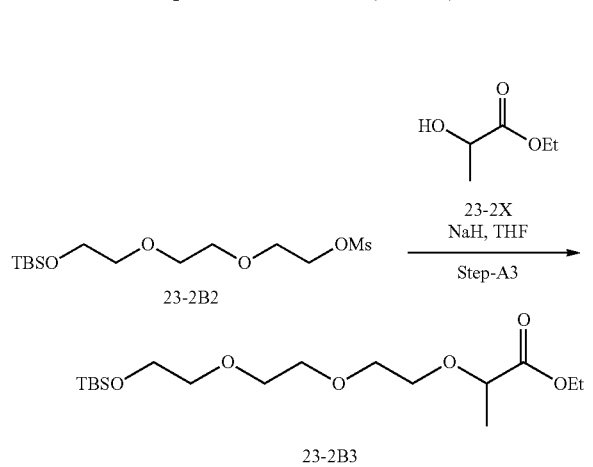

To a stirred solution of 23-2X (0.35 g, 2.96 mmol) in THF (5 mL) was added NaH (0.23 g, 5.92 mmol) in THF (10 mL) at 0° C., and the reaction was continued at RT for 30 min. 23-2B2 (1.1 g, 3.21 mmol) in THF (5 ml) was added to reaction mixture at 0° C. for 5 min, and reaction was warmed to RT and continued stirring for 16 hr. The reaction mixture quenched with ice cold water (50 mL) and extracted with EtOAc (3×30 mL). The combined organic layers were washed with water (2×20 mL), brine (15 mL), dried over $Na_2SO_4$ and concentrated. The crude residue was purified by flash column chromatography (100-200 silica) using 20% EtOAc/hexanes to afford 23-2B3 (0.14 g, 0.38 mmol, 11% yield) as a colorless liquid.

Ethyl 2-(2-(2-(2-hydroxyethoxy)ethoxy)ethoxy)propanoate (23-3B)

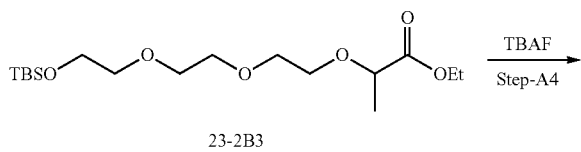

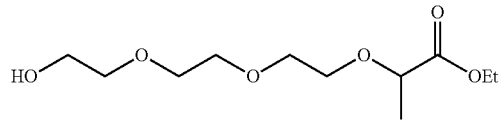

To a stirred solution of 23-2B3 (1.7 g, 4.67 mmol) in THF (20 mL) was added 1M TBAF in THF solution (8.0 mL, 8.0 mmol) at 0° C., and stirred at RT for 2 hr. The reaction mixture was diluted with water and extracted with EtOAc (3×50 mL), the combined organic layers were washed with brine (25 mL), dried over $Na_2SO_4$ and concentrated to afford 23-3B (1 g, 4 mmol, 86%) as a yellow thick liquid.

{2-[2-(2-Methanesulfonyloxy-ethoxy)-ethoxy]-ethoxy}-acetic Acid Tert-butyl Ester (23-4A)

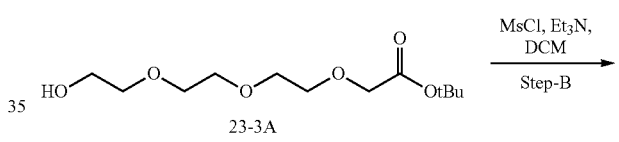

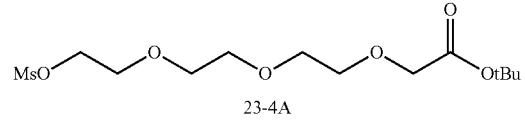

Methane sulfonyl chloride (0.13 mL, 1.59 mmol) was added to a solution of 23-3A (0.42 g, 1.59 mmol) in DCM (15 mL) and triethylamine (0.33 mL, 2.38 mmol) at 0° C. and stirred at RT for 1 hr. The reaction mixture was diluted with water (50 mL) extracted with DCM (3×20 mL). The combined organic layers were washed with brine (25 mL), dried over $Na_2SO_4$ and concentrated. The crude residue was purified by flash column chromatography (100-200 silica) using 20% EtOAc in hexanes to afford 23-4A (0.3 g, 0.87 mmol, 55% yield) as gummy liquid.

2-{2-[2-(2-Methanesulfonyloxy-ethoxy)-ethoxy]-ethoxy}-propionic Acid Ethyl Ester (23-4B)

Step-B above was adapted using 23-3B (1 g, 4.0 mmol) to prepare 23-4B (1.3 g, 99%).

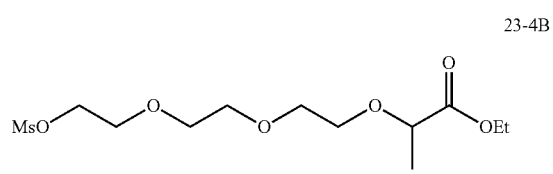 [SMILES: CCOC(=O)C(C)OCCOCCOCCOS(C)(=O)=O]

{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-acetic Acid Tert-butyl Ester (23-5A)

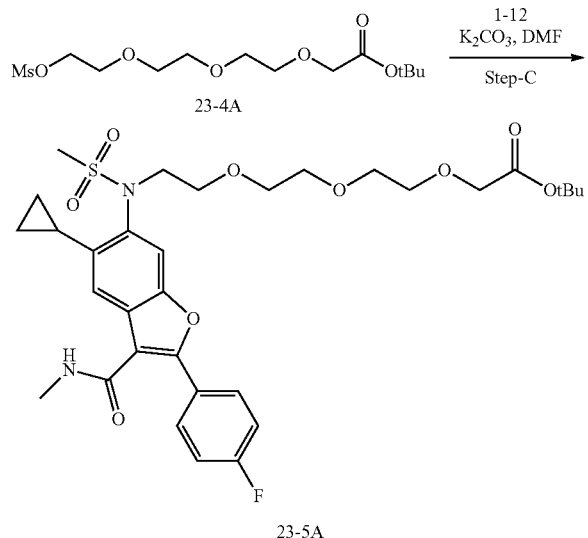

To a stirred solution of 1-12 (0.1 g, 0.24 mmol) in DMF (15 mL) was added potassium carbonate (0.10 g, 0.74 mmol) followed by 23-4A (0.12 g, 0.37 mmol), catalytic amount of TBAI at 80° C. for 10 hr. The reaction mixture was cooled to RT and diluted with EtOAc (25 mL) washed with water (2×20 mL), brine (25 mL) and dried over $Na_2SO_4$ and concentrated. The residue was purified by flash column chromatography (100-200 silica) using 30% EtOAc/pet. ether to afford 23-5A (0.06 g, 0.09 mmol, 62% yield) as an off-white solid. MS (ESI): m/z 693.3 (M+1)⁺.

2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-propionic Acid Ethyl Ester (23-5B)

Step C above was adapted using 23-4B (0.15 g, 0.37 mmol) to prepare 23-5B (0.14 g, 59%). MS (ESI): m/z 635.1 (M+1)⁺.

{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-acetic Acid Ethyl Ester (23-5C)

Step C above was also adapted using 23-4C (382 mg, 1.22 mmol) to prepare 23-5C (355 mg 70%). MS (ESI): m/z 621.1 (M+1)⁺.

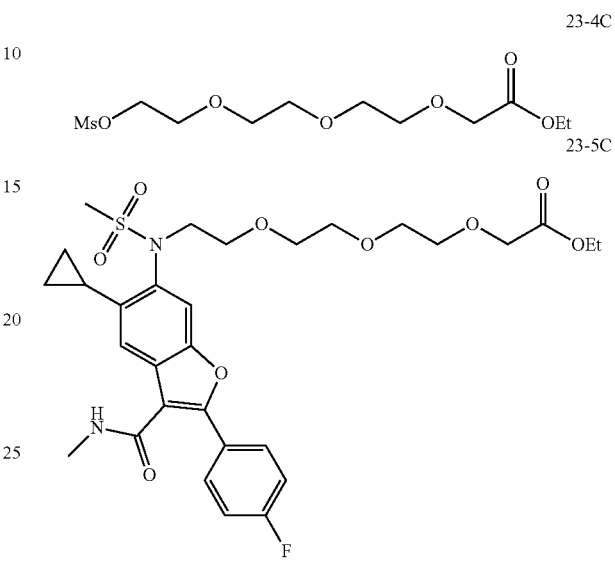

Method-A:

{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-acetic Acid (23-6A)

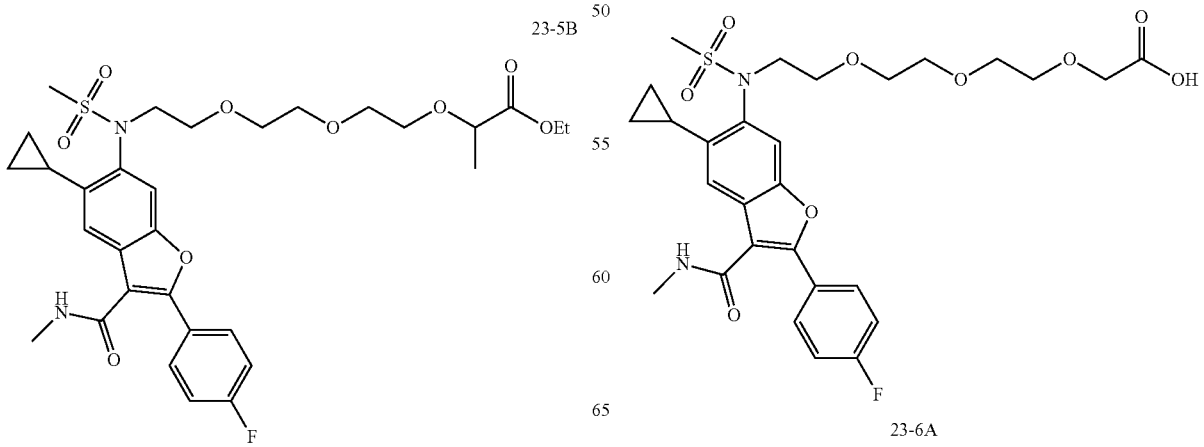

To a stirred solution of 23-5A (0.06 g, 0.09 mmol) in DCM (3 mL) was added TFA (1 mL) at 0° C. and reaction was continued stirring at RT for 1 hr. After completion of the reaction (TLC), solvents removed by rotavapor. The crude residue was purified by flash column chromatography (100-200 silica) using 2% MeOH/DCM to afford 23-6A (0.005 g, 0.008 mmol, 8.9% yield) as an off-white solid. MS (ESI): m/z 615.3 (M+23)$^+$.

Method-B:

2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-propionic Acid (23-6B)

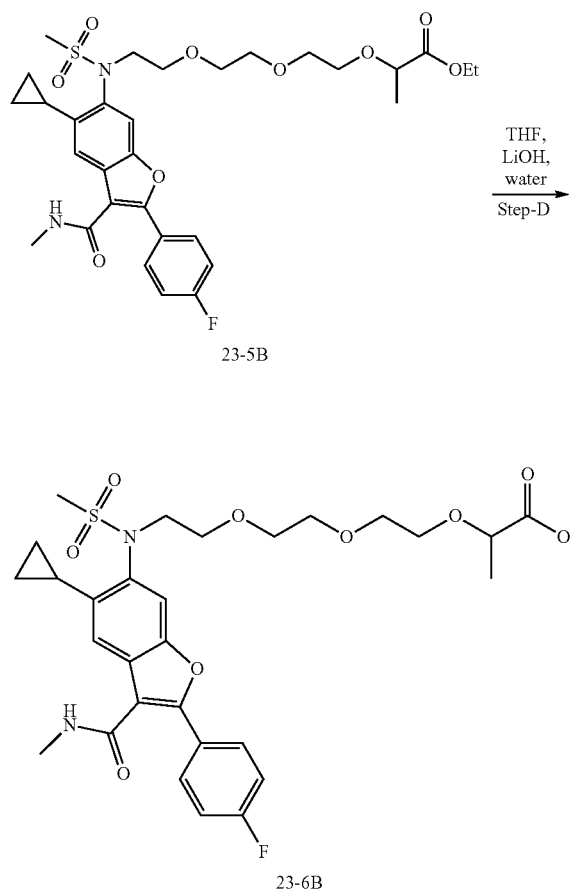

To a stirred solution of 23-5B (0.14 g, 0.220 mmol) in THF and water (8 mL; 4:1) was added LiOH (0.02 g, 0.66 mmol) at 0° C. and the reaction was continued at RT for 3 hr. After completion of the reaction (TLC), solvents evaporated at rotary evaporator, residue extracted with ether (20 mL). Then aqueous layer was neutralized with 1N HCl (5 mL) followed by extracted with EtOAc (3×30 mL). The combined organic layers were washed with brine (2×25 mL), dried over Na$_2$SO$_4$ and concentrated. The crude residue was purified by washed with pentane and ether to afford 23-6B (0.08 g, 0.13 mmol, 60% yield) as an off-white solid. MS (ESI): m/z 607.0 (M+1)$^+$.

5-Cyclopropyl-2-(4-fluoro-phenyl)-6-({2-[2-(2-hydroxycarbamoylmethoxy-ethoxy)-ethoxy]-ethyl}-methanesulfonyl-amino)-benzofuran-3-carboxylic Acid Methylamide (23-6C)

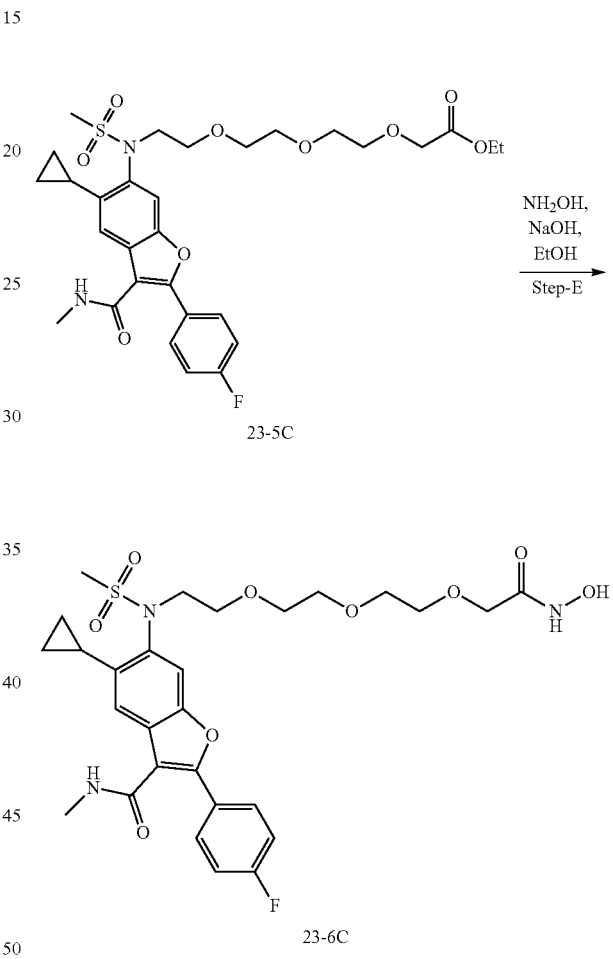

To a stirred solution of NH$_2$OH.HCl (1 g, 14.34 mmol) in MeOH (1.5 mL) was added KOH (1.2 g, 21.51 mmol) in MeOH at 0° C. Freshly prepared solution of hydroxylamine (2 mL) in MeOH was added to the solution of 23-5C (50 mg, 0.08 mmol) in MeOH at 0° C. and reaction was continued at RT for 1 hr. After completion of the reaction (TLC), solvents evaporated under reduced pressure, then added water and neutralized with 1N HCl (5 mL) followed by extraction with EtOAc (3×20 mL). The combined organic layers were washed with brine (2×20 mL), dried over Na$_2$SO$_4$ and concentrated. The crude residue was purified with prep-TLC to afford 23-6C (15 mg, 0.02 mmol, 30% yield) as an off-white solid. MS (ESI): m/z 608.7 (M+1)$^+$.

6-({2-[2-(2-Carbamoylmethoxy-ethoxy)-ethoxy]-ethyl}-methanesulfonyl-amino)-5-cyclopropyl-2-(4-fluoro-phenyl)-benzofuran-3-carboxylic Acid Methylamide (23-7A)

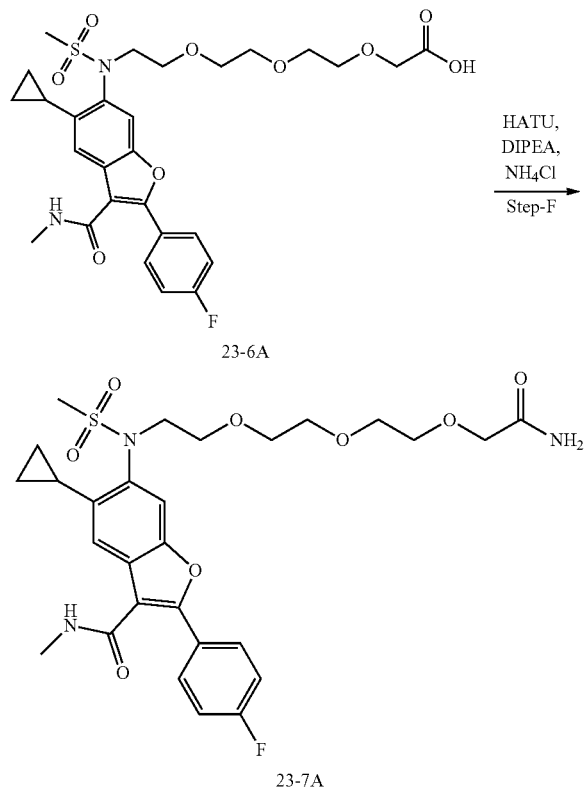 [SMILES: CNC(=O)c1c(-c2ccc(F)cc2)oc2cc(N(CCOCCOCCOCC(=O)O)S(C)(=O)=O)c(C3CC3)cc12 ; CNC(=O)c1c(-c2ccc(F)cc2)oc2cc(N(CCOCCOCCOCC(N)=O)S(C)(=O)=O)c(C3CC3)cc12]

To a stirred solution of 23-6A (0.03 g, 0.50 mmol) in DCM (20 mL) was added HATU (0.57 g, 1.52 mmol), DIPEA (0.4 mL, 2.53 mmol) and ammonium chloride (0.054 g, 1.01 mmol) at 0° C. and stirred at RT for 4 hr. The reaction mixture was diluted with water and extracted with DCM (3×25 mL). The combined organic layer washed with brine (25 mL), dried over Na$_2$SO$_4$ and concentrated. The residue was purified by flash column chromatography (100-200 silica) using 5% MeOH-DCM to afford 23-7A (0.15 g, 0.25 mmol, 51% yield) as gummy liquid. MS (ESI): m/z 592.2 (M+1)$^+$.

Example 24

Ethyl 3-(2-(2-(2-hydroxyethoxy)-ethoxy)-ethoxy)-propanoate (24-1)

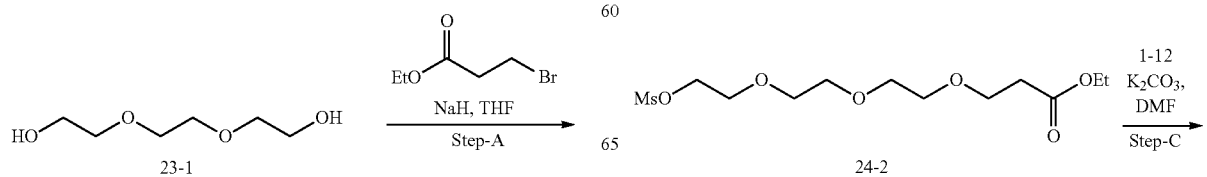

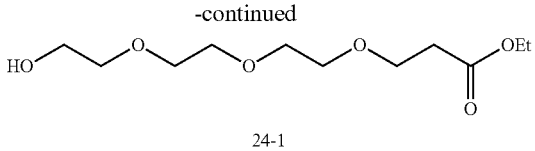

To a stirred solution of 2,2'-(ethane-1,2-diylbis(oxy))diethanol 23-1 (2 g, 13.3 mmol) in THF (30 mL) was added NaH (0.48 g, 0.012 mmol) at 0° C., and reaction was continued at RT for 2 hr. Ethyl 3-bromopropanoate (2.16 g, 0.012 mmol) in THF (10 mL) was added to reaction mixture at 0° C. for 5 min and reaction was continued at RT for 16 hr. The reaction mixture was quenched with ice cold water (100 mL) and extracted with EtOAc (3×200 mL). The combined organic layers were washed with water (2×50 mL), brine (50 mL), dried over Na$_2$SO$_4$ and concentrated. The crude residue was purified by flash column chromatography (230-400 silica) using 50% EtOAc/hexanes to afford 24-1 (150 mg, 0.6 mmol, 5% yield) as a colorless liquid.

2-(2-(Tetrahydro-2H-pyran-2-yloxy)-ethoxy Ethanol (24-2)

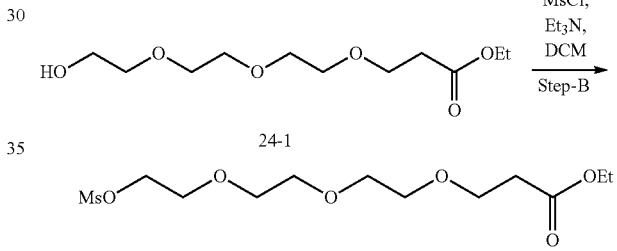

To a stirred solution of 24-1 (500 mg, 2 mmol) in DCM (5 mL) was added triethylamine (0.36 mL, 2.6 mmol) and methane sulfonyl chloride (0.2 mL, 2.4 mmol) at 0° C. and stirred at RT for 2 hr. The reaction mixture was diluted with excess DCM (40 mL) and washed with water (2×20 mL), brine (20 mL) and dried over Na$_2$SO$_4$, and the organic phase concentrated under reduced pressure. The crude compound was purified using 230-400 silica gel column chromatography using 80% EtOAc/hexanes to afford 24-2 (390 mg, 1.18 mmol, 60% yield) as a colorless liquid.

3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-propionic Acid Ethyl Ester (24-3)

-continued

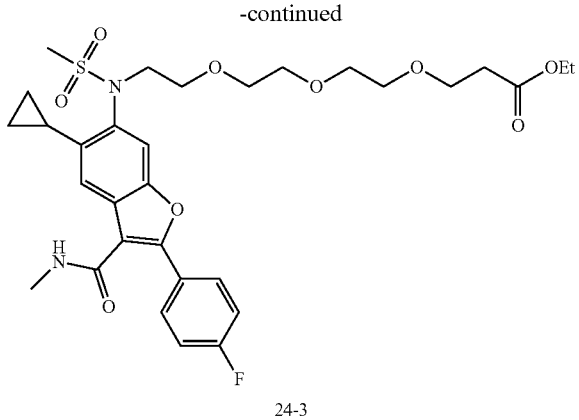

24-3

To a solution of 1-12 (370 mg, 0.92 mmol) in DMF (5 mL) was added potassium carbonate (470 mg, 1.15 mmol) followed by 24-2 (380 mg, 1.15 mmol), catalytic amount of TBAI and stirred at 70° C. for 16 hr. The reaction mixture was cooled to RT and diluted with EtOAc (30 mL) washed with water (2×20 mL), brine (15 mL) and dried over $Na_2SO_4$, and the organic phase was concentrated under reduced pressure. The crude compound was purified using 230-400 silica gel column chromatography using 5% acetone in DCM to afford the title compound 24-3 (420 mg, 0.66 mmol, 71% yield) as an off-white solid. MS (ESI): m/z 634.80 (M+1)⁺.

3-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-propionic Acid (24-4)

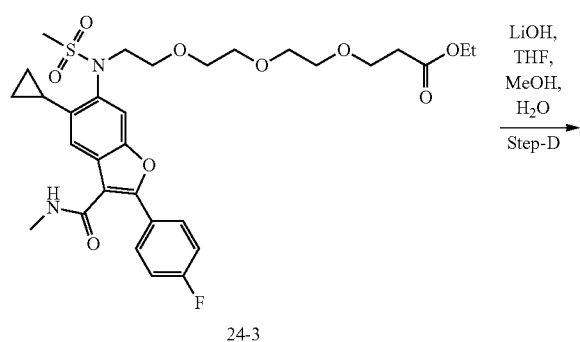

24-3

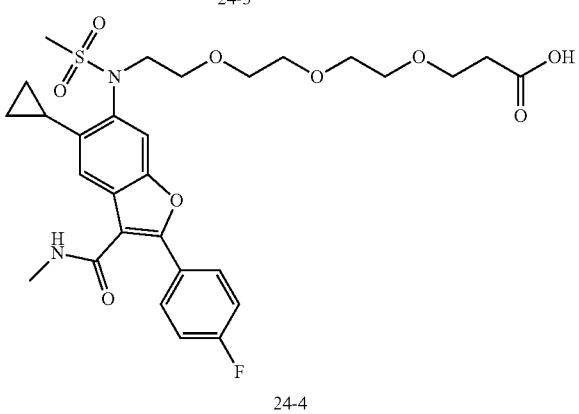

24-4

To a stirred solution of 24-3 (250 mg, 0.4 mmol) in THF and water (4 mL, 4:1) was added LiOH (56 mg, 2.0 mmol) at 0° C. and reaction was continued at RT for 16 hr. After completion of the reaction (TLC), solvents were evaporated at rotary evaporator. The crude residue extracted with ether (2×30 mL). Aqueous layer was neutralized with 1N HCl (10 mL) followed by extracted with EtOAc (3×50 mL). The combined organic layers were washed with brine (20 mL), dried over $Na_2SO_4$ and concentrated. The crude residue was purified by washings with diethyl ether and pentane to afford 24-4 (50 mg, 0.08 mmol, 20% yield) as white solid. MS (ESI): m/z 606.85 (M+1)+.

Example 25

Ethyl 2-phenyl-2-(2-(2-(2-(tetrahydro-2H-pyran-2-yloxy)-ethoxy)-ethoxy)-ethoxy)acetate (25-1

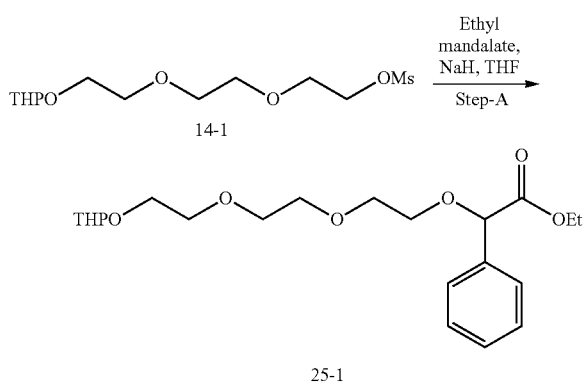

25-1

To a stirred solution of ethyl mandalate (0.6 g, 3.33 mmol) in THF (30 mL) was added NaH (0.16 g, 42.1 mmol) at 0° C., and the reaction was continued at RT for 30 min. 2-(2-(2-(tetrahydro-2H-pyran-2-yloxy)-ethoxy)-ethoxy)-ethyl methane sulfonate 14-1 (1.14 g, 3.66 mmol) in THF (10 mL) was added to reaction mixture at 0° C. for 5 min, and reaction was warmed to RT and continued stirring for 16 hr. The reaction mixture was quenched with ice cold water (50 mL) and extracted with EtOAc (3×30 mL). The combined organic layers were washed with water (2×20 mL), brine (15 mL), dried over $Na_2SO_4$ and concentrated. The crude residue was purified by flash column chromatography (100-200 silica) using 20% EtOAc/hexanes to afford 25-1 (0.14 g, 0.36 mmol, 11% yield) as a yellow thick liquid. MS (ESI): m/z 414.3 (M+18)⁺.

Ethyl 2-(2-(2-(2-hydroxyethoxy)-ethoxy)-ethoxy)-2-phenylacetate (25-2)

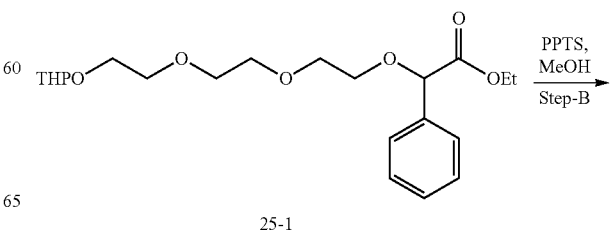

25-1

207
-continued

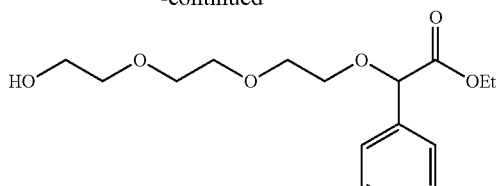

25-2

To a stirred solution of 25-1 (1.6 g, 4.04 mmol) in MeOH (20 mL) was added pyridinium p-toluenesulfonate (0.1 g, 0.40 mmol) at 0° C., and stirred at RT for 1 h. The solvents were distilled off under reduced pressure. The crude residue was extracted with EtOAc (3×20 mL), the combined organic layers were washed with brine (25 mL), dried over $Na_2SO_4$ and concentrated. The residue was purified by flash column chromatography (100-200 silica) using 5% MeOH/DCM to afford 25-2 (0.74 g, 2.37 mmol, 58% yield) as a yellow thick liquid. MS (ESI): m/z 330.2 $(M+18)^+$.

{2-[2-(2-Methanesulfonyloxy-ethoxy)-ethoxy]-ethoxy}-phenyl-acetic Acid Ethyl Ester (25-3)

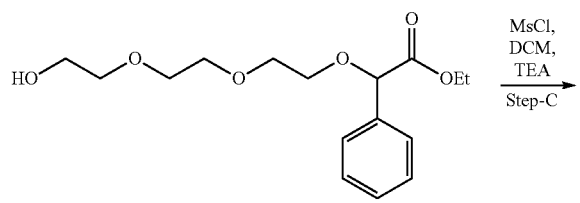

Methane sulfonyl chloride (0.1 mL, 1.28 mmol) was added to a solution of 25-2 (0.4 g, 1.28 mmol) in DCM (10 mL) and triethylamine (0.27 mL, 1.92 mmol) at 0° C. and stirred at RT for 1 hr. The reaction mixture was diluted with water (25 mL), extracted with DCM (3×25 mL). The combined organic layers were washed with brine (25 mL), dried over $Na_2SO_4$ and concentrated. The crude residue was purified by flash column chromatography (100-200 silica) using 20% EtOAc in hexanes to afford 25-3 (0.4 g, 1.025 mmol, 80% yield) as gummy liquid. MS (ESI): m/z 408.2 $(M+18)^+$.

208

{2-[2-(2-{[5-Cyclopropyl-2-(4-fluoro-phenyl)-3-methylcarbamoyl-benzofuran-6-yl]-methanesulfo-nyl-amino}-ethoxy)-ethoxy]-ethoxy}-phenyl-acetic Acid Ethyl Ester (25-4)

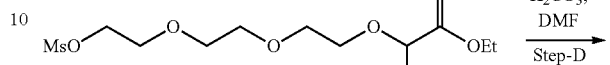

25-3

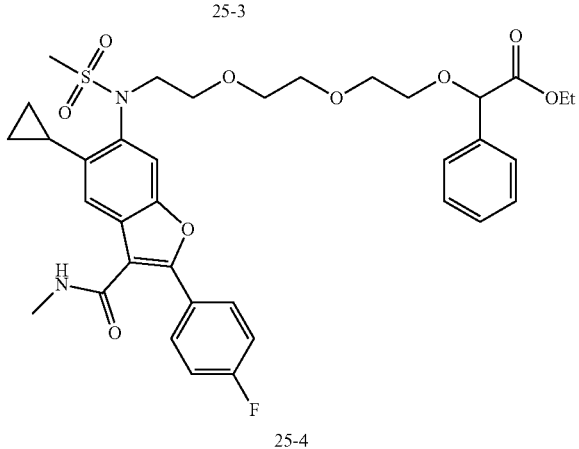

25-4

To a stirred solution of 1-12 (0.29 g, 0.721 mmol) in DMF (15 mL) was added $K_2CO_3$ (0.2 g, 2.163 mmol) followed by 25-3 (0.33 g, 0.86 mmol), catalytic amount of TBAI at 80° C. for 16 hr. The reaction mixture was cooled to RT and diluted with EtOAc (25 mL) washed with water (2×20 mL), brine (25 mL) and dried over $Na_2SO_4$ and concentrated. The crude residue was purified by flash column chromatography (100-200 silica) using 5% MeOH-DCM to afford 25-4 (0.2 g, 0.28 mmol, 40% yield) as an off-white solid. MS (ESI): m/z 718.9 $(M+23)^+$.

{2-[2-(2-{[5-Cyclopropyl-2-(4-fluoro-phenyl)-3-methylcarbamoyl-benzofuran-6-yl]-methanesulfo-nyl-amino}-ethoxy)-ethoxy]-ethoxy}-phenyl-acetic Acid (25-5)

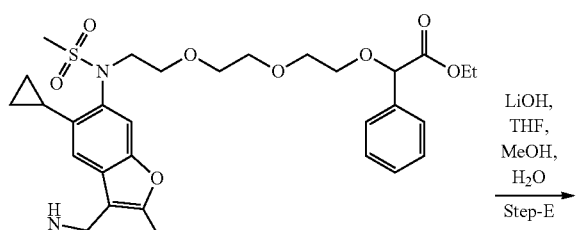

25-4

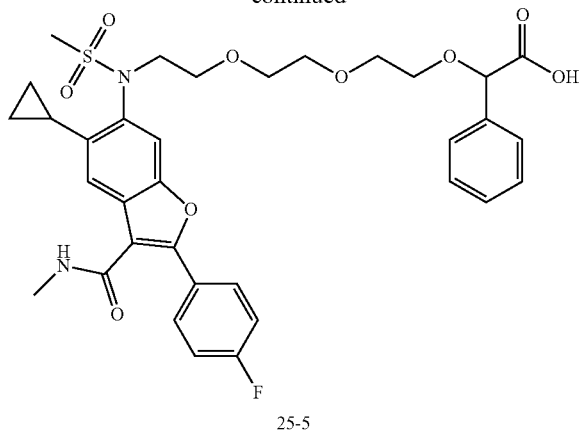

25-5

To a stirred solution of 25-4 (0.08 g, 0.114 mmol) in THF and water (6 mL; 4:1) was added LiOH (0.02 g, 0.46 mmol) at 0° C. and reaction was continued at RT for 2 hr. After completion of the reaction (by TLC), solvents were evaporated at rotary evaporator, residue extracted with ether (25 mL). The aqueous layer was neutralized with 1N HCl (5 mL) followed by extracted with EtOAc (3×15 mL). The combined organic layers were washed with brine (2×15 mL), dried over $Na_2SO_4$ and concentrated. The crude residue was purified by washed with pentane and ether gave 25-5 (40 mg, 0.06 mmol, 52% yield) as an off-white solid. MS (ESI): m/z 669.1 $(M+1)^+$.

5-Cyclopropyl-2-(4-fluoro-phenyl)-6-[(2-{2-[2-(hydroxycarbamoyl-phenyl-methoxy)-ethoxy]-ethoxy}-ethyl)-methanesulfonyl-amino]-benzofuran-3-carboxylic Acid Methylamide (25-6)

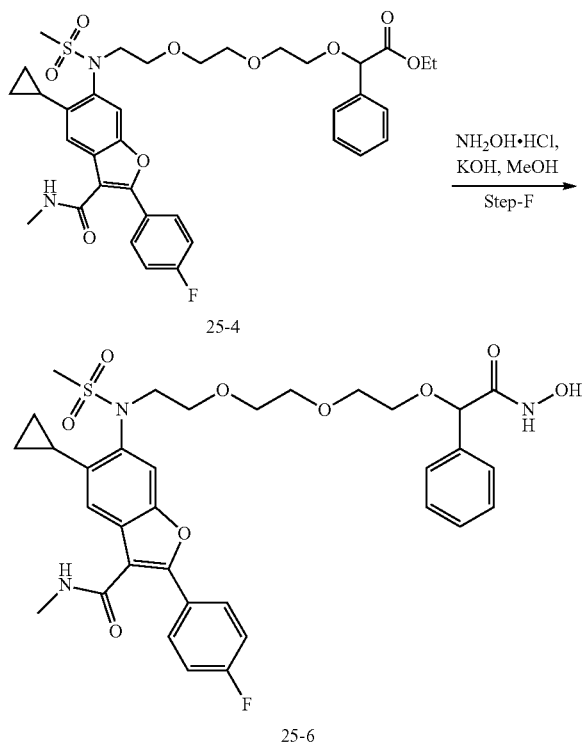 [SMILES: CCOC(=O)C(OCCOCCOCCN(c1cc2oc(-c3ccc(F)cc3)c(C(=O)NC)c2cc1C1CC1)S(C)(=O)=O)c1ccccc1 ; CNC(=O)c1c(-c2ccc(F)cc2)oc2cc(N(CCOCCOCCOC(C(=O)NO)c3ccccc3)S(C)(=O)=O)c(C3CC3)cc12]

To a stirred solution of hydroxyl amine hydrochloride (1 g, 14.34 mmol) in MeOH (1.5 mL) was added KOH (1.2 g, 21.51 mmol) in MeOH at 0° C. Freshly prepared solution of hydroxylamine (1 mL) in MeOH was added to the solution of 25-4 (150 mg, 0.22 mmol) in MeOH at 0° C. and reaction was continued at RT for 1 hr. After completion of the reaction (TLC), solvents were evaporated under reduced pressure, then added water and neutralized with 1N HCl (5 mL) followed by extraction with EtOAc (3×20 mL). The combined organic layers were washed with brine (2×20 mL), dried over $Na_2SO_4$ and concentrated. The crude residue was purified with prep-TLC to afford 25-6 (70 mg, 0.12 mmol, 50% yield) as an off-white solid. MS (ESI): m/z 683.9 $(M+1)^+$.

Example 26

2-(2-(2-(Trityloxy)-ethoxy)-ethoxy)-ethanol (26-1)

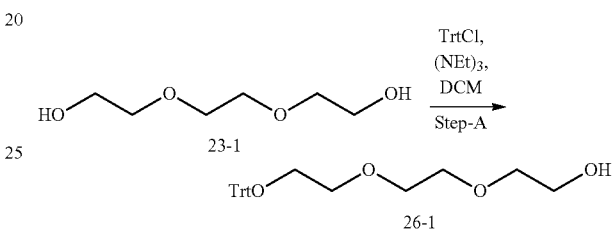

To a stirred solution of 23-1 (1 g, 6.66 mmol) in DCM (25 mL) was added Trityl chloride (1.67 g, 5.99 mmol) and triethylamine (1.7 mL, 13.32 mmol) at 0° C. and stirring continued at RT for 4 hr under nitrogen atmosphere. The reaction mixture was diluted with water (2×50 mL) and extracted with DCM (3×50 mL). The combined organic layers were evaporated under reduced pressure and the crude residue was purified by flash column chromatography (100-200 silica) using 25% EtOAc/pet. ether to afford 26-1 (900 mg, 2.29 mmol, 34% yield) as an off-white solid.

Tert-Butyl 1-(2-(2-(2-(trityloxy)-ethoxy)-ethoxy)-ethoxy)cyclopentanecarboxylate (26-2)

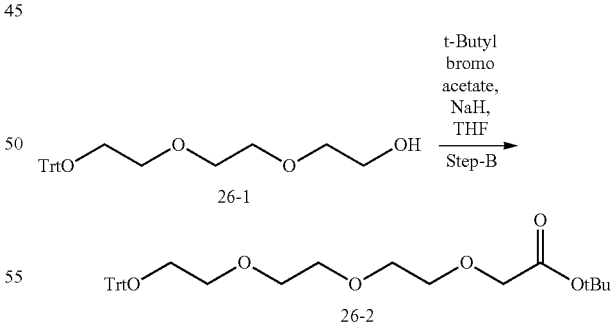

To a solution of 26-1 (8 g, 20.4 mmol) in THF (100 mL) added NaH (880 mg, 18.37 mmol) portion wise at 0° C. then stirred for 1 hr and then added the solution of t-butylbromo acetate (8 g, 40.82 mmol) in THF (50 mL) at 0° C. and stirred at RT for 24 hr. The reaction mixture was quenched with saturated ammonium chloride solution (300 mL) and diluted with EtOAc (400 mL), washed with water (100 mL), and dried over $Na_2SO_4$, and the organic phase was concentrated under reduced pressure to get crude compound.

Obtained crude was purified using silica gel chromatography (10% EtOAc in hexanes) to afford 26-2 (4.5 g, 8.9 mmol, 43% yield) as a colorless gummy liquid. MS (ESI): m/z 524.2 (M+1)+.

Tert-Butyl 1-(2-(2-(2-(trityloxy)-ethoxy)-ethoxy)-ethoxy)cyclopentanecarboxylate (26-3A)

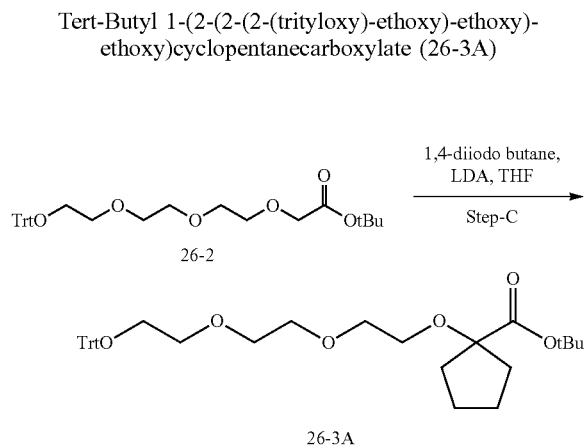

To a solution of 26-2 (500 mg, 0.98 mmol) and 1,4-diiodobutane (459 mg, 1.48 mmol) in THF (10 mL) was added lithium diisopropylamide (LDA; 2 M in THF) (1.97 mL, 1.97 mmol) at −40° C., and the reaction was stirred at RT for 1 hr. The reaction was quenched with saturated NH₄Cl solution (50 mL) and diluted with EtOAc (50 mL), washed with water (20 mL), and dried over Na₂SO₄, and the organic phase was concentrated under reduced pressure. The crude compound was purified using silica gel chromatography (10% EtOAc in hexanes) to afford 26-3A (170 mg, 0.30 mmol, 40% yield) as a colorless oily liquid. Confirmed by ¹H NMR.

Tert-Butyl 12,12-dimethyl-1,1,1-triphenyl-2,5,8,11-tetraoxatridecan-13-oate (26-3B)

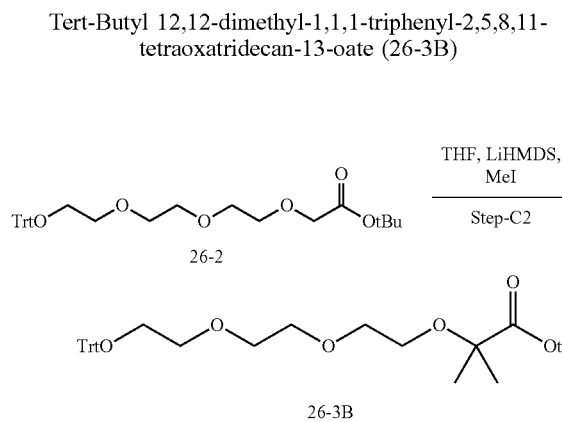

To a solution of 26-2 (700 mg, 1.78 mmol) in THF (10 mL) at −78° C. was added LiHMDS (1 M in THF) (4.1 mL, 4.1 mmol) followed by methyl iodide (0.4 mL, 5.35 mmol) in THF (8 mL) was added and stirred at same temperature for 2 hr. The reaction mixture was quenched with saturated ammonium chloride solution (50 mL) and diluted with EtOAc (50 mL), washed with water (20 mL), and dried over Na₂SO₄. The organic phase was concentrated under reduced pressure. The crude compound was purified using silica gel chromatography (5% EtOAc in hexanes) to afford 26-3B (500 mg, 0.93 mmol, 67% yield) as a colorless oily liquid. MS (ESI): m/z 566.3[M+1]⁺.

Tert-Butyl 5-((5-hydroxypentyl)-oxy)-2-methylpentanoate (26-4A)

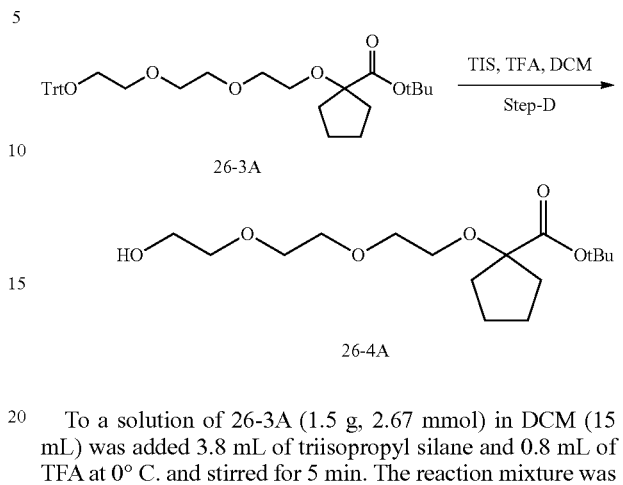

To a solution of 26-3A (1.5 g, 2.67 mmol) in DCM (15 mL) was added 3.8 mL of triisopropyl silane and 0.8 mL of TFA at 0° C. and stirred for 5 min. The reaction mixture was diluted with EtOAc (100 mL) washed with water (100 mL), brine (50 mL) and dried over Na₂SO₄, and the organic phase was concentrated under reduced pressure. The crude compound was purified using silica gel chromatography (60% EtOAc in hexanes) to afford 26-4A (800 mg, 2.51 mmol, 94% yield) as a colorless oily liquid.

(26-3B) (500 mg, 0.94 mmol) was substituted for [26-3A in the above procedure to prepare [26-4B (210 mg, 77%).

Ethyl 4-((2-(2-hydroxyethoxy)-ethoxy)-methyl)-1-naphthoate1-{2-[2-(2-Methanesulfonyloxy-ethoxy)-ethoxy]-ethoxy}-cyclopentanecarboxylic Acid Tert-butyl Ester (26-5A)

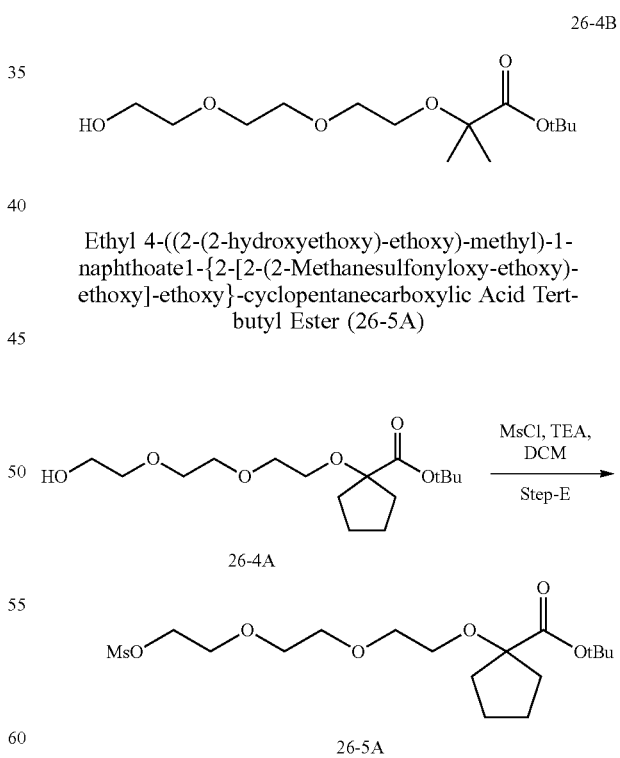

Methanesulfonyl chloride (430 mg, 3.77 mmol) at 0° C. was added to a solution of 26-4A (800 mg, 2.51 mmol) in DCM (10 mL) and triethylamine (635 mg, 6.28 mmol) and stirred at RT for 1 hr. The reaction mixture was diluted with excess DCM (100 mL) and washed with water (100 mL), brine (50 mL) and dried over Na₂SO₄, and the organic phase concentrated under reduced pressure. The crude compound was purified using 100-200 silica gel filter column chromatography to afford 26-5A (600 mg, 1.515 mmol, 60% yield) as a pale brownish oily liquid.

Step-E above was adapted using 26-4B (210 mg, 0.72 mmol) substituted for 26-4A to prepare 26-5B (200 mg, 75%).

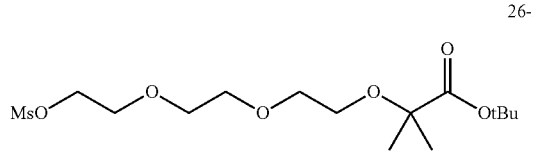

26-5B

1-[2-(2-{2-[(5-Cyclopropyl-3-methylcarbamoyl-2-p-tolyl-benzofuran-6-yl)-methanesulfonyl-amino]-ethoxy}-ethoxy)-ethoxy]-cyclopentanecarboxylic Acid Tert-butyl Ester (26-6A)

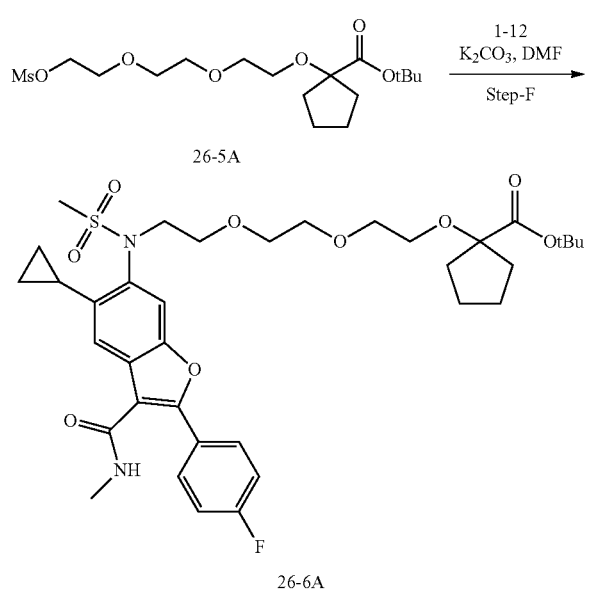

To a solution of 1-12 (507 mg, 1.26 mmol) in DMF (6 mL) was added potassium carbonate (528 mg, 3.78 mmol) followed by 26-5A (600 mg, 1.51 mmol), catalytic amount of TBAI then stirred at 70° C. for 16 hr. The reaction mixture was cooled to RT and diluted with EtOAc (100 mL) washed with water (100 mL), brine (50 mL) and dried over Na₂SO₄, and the organic phase was concentrated under reduced pressure. The crude compound was purified using 100-200 silica gel column chromatography (50% EtOAc in hexanes) to afford 26-6A (156 mg, 0.22 mmol, 17% yield) as a colorless gummy liquid. MS (ESI): m/z 720.3 (M+18)⁺.

2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-2-methyl-propionic Acid Tert-butyl Ester (26-6B)

26-5B (100 mg, 0.26 mmol) was substituted for 26-5A in the above procedure to prepare 26-6B (102 mg, 84%). MS (ESI): m/z 694.3 (M+23)⁺.

1-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-cyclopentanecarboxylic Acid (26-7A)

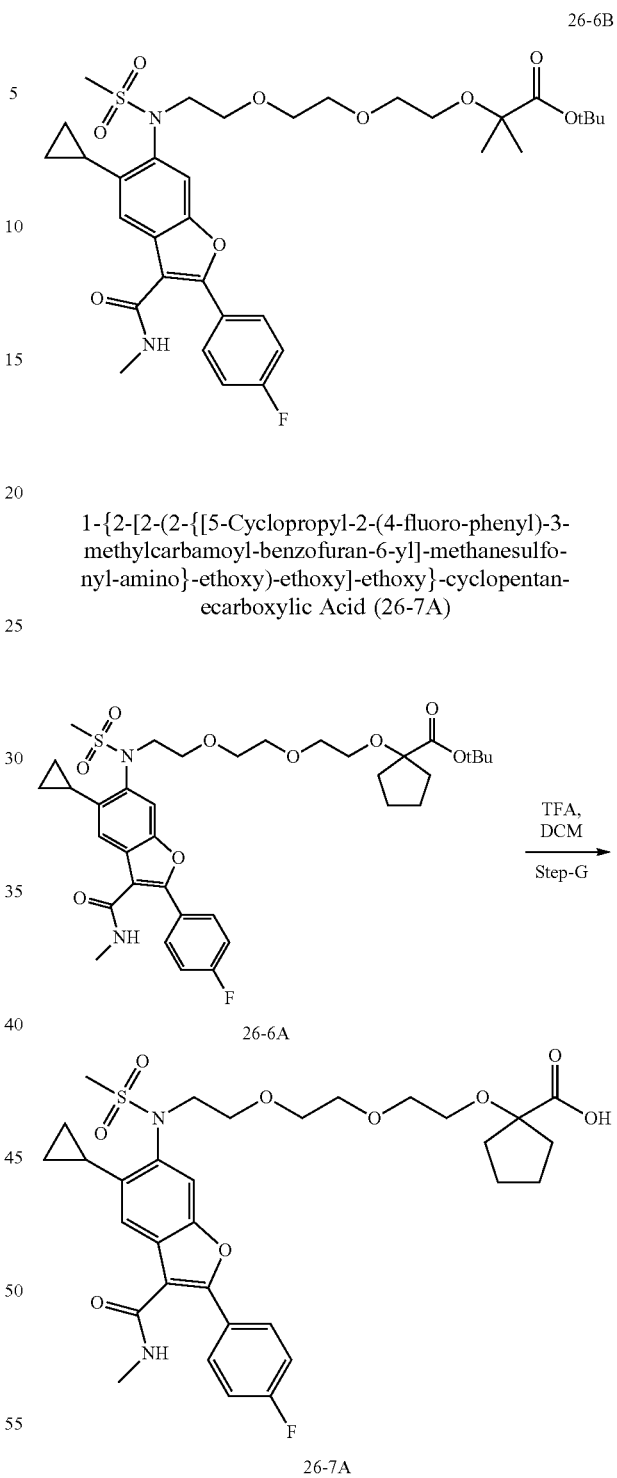

To a solution of 26-6A (80 mg, 0.12 mmol) in DCM (2 mL) was added TFA at 0° C. and stirred at RT for 2 hr. After completion of the reaction as indicated by TLC, to the reaction mixture added water and then extracted with excess DCM. The organic layer was washed with brine, dried over Na₂SO₄ and concentrated. The crude compound was purified by Prep TLC to afford 26-7A (50 mg, 0.07 mmol, 68% yield) as white solid. MS (ESI): m/z 646.9 (M+1)⁺.

2-{2-[2-(2-{[5-Cyclopropyl-2-(4-fluoro-phenyl)-3-methylcarbamoyl-benzofuran-6-yl]-methanesulfonyl-amino}-ethoxy)-ethoxy]-ethoxy}-2-methyl-propionic Acid (26-7B)

Starting from Step-D in the procedure described above, 26-3B was substituted for 26-3A, and Steps D-G were adapted to prepare 26-7B. MS (ESI): m/z 620.95 [M+1]$^+$.

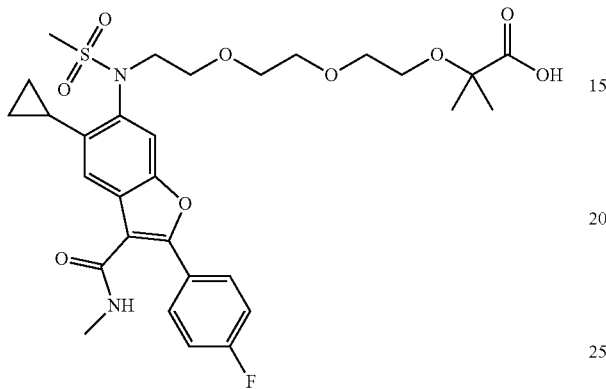

5-Cyclopropyl-2-(4-fluoro-phenyl)-6-[(2-{2-[2-(1-hydroxycarbamoyl-1-methyl-ethoxy)-ethoxy]-ethoxy}-ethyl)-methanesulfonyl-amino]-benzofuran-3-carboxylic Acid Methylamide (26-8B)

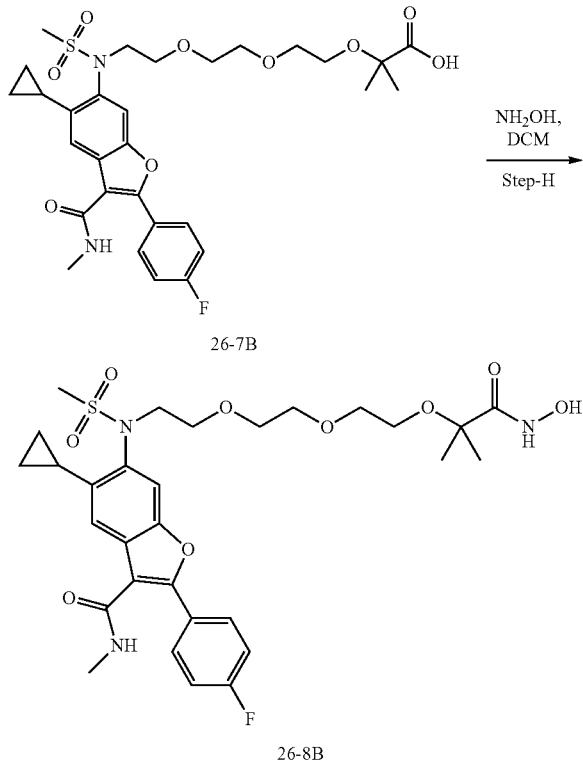

To a stirred solution of 26-7B (30 mg, 0.048 mmol) in DCM (2 mL) was added NH$_2$OH.HCl (5 mg, 0.07 mmol), HATU (36.8 mg, 0.09 mmol) and DIPEA (187 mg, 1.45 mmol) at 0° C. and the reaction was continued at RT for 16 hr. After completion of the reaction (TLC), solvents evaporated under reduced pressure, then added water and neutralized with 1N HCl (5 mL) followed by extraction with EtOAc (3×20 mL). The combined organic layers were washed with brine (2×20 mL), dried over Na$_2$SO$_4$ and concentrated. The residue was purified with preparative HPLC to afford 26-8B (5 mg, 0.07 mmol, 16% yield) as a brown solid. MS (ESI): m/z 636.26 [M+1]$^+$.

Example 27

((2-Bromoethoxy)-methanetrityl)tribenzene (27-2)

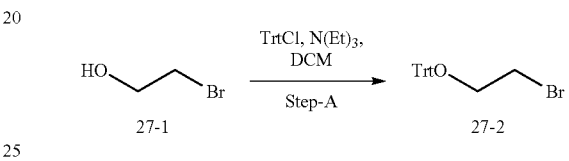

To a stirred solution of 2-bromoethanol 27-1 (10 g, 80.0 mmol) in DCM (250 mL) was added trityl chloride (20 g, 72 mmol) and triethylamine (22.4 mL, 160 mmol) at 0° C. The reaction mixture was stirred at RT for 10 hr under nitrogen atmosphere. The reaction mixture was diluted with water and extracted with DCM (3×500 mL). The combined organic layers were evaporated under reduced pressure and the crude residue was purified by flash column chromatography (100-200 silica) using 5% EtOAc/pet. ether to afford 27-2 (16 g, 43.71 mmol, 54% yield) as an off-white solid.

5-(2-(Trityloxy)-ethoxy)-pentan-1-ol (27-3)

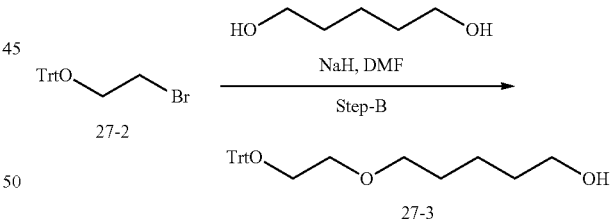

To a stirred solution of 27-2 (3 g, 15.95 mmol) in DMF (50 mL) was added NaH (0.96 g, 23.96 mmol) at 0° C. and reaction was warmed to RT for 30 min. Pentane-1,5-diol (6 g, 17.55 mmol) in DMF (10 mL) was added to reaction mixture at 0° C. for 5 min. and the reaction was continued at RT for 16 hr. The reaction was quenched with ice cold water (100 mL) and extracted with EtOAc (3×150 mL). The combined organic layers were washed with water (2×100 mL), brine (150 mL), dried over Na$_2$SO$_4$ and concentrated. The crude residue was purified by flash column chromatography (100-200 silica) using 20% EtOAc/hexanes to afford 27-3 (1 g, 2.56 mmol, 17% yield) as a yellow thick liquid.

Tert-Butyl 2-(5-(2-(trityloxy)-ethoxy)-pentyloxy) acetate (27-5A)

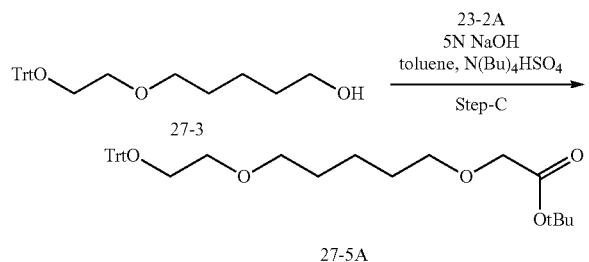

To a solution of 27-3 (1.95 g, 10.25 mmol) and 23-2A (1.95 g, 10.25 mmol) in toluene (20 mL) and 5N NaOH (aq.) (20 mL) was added tetra n-butyl ammonium hydrogen sulfate (800 mg, 2.05 mmol) and stirred at RT for 48 hr. The reaction mixture was diluted with EtOAc (100 mL), washed with water (100 mL), brine (50 mL) and dried over $Na_2SO_4$, and the organic phase was concentrated under reduced pressure. The crude compound was purified using silica gel chromatography (6% EtOAc in hexanes) to afford 27-5A (1 g, 1.984 mmol, 77% yield) as a colorless oily liquid.

Tert-Butyl 2-(5-(2-hydroxyethoxy) pentyloxy)acetate (27-6A)

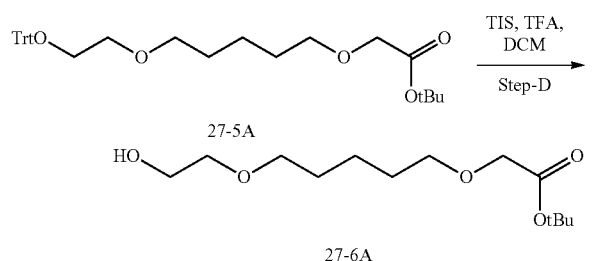

To a solution of 27-5A (1 g, 1.98 mmol) in DCM (10 mL) was added 0.5 mL of tri isopropyl silane (TIS) and 0.5 mL of TFA at 0° C. and stirred for 5 min. The reaction was diluted with EtOAc (100 mL) washed with water (100 mL), brine (50 mL) and dried over $Na_2SO_4$, and the organic phase was concentrated under reduced pressure. The crude residue was purified using silica gel chromatography (40% EtOAc in hexanes) to afford 27-6A (300 mg, 1.14 mmol, 58% yield) as a colorless oily liquid.

[5-(2-Methanesulfonyloxy-ethoxy)-pentyloxy]-acetic Acid Tert-butyl Ester (27-7A)

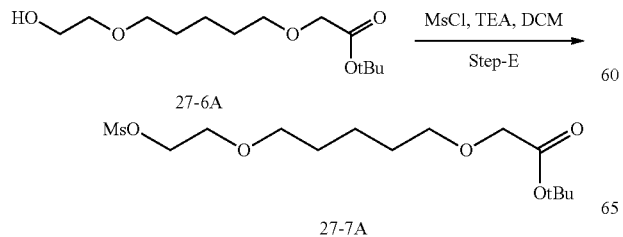

Methanesulfonyl chloride (195 mg, 1.71 mmol) at 0° C. was added to a solution of 27-6A (300 mg, 1.14 mmol) in DCM (5 mL) and triethylamine (231 mg, 2.29 mmol) and stirred at RT for 2 hr. The reaction mixture was diluted with excess DCM (50 mL) and washed with water (50 mL), brine (20 mL) and dried over $Na_2SO_4$. The organic layer was concentrated under reduced pressure. The crude residue was purified using 100-200 silica gel column chromatography (30% EtOAc in hexanes) to afford 27-7A (320 mg, 0.94 mmol, 82% yield) as a colorless oily liquid.

[5-(2-{[5-Cyclopropyl-2-(4-fluoro-phenyl)-3-methylcarbamoyl-benzofuran-6-yl]-methanesulfonylamino}-ethoxy)-pentyloxy]-acetic Acid Tert-butyl Ester (27-8A)

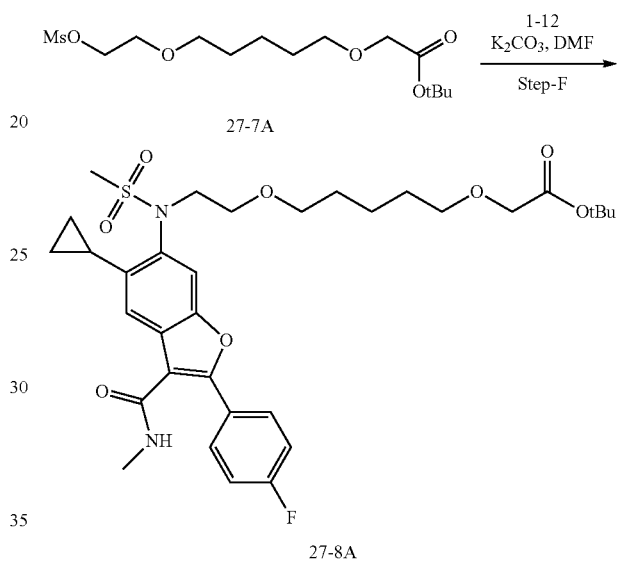

To a solution of 1-12 (315 mg, 0.78 mmol) in DMF (3 mL) was added potassium carbonate (325 mg, 2.35 mmol) followed by 27-7A (320 mg, 0.94 mmol), catalytic amount of TBAI then stirred at 70° C. for 16 hr. The reaction was cooled to RT and diluted with EtOAc (50 mL) washed with water (50 mL), brine (20 mL) and dried over $Na_2SO_4$, and the organic phase was concentrated under reduced pressure. The crude residue was purified using 100-200 silica gel column chromatography (40% EtOAc in hexanes) to afford 27-8A (250 mg, 0.38 mmol, 49% yield) as a grayish solid. MS (ESI): m/z 647.1 $(M+1)^+$.

[5-(2-{[5-Cyclopropyl-2-(4-fluoro-phenyl)-3-methylcarbamoyl-benzofuran-6-yl]-methanesulfonylamino}-ethoxy)-pentyloxy]-acetic Acid (27-9A)

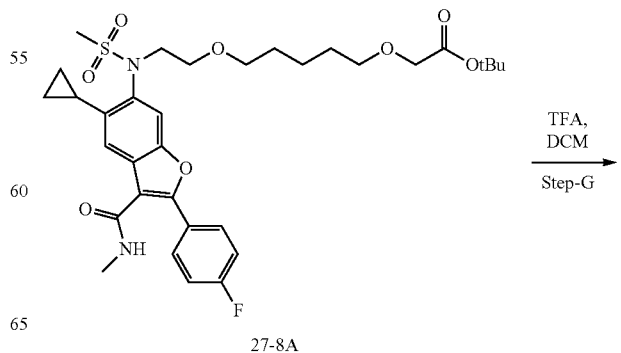

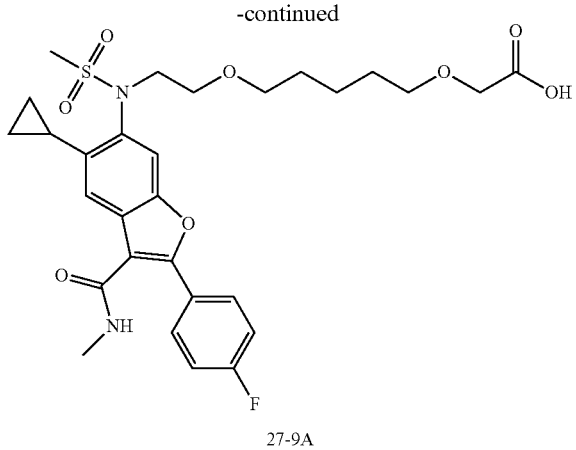

27-9A

To a solution of 27-8A (50 mg, 0.07 mmol) in DCM (2 mL) was added 0.5 mL of TFA at 0° C. and stirred at RT for 2 hr. After completion as indicated by TLC, to the reaction mixture add water (20 mL) and then extracted with excess DCM (20 mL). The organic layer was washed with brine, dried ($Na_2SO_4$) and concentrated at reduced pressure. The crude residue was purified by prep TLC to afford 27-9A (12 mg, 0.02 mmol, 25% yield) as a white solid. MS (ESI): m/z 589.6 (M+1)$^+$.

2-[5-(2-{[5-Cyclopropyl-2-(4-fluoro-phenyl)-3-methylcarbamoyl-benzofuran-6-yl]-methanesulfonyl-amino}-ethoxy)-pentyloxy]-propionic Acid (27-9B)

Starting from Step-C in the procedure described above, 2-bromo-propionic acid tert-butyl ester 27-4B was substituted for 27-4A, and Steps C-G were adapted to prepare 27-9B. MS (ESI): m/z 603.5 (M+1)$^+$.

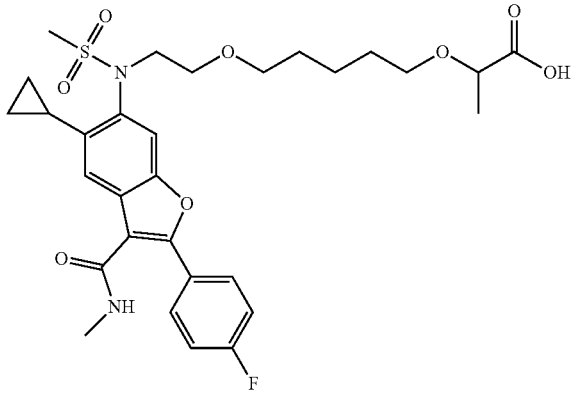

27-9B

Example 28

Tert-Butyl 5-bromopentanoate (28-2A)

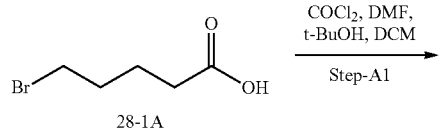

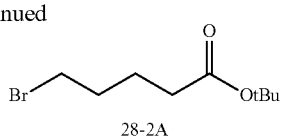

28-2A

To a solution of 28-1A (5 g, 27.62 mmol) in DCM, added oxalyl chloride (5.2 g, 41.436 mmol) and catalytic amount of DMF at 0° C. and stirred at RT for 30 min, then added t-BuOH (8.2 g, 110.49 mmol) at 0° C. and stirred at RT for 15 min. The reaction mixture completely distilled off, then added water (100 mL) and extracted with EtOAc (100 mL). The organic layer washed with water (50 mL), $NaHCO_3$ solution (50 mL) and dried over $Na_2SO_4$, and the organic phase was concentrated under reduced pressure. The crude compound was purified using silica gel chromatography (3% EtOAc in hexanes) to afford 28-2A (5 g, 21.18 mmol, 77% yield) as a colorless oily liquid.

Tert-Butyl 5-bromo-2-methylpentanoate (28-2B)

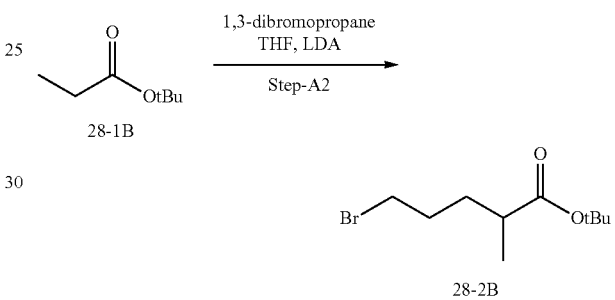

To a solution of propionic acid tert-butyl ester 28-1B (300 mg, 2.30 mmol) in THF (5 mL) was added 1,3-dibromopropane (0.35 mL, 3.46 mmol) and LDA in THF (2.3 mL, 4.61 mmol) at −40° C. and stirred for 2 hr. The reaction was quenched with saturated ammonium chloride solution and extracted with EtOAc (100 mL) washed with water (100 mL), brine (50 mL) and dried over $Na_2SO_4$, and the organic phase was concentrated under reduced pressure. The crude compound was purified using silica gel chromatography (40% EtOAc in hexanes) to afford 28-2B (290 mg, 1.16 mmol, 51% yield) as a pale yellow oily liquid.

Tert-Butyl 5-(5-(trityloxy)-pentyloxy)-pentanoate (28-4A)

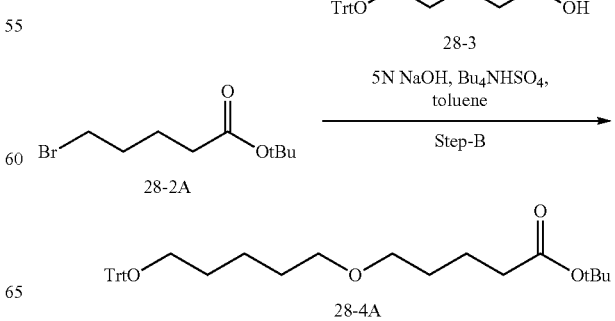

221

To a solution of 5-trityloxy-pentan-1-ol 28-3 (551 mg, 1.588 mmol) and 28-2A (1.5 g, 6.35 mmol) in toluene (6 mL) and 5N aq. NaOH (20 mL) was added tetra n-butyl ammonium hydrogen sulfate (495 mg, 1.27 mmol) and stirred at 50° C. for 48 hr. The reaction mixture was diluted with EtOAc (100 mL), washed with water (100 mL), brine (50 mL) and dried over Na$_2$SO$_4$, and the organic phase was concentrated under reduced pressure. The crude compound was purified using silica gel chromatography (3% EtOAc in hexanes) to afford 28-4A (220 mg, 0.43 mmol, 27% yield) as a colorless oily liquid.

Tert-Butyl 5-((5-hydroxypentyl)-oxy)-pentanoate (28-5A)

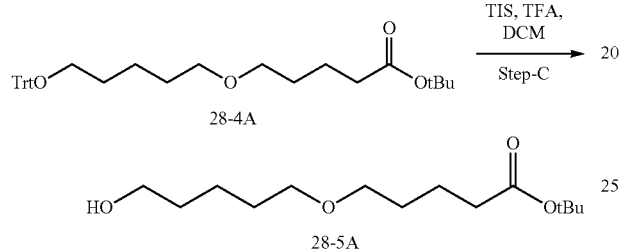

To a solution of 28-4A (220 mg, 0.44 mmol) in DCM (5 mL) was added triisopropyl silane (TIS; 5 mL) and TFA (0.1 mL) at 0° C. and stirred for 5 min. The reaction was diluted with EtOAc (50 mL) washed with water (50 mL), brine (25 mL) and dried over Na$_2$SO$_4$, and the organic phase was concentrated under reduced pressure. The crude compound was purified using silica gel chromatography (50% EtOAc in hexanes) to afford 28-5A (40 mg, 0.15 mmol, 33% yield) as a colorless oily liquid.

Tert-Butyl 5-((5-((methylsulfonyl)-oxy)-pentyl)-oxy)-pentanoate (28-6A

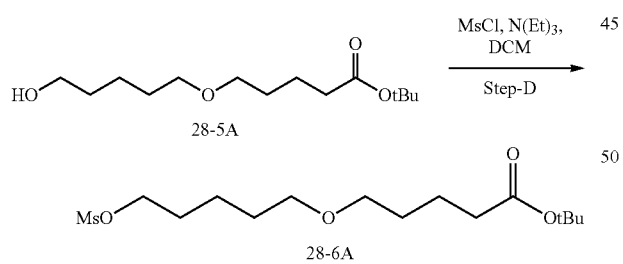

Methanesulfonyl chloride (26 mg, 0.23 mmol) at 0° C. was added to a solution of 28-5A (40 mg, 0.15 mmol) in DCM (2 mL) and triethylamine (39 mg, 0.38 mmol) and stirred at RT for 1 hr. The reaction mixture was diluted with excess DCM (20 mL) and washed with water (20 mL), brine (10 mL) and dried over Na$_2$SO$_4$, and the organic phase concentrated under reduced pressure. The crude compound was purified using 100-200 silica gel column chromatography (40% EtOAc in hexanes) to afford 28-6A (45 mg, 0.133 mmol, 86% yield) as a brownish oily liquid.

222

5-(5-{[5-Cyclopropyl-2-(4-fluoro-phenyl)-3-methyl-carbamoyl-benzofuran-6-yl]-methanesulfonyl-amino}-pentyloxy)-pentanoic Acid Tert-butyl Ester (28-7A)

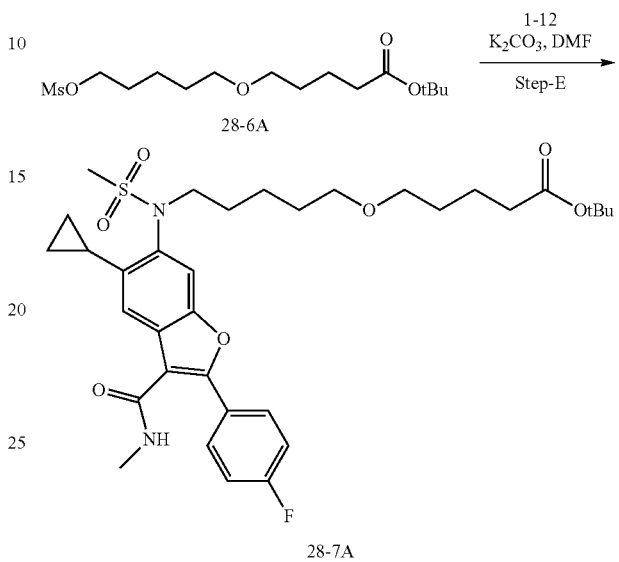

To a solution of 1-12 (281 mg, 0.69 mmol) in DMF (1 mL) was added potassium carbonate (290 mg, 2.09 mmol) followed by 28-6A (260 mg, 0.76 mmol), catalytic amount of TBAI then stirred at 70° C. for 16 hr. The reaction was cooled to RT and diluted with EtOAc (50 mL) washed with water (50 mL), brine (20 mL) and dried over Na$_2$SO$_4$, and the organic phase was concentrated under reduced pressure. The crude compound was purified using 100-200 silica gel column chromatography (40% EtOAc in hexanes) to afford 28-7A (180 mg, 0.279 mmol, 36% yield) as a grayish solid. MS (ESI): m/z 645.0 (M+1)$^+$.

5-((5-(N-(5-cyclopropyl-2-(4-fluorophenyl)-3-(methylcarbamoyl)benzofuran-6-yl)-methyl sulfonamido)-pentyl)-oxy)-pentanoic Acid (28-8A)

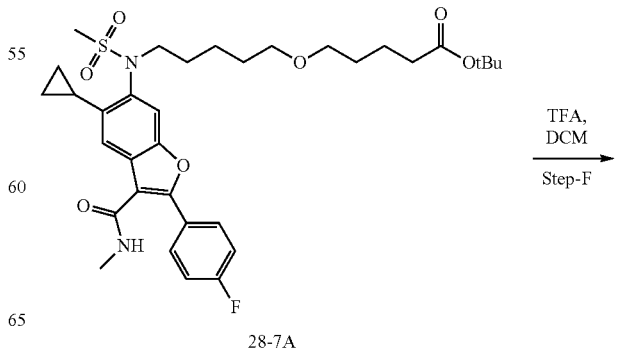

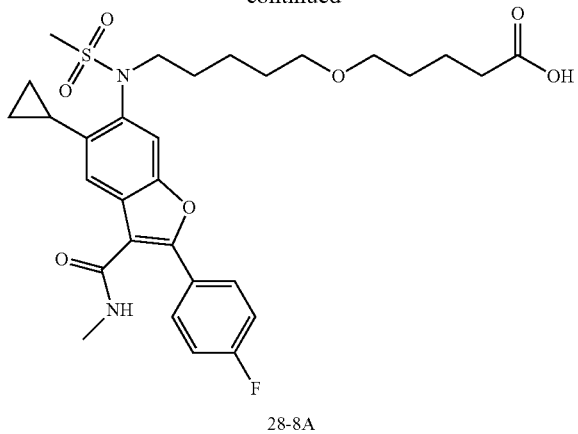

28-8A

To a solution of 28-7A (18 mg, 0.03 mmol) in DCM (1 mL) was added TFA at 0° C. and stirred at RT for 16 hr. After completion of the reaction (by TLC), water (10 mL) was added, and the mixture was extracted with EtOAc (10 mL). The organic layer was washed with brine, dried over $Na_2SO_4$ and concentrated. The crude compound was purified by prep TLC to afford 28-8A (8 mg, 0.014 mmol, 50% yield) as a grayish solid. MS (ESI): m/z 586.9 $(M+1)^+$.

5-(5-{[5-Cyclopropyl-2-(4-fluoro-phenyl)-3-methyl-carbamoyl-benzofuran-6-yl]-methanesulfonyl-amino}-pentyloxy)-2-methyl-pentanoic Acid (28-8B)

Starting from Step-B in the procedure described above, 28-2B was substituted for 28-2A, and Steps B-F were adapted to prepare 28-8B. MS (ESI): m/z 603.5 $(M+1)^+$.

28-8B

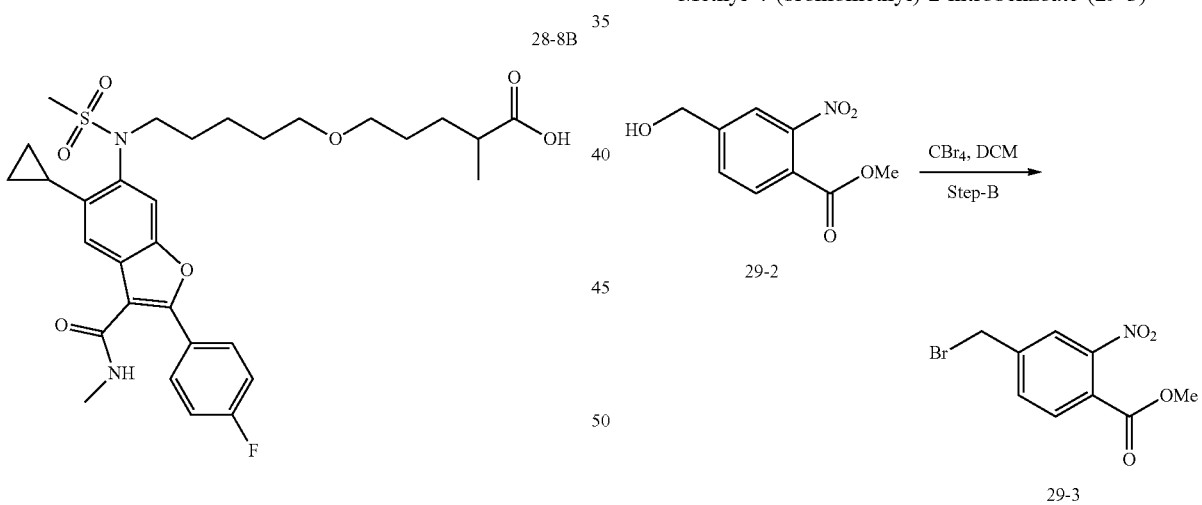

Example 29

Methyl 4-(hydroxymethyl)-2-nitrobenzoate (29-2)

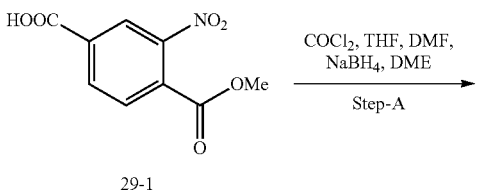

To a stirred solution of 4-(methoxycarbonyl)-3-nitrobenzoic acid 29-1 (5 g, 22.2 mmol) in THF (100 mL) was added, and oxalyl chloride (2.27 mL, 26.6 mmol) and DMF (0.3 mL) was added at 0° C. The reaction mixture was stirred at the same temperature for 1 hr. The organic solvent was removed under reduced pressure, and the residue was dissolved in DME (30 mL). This solution was added to a suspension of sodium borohydride (3.3 g, 88.8 mmol) in DME (20 mL) at 0° C., and the mixture was stirred for 4 hr. After completion of the reaction (by TLC), 1N hydrochloric acid (50 mL) was poured into the reaction mixture and extracted with EtOAc. The organic layer was washed with brine, dried ($Na_2SO_4$) and concentrated. The crude compound was purified by column chromatography (100-200 silica) using 25% EtOAc/pet. ether to afford 29-2 (3.7 g, 20.6 mmol, yield 80%) as an off-white solid. MS (ESI): m/z 180.0 $(M+1)^+$.

Methyl 4-(bromomethyl)-2-nitrobenzoate (29-3)

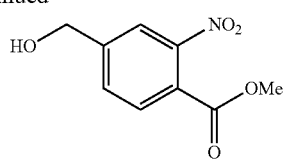

To a solution of 29-2 (3 g, 14.2 mmol) in DCM (80 mL) was added carbon tetra bromide (5.17 g, 15.6 mmol), triphenyl phosphine (4.08 g, 15.6 mmol), and stirred at 0° C. to RT for 4 hr. The reaction mixture was diluted with DCM (50 mL), washed with water (100 mL), brine (100 mL) and dried over $Na_2SO_4$, and the organic phase was concentrated under reduced pressure. The crude compound was purified by column chromatography (100-200 silica) using 10% EtOAc in hexane) to afford 29-3 (2.5 g, 9.19 mmol, 65% yield). MS (ESI): m/z 244.0 $(M-NO_2+18)^+$.

Methyl 2-nitro-4-((2-(2-(tetrahydro-2H-pyran-2-yloxy)-ethoxy)-ethoxy)-methyl)benzoate (29-4)

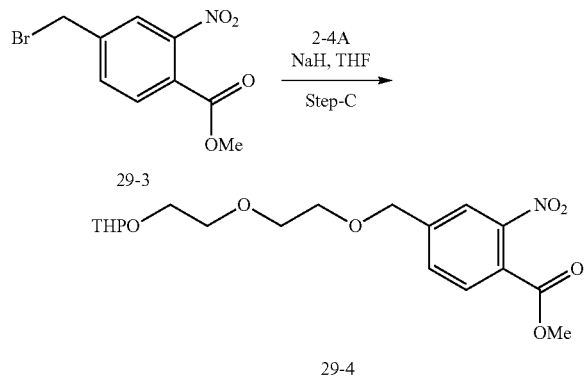

To a stirred solution of 2-4A (1.5 g, 7.8 mmol) in THF (5 mL) was added NaH (187 mg, 7.8 mmol) at 0° C., and reaction was continued at RT for 30 min. Then, 29-3 (2.34 g, 8.58 mmol) in THF (10 mL) was added to the reaction mixture at 0° C. over 5 min. and reaction was continued at RT for 16 hr. The reaction mixture was quenched with ice cold water (100 mL) and extracted with EtOAc (3×100 mL), the combined organic layers were washed with water (2×100 mL), brine (100 mL), dried over $Na_2SO_4$ and concentrated. The residue was purified by flash column chromatography (100-200 silica) using 20% EtOAc/hexanes to afford 29-4 (1.1 g, 2.87 mmol, 31% yield) as a yellow thick liquid. MS (ESI): m/z 300.0 (M-THP+1)$^+$.

Methyl 4-((2-(2-hydroxyethoxy)-ethoxy)-methyl)-2-nitrobenzoate (29-5)

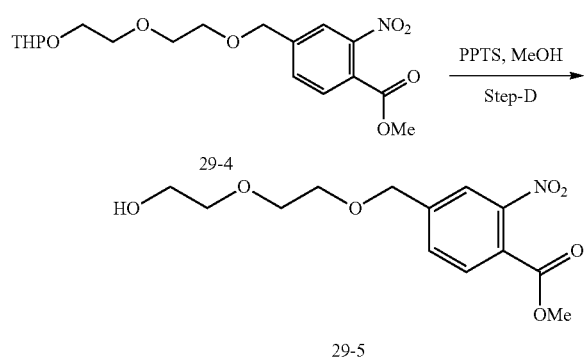

To a stirred solution of 29-4 (1.1 g, 2.87 mmol) in MeOH (10 mL) was added PPTS (72 mg, 0.28 mmol) at 0° C. and stirred at RT for 12 hr. The reaction mixture was distilled off and diluted with excess EtOAc (20 mL), washed with water (20 mL), brine (10 mL) and dried over $Na_2SO_4$, and the organic phase was concentrated under reduced pressure to get crude compound. The crude was purified by flash column chromatography (100-200 silica) using 40% EtOAc/hexanes to afford 29-5 (600 mg, 2.01 mmol, 69% yield) as light yellow liquid. MS (ESI): m/z 300.0 (M+1)$^+$.

4-[2-(2-Methanesulfonyloxy-ethoxy)-ethoxymethyl]-2-nitro-benzoic Acid Methyl Ester (29-6)

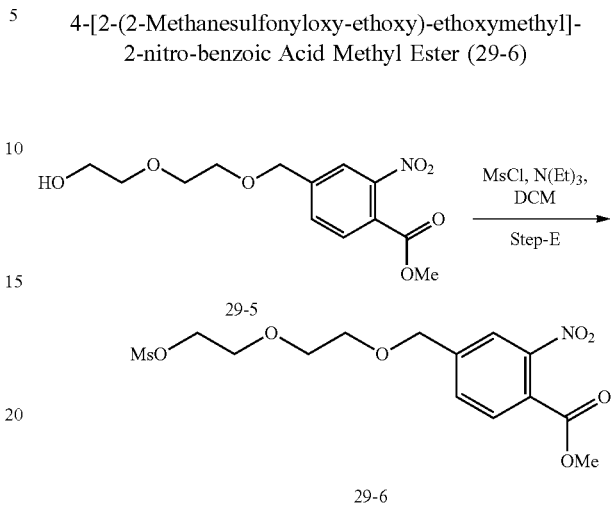

To a stirred solution of 29-5 (600 mg, 2.01 mmol) in DCM (10 mL) was added triethylamine (0.67 mL, 4.81 mmol) and methanesulfonyl chloride (0.19 mL, 2.41 mmol) at 0° C. and stirred at RT for 1 hr. The reaction mixture was diluted with excess DCM (50 mL) and washed with water (50 mL), brine (30 mL) and dried over $Na_2SO_4$, and the organic phase concentrated under reduced pressure. The crude compound was purified by column chromatography (100-200 silica) using 30% EtOAc/hexane to afford 29-6 (610 mg, 1.62 mmol, 80% yield). MS (ESI): m/z 378.0 (M+1)$^+$.

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-2-nitro-benzoic Acid Methyl Ester

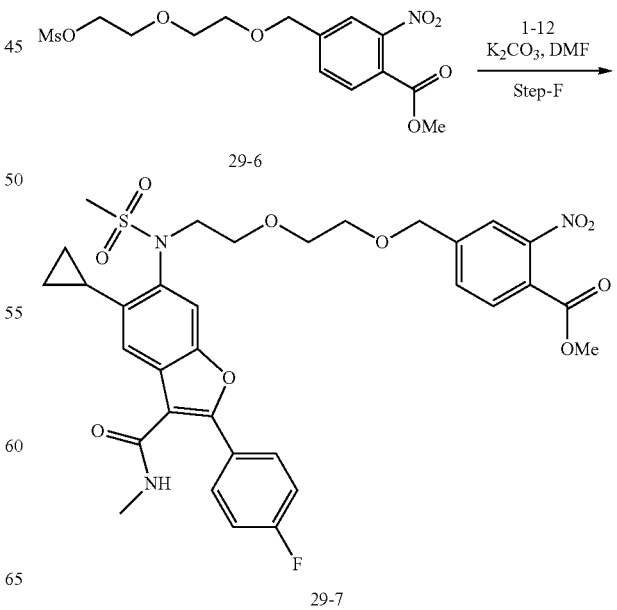

To a stirred solution of 1-12 (544 mg, 1.35 mmol) in DMF (10 mL) was added potassium carbonate (560 mg, 4.06 mmol) followed by 29-6 (610 mg, 1.62 mmol), catalytic amount of TBAI then stirred at 70° C. for 16 hr. The reaction was cooled to RT and diluted with EtOAc (40 mL) washed with water (20 mL), brine (20 mL) and dried over $Na_2SO_4$, and the organic phase was concentrated under reduced pressure. The crude compound was purified by column chromatography (100-200 silica) using 30% EtOAc/hexane to afford 29-7 (530 mg, 0.775 mmol, 57% yield) as a pale yellow solid. MS (ESI): m/z 683.0 $(M+1)^+$.

4-[2-(2-{[5-Cyclopropyl-2-(4-fluoro-phenyl)-3-methylcarbamoyl-benzofuran-6-yl]-methanesulfonyl-amino}-ethoxy)-ethoxymethyl]-2-nitro-benzoic Acid

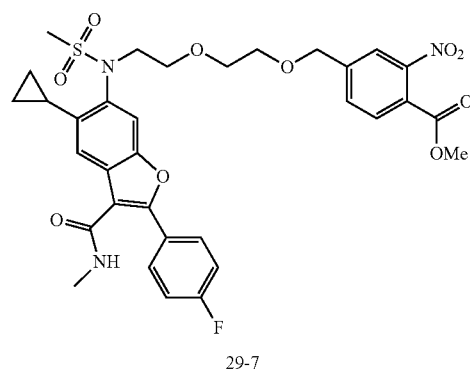

29-8

To a solution of 29-7 (200 mg, 0.292 mmol) in MeOH, THF and water (1:4:1) (8 mL) was added $LiOH \cdot H_2O$ (42 mg, 1.75 mmol) and stirred at RT for 16 hr. After completion of the reaction as indicated by TLC, the reaction mixture was neutralized with 1N HCl and then extracted with EtOAc. The organic layer was washed with brine, dried ($Na_2SO_4$) and concentrated. The crude compound was purified by column chromatography (100-200 silica) using 2% MeOH/DCM to afford 29-8 (80 mg, 0.12 mmol, 40% yield) as an off-white solid. MS (ESI): m/z 670.0 $(M+1)^+$.

2-Amino-4-[2-(2-{[5-cyclopropyl-2-(4-fluoro-phenyl)-3-methylcarbamoyl-benzofuran-6-yl]-methanesulfonyl-amino}-ethoxy)-ethoxymethyl]-benzoic Acid Methyl Ester (29-9)

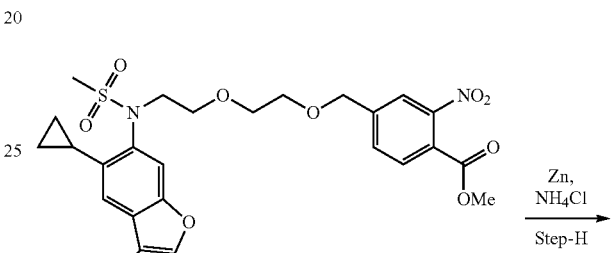

29-7

29-9

To a stirred solution of 29-7 (200 mg, 0.292 mmol) in THF/water (1:1, 8 mL) was added zinc (114 mg, 1.756 mmol) and $NH_4Cl$ (93 mg, 1.756 mmol) at RT and stirred at 70° C. for 4 hr. After completion of the reaction as indicated by TLC, the reaction mixture was filtered. The reaction mixture was distilled off and diluted with excess EtOAc (20 mL), washed with water (20 mL), brine (10 mL) and dried over $Na_2SO_4$, and the organic phase was concentrated under reduced pressure. The crude compound was purified by flash column chromatography (100-200 silica) using 40% EtOAc in hexane to afford 29-9 (140 mg, 0.21 mmol, 73% yield) as a yellowish solid. MS (ESI): m/z 654.0 (M+1)+.

2-Amino-4-[2-(2-{[5-cyclopropyl-2-(4-fluoro-phenyl)-3-methylcarbamoyl-benzofuran-6-yl]-methanesulfonyl-amino}-ethoxy)-ethoxymethyl]-benzoic Acid (29-10)

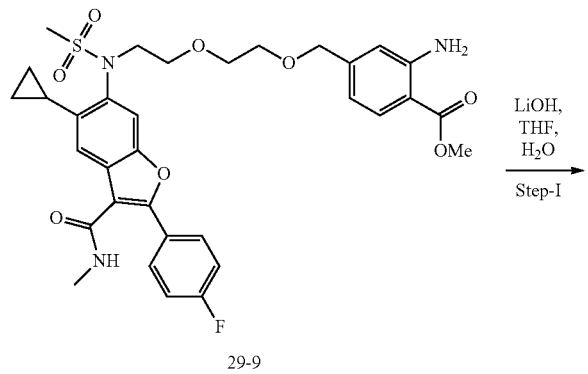

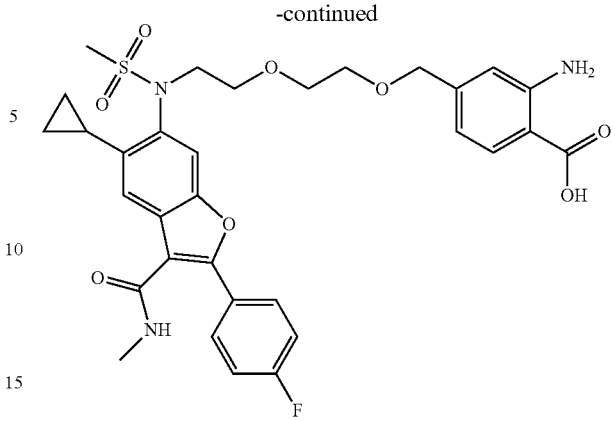

29-10

To a solution of 29-9 (90 mg, 0.137 mmol) in MeOH, THF and water (1:4:1, 4 mL) was added LiOH.H$_2$O (20 mg, 0.826 mmol) and stirred at RT for 16 hr. After completion of the reaction as indicated by TLC, the reaction mixture was neutralized with 1N HCl and then extracted with EtOAc. The organic layer was washed with brine, dried (Na$_2$SO$_4$) and concentrated to get crude compound. This crude was purified by column chromatography (100-200 silica) using 2% MeOH/DCM, followed by washing with DCM and pentane to afford 29-10 (40 mg, 0.119 mmol, 45% yield) as an off-white solid. MS (ESI): m/z 640.0 (M+1)+.

Example 30

The following compounds were made by methods generally in accord with those described above, using suitable reagents and conventional adaptation of reaction conditions. Esters and other carboxylic acid derivatives were prepared from, or converted to, the corresponding carboxylic acid compounds using conventional methods.

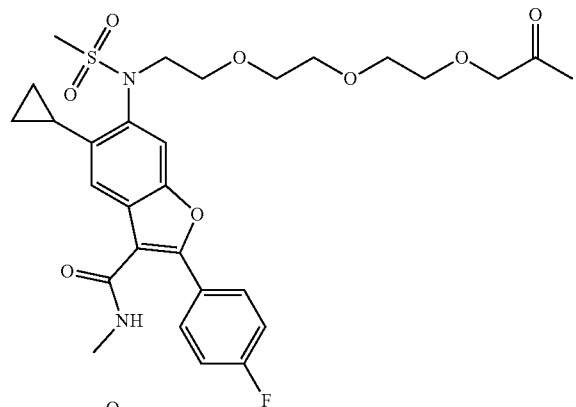

30-1

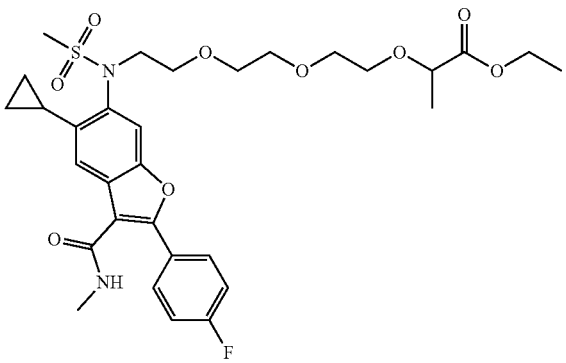

30-2

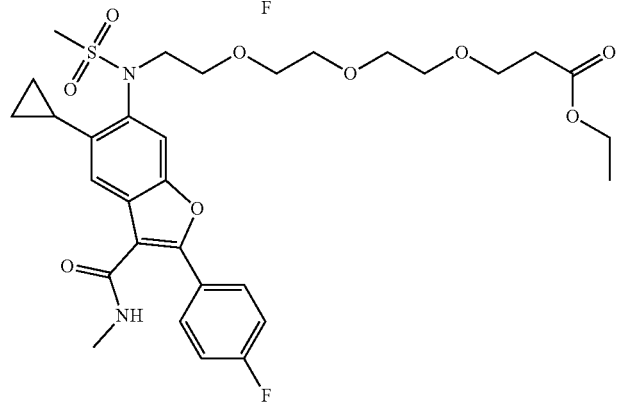

30-3

30-4
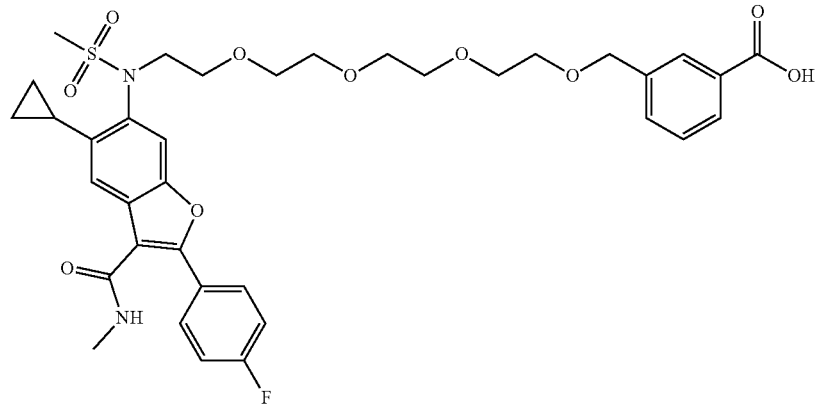
30-5
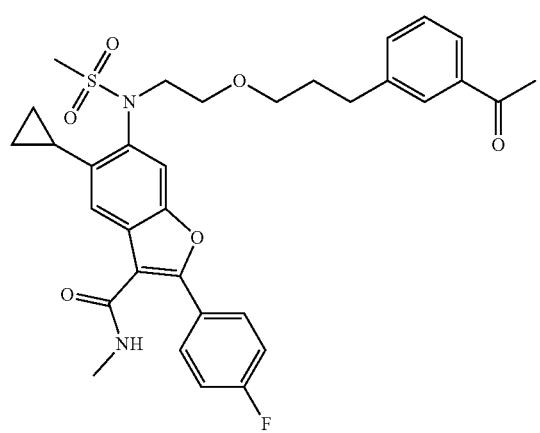
30-6
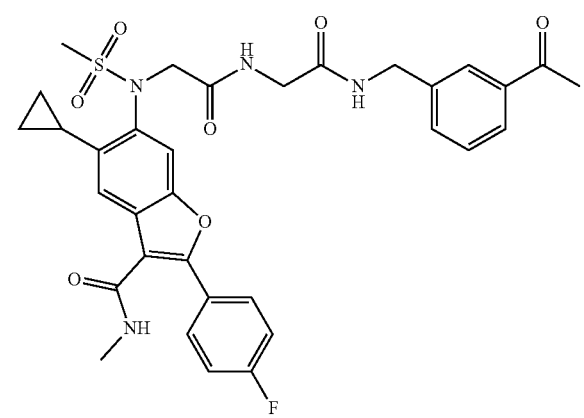
30-7
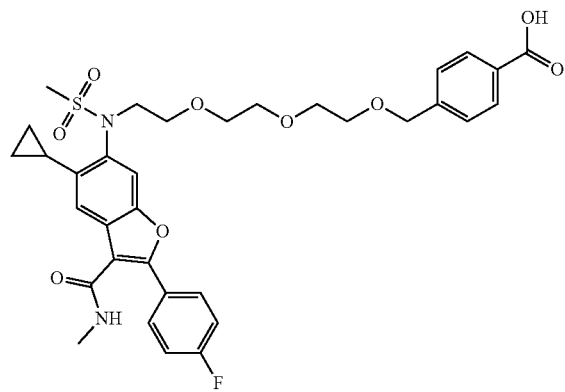
30-8
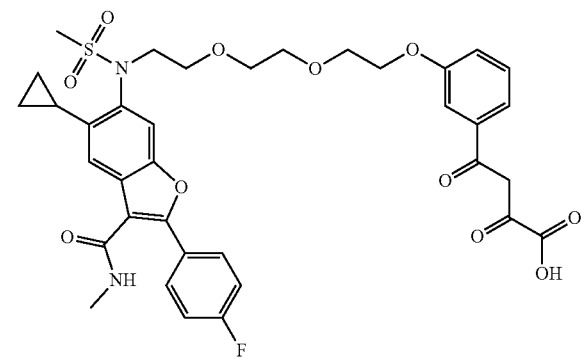

-continued
30-9
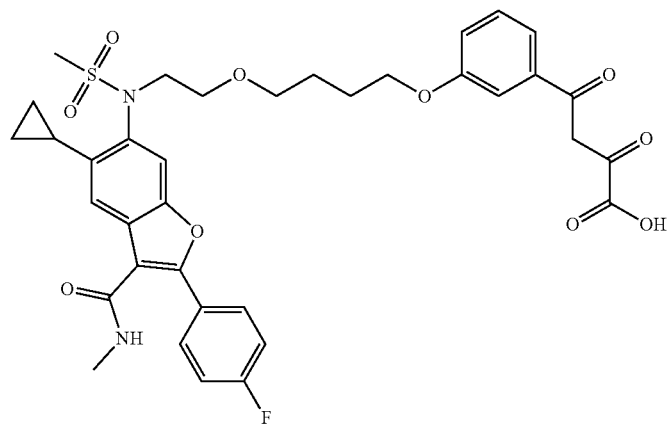
30-10
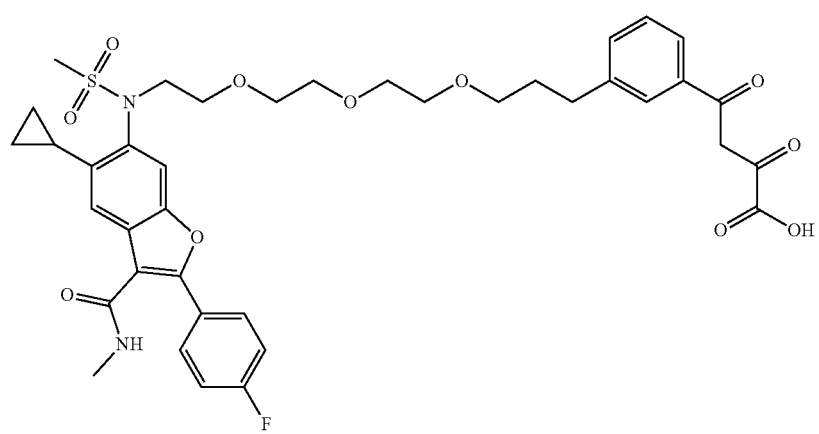
30-11
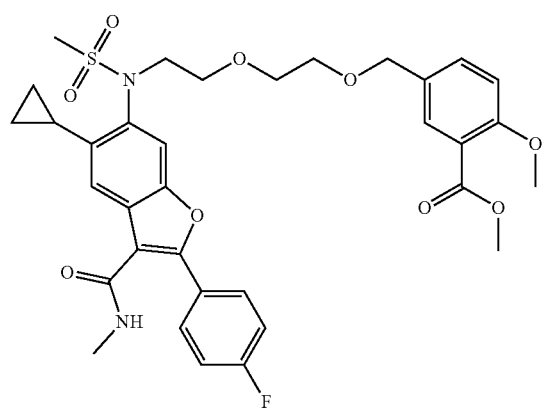
30-12
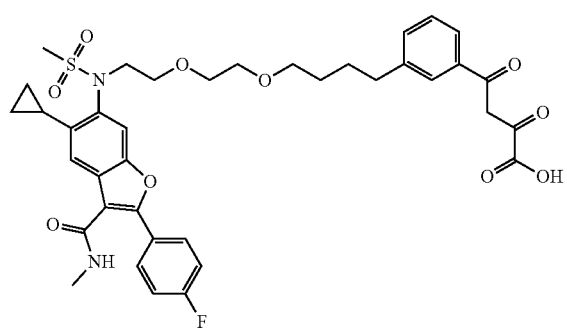

-continued
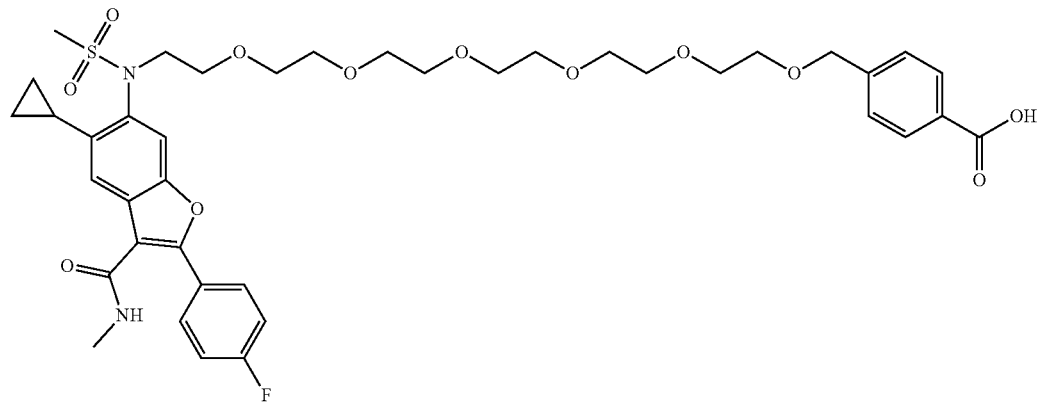
30-13
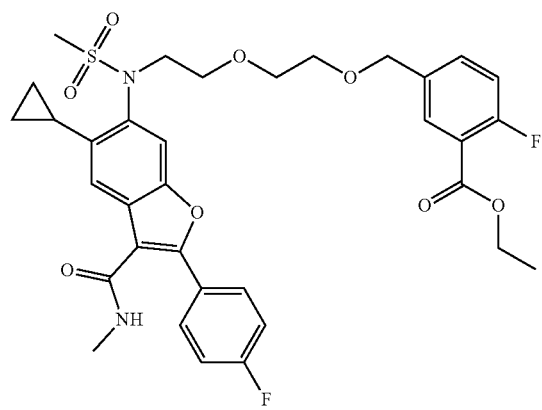
30-14
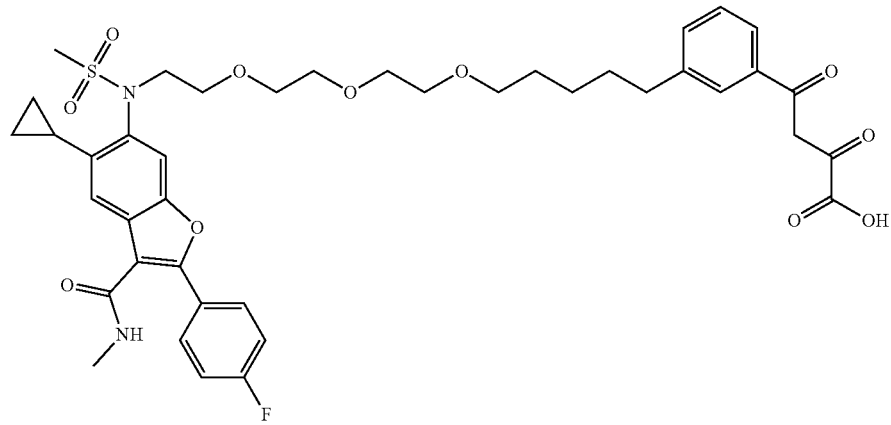
30-15
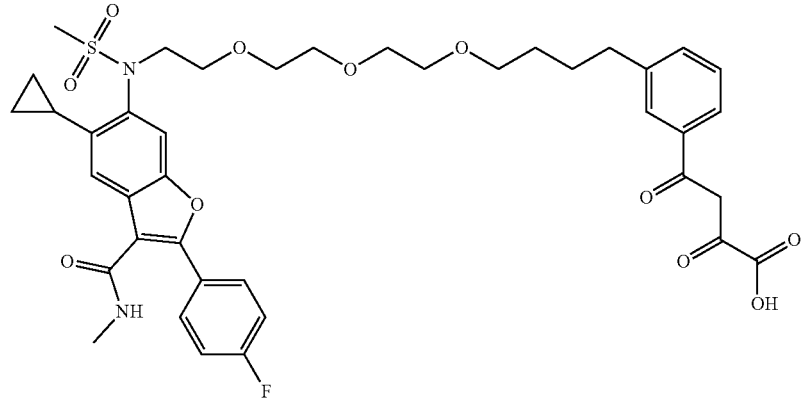
30-16

Example 31

RNA-Dependent RNA HCV NS5B (polymerase) Assay and IC$_{50}$ Determination.

The reaction mixtures consisted of 50 mM Hepes-KOH, pH 7.5, 5 mM MgCl$_2$, 5 mM DTT, 2% glycerol, 0.01% Triton® X-100, 0.5 uM polyA:U16 substrate, purified HCV RNA-dependent RNA polymerase, 10 μM UTP, and $^{32}$P-UTP (Perkin Elmer). The reaction mixtures incubated at 30° C. for 60 minutes, and then filtered through Zeta probe membrane (BioRad). The filter was washed with 5×SSC (75 mM sodium citrate, pH 7 and 750 mM NaCl), and the radiolabeled RNA products were quantitated by microbeta (Perkin Elmer). For IC$_{50}$ determination, different concentrations of inhibitors were added to the polymerase reaction mixtures, and incubated at 37° C. for 60 minutes. IC$_{50}$ values were determined using GraFit (Erithaus software).

Table 1 presents IC$_{50}$ data obtained using the biochemical assay to test representative compounds. Data are presented as follows: "+++" means <0.1 μM; "++" means ≥0.1 μM but <1.0 μM; "+" means ≥1.0 μM.

TABLE 1

| Compound | IC$_{50}$ (μM) |
| --- | --- |
| 02-10A | ++ |
| 02-10B | + |
| 02-10B | + |
| 02-10C | ++ |
| 02-10E | + |
| 02-10F | + |
| 02-10G | + |
| 02-10H | + |
| 02-10I | + |
| 02-10J | + |
| 02-8A | + |
| 02-8B | + |
| 02-8D | + |
| 02-8E | + |
| 02-8F | + |
| 02-8H | + |
| 02-8I | + |
| 02-9C | + |
| 02-9H | + |
| 03-6A | + |
| 03-8A | ++ |
| 03-8B | + |
| 04-10 | + |
| 04-5 | + |
| 05-4A | + |
| 05-4B | + |
| 06-6A | ++ |
| 06-6B | + |
| 06-6C | + |
| 06-6D | ++ |
| 06-6E | ++ |
| 06-6F | + |
| 06-7A | ++ |
| 06-7B | ++ |
| 06-7C | ++ |
| 06-7D | ++ |
| 06-7E | ++ |
| 06-7F | +++ |
| 06-8B1 | + |
| 06-8B2 | + |
| 06-8B3 | ++ |
| 06-8B4 | ++ |
| 06-8B5 | ++ |
| 06-8B6 | ++ |
| 06-8B7 | ++ |
| 06-8B8 | ++ |
| 07-7 | + |
| 07-10 | + |
| 08-6 | ++ |
| 09-14A | ++ |
| 09-14B | + |
| 09-14C | + |
| 09-14D | + |
| 09-14E | + |
| 09-14F | + |
| 10-3A | + |
| 10-3B | + |
| 10-4A | + |
| 10-4B | + |
| 11-5A | ++ |
| 11-5B | + |
| 11-5C | + |
| 11-6A | +++ |
| 11-6B | +++ |
| 11-6C | ++ |
| 12-6A | ++ |
| 12-7A | +++ |
| 12-7B | +++ |
| 12-7C | ++ |
| 13-7A | ++ |
| 13-7B | ++ |
| 13-7C | ++ |
| 13-7D | ++ |
| 13-8A | ++ |
| 13-8B | ++ |
| 13-8C | ++ |
| 13-8D | ++ |
| 14-6A | ++ |
| 14-6B | + |
| 14-6C | + |
| 14-7A | +++ |
| 14-7B | ++ |
| 14-7C | ++ |
| 15-7 | ++ |
| 15-8 | ++ |
| 16-6 | + |
| 16-7 | ++ |
| 17A-8A | ++ |
| 17A-8B | + |
| 17B-8 | ++ |
| 18-9A | + |
| 18-9B | + |
| 18-10A | ++ |
| 18-10B | +++ |
| 19-8A | +++ |
| 19-8B | +++ |
| 20-7 | ++ |
| 20-8 | +++ |
| 21-5 | +++ |
| 22-12 | + |
| 23-5A | + |
| 23-6A | ++ |
| 23-6B | ++ |
| 23-6C | ++ |
| 23-7A | ++ |
| 24-4 | ++ |
| 25-4 | + |
| 25-5 | ++ |
| 25-6 | + |
| 26-6A | + |
| 26-6B | + |
| 26-7A | +++ |
| 26-7B | ++ |
| 26-8B | + |
| 27-8A | + |
| 27-9A | ++ |
| 27-9B | ++ |
| 28-7A | + |
| 28-8A | +++ |
| 28-8B | +++ |
| 29-7 | ++ |
| 29-8 | ++ |
| 29-9 | ++ |
| 29-10 | ++ |
| 30-1 | + |
| 30-2 | + |
| 30-3 | + |
| 30-4 | + |

TABLE 1-continued

| Compound | IC$_{50}$ (μM) |
|---|---|
| 30-5 | + |
| 30-6 | + |
| 30-7 | + |
| 30-8 | + |
| 30-9 | + |
| 30-10 | + |
| 30-11 | + |
| 30-12 | + |
| 30-13 | + |
| 30-14 | + |
| 30-15 | + |
| 30-16 | + |

Example 32

HCV Replicon Assay and EC$_{50}$ Determination.

HCV replicon assay is based on the luciferase reporter cell line (Huh-luc/neo-ET). This reporter cell line is a human liver carcinoma cell line (Huh-7) stably transfected with an autonomously replicating bicistronic HCV subgenomic RNA replicon (Lohmann et al., 1999, Science, 285, 110-113). Inhibition of HCV RNA replication was monitored through analysis of reporter luciferase activity. Briefly, HCV replicon cells were incubated with inhibitors for 72 hours at 37° C. After the incubation, duplicate plates were treated and incubated in parallel for assessment of cellular toxicity by XTT staining and anti-HCV activity by measurement of luciferase reporter activity. Either human interferon alpha 2B or ribavirin was used as a reference compound. EC$_{50}$ values were determined using GraFit (Erithaus software) or Excel.

Table 2 presents EC$_{50}$ data obtained using this HCV replicaon assay to test representative compounds. Data are presented as follows: "+++" means <0.1 μM; "++" means ≥0.1 μM and <1.0 μM; "+" means ≥1.0 μM.

TABLE 2

| Compound | EC$_{50}$ (μM) |
|---|---|
| 2-8A | +++ |
| 2-10A | +++ |
| 2-10E | ++ |
| 2-10F | +++ |
| 3-8B | +++ |
| 04-5 | ++ |
| 06-7A | +++ |
| 06-7B | ++ |
| 06-7C | +++ |
| 08-6 | ++ |
| 09-14A | ++ |
| 09-14C | ++ |
| 09-14E | ++ |
| 09-14F | ++ |
| 13-8C | +++ |
| 13-8D | +++ |
| 16-7 | +++ |
| 17A-8A | +++ |
| 17B-8 | ++ |
| 22-12 | +++ |
| 23-6A | ++ |
| 23-6B | +++ |
| 23-6C | +++ |
| 25-5 | ++ |

All publications, including but not limited to patents and patent applications, cited in this specification are incorporated by reference herein for all that they disclose, as if each individual publication were specifically and individually set forth in its entirety.

While a number of aspects and embodiments of this invention have been described, the basic examples and general formulas and schemata may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A compound having the structure:

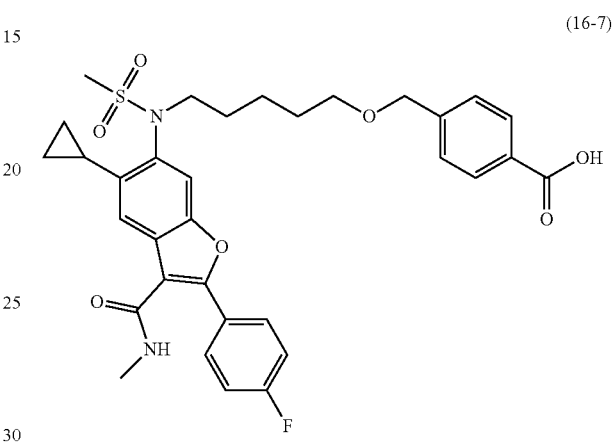

(16-7)

or a pharmaceutically acceptable salt thereof.

2. A pharmaceutical composition comprising the compound or salt of claim 1 and a pharmaceutically acceptable excipient.

3. A method for reducing a hepatitis C virus polymerase activity in a host, comprising administering to the host a therapeutic amount of the compound or salt of claim 1.

4. A method for reducing hepatitis C virus replication in a host, comprising administering to the host a therapeutic amount of the compound or salt of claim 1.

5. A method for treating or preventing hepatitis C virus infection or reactivation in a host, comprising administering to the host a therapeutic amount of the compound or salt of claim 4.

6. The method of claim 5, further comprising administering to the host at least one active agent selected from the group consisting of interferons, ribavirin, nucleoside HCV NS5B polymerase inhibitors, non-nucleoside HCV NS5B polymerase inhibitors, HCV NS3-4A protease inhibitors, HCV NS5A inhibitors, HCV entry inhibitors, HCV NS3 inhibitors, HCV NS3 helicase inhibitors, HCV NS4B inhibitors, and human cyclophilin inhibitors.

7. A combination, comprising the compound or salt of claim 1, together with at least one active agent selected from interferons, ribavirin, nucleoside HCV NS5B polymerase inhibitors, non-nucleoside HCV NS5B polymerase inhibitors, HCV NS3-4A protease inhibitors, HCV NS5A inhibitors, HCV entry inhibitors, HCV NS3 inhibitors, HCV NS3 helicase inhibitors, HCV NS4B inhibitors, and human cyclophilin inhibitors.

8. A combination, comprising the composition of claim 2, together with a composition comprising at least one active agent selected from interferons, ribavirin, nucleoside HCV NS5B polymerase inhibitors, non-nucleoside HCV NS5B polymerase inhibitors, HCV NS3-4A protease inhibitors, HCV NS5A inhibitors, HCV entry inhibitors, HCV NS3 inhibitors, HCV NS3 helicase inhibitors, HCV NS4B inhibitors, and human cyclophilin inhibitors and a pharmaceutically acceptable excipient.

* * * * *